US012774458B2

(12) United States Patent
Lin et al.

(10) Patent No.: US 12,774,458 B2
(45) Date of Patent: Oct. 27, 2026

(54) BASE EDITING ENZYMES

(71) Applicant: Metagenomi Therapeutics, Inc., Emeryville, CA (US)

(72) Inventors: Jyun-Liang Lin, Emeryville, CA (US); Alan Brooks, Emeryville, CA (US); Cristina Butterfield, Emeryville, CA (US); Christopher Brown, Emeryville, CA (US); Cindy Castelle, Emeryville, CA (US); Brian C. Thomas, Emeryville, CA (US)

(73) Assignee: Metagenomi Therapeutics, Inc., Emeryville, CA (US)

( * ) Notice: Subject to any disclaimer, the term of this patent is extended or adjusted under 35 U.S.C. 154(b) by 730 days.

(21) Appl. No.: 18/180,009

(22) Filed: Mar. 7, 2023

(65) Prior Publication Data

US 2023/0348876 A1 Nov. 2, 2023

Related U.S. Application Data

(63) Continuation of application No. PCT/US2021/049962, filed on Sep. 10, 2021.
(Continued)

(51) Int. Cl.
*C12N 9/22* (2006.01)
*C12N 9/78* (2006.01)
(Continued)

(52) U.S. Cl.
CPC ................. *C12N 9/22* (2013.01); *C12N 9/78* (2013.01); *C12N 15/11* (2013.01); *C12N 15/111* (2013.01); *C12N 15/1137* (2013.01); *C12N 15/85* (2013.01); *C12N 15/907* (2013.01); *C12Y 302/02027* (2013.01);
(Continued)

(58) Field of Classification Search
CPC .................. C12N 9/22; C12N 2310/20; C12Y 305/04004; C07K 2319/00
See application file for complete search history.

(56) References Cited

U.S. PATENT DOCUMENTS 12,286,654 B2 4/2025 Lin et al.
12,503,710 B2 12/2025 Thomas et al.
(Continued)

FOREIGN PATENT DOCUMENTS

EP 3617311 A1 3/2020
WO WO-2018027078 A1 * 2/2018 .............. A61P 43/00
(Continued)

OTHER PUBLICATIONS

GenBank. "Corynebacterium Ulcerans BR-AD22, Complete Genome, NCBI Reference Sequence: NC_015683.1—Nucleotide—NCBI." Nih.gov, Mar. 30, 2017, www.ncbi.nlm.nih.gov/nuccore/337289620?sat=47&satkey=89452374. Accessed Jan. 29, 2026. (Year: 2017).*
(Continued)

*Primary Examiner* — Kimberly Chong
*Assistant Examiner* — Africa M Mcleod
(74) *Attorney, Agent, or Firm* — Wilson Sonsini Goodrich & Rosati

(57) ABSTRACT

The present disclosure provides for endonuclease enzymes having distinguishing domain features, as well as methods of using such enzymes or variants thereof.

14 Claims, 25 Drawing Sheets

Specification includes a Sequence Listing.

Related U.S. Application Data

(60) Provisional application No. 63/222,351, filed on Jul. 15, 2021, provisional application No. 63/077,057, filed on Sep. 11, 2020.

(51) Int. Cl.

| | |
|---|---|
| ***C12N 15/10*** | (2006.01) |
| ***C12N 15/11*** | (2006.01) |
| ***C12N 15/113*** | (2010.01) |
| ***C12N 15/85*** | (2006.01) |
| ***C12N 15/90*** | (2006.01) |

(52) U.S. Cl.
CPC .. *C12Y 305/04004* (2013.01); *C07K 2319/00* (2013.01); *C07K 2319/09* (2013.01); *C12N 15/102* (2013.01); *C12N 2310/20* (2017.05); *C12N 2800/107* (2013.01); *C12N 2800/80* (2013.01)

(56) References Cited

U.S. PATENT DOCUMENTS

| | | | |
|---|---|---|---|
| 2018/0170984 A1 | 6/2018 | Harris et al. |
| 2018/0258418 A1 | 9/2018 | Kim |
| 2018/0371498 A1 | 12/2018 | Gill et al. |
| 2022/0364067 A1 | 11/2022 | Lin et al. |
| 2023/0348877 A1 | 11/2023 | Lin et al. |
| 2023/0374482 A1 | 11/2023 | Thomas et al. |
| 2024/0309404 A1 | 9/2024 | Thomas et al. |

FOREIGN PATENT DOCUMENTS

| | | |
|---|---|---|
| WO | WO-2018176009 A1 | 9/2018 |
| WO | WO-2018179578 A1 | 10/2018 |
| WO | WO-2019005884 A1 | 1/2019 |
| WO | WO-2019118935 A1 | 6/2019 |
| WO | WO-2020163396 A1 | 8/2020 |
| WO | WO-2020168234 A1 | 8/2020 |
| WO | WO-2020168291 A1 | 8/2020 |
| WO | WO-2021097118 A1 | 5/2021 |
| WO | WO-2021202568 A1 | 10/2021 |
| WO | WO-2022056301 A1 | 3/2022 |
| WO | WO-2022056324 A1 | 3/2022 |
| WO | WO-2023081855 A1 | 5/2023 |

OTHER PUBLICATIONS

GenPept. "TRNA Adenosine(34) Deaminase TadA [Lacimicrobium Alkaliphilum], NCBI Reference Sequence: WP_062484216.1—Protein—NCBI." Nih.gov, Jul. 12, 2017, www.ncbi.nlm.nih.gov/protein/1011634138?sat=47&satkey=44006920. (Year: 2017).*

Rathore, A. et al., "The Local Dinucleotide Preference of APOBEC3G Can Be Altered from 5'-CC to 5'-TC by a Single Amino Acid Substitution", J. Mol Biol., 2013, vol. 425, pp. 4442-4454.

Feng, Y. et al., "FAM72A antagonizes UNG2 to promote mutagenic repair during antibody maturation", Nature, Dec. 2021, vol. 600, No. 7888, pp. 324-328.

Kohli, R. et al., "A Portable Hot Spot Recognition Loop Transfers Sequence Preferences from APOBEC Family Members to Activation-induced Cytidine Deaminase", The Journal of Biological Chemistry, 2009, vol. 284, No. 34, pp. 22898-22904.

Rogier, M. et al., "Fam72a enforces error-prone DNA repair during antibody diversification", Nature, 2021, vol. 600, pp. 329-333.

U.S. Appl. No. 17/841,082 Office Action dated Dec. 7, 2023.

Conticello, The AID/APOBEC family of nucleic acid mutators. Genome Biol. 2008;9(6):229. doi: 10.1186/GB-2008-9-6-229. Epub Jun. 17, 2008.

Hu, Z. et al. A compact Cas9 ortholog from *Staphylococcus auricularis* (SauriCas9) expands the DNA targeting scope. PLOS Biology 18(3): 1-18 (2020).

Kim et al. Evaluating and Enhancing Target Specificity of Gene-Editing Nucleases and Deaminases. Annu Rev Biochem. 2019. 88:191-220. First published as a Review in Advance on Mar. 18, 2019.

U.S. Appl. No. 17/841,082 Notice of Allowance dated Feb. 24, 2025.

Zhao, Yawei et al. Multiplex genome editing using a dCas9-cytidine deaminase fusion in Streptomyces. Science china life sciences 63(7):1053-1062 (2020).

U.S. Appl. No. 17/841,082 Final Office Action dated Apr. 25, 2023.

Humphrey W. et al. VMD: Visual Molecular Dynamics. Journal of Molecular Graphics vol. 14,1: pp. 33-38 (1996).

Jinek, Martin et al. A Programmable Dual-RNA-guided DNA Endonuclease in Adaptive Bacterial Immunity. Science 337(6096):816-821 (2012).

U.S. Appl. No. 17/841,082 Office Action dated Sep. 18, 2024.

Yu, Y et al. Cytosine Base Editors with Minimized Unguided DNA and RNA off-Target Events and High on-Target Activity. Nature Communications vol. 2052: pp. 1-10 (2020).

Zhang, Y. et al. In Vivo Gene Delivery by Nonviral Vectors: Overcoming Hurdles?. Molecular Therapy vol. 20,7: pp. 1298-1304 (2012).

Baker et al.: Did Dendritic Cell Activation, Induced by Adenovirus-Antibody Complexes, Play a Role in the Death of Jesse Gelsinger? Mol Ther. 28(3):704-706 doi:10.1016/j.ymthe.2020.02.010 (2020).

Brinkman et al.: Easy quantitative assessment of genome editing by sequence trace decomposition. Nucleic Acids Research 42(22): e168 , pp. 1-8 doi: 10.1093/nar/gku936 (2014).

Carreras et al.: In vivo genome and base editing of a human PCSK9 knock-in hypercholesterolemic mouse model. BMC Biol. 17(1):4 doi: 10.1186/s12915-018-0624-2 [1-14](2019).

Deyle et al.: Adeno-associated virus vector integration. Curr Opin Mol Ther.11(4):442-447 (2009).

Finn et al.: A Single Administration of CRISPR/Cas9 Lipid Nanoparticles Achieves Robust and Persistent In Vivo Genome Editing. Cell Rep. 22(9):2227-2235 doi:10.1016/j.celrep.2018.02.014 (2018).

Gaudelli et al.: Directed evolution of adenine base editors with increased activity and therapeutic application. Nat Biotechnol. 38(7):892-900 doi:10.1038/s41587-020-0491-6 (2020).

Gaudelli, et al. Programmable base editing of A•T to G•C in genomic DNA without DNA cleavage. Nature. Nov. 23, 2017; 551(7681): 464-471. Published online Oct. 25, 2017. doi: 10.1038/nature24644.

Herbert et al.: Increased secretion of lipoproteins in transgenic mice expressing human D374Y PCSK9 under physiological genetic control. Arterioscler Thromb Vasc Biol. 30(7):1333-1339 doi:10.1161/ATVBAHA.110.204040 (2010).

Jeong et al.: Adenine base editor engineering reduces editing of bystander cytosines. Nat Biotechnol. 39(11):1426-1433 doi:10.1038/s41587-021-00943-2 (2021).

Jinek et al. A programmable dual-RNA-guided DNA endonuclease in adaptive bacterial immunity. Science 337(6096):816-821 (2012).

Kim et al.: Genome-wide target specificities of CRISPR RNA-guided programmable deaminases. Nat Biotechnol. 35(5):475-480 (2017).

Kim et al., Highly efficient RNA-guided bases editing in mouse embryos. Nat Biotech 35: 435-437 (2017).

Kohli et al.: A portable hot spot recognition loop transfers sequence preferences from APOBEC family members to activation-induced cytidine deaminase. J Biol Chem. 284(34):22898-22904 doi:10.1074/jbc.M109.025536 (2009).

Levy et al.: Cytosine and adenine base editing of the brain, liver, retina, heart and skeletal muscle of mice via adeno-associated viruses. Nat Biomed Eng. 4(1):97-110 doi:10.1038/s41551-019-0501-5 (2020).

Liu et al.: Application of different types of CRISPR/Cas-based systems in bacteria. Microb Cell Fact. 19(1):172:1-14 doi:10.1186/s12934-020-01431-z (2020).

Mali et al. RNA-guided human genome engineering via Cas9. Science 339(6121):823-826 (2013).

Mishra et al.: Base editing in crops: current advances, limitations and future implications. Plant Biotechnol J. 18(1):20-31 doi:10.1111/pbi.13225 (2020).

(56) References Cited

OTHER PUBLICATIONS

Mok, et al. A bacterial cytidine deaminase toxin enables CRISPR-free mitochondrial base editing. Nature. Jul. 2020;583(7817):631-637. doi: 10.1038/s41586-020-2477-4. Epub Jul. 8, 2020.
Moon et al.: Recent advances in the CRISPR genome editing tool set. Exp Mol Med. 51(11):1-11 (2019).
NCBI GenBank Accession No. EDV12729.1: tRNA-specific adenosine deaminase 2 [*Saccharomyces cerevisiae* RM11-1a], Published Jul. 26, 2016.
NCBI GenBank Accession No. WP_094758060.1: HNH endonuclease [*Rothia* sp. Olga], Published Jul. 27, 2021.
PCT/US2021/049931 International Search Report and Written Opinion dated Jan. 12, 2022.
PCT/US2021/049962 International Search Report and Written Opinion dated Feb. 25, 2022.
PCT/US2022/079345 International Search Report and Written Opinion dated Mar. 2, 2023.
Ribeiro, et al. Protein Engineering Strategies to Expand CRISPR-Cas9 Applications. International Journal of Genomics, vol. 2018, Aug. 2, 2018, pp. 1-12.
Richter et al.: Phage-assisted evolution of an adenine base editor with improved Cas domain compatibility and activity. Nat Biotechnol. 38(7):883-891 doi:10.1038/s41587-020-0453-z (2020).
Sabatine: PCSK9 inhibitors: clinical evidence and implementation. Nature Reviews Cardiology 16(3):155-165 doi:10.1038/s41569-018-0107-8 (2019).
Sadowski, M. et al., "The sequence-structure relationship and protein function prediction", Current Opinion in Structural Biology, 2009, vol. 19, pp. 357-362.
Seffernick, J. et al., "Melamine Deaminase and Atrazine Chlorohydrolase: 98 Percent Identical but Functionally Different", Journal of Bacteriology, 2001, vol. 183, No. 8, pp. 2405-2410.
Shi et al. Structural Basis for Targeted DNA Cytosine Deamination and Mutagenesis by APOBEC3A and APOBEC3B. Nature Structural & Molecular Biology 24(2):131-139 (2017).
Singh et al.: Protein Engineering Approaches in the Post-Genomic Era. Curr Protein Pept Sci. 19(1):5-15 doi:10.2174/1389203718666161117114243 (2018).
Tang et al. Identification of Dehalobacter reductive dehalogenases that catalyse dechlorination of chloroform, 1,1, 1-trichloroethane and 1,1-dichloroethane. Philos Trans R Soc Lond B Biol Sci. 368(1616):20120318 (2013).
UniProt Accession No. A0A2K5RDN7:CMP/dCMP-type deaminase domain-containing protein (2018).
UniProt accession No. A0A8S5MVN9, pp. 1-2 (Oct. 12, 2022).
UniProt accession No. A0A8S5N1WO, pp. 1-2 (Oct. 12, 2022).
UniProt accession No. A0A8S5UMQ3, pp. 1-2 (Oct. 12, 2022).
U.S. Appl. No. 17/841,082 Non-Final Office Action dated Dec. 20, 2022.
Witkowski et al., Conversion of a beta-ketoacyl synthase to a malonyl decarboxylase by replacement of the active-site cysteine with glutamine. Biochemistry. 38(36):11643-11650 (1999).
Wolfe et al.: The structure of APOBEC1 and insights into its RNA and DNA substrate selectivity. NAR Cancer. 2(4):zcaa027:1-15 doi:10.1093/narcan/zcaa027 (2020).
Workman et al.: A natural single-guide RNA repurposes Cas9 to autoregulate CRISPR-Cas expression. Cell. 184(3):675-688.e19:1-34 doi:10.1016/j.cell.2020.12.017 (2021).
Yin et al.: Therapeutic genome editing by combined viral and non-viral delivery of CRISPR system components in vivo. Nat Biotechnol. 34(3):328-333 doi:10.1038/nbt.3471 (2016).
Young et al.: The promise and potential hazards of adenovirus gene therapy. Gut 48(5):733-736 doi:10.1136/gut.48.5.733 (2001).
Yu et al.: Cytosine base editors with minimized unguided DNA and RNA off-target events and high on-target activity. Nat Commun. 11(1):2052:1-10 doi:10.1038/s41467-020-15887-5 (2020).
Yuan Zong et al.: "Precise base editing in rice, wheat and maize with aCas9-cytidine deaminase fusion", Nature Biotechnology, vol. 35,No. 5, Feb. 27, 2017, pp. 438-440.
Zhang et al.: In Vivo Gene Delivery by Nonviral Vectors: Overcoming Hurdles? Molecular Therapy 20(7):1298-1304 doi:10.1038/mt.2012.79 (2012).
Co-pending U.S. Appl. No. 19/386,855, inventor Thomas; Brian C., filed on Nov. 12, 2025.
Zheng, K. et al., Highly efficient base editing in bacteria using a Cas9-cytidine deaminase fusion, Commun Biol 1:32, pp. 1-6 (2018).

* cited by examiner

| Candidate | sgRNA sequence | PAM | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| MGA1-4 | CGTTTGCCGTCTGAATTTGACC | TGAG | C | G | T | T | T | G | C | C | G | T | C | T | G | A | A | T | T | T | G | A | C | C |
| | GAAGATCAGGATATGTGGCGGA | TGAG | G | A | A | G | A | T | C | A | G | G | A | T | A | T | G | T | G | G | C | G | G | A |
| | ACGGGTAACAGTTTCTTTATGG | CAGG | A | C | G | G | G | T | A | A | C | A | G | T | T | T | C | T | T | T | A | T | G | G |
| MGA1-6 | CGTTGCTGCATAAACCGACTAC | ACAAAT | C | G | T | T | G | C | T | G | C | A | T | A | A | A | C | C | G | A | C | T | A | C |
| | AAAACCCGAAACTGTGGAGCGC | CGAAAT | A | A | A | A | C | C | C | G | A | A | A | C | T | G | T | G | G | A | G | C | G | C |
| | GATTGAAAATGGTCTGCTGCTG | CTGAAC | G | A | T | T | G | A | A | A | A | T | G | G | T | C | T | G | C | T | G | C | T | G |
| MGA3-6 | TACGGGTAACAGTTTCTTTATG | GCAGGGT | T | A | C | G | G | G | T | A | A | C | A | G | T | T | T | C | T | T | T | A | T | G |
| | GCGTTGGCAATTTAACCGCCAG | TCAGGGT | G | C | G | T | T | G | G | C | A | A | T | T | T | A | A | C | C | G | C | C | A | G |
| | CTGAATATCGACGGTTTCCATA | TGGGGAT | C | T | G | A | A | T | A | T | C | G | A | C | G | G | T | T | T | C | C | A | T | A |
| MGA3-7 | CACATTTAATGTTGATGAAAGC | TGGCTAC | C | A | C | A | T | T | T | A | A | T | G | T | T | G | A | T | G | A | A | A | G | C |
| | ACACAAATCAGCGATTTCCATG | TTGCCAC | A | C | A | C | A | A | A | T | C | A | G | C | G | A | T | T | T | C | C | A | T | G |
| | ATGGATGAGCAGACGATGGTGC | AGGATAT | A | T | G | G | A | T | G | A | G | C | A | G | A | C | G | A | T | G | G | T | G | C |
| MGA3-8 | TTCATCTGTGGTGCAACGGGCG | CTGGGTC | T | T | C | A | T | C | T | G | T | G | G | T | G | C | A | A | C | G | G | G | C | G |
| | ACGAGCATCATCCTCTGCATGG | TCAGGTC | A | C | G | A | G | C | A | T | C | A | T | C | C | T | C | T | G | C | A | T | G | G |
| | CGACCCGCATTGACCCTAACGC | CTGGGTC | C | G | A | C | C | C | G | C | A | T | T | G | A | C | C | C | T | A | A | C | G | C |
| MGA4-5 | CACAAATCAGCGATTTCCATGT | TGCCA | C | A | C | A | A | A | T | C | A | G | C | G | A | T | T | T | C | C | A | T | G | T |
| | TGATGAAGCAGAACAACTTTAA | CGCCG | T | G | A | T | G | A | A | G | C | A | G | A | A | C | A | A | C | T | T | T | A | A |
| | AATATTGAAACCCACGGCATGG | TGCCA | A | A | T | A | T | T | G | A | A | A | C | C | C | A | C | G | G | C | A | T | G | G |
| MGA7-1 | GAAGATCAGGATATGTGGCGGA | TGAGCG | G | A | A | G | A | T | C | A | G | G | A | T | A | T | G | T | G | G | C | G | G | A |
| | AACGTCGAAAACCCGAAACTGT | GGAGCG | A | A | C | G | T | C | G | A | A | A | A | C | C | C | G | A | A | A | C | T | G | T |
| | AAACCCACGGCATGGTGCCAAT | GAATGG | A | A | A | C | C | C | A | C | G | G | C | A | T | G | G | T | G | C | C | A | A | T |
| MGA14-1 | TCAAAAAATGGCTTTCGCTACC | TGGAGAGA | T | C | A | A | A | A | A | A | T | G | G | C | T | T | T | C | G | C | T | A | C | C |
| | AAGCAGCGTTGTTGCAGTGCAC | GGCAGATA | A | A | G | C | A | G | C | G | T | T | G | T | T | G | C | A | G | T | G | C | A | C |
| | TCAGCCGGAAAACCTACCGGAT | TGATGGTA | T | C | A | G | C | C | G | G | A | A | A | A | C | C | T | A | C | C | G | G | A | T |
| MGA15-1 | GAAGATCAGGATATGTGGCGGA | TGAGCG | G | A | A | G | A | T | C | A | G | G | A | T | A | T | G | T | G | G | C | G | G | A |
| | AACGTCGAAAACCCGAAACTGT | GGAGCG | A | A | C | G | T | C | G | A | A | A | A | C | C | C | G | A | A | A | C | T | G | T |
| | AAACCCACGGCATGGTGCCAAT | GAATGG | A | A | A | C | C | C | A | C | G | G | C | A | T | G | G | T | G | C | C | A | A | T |
| MGA16-1 | GCCAGCTGGCGTAATAGCGAAG | AGGCCC | G | C | C | A | G | C | T | G | G | C | G | T | A | A | T | A | G | C | G | A | A | G |
| | AGGGTGAAACGCAGGTCGCCAG | CGGCAC | A | G | G | G | T | G | A | A | A | C | G | C | A | G | G | T | C | G | C | C | A | G |
| | CTACGTCTGAACGTCGAAAACC | CGAAAC | C | T | A | C | G | T | C | T | G | A | A | C | G | T | C | G | A | A | A | A | C | C |
| MGA18-1 | AAAACCCGAAACTGTGGAGCGC | CGAAAT | A | A | A | A | C | C | C | G | A | A | A | C | T | G | T | G | G | A | G | C | G | C |
| | GGCAACTCTGGCTCACAGTACG | CGTAGT | G | G | C | A | A | C | T | C | T | G | G | C | T | C | A | C | A | G | T | A | C | G |
| | CCGGAAAACCTACCGGATTGAT | GGTAGT | C | C | G | G | A | A | A | A | C | C | T | A | C | C | G | G | A | T | T | G | A | T |
| ABE8.17m | TTTCTTTCACAGATGTGGAT | TGG | T | T | T | C | T | T | T | C | A | C | A | G | A | T | G | T | G | G | A | T | | |
| | CAGGATATGTGGCGGATGAG | CGG | C | A | G | G | A | T | A | T | G | T | G | G | C | G | G | A | T | G | A | G | | |
| | TGCGAATACGCCCACGCGAT | GGG | T | G | C | G | A | A | T | A | C | G | C | C | C | A | C | G | C | G | A | T | | |

FIG. 6A

| Candidate | sgRNA sequence | PAM | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|---|
| MGC1-4 | CGGCGTTTCATCTGTGGTGCAA | CGGG | C | G | G | C | G | T | T | T | C | A | T | C | T | G | T | G | G | T | G | C | A | A |
| | GCCAGGACAGTCGTTTGCCGTC | TGAA | G | C | C | A | G | G | A | C | A | G | T | C | G | T | T | T | G | C | C | G | T | C |
| | TCAGCCGCGCTGTACTGGAGGC | TGAA | T | C | A | G | C | C | G | C | G | C | T | G | T | A | C | T | G | G | A | G | G | C |
| MGC1-6 | CCCTTCCCAACAGTTGCGCAGC | CTGAAT | C | C | C | T | T | C | C | C | A | A | C | A | G | T | T | G | C | G | C | A | G | C |
| | CTGTCGTCGTCCCCTCAAACTG | GCAGAT | C | T | G | T | C | G | T | C | G | T | C | C | C | C | T | C | A | A | A | C | T | G |
| | CTACGTCTGAACGTCGAAAACC | CGAAAC | C | T | A | C | G | T | C | T | G | A | A | C | G | T | C | G | A | A | A | A | C | C |
| MGC3-5 | GTGACGGCAGTTATCTGGAAGA | TCAGGAT | G | T | G | A | C | G | G | C | A | G | T | T | A | T | C | T | G | G | A | A | G | A |
| | ATGATTTCAGCCGCGCTGTACT | GGAGGCT | A | T | G | A | T | T | T | C | A | G | C | C | G | C | G | C | T | G | T | A | C | T |
| | TTACTGCCGCCTGTTTTGACCG | CTGGGAT | T | T | A | C | T | G | C | C | G | C | C | T | G | T | T | T | T | G | A | C | C | G |
| MGC3-7 | CGAATGGCGCTTTGCCTGGTTT | CCGGCAC | C | G | A | A | T | G | G | C | G | C | T | T | T | G | C | C | T | G | G | T | T | T |
| | TCCCCTCAAACTGGCAGATGCA | CGGTTAC | T | C | C | C | C | T | C | A | A | A | C | T | G | G | C | A | G | A | T | G | C | A |
| | ATCTACACCAACGTGACCTATC | CCATTAC | A | T | C | T | A | C | A | C | C | A | A | C | G | T | G | A | C | C | T | A | T | C |
| MGC3-8 | TTCATCTGTGGTGCAACGGGCG | CTGGGTC | T | T | C | A | T | C | T | G | T | G | G | T | G | C | A | A | C | G | G | G | C | G |
| | ACGAGCATCATCCTCTGCATGG | TCAGGTC | A | C | G | A | G | C | A | T | C | A | T | C | C | T | C | T | G | C | A | T | G | G |
| | CGACCCGCATTGACCCTAACGC | CTGGGTC | C | G | A | C | C | C | G | C | A | T | T | G | A | C | C | C | T | A | A | C | G | C |
| MGC4-5 | CAACGGGCGCTGGGTCGGTTAC | GGCCA | C | A | A | C | G | G | G | C | G | C | T | G | G | G | T | C | G | G | T | T | A | C |
| | CACAAATCAGCGATTTCCATGT | TGCCA | C | A | C | A | A | A | T | C | A | G | C | G | A | T | T | T | C | C | A | T | G | T |
| | AAGGCGGCGGAGCCGACACCAC | GGCCA | A | A | G | G | C | G | G | C | G | G | A | G | C | C | G | A | C | A | C | C | A | C |
| MGC7-1 | GCCGATCGCGTCACACTACGTC | TGAACG | G | C | C | G | A | T | C | G | C | G | T | C | A | C | A | C | T | A | C | G | T | C |
| | GATCCGCGCTGGCTACCGGCGA | TGAGCG | G | A | T | C | C | G | C | G | C | T | G | G | C | T | A | C | C | G | G | C | G | A |
| | CCTTCCCGCCCGGTGCAGTATG | AAGGCG | C | C | T | T | C | C | C | G | C | C | C | G | G | T | G | C | A | G | T | A | T | G |
| MGC14-1 | CGGTCAATCCGCCGTTTGTTCC | CACGGAGA | C | G | G | T | C | A | A | T | C | C | G | C | C | G | T | T | T | G | T | T | C | C |
| | TCCTTTGCGAATACGCCCACGC | GATGGGTA | T | C | C | T | T | T | G | C | G | A | A | T | A | C | G | C | C | C | A | C | G | C |
| | GGTCGGCTTACGGCGGTGATTT | TGGCGATA | G | G | T | C | G | G | C | T | T | A | C | G | G | C | G | G | T | G | A | T | T | T |
| MGC15-1 | GCCGATCGCGTCACACTACGTC | TGAACG | G | C | C | G | A | T | C | G | C | G | T | C | A | C | A | C | T | A | C | G | T | C |
| | GATCCGCGCTGGCTACCGGCGA | TGAGCG | G | A | T | C | C | G | C | G | C | T | G | G | C | T | A | C | C | G | G | C | G | A |
| | CCTTCCCGCCCGGTGCAGTATG | AAGGCG | C | C | T | T | C | C | C | G | C | C | C | G | G | T | G | C | A | G | T | A | T | G |
| MGC16-1 | ACGTGACCTATCCCATTACGGT | CAATCC | A | C | G | T | G | A | C | C | T | A | T | C | C | C | A | T | T | A | C | G | G | T |
| | ATCCGCCGTTTGTTCCCACGGA | GAATCC | A | T | C | C | G | C | C | G | T | T | T | G | T | T | C | C | C | A | C | G | G | A |
| | CGACGGCACGCTGATTGAAGCA | GAAGCC | C | G | A | C | G | G | C | A | C | G | C | T | G | A | T | T | G | A | A | G | C | A |
| MGC18-1 | TCAGCCGCGCTGTACTGGAGGC | TGAAGT | T | C | A | G | C | C | G | C | G | C | T | G | T | A | C | T | G | G | A | G | G | C |
| | GACCAGCCCTTCCCGGCTGTGC | CGAAAT | G | A | C | C | A | G | C | C | C | T | T | C | C | C | G | G | C | T | G | T | G | C |
| | TCCGTTTATCCGGGCAAACCAT | CGAAGT | T | C | C | G | T | T | T | A | T | C | C | G | G | G | C | A | A | A | C | C | A | T |
| 8E3 | CCTCTGGATGTCGCTCCACA | AGG | C | C | T | C | T | G | G | A | T | G | T | C | G | C | T | C | C | A | C | A | | |
| | GGGACGCGCGAATTGAATTA | TGG | G | G | G | A | C | G | C | G | C | G | A | A | T | T | G | A | A | T | T | A | | |
| | CGTTTTACAACGTCGTGACT | GGG | C | G | T | T | T | T | A | C | A | A | C | G | T | C | G | T | G | A | C | T | | |

FIG. 6B (a)

| sgRNA | TadA variant | Tested/edited |
|---|---|---|
| - | TadA | 0/10 |
| + | TadA | 1/10 |
| | TadA (D108N) | 7/9 |
| | TadA (ABE8.17m) | 10/10 |

| sgRNA | TadA variant | Tested/edited |
|---|---|---|
| - | EcTadA | 1/0 |
| + | EcTadA | 12/0 |
| | MG68-1 | 4/0 |
| | MG68-2 | 8/0 |
| | MG68-3 | 8/2 |
| | MG68-4 | 11/3 |
| | MG68-5 | 8/0 |
| | MG68-6 | 5/0 |
| | MG68-7 | 6/0 |
| | MG68-8 | 1/1 |

*FIG. 16B*

| Gene | Tested/edited |
|---|---|
| MG68-4 | 12/4 |
| MG68-4 (D109N) | 13/13 |

(a)

(b)

| sgRNA | Tested/edited |
|---|---|
| - | 0/0 |
| + | 7/7 |

| MG68-4 | 24 | 83 | 85 | 107 | 109 | 112 | 124 | 143 | 147 | 148 | 154 | 158 |
|---|---|---|---|---|---|---|---|---|---|---|---|---|
| | W | V | L | A | D | T | H | A | S | D | R | K |
| MG68-4_V1 | | | | | N | | | | | | | |
| MG68-4_V2 | | | | V | N | | | | | | | |
| MG68-4_V3 | | | | | N | | | | | Y | | |
| MG68-4_V4 | | | F | | N | | | | | | | |
| MG68-4_V5 | | | | | N | | Y | | | | | |
| MG68-4_V6 | | | | | N | | | N | | | | |
| MG68-4_V7 | | | | | N | | | | C | | | |
| MG68-4_V8 | | | | | N | | | | | | | N |
| MG68-4_V9 | R | | | | N | | | | | | | |
| MG68-4_V10 | | S | | | N | | | | | | | |
| MG68-4_V11 | | | | | N | R | | | | | | |
| MG68-4_V12 | | | | | N | | | | | R | | |
| MG68-4_V13 | | | | | N | | | | | | P | |
| MG68-4_V14 | | | | V | N | | | | | Y | | |
| MG68-4_V15 | | | F | V | N | | | | | Y | | |
| MG68-4_V16 | | | F | V | N | | Y | | | | | |
| MG68-4_V17 | | | F | V | N | | Y | N | | Y | | |
| MG68-4_V18 | | | F | V | N | | Y | | C | Y | | |
| MG68-4_V19 | | | F | V | N | | Y | | | Y | | N |
| MG68-4_V20 | | | F | V | N | | Y | | C | Y | | N |
| MG68-4_V21 | R | | F | V | N | | Y | | C | Y | | N |
| MG68-4_V22 | R | | F | V | N | | Y | N | C | Y | | N |
| MG68-4_V23 | R | | F | V | N | | Y | N | C | Y | P | N |
| MG68-4_V24 | R | S | F | V | N | | Y | N | C | Y | P | N |
| MG68-4_V25 | R | S | F | V | N | | H | N | C | Y | P | N |
| MG68-4_V26 | R | S | F | V | N | | H | N | C | R | P | N |
| MG68-4_V27 | R | S | F | V | N | R | H | N | C | R | P | N |
| MG68-4_V28 | R | S | F | V | N | R | H | N | C | D | P | N |

*FIG. 19*

BASE EDITING ENZYMES

CROSS-REFERENCE

This application is a continuation application of International Application No. PCT/US2021/049962 filed Sep. 10, 2021, entitled "BASE EDITING ENZYMES", which claims the benefit of U.S. Provisional Application No. 63/077,057, filed on Sep. 11, 2020, entitled "BASE EDITING ENZYMES"; and U.S. Provisional Application No. 63/222,351, filed on Jul. 15, 2021, entitled "BASE EDITING ENZYMES", each of which is incorporated by reference in its entirety herein.

BACKGROUND

Cas enzymes along with their associated Clustered Regularly Interspaced Short Palindromic Repeats (CRISPR) guide ribonucleic acids (RNAs) appear to be a pervasive (~45% of bacteria, ~84% of archaea) component of prokaryotic immune systems, serving to protect such microorganisms against non-self nucleic acids, such as infectious viruses and plasmids by CRISPR-RNA guided nucleic acid cleavage. While the deoxyribonucleic acid (DNA) elements encoding CRISPR RNA elements may be relatively conserved in structure and length, their CRISPR-associated (Cas) proteins are highly diverse, containing a wide variety of nucleic acid-interacting domains. While CRISPR DNA elements have been observed as early as 1987, the programmable endonuclease cleavage ability of CRISPR/Cas complexes has only been recognized relatively recently, leading to the use of recombinant CRISPR/Cas systems in diverse DNA manipulation and gene editing applications.

SEQUENCE LISTING

The instant application contains a Sequence Listing which has been submitted electronically in XML format and is hereby incorporated by reference in its entirety. Said XML copy, created on Mar. 19, 2026, is named 55921-715_302_SL.xml and is 1,501,940 bytes in size.

SUMMARY

In some aspects, the present disclosure provides for an engineered nucleic acid editing system, comprising: an endonuclease comprising a RuvC domain and an HINH domain, wherein said endonuclease is derived from an uncultivated microorganism, wherein said endonuclease is a class 2, type II Cas endonuclease, wherein said endonuclease is configured to be deficient in nuclease activity; a base editor coupled to said endonuclease; and an engineered guide ribonucleic acid structure configured to form a complex with said endonuclease comprising: a guide ribonucleic acid sequence configured to hybridize to a target deoxyribonucleic acid sequence; and a ribonucleic acid sequence configured to bind to said endonuclease. In some embodiments, said RuvC domain lacks nuclease activity. In some embodiments, said class 2, type II Cas endonuclease comprises a nickase mutation. In some embodiments, said class 2, type II cas endonuclease comprises the aspartate to alanine mutation at residue 9 relative to SEQ ID NO: 70, residue 13 relative to SEQ ID NOs: 71, 72, or 74, residue 12 relative to SEQ ID NO: 73, residue 17 relative to SEQ ID NO: 75, residue 23 relative to SEQ ID NO: 76, or residue 10 relative to SEQ ID NO: 597 when optimally aligned. In some embodiments, said endonuclease comprises an aspartate to alanine mutation at residue 9 relative to SEQ ID NO: 70, residue 13 relative to SEQ ID NO: 72, or residue 17 relative to SEQ ID NO: 75 when optimally aligned. In some embodiments, said endonuclease comprises a sequence with at least 95% sequence identity to any one of SEQ ID NOs: 70-78 or 597 or a variant thereof. In some aspects, the present disclosure provides for an engineered nucleic acid editing system comprising: an endonuclease having at least 95% sequence identity to any one of SEQ ID NOs: 70-78 or 597 or a variant thereof; a base editor coupled to said endonuclease; and an engineered guide ribonucleic acid structure configured to form a complex with said endonuclease comprising: a guide ribonucleic acid sequence configured to hybridize to a target deoxyribonucleic acid sequence; and a ribonucleic acid sequence configured to bind to said endonuclease. In some aspects, the present disclosure provides for an engineered nucleic acid editing system comprising: an endonuclease configured to bind to a protospacer adjacent motif (PAM) sequence comprising any one of SEQ ID NOs: 360-368 or 598 or a variant thereof, wherein said endonuclease is a class 2, type II Cas endonuclease, and wherein said endonuclease is configured to be deficient in nuclease activity; a base editor coupled to said endonuclease; and an engineered guide ribonucleic acid structure configured to form a complex with said endonuclease comprising: a guide ribonucleic acid sequence configured to hybridize to a target deoxyribonucleic acid sequence; and a ribonucleic acid sequence configured to bind to said endonuclease. In some embodiments, said endonuclease comprises a nickase mutation. In some embodiments, said endonuclease is configured to cleave one strand of a double-stranded target deoxyribonucleic acid. In some embodiments, said class 2, type II cas endonuclease comprises an aspartate to alanine mutation at residue 9 relative to SEQ ID NO: 70, residue 13 relative to SEQ ID NOs: 71, 72, or 74, residue 12 relative to SEQ ID NO: 73, residue 17 relative to SEQ ID NO: 75, residue 23 relative to SEQ ID NO: 76, or residue 10 relative to SEQ ID NO: 597 when optimally aligned. In some embodiments, said base editor comprises a sequence having at least 70%, 80%, 90% or 95% identity to any one of SEQ ID NOs: 1-51, 57-66, 385-443, 444-475, or 594-595 or a variant thereof. In some embodiments, said base editor comprises a sequence having at least 70%, 80%, 90% or 95% identity to any one of SEQ ID NOs: 50-51 or 385-390. In some embodiments, said RuvC domain lacks nuclease activity. In some embodiments, said endonuclease is derived from an uncultivated microorganism. In some embodiments, said endonuclease has less than 80% identity to a Cas9 endonuclease. In some embodiments, said endonuclease further comprises an HNH domain. In some embodiments, said engineered guide ribonucleic acid sequence comprises a sequence with at least 80% sequence identity to non-degenerate nucleotides of any one of SEQ ID NOs: 88-96 or 488-489 or a variant thereof. In some aspects, the present disclosure provides for an engineered nucleic acid editing system comprising, an engineered guide ribonucleic acid structure comprising: a guide ribonucleic acid sequence configured to hybridize to a target deoxyribonucleic acid sequence; and a ribonucleic acid sequence configured to bind to an endonuclease, wherein said engineered ribonucleic acid sequence comprises a sequence with at least 80% sequence identity to non-degenerate nucleotides of any one of SEQ ID NOs: 88-96 or 488-489 or a variant thereof; a class 2, type II Cas endonuclease configured to bind to said engineered guide ribonucleic acid; and a base editor coupled to said endonuclease. In some embodiments, said base editor comprises a sequence having at least 70%, 80%, 90% or 95% identity to any one of SEQ ID NOs: 50-51 or 385-390. In some embodiments, said endonuclease is configured to bind to a protospacer adjacent motif (PAM) sequence selected from the group consisting of SEQ ID NOs: 360-368 or 598. In some embodiments, said base editor comprises a sequence with at least 70%, 80%, 90% or 95% identity to any one of SEQ ID NOs: 1-51, 57-66, 385-443, 444-475, or 594-595 or a variant thereof. In some embodiments, said base editor is an adenine deaminase. In some embodiments, said adenosine deaminase comprises a sequence with at least 70%, 80%, 90% or 95% identity to any one of SEQ ID NOs: 50-51, 57, 385-443, 448-475, or 595 or a variant thereof. In some embodiments, said base editor is a cytosine deaminase. In some embodiments, said cytosine deaminase comprises a sequence with at least 70%, 80%, 90% or 95% identity to any one of SEQ ID NOs: 1-49, 444-447, 594, or 58-66 or a variant thereof. In some embodiments, the system further comprises a uracil DNA glycosylase inhibitor coupled to said endonuclease or said base editor. In some embodiments, said uracil DNA glycosylase inhibitor comprises a sequence with at least 70%, 80%, 90% or 95% identity to any one of SEQ ID NOs: 52-56 or SEQ ID NO: 67. In some embodiments, said engineered guide ribonucleic acid structure comprises at least two ribonucleic acid polynucleotides. In some embodiments, said engineered guide ribonucleic acid structure comprises one ribonucleic acid polynucleotide comprising said guide ribonucleic acid sequence and said tracr ribonucleic acid sequence. In some embodiments, said guide ribonucleic acid sequence is complementary to a prokaryotic, bacterial, archaeal, eukaryotic, fungal, plant, mammalian, or human genomic sequence. In some embodiments, said guide ribonucleic acid sequence is 15-24 nucleotides in length. In some embodiments, said endonuclease comprises one or more nuclear localization sequences (NLSs) proximal to an N- or C-terminus of said endonuclease. In some embodiments, said NLS comprises a sequence with at least 90% identity to a selected from SEQ ID NOs: 369-384 or a variant thereof. In some embodiments, said endonuclease is covalently coupled directly to said base editor or covalently coupled to said base editor through a linker. In some embodiments, said endonuclease comprises an aspartate to alanine mutation at residue 9 relative to SEQ ID NO: 70, residue 13 relative to SEQ ID NOs: 71, 72, or 74, residue 12 relative to SEQ ID NO: 73 or 78, residue 17 relative to SEQ ID NO: 75, residue 23 relative to SEQ ID NO: 76, residue 8 relative to SEQ ID NO: 77, or residue 10 relative to SEQ ID NO: 597 when optimally aligned. In some embodiments, said endonuclease comprises an aspartate to alanine mutation at residue 9 relative to SEQ ID NO: 70, residue 13 relative to SEQ ID NO: 72, or residue 17 relative to SEQ ID NO: 75 when optimally aligned. In some embodiments, a polypeptide comprises said endonuclease and said base editor. In some embodiments, said endonuclease is configured to cleave one strand of a double-stranded target deoxyribonucleic acid. In some embodiments, said system further comprises a source of $Mg^{2+}$. In some embodiments: (a) said endonuclease comprises a sequence at least 70%, at least 80%, or at least 90% identical to any one of SEQ ID NOs: 70, 71, 73, 74, 76, 78, 77, or 78 or a variant thereof; (b) said guide RNA structure comprises a sequence at least 70%, at least 80%, or at least 90% identical to non-degenerate nucleotides of any one of SEQ ID NOs: 88, 89, 91, 92, 94, 96, 95, or 488; (c) said endonuclease is configured to bind to a PAM comprising any one of SEQ ID NOs: 360, 361, 363, 365, 367, or 368; or (d) said base editor comprises a sequence at least 70%, at least 80%, or at least 90% identical to SEQ ID NOs: 58 or 595 or a variant thereof. In some embodiments: (a) said endonuclease comprises a sequence at least 70%, at least 80%, or at least 90% identical to any one of SEQ ID NOs: 70, 71, or 78 or a variant thereof; (b) said guide RNA structure comprises a sequence at least 70%, at least 80%, or at least 90% identical to non-degenerate nucleotides of at least one of SEQ ID NOs: 88, 89, or 96; (c) said endonuclease is configured to bind to a PAM comprising any one of SEQ ID NOs: 360, 362, or 368; or (d) said base editor comprises a sequence at least 70%, at least 80%, or at least 90% identical to SEQ ID NO: 594 or a variant thereof. In some embodiments, said sequence identity is determined by a BLASTP, CLUSTALW, MUSCLE, MAFFT, or Smith-Waterman homology search algorithm. In some embodiments, said sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment. In some embodiments, said endonuclease is configured to be catalytically dead. In some embodiments, said endonuclease is configured to cleave one strand of a double-stranded target deoxyribonucleic acid.

In some aspects, the present disclosure provides for a nucleic acid comprising an engineered nucleic acid sequence optimized for expression in an organism, wherein said nucleic acid encodes a class 2, type II Cas endonuclease coupled to a base editor, and wherein said endonuclease is derived from an uncultivated microorganism.

In some aspects, the present disclosure provides for a nucleic acid comprising an engineered nucleic acid sequence optimized for expression in an organism, wherein said nucleic acid encodes an endonuclease having at least 70% sequence identity to any one of SEQ ID NOS: 70-78 coupled to a base editor. In some embodiments, said endonuclease comprises a sequence encoding one or more nuclear localization sequences (NLSs) proximal to an N- or C-terminus of said endonuclease. In some embodiments, said NLS comprises a sequence with at least 90% identity to a selected from SEQ ID NOs: 369-384 or a variant thereof. In some embodiments, said organism is prokaryotic, bacterial, eukaryotic, fungal, plant, mammalian, rodent, or human.

In some aspects, the present disclosure provides for a vector comprising a nucleic acid sequence encoding a class 2, type II Cas endonuclease coupled to a base editor, wherein said endonuclease is derived from an uncultivated microorganism.

In some aspects, the present disclosure provides for a vector comprising the nucleic acid of any of the aspects or embodiments described herein. In some embodiments, the vector further comprises a nucleic acid encoding an engineered guide ribonucleic acid structure configured to form a complex with said endonuclease comprising: a guide ribonucleic acid sequence configured to hybridize to a target deoxyribonucleic acid sequence; and a ribonucleic acid sequence configured to binding to said endonuclease. In some embodiments, the vector is a plasmid, a minicircle, a CELiD, an adeno-associated virus (AAV) derived virion, or a lentivirus.

In some aspects, the present disclosure provides for a cell comprising the vector of any of the aspects or embodiments described herein.

In some aspects, the present disclosure provides for a method of manufacturing an endonuclease, comprising cultivating the cell of any of the aspects or embodiments described herein.

In some aspects, the present disclosure provides for a method for modifying a double-stranded deoxyribonucleic acid polynucleotide comprising contacting said double-stranded deoxyribonucleic acid polynucleotide with a complex comprising: an endonuclease comprising a RuvC domain and an HNH domain, wherein said endonuclease is derived from an uncultivated microorganism, wherein said endonuclease is a class 2, type II Cas endonuclease, and wherein the endonuclease is configured to be deficient in nuclease activity; a base editor coupled to said endonuclease; and an engineered guide ribonucleic acid structure configured to bind to said endonuclease and said double-stranded deoxyribonucleic acid polynucleotide; wherein said double-stranded deoxyribonucleic acid polynucleotide comprises a protospacer adjacent motif (PAM). In some embodiments, said endonuclease comprising a RuvC domain and an HNH domain is covalently coupled directly to said base editor or covalently coupled to said base editor through a linker. In some embodiments, said endonuclease comprising a RuvC domain and an HINH domain comprises a sequence with at least 95% sequence identity to any one of SEQ ID NOs: 70-78 or 597 or a variant thereof.

In some aspects, the present disclosure provides for a method for modifying a double-stranded deoxyribonucleic acid polynucleotide, comprising contacting said double-stranded deoxyribonucleic acid polynucleotide with a complex comprising: a class 2, type II Cas endonuclease, a base editor coupled to said endonuclease, and an engineered guide ribonucleic acid structure configured to bind to said endonuclease and said double-stranded deoxyribonucleic acid polynucleotide; wherein said double-stranded deoxyribonucleic acid polynucleotide comprises a protospacer adjacent motif (PAM); and wherein said PAM comprises a sequence selected from the group consisting of SEQ ID NOs: 70-78 or 597. In some embodiments, said class 2, type II Cas endonuclease is covalently coupled to said base editor or coupled to said base editor through a linker. In some embodiments, said base editor comprises a sequence with at least 70%, at least 80%, at least 90% or at least 95% identity to a sequence selected from SEQ ID NOs: 1-51, 57-66, 385-443, 444-475, or 594-595 or a variant thereof. In some embodiments, said base editor comprises an adenine deaminase; said double-stranded deoxyribonucleic acid polynucleotide comprises an adenine; and modifying said double-stranded deoxyribonucleic acid polypeptide comprises converting said adenine to guanine. In some embodiments, said adenine deaminase comprises a sequence with at least 70%, 80%, 90% or 95% sequence identity to any one of SEQ ID NOs: 50-51, 57, 385-443, 448-475, or 595 or a variant thereof. In some embodiments, said base editor comprises a cytosine deaminase; said double-stranded deoxyribonucleic acid polynucleotide comprises a cytosine; and modifying said double-stranded deoxyribonucleic acid polypeptide comprises converting said cytosine to uracil. In some embodiments, said cytosine deaminase comprises a sequence with at least 70%, 80%, 90% or 95% sequence identity to any one of SEQ ID NOs: 1-49, 444-447, 594, or 58-66 or a variant thereof. In some embodiments, said complex further comprises a uracil DNA glycosylase inhibitor coupled to said endonuclease or said base editor. In some embodiments, said uracil DNA glycosylase inhibitor comprises a sequence with at least 70%, 80%, 90% or 95% identity to any one of SEQ ID NOs: 52-56 or SEQ ID NO: 67 or a variant thereof. In some embodiments, said double-stranded deoxyribonucleic acid polynucleotide comprises a first strand comprising a sequence complementary to a sequence of said engineered guide ribonucleic acid structure and a second strand comprising said PAM. In some embodiments, said PAM is directly adjacent to the 3' end of said sequence complementary to said sequence of said engineered guide ribonucleic acid structure. In some embodiments, said class 2, type II Cas endonuclease is not a Cas9 endonuclease, a Cas14 endonuclease, a Cas12a endonuclease, a Cas12b endonuclease, a Cas 12c endonuclease, a Cas12d endonuclease, a Cas12e endonuclease, a Cas13a endonuclease, a Cas13b endonuclease, a Cas13c endonuclease, or a Cas 13d endonuclease. In some embodiments, said class 2, type II Cas endonuclease is derived from an uncultivated microorganism. In some embodiments, said double-stranded deoxyribonucleic acid polynucleotide is a eukaryotic, plant, fungal, mammalian, rodent, or human double-stranded deoxyribonucleic acid polynucleotide.

In some aspects, the present disclosure provides for a method of modifying a target nucleic acid locus, said method comprising delivering to said target nucleic acid locus said engineered nucleic acid editing system of any of the aspects or embodiments described herein, wherein said endonuclease is configured to form a complex with said engineered guide ribonucleic acid structure, and wherein said complex is configured such that upon binding of said complex to said target nucleic acid locus, said complex modifies a nucleotide of said target nucleic locus. In some embodiments, said engineered nucleic acid editing system comprises an adenine deaminase, said nucleotide is an adenine, and modifying said target nucleic acid locus comprises converting said adenine to a guanine. In some embodiments, said engineered nucleic acid editing system comprises a cytidine deaminase and a uracil DNA glycosylase inhibitor, said nucleotide is a cytosine and modifying said target nucleic acid locus comprises converting said adenine to a uracil. In some embodiments, said target nucleic acid locus comprises genomic DNA, viral DNA, or bacterial DNA. In some embodiments, said target nucleic acid locus is in vitro. In some embodiments, said target nucleic acid locus is within a cell. In some embodiments, said cell is a prokaryotic cell, a bacterial cell, a eukaryotic cell, a fungal cell, a plant cell, an animal cell, a mammalian cell, a rodent cell, a primate cell, or a human cell. In some embodiments, said cell is within an animal. In some embodiments, said cell is within a cochlea. In some embodiments, said cell is within an embryo. In some embodiments, said embryo is a two-cell embryo. In some embodiments, said embryo is a mouse embryo. In some embodiments, delivering said engineered nucleic acid editing system to said target nucleic acid locus comprises delivering the nucleic acid of any of the aspects or embodiments described herein or the vector of any of the aspects or embodiments described herein. In some embodiments, delivering said engineered nucleic acid editing system to said target nucleic acid locus comprises delivering a nucleic acid comprising an open reading frame encoding said endonuclease. In some embodiments, said nucleic acid comprises a promoter to which said open reading frame encoding said endonuclease is operably linked. In some embodiments, delivering said engineered nucleic acid editing system to said target nucleic acid locus comprises delivering a capped mRNA containing said open reading frame encoding said endonuclease. In some embodiments, delivering said engineered nucleic acid editing system to said target nucleic acid locus comprises delivering a translated polypeptide. In some embodiments, delivering said engineered nucleic acid editing system to said target nucleic acid locus comprises delivering a deoxyribonucleic acid (DNA) encoding said engineered guide ribonucleic acid structure operably linked to a ribonucleic acid (RNA) pol III promoter.

In some aspects, the present disclosure provides for an engineered nucleic acid editing polypeptide, comprising: an endonuclease comprising a RuvC domain and an HNH domain, wherein said endonuclease is derived from an uncultivated microorganism, wherein said endonuclease is a class 2, type II Cas endonuclease, and wherein the endonuclease is configured to be deficient in nuclease activity; and a base editor coupled to said endonuclease. In some embodiments, said endonuclease comprises a sequence with at least 95% sequence identity to any one of SEQ ID NOs: 70-78 or 597 or a variant thereof.

In some aspects, the present disclosure provides for an engineered nucleic acid editing polypeptide, comprising: an endonuclease having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof, wherein the endonuclease is configured to be deficient in nuclease activity; and a base editor coupled to said endonuclease. In some aspects, the present disclosure provides for an engineered nucleic acid editing polypeptide, comprising: an endonuclease configured to bind to a protospacer adjacent motif (PAM) sequence comprising any one of SEQ ID NOs: 360-368 or 598, wherein said endonuclease is a class 2, type II Cas endonuclease, and wherein the endonuclease is configured to be deficient in nuclease activity; and a base editor coupled to said endonuclease. In some embodiments, said endonuclease is derived from an uncultivated microorganism. In some embodiments, said endonuclease has less than 80% identity to a Cas9 endonuclease. In some embodiments, said endonuclease further comprises an HNH domain. In some embodiments, said tracr ribonucleic acid sequence comprises a sequence with at least 80% sequence identity to about 60 to 90 consecutive nucleotides selected from any one of SEQ ID NOs: 88-96, 488, and 489. In some embodiments, said base editor comprises a sequence with at least 70%, 80%, 90% or 95% identity to any one of SEQ ID NOs: 1-51, 57-66, 385-443, 444-475, or 594-595 or a variant thereof. In some embodiments, said base editor is an adenine deaminase. In some embodiments, said adenosine deaminase comprises a sequence with at least 70%, 80%, 90% or 95% sequence identity to any one of SEQ ID NOs: 50-51, 57, 385-443, 448-475, or 595 or a variant thereof. In some embodiments, said base editor is a cytosine deaminase. In some embodiments, said cytosine deaminase comprises a sequence with at least 70%, 80%, 90% or 95% sequence identity to any one of SEQ ID NOs: 1-49, 444-447, 594, or 58-66 or a variant thereof.

In some aspects, the present disclosure provides for an engineered nucleic acid editing polypeptide, comprising: an endonuclease, wherein said endonuclease is configured to be deficient in endonuclease activity; and a base editor coupled to said endonuclease, wherein said base editor comprises a sequence with at least 70%, 80%, 90% or 95% sequence identity to any one of SEQ ID NOs: 1-51, 385-386, 387-443, 444-447, 488-475, or 595, or a variant thereof. In some embodiments, said endonuclease is configured to cleave one strand of a double-stranded target deoxyribonucleic acid. In some embodiments, said endonuclease is configured to be catalytically dead. In some embodiments, said endonuclease is a Cas endonuclease. In some embodiments, said Cas endonuclease is a Class II, type II Cas endonuclease or a Class II, type V Cas endonuclease. In some embodiments, said endonuclease comprises a sequence having at least 70%, 80%, 90% or 95% sequence identity to any one of SEQ ID NOs: 70-78 or 597 or a variant thereof. In some embodiments, said Cas endonuclease comprises a nickase mutation. In some embodiments, said Cas endonuclease comprises the aspartate to alanine mutation at residue 9 relative to SEQ ID NO: 70, residue 13 relative to SEQ ID NOs: 71, 72, or 74, residue 12 relative to SEQ ID NO: 73, residue 17 relative to SEQ ID NO: 75, residue 23 relative to SEQ ID NO: 76, or residue 10 relative to SEQ ID NO: 597 when optimally aligned. In some embodiments, said endonuclease is configured to bind to a protospacer adjacent motif (PAM) sequence selected from the group consisting of SEQ ID NOs: 360-368 or 598. In some embodiments, said base editor is an adenine deaminase. In some embodiments, said adenosine deaminase comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 50-51, 385-443, or 448-475 or a variant thereof. In some embodiments, said adenosine deaminase comprises a sequence with at least 70%, 80%, 90% or 95% identity to any one of SEQ ID NOs: 50-51, 385-390, or 595, or a variant thereof. In some embodiments, said base editor is a cytosine deaminase. In some embodiments, said cytosine deaminase comprises a sequence with at least 70%, 80%, 90% or 95% identity to any one of SEQ ID NOs: 1-49, 444-447 or a variant thereof. In some embodiments, the polypeptide further comprises a uracil DNA glycosylase inhibitor coupled to said endonuclease or said base editor. In some embodiments, said uracil DNA glycosylase inhibitor comprises a sequence with at least 70%, 80%, 90% or 95% identity to any one of SEQ ID NOs: 52-56 or SEQ ID NO: 67 or a variant thereof. In some embodiments, said endonuclease comprises one or more nuclear localization sequences (NLSs) proximal to an N- or C-terminus of said endonuclease. In some embodiments, said NLS comprises a sequence with at least 90% identity to a selected from SEQ ID NOs: 369-384 or a variant thereof. In some embodiments, said endonuclease is covalently coupled directly to said base editor or covalently coupled to said base editor through a linker.

In some aspects, the present disclosure provides for a nucleic acid comprising an engineered nucleic acid sequence optimized for expression in an organism, wherein said nucleic acid encodes a sequence having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-51, 385-386, 387-443, 444-447, or 488-475 or a variant thereof. In some embodiments, said organism is prokaryotic, bacterial, eukaryotic, fungal, plant, mammalian, rodent, or human.

In some aspects, the present disclosure provides for a vector comprising the nucleic acid of any of the aspects or embodiments described herein. In some embodiments, the vector is a plasmid, a minicircle, a CELiD, an adeno-associated virus (AAV) derived virion, or a lentivirus.

In some aspects, the present disclosure provides for a cell comprising the vector of any one of the aspects or embodiments described herein.

In some aspects, the present disclosure provides for a method of manufacturing a base editor, comprising cultivating said cell of any one of the aspects or embodiments described herein.

In some aspects, the present disclosure provides for a system comprising: (a) the nucleic acid editing polypeptide of any of the aspects or embodiments described herein; and (b) an engineered guide ribonucleic acid structure configured to form a complex with said nucleic acid editing polypeptide comprising: a guide ribonucleic acid sequence configured to hybridize to a target deoxyribonucleic acid sequence; and a ribonucleic acid sequence configured to bind to said endonuclease. In some embodiments, said engineered guide ribonucleic acid sequence comprises a sequence with at least 80% sequence identity to non-degenerate nucleotides of any one of SEQ ID NOs: 88-96 or 488-489.

In some aspects, the present disclosure provides for a method of modifying a target nucleic acid locus, said method comprising delivering to said target nucleic acid locus said engineered nucleic acid editing polypeptide of any of the aspects or embodiments described herein or said system of any of the aspects or embodiments described herein, wherein said complex is configured such that upon binding of said complex to said target nucleic acid locus, said complex modifies a nucleotide of said target nucleic locus.

In some aspects, the present disclosure provides for an engineered nucleic acid editing system, comprising: (a) an endonuclease comprising a RuvC domain and an HINH domain, wherein the endonuclease is derived from an uncultivated microorganism, wherein the endonuclease is a class 2, type II Cas endonuclease, and wherein the RuvC domain lacks nuclease activity; (b) a base editor coupled to the endonuclease; and (c) an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease. In some embodiments, the endonuclease comprises a sequence with at least 95% sequence identity to any one of SEQ ID NOs: 70-78.

In some aspects, the present disclosure provides for an engineered nucleic acid editing system comprising: (a) an endonuclease having at least 95% sequence identity to any one of SEQ ID NOs: 70-78, wherein the endonuclease comprises a RuvC domain lacking nuclease activity; a base editor coupled to the endonuclease; and an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease.

In some aspects, the present disclosure provides for an engineered nucleic acid editing system comprising: (a) an endonuclease configured to bind to a protospacer adjacent motif (PAM) sequence comprising SEQ ID NOs: 360-368, wherein the endonuclease is a class 2, type II Cas endonuclease, and wherein the endonuclease comprises a RuvC domain lacking nuclease activity; and (b) a base editor coupled to the endonuclease; and (c) an engineered guide ribonucleic acid structure configured to form a complex with the endonuclease comprising: (i) a guide ribonucleic acid sequence configured to hybridize to a target deoxyribonucleic acid sequence; and (ii) a tracr ribonucleic acid sequence configured to bind to the endonuclease.

In some embodiments, the endonuclease is derived from an uncultivated microorganism. In some embodiments, the endonuclease has less than 80% identity to a Cas9 endonuclease. In some embodiments, the endonuclease further comprises an HINH domain. In some embodiments, the tracr ribonucleic acid sequence comprises a sequence with at least 80% sequence identity to about 60 to 90 consecutive nucleotides selected from any one of SEQ ID NOs: 88-96, 488, and 489.

In some aspects, the present disclosure provides an engineered nucleic acid editing system comprising, (a) an engineered guide ribonucleic acid structure comprising: (i) a guide ribonucleic acid sequence configured to hybridize to a target deoxyribonucleic acid sequence; and (ii) a tracr ribonucleic acid sequence configured to bind to an endonuclease, wherein the tracr ribonucleic acid sequence comprises a sequence with at least 80% sequence identity to about 60 to 90 consecutive nucleotides selected from any one of SEQ ID NOs: 88-96, 488, and 489; and a class 2, type II Cas endonuclease configured to bind to the engineered guide ribonucleic acid.

In some embodiments, the endonuclease is configured to bind to a protospacer adjacent motif (PAM) sequence selected from the group consisting of SEQ ID NOs: 360-368. In some embodiments, the base editor comprises a sequence with at least 70%, 80%, 90% or 95% identity to any one of SEQ ID NOs: 1-51 and 385-475. In some embodiments, the base editor is an adenine deaminase. In some embodiments, the adenosine deaminase comprises a sequence with at least 95% identity to SEQ ID NO: 57. In some embodiments, the base editor is a cytosine deaminase. In some embodiments, the cytosine deaminase comprises a sequence with at least 95% identity to SEQ ID NO: 58. In some embodiments, the cytosine deaminase comprises a sequence with at least 95% identity to any one of SEQ ID NOs: 59-66.

In some embodiments, the engineered nucleic acid editing system further comprises a uracil DNA glycosylase inhibitor. In some embodiments, the uracil DNA glycosylase inhibitor comprises a sequence with at least 70%, 80%, 90% or 95% identity to any one of SEQ ID NOs: 52-56 or SEQ ID NO: 67.

In some embodiments, the engineered guide ribonucleic acid structure comprises at least two ribonucleic acid polynucleotides. In some embodiments, the engineered guide ribonucleic acid structure comprises one ribonucleic acid polynucleotide comprising the guide ribonucleic acid sequence and the tracr ribonucleic acid sequence. In some embodiments, the guide ribonucleic acid sequence is complementary to a prokaryotic, bacterial, archaeal, eukaryotic, fungal, plant, mammalian, or human genomic sequence. In some embodiments, the guide ribonucleic acid sequence is 15-24 nucleotides in length. In some embodiments, the endonuclease comprises one or more nuclear localization sequences (NLSs) proximal to an N- or C-terminus of said endonuclease. In some embodiments, the endonuclease is covalently coupled directly to the base editor or covalently coupled to the base editor through a linker. In some embodiments, a polypeptide comprises the endonuclease and the base editor. In some embodiments, the endonuclease is configured to cleave one strand of a double-stranded target deoxyribonucleic acid. In some embodiments, the endonuclease comprises SEQ ID NO: 370. In some embodiments, the system further comprises a source of $Mg^{2+}$.

In some embodiments, the endonuclease comprises a sequence at least 70%, at least 80%, or at least 90% identical to SEQ ID NO: 70; the guide RNA structure comprises a sequence at least 70%, at least 80%, or at least 90% identical to SEQ ID NO: 88; and the endonuclease is configured to bind to a PAM comprising SEQ ID NO: 360.

In some embodiments, the endonuclease comprises a sequence at least 70%, at least 80%, or at least 90% identical to SEQ ID NO: 71; the guide RNA structure comprises a sequence at least 70%, at least 80%, or at least 90% identical to SEQ ID NO: 89; and the endonuclease is configured to bind to a PAM comprising SEQ ID NO: 361.

In some embodiments, the endonuclease comprises a sequence at least 70%, at least 80%, or at least 90% identical to SEQ ID NO: 73; the guide RNA structure comprises a sequence at least 70%, at least 80%, or at least 90% identical to SEQ ID NO: 91; and the endonuclease is configured to bind to a PAM comprising SEQ ID NO: 363.

In some embodiments, the endonuclease comprises a sequence at least 70%, at least 80%, or at least 90% identical to SEQ ID NO: 75; the guide RNA structure comprises a sequence at least 70%, at least 80%, or at least 90% identical to SEQ ID NO: 93; and the endonuclease is configured to bind to a PAM comprising SEQ ID NO: 365.

In some embodiments, the endonuclease comprises a sequence at least 70%, at least 80%, or at least 90% identical to SEQ ID NO: 76; the guide RNA structure comprises a sequence at least 70%, at least 80%, or at least 90% identical to SEQ ID NO: 94; and the endonuclease is configured to bind to a PAM comprising SEQ ID NO: 366.

In some embodiments, the endonuclease comprises a sequence at least 70%, at least 80%, or at least 90% identical to SEQ ID NO: 77; the guide RNA structure comprises a sequence at least 70%, at least 80%, or at least 90% identical to SEQ ID NO: 95; and the endonuclease is configured to bind to a PAM comprising SEQ ID NO: 367.

In some embodiments, the endonuclease comprises a sequence at least 70%, at least 80%, or at least 90% identical to SEQ ID NO: 78; the guide RNA structure comprises a sequence at least 70%, at least 80%, or at least 90% identical to SEQ ID NO: 96; and the endonuclease is configured to bind to a PAM comprising SEQ ID NO: 368.

In some embodiments, the base editor comprises an adenine deaminase. In some embodiments, the adenine deaminase comprises SEQ ID NO: 57. In some embodiments, the base editor comprises a cytosine deaminase. In some embodiments, the cytosine deaminase comprises SEQ ID NO: 58. In some embodiments, the engineered nucleic acid editing system described herein further comprises a uracil DNA glycosylation inhibitor. In some embodiments, the uracil DNA glycosylation inhibitor comprises SEQ ID NO: 67.

In some embodiments, the sequence identity is determined by a BLASTP, CLUSTALW, MUSCLE, MAFFT, or Smith-Waterman homology search algorithm. In some embodiments, the sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some aspects, the present disclosure provides a nucleic acid comprising an engineered nucleic acid sequence optimized for expression in an organism, wherein the nucleic acid encodes a class 2, type II Cas endonuclease coupled to a base editor, and wherein the endonuclease is derived from an uncultivated microorganism.

In some aspects, the present disclosure provides a nucleic acid comprising an engineered nucleic acid sequence optimized for expression in an organism, wherein the nucleic acid encodes an endonuclease having at least 70% sequence identity to any one of SEQ ID NOs: 70-78 coupled to a base editor. In some embodiments, the endonuclease comprises a sequence encoding one or more nuclear localization sequences (NLSs) proximal to an N- or C-terminus of said endonuclease. In some embodiments, the organism is prokaryotic, bacterial, eukaryotic, fungal, plant, mammalian, rodent, or human.

In some aspects, the present disclosure provides a vector comprising a nucleic acid sequence encoding a class 2, type II Cas endonuclease coupled to a base editor, wherein said endonuclease is derived from an uncultivated microorganism. In some embodiments, the vector comprises the nucleic acid described herein. In some embodiments, the vector further comprises a nucleic acid encoding an engineered guide ribonucleic acid structure configured to form a complex with the endonuclease comprising: a guide ribonucleic acid sequence configured to hybridize to a target deoxyribonucleic acid sequence; and a tracr ribonucleic acid sequence configured to binding to the endonuclease. In some embodiments, the vector is a plasmid, a minicircle, a CELiD, an adeno-associated virus (AAV) derived virion, or a lentivirus. In some aspects, the present disclosure provides a cell comprising the vector described herein. In some aspects, the present disclosure provides a method of manufacturing an endonuclease, comprising cultivating the cell described herein.

In some aspects, the present disclosure provides a method for modifying a double-stranded deoxyribonucleic acid polynucleotide comprising contacting the double-stranded deoxyribonucleic acid polynucleotide with a complex comprising: an endonuclease comprising a RuvC domain and an HINH domain, wherein the endonuclease is derived from an uncultivated microorganism, wherein the endonuclease is a class 2, type II Cas endonuclease, and wherein the RuvC domain lacks nuclease activity; a base editor coupled to the endonuclease; and an engineered guide ribonucleic acid structure configured to bind to the endonuclease and the double-stranded deoxyribonucleic acid polynucleotide; wherein the double-stranded deoxyribonucleic acid polynucleotide comprises a protospacer adjacent motif (PAM).

In some embodiments, the endonuclease comprising a RuvC domain and an HNH domain is covalently coupled directly to the base editor or covalently coupled to the base editor through a linker. In some embodiments, the endonuclease comprising a RuvC domain and an HNH domain comprises a sequence with at least 95% sequence identity to any one of SEQ ID NOs: 70-78.

In some aspects, the present disclosure provides a method for modifying a double-stranded deoxyribonucleic acid polynucleotide, comprising contacting the double-stranded deoxyribonucleic acid polynucleotide with a complex comprising: a class 2, type II Cas endonuclease, a base editor coupled to the endonuclease, and an engineered guide ribonucleic acid structure configured to bind to the endonuclease and the double-stranded deoxyribonucleic acid polynucleotide; wherein the double-stranded deoxyribonucleic acid polynucleotide comprises a protospacer adjacent motif (PAM); and wherein the PAM comprises a sequence selected from the group consisting of SEQ ID NOs: 360-368.

In some embodiments, the class 2, type II Cas endonuclease is covalently coupled to the base editor or coupled to the base editor through a linker. In some embodiments, the base editor comprises a sequence with at least 70%, at least 80%, at least 90% or at least 95% identity to a sequence selected from SEQ ID NOs: 1-51 and 385-475. In some embodiments, the base editor comprises an adenine deaminase; the double-stranded deoxyribonucleic acid polynucleotide comprises an adenine; and modifying the double-stranded deoxyribonucleic acid polypeptide comprises converting the adenine to guanine. In some embodiments, the adenine deaminase comprises a sequence with at least 95% identity to SEQ ID NO: 57.

In some embodiments, the base editor comprises a cytosine deaminase; the double-stranded deoxyribonucleic acid polynucleotide comprises a cytosine; and modifying the double-stranded deoxyribonucleic acid polypeptide comprises converting the cytosine to uracil. In some embodiments, the cytosine deaminase comprises a sequence with at least 95% identity to SEQ ID NO: 58. In some embodiments, the cytosine deaminase comprises a sequence with at least 95% identity to any one of SEQ ID NOs: 59-66.

In some embodiments, the complex further comprises a uracil DNA glycosylase inhibitor. In some embodiments, the uracil DNA glycosylase inhibitor comprises a sequence with at least 70%, 80%, 90% or 95% identity to any one of SEQ ID NOs: 52-56 or SEQ ID NO: 67. In some embodiments, the double-stranded deoxyribonucleic acid polynucleotide comprises a first strand comprising a sequence complementary to a sequence of the engineered guide ribonucleic acid structure and a second strand comprising said PAM. In some embodiments, the PAM is directly adjacent to the 3' end of the sequence complementary to the sequence of the engineered guide ribonucleic acid structure.

In some embodiments, the class 2, type II Cas endonuclease is not a Cas9 endonuclease, a Cas 14 endonuclease, a Cas12a endonuclease, a Cas12b endonuclease, a Cas 12c endonuclease, a Cas 12d endonuclease, a Cas12e endonuclease, a Cas13a endonuclease, a Cas13b endonuclease, a Cas 13c endonuclease, or a Cas 13d endonuclease. In some embodiments, the class 2, type II Cas endonuclease is derived from an uncultivated microorganism. In some embodiments, the double-stranded deoxyribonucleic acid polynucleotide is a eukaryotic, plant, fungal, mammalian, rodent, or human double-stranded deoxyribonucleic acid polynucleotide.

In some aspects, the present disclosure provides a method of modifying a target nucleic acid locus, said method comprising delivering to said target nucleic acid locus the engineered nucleic acid editing system described herein, wherein the endonuclease is configured to form a complex with the engineered guide ribonucleic acid structure, and wherein the complex is configured such that upon binding of the complex to the target nucleic acid locus, the complex modifies a nucleotide of the target nucleic locus.

In some embodiments, the engineered nucleic acid editing system comprises an adenine deaminase, the nucleotide is an adenine, and modifying the target nucleic acid locus comprises converting the adenine to a guanine. In some embodiments, the engineered nucleic acid editing system comprises a cytidine deaminase and a uracil DNA glycosylase inhibitor, the nucleotide is a cytosine and modifying the target nucleic acid locus comprises converting the adenine to a uracil. In some embodiments, the target nucleic acid locus comprises genomic DNA, viral DNA, or bacterial DNA. In some embodiments, the target nucleic acid locus is in vitro. In some embodiments, the target nucleic acid locus is within a cell. In some embodiments, the cell is a prokaryotic cell, a bacterial cell, a eukaryotic cell, a fungal cell, a plant cell, an animal cell, a mammalian cell, a rodent cell, a primate cell, or a human cell. In some embodiments, the cell is within an animal.

In some embodiments, the cell is within a cochlea. In some embodiments, the cell is within an embryo. In some embodiments, the embryo is a two-cell embryo. In some embodiments, the embryo is a mouse embryo. In some embodiments, delivering the engineered nucleic acid editing system to the target nucleic acid locus comprises delivering the nucleic acid described herein or the vector described herein. In some embodiments, delivering the engineered nucleic acid editing system to the target nucleic acid locus comprises delivering a nucleic acid comprising an open reading frame encoding the endonuclease.

In some embodiments, the nucleic acid comprises a promoter to which the open reading frame encoding the endonuclease is operably linked. In some embodiments, delivering the engineered nucleic acid editing system to said target nucleic acid locus comprises delivering a capped mRNA containing the open reading frame encoding the endonuclease. In some embodiments, delivering the engineered nucleic acid editing system to the target nucleic acid locus comprises delivering a translated polypeptide. In some embodiments, delivering the engineered nucleic acid editing system to the target nucleic acid locus comprises delivering a deoxyribonucleic acid (DNA) encoding the engineered guide ribonucleic acid structure operably linked to a ribonucleic acid (RNA) pol III promoter.

In some aspects, the present disclosure provides an engineered nucleic acid editing polypeptide, comprising: an endonuclease comprising a RuvC domain and an HINH domain, wherein the endonuclease is derived from an uncultivated microorganism, wherein the endonuclease is a class 2, type II Cas endonuclease, and wherein the RuvC domain lacks nuclease activity; and a base editor coupled to the endonuclease. In some embodiments, the endonuclease comprises a sequence with at least 95% sequence identity to any one of SEQ ID NOs: 70-78.

In some aspects, the present disclosure provides an engineered nucleic acid editing polypeptide, comprising: an endonuclease having at least 95% sequence identity to any one of SEQ ID NOs: 70-78, wherein the endonuclease comprises a RuvC domain lacking nuclease activity; and a base editor coupled to the endonuclease.

In some aspects, the present disclosure provides an engineered nucleic acid editing polypeptide, comprising: an endonuclease configured to bind to a protospacer adjacent motif (PAM) sequence comprising SEQ ID NOs: 360-368, wherein the endonuclease is a class 2, type II Cas endonuclease, and wherein the endonuclease comprises a RuvC domain lacks nuclease activity; and a base editor coupled to the endonuclease.

In some embodiments, the endonuclease is derived from an uncultivated microorganism. In some embodiments, the endonuclease has less than 80% identity to a Cas9 endonuclease. In some embodiments, the endonuclease further comprises an HINH domain. In some embodiments, the tracr ribonucleic acid sequence comprises a sequence with at least 80% sequence identity to about 60 to 90 consecutive nucleotides selected from any one of SEQ ID NOs: 88-96, 488, and 489. In some embodiments, the base editor comprises a sequence with at least 70%, 80%, 90% or 95% identity to any one of SEQ ID NOs: 1-51 and 385-475. In some embodiments, the base editor is an adenine deaminase. In some embodiments, the adenosine deaminase comprises a sequence with at least 95% identity to SEQ ID NO: 57. In some embodiments, the base editor is a cytosine deaminase. In some embodiments, the cytosine deaminase comprises a sequence with at least 95% identity to SEQ ID NO: 58. In some embodiments, the adenosine cytosine deaminase comprises a sequence with at least 95% identity to any one of SEQ ID NOs: 59-66.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure.

Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 6A and 6B show sgRNA designs for lacZ targeting in *E. coli*. The spacer length used for the systems described herein was 22 nucleotides. For selected systems described herein, three sgRNAs targeting lacZ in *E. coli* were designed to determine editing windows. FIG. 6A (left column) discloses SEQ ID NOs: 613-630, 614, 631-635, 614, 631, 632, 636-638, 617, and 639-643, respectively, in order of appearance. FIG. 6A (right column) discloses SEQ ID NOs: 613-630, 614, 631-635, 614, 631, 632, 636-638, 617, and 639-643, respectively, in order of appearance. FIG. 6B (left column) discloses SEQ ID NOs: 644-648, 638, 649-654, 625-627, 655, 628, 656-662, 657-659, 663-665, 646, and 666-670, respectively, in order of appearance. FIG. 6B (right column) discloses SEQ ID NOs: 644-648, 638, 649-654, 625-627, 655, 628, 656-662, 657-659, 663-665, 646, and 666-670, respectively in order of appearance.

FIG. 8A discloses SEQ ID NOs: 99, 695, 99, 696, 695, 106, 697, 698, 697, 107, 699, 700, 699, 108, 701, 702, 108, 108, 108, 101, 703, 703, 122, 704, 704, and 704, respectively, in order of columns. FIG. 8B discloses SEQ ID NOs: 132, 705, 705, 705, 136, 706, 136, 137, 707, 708, 708, 112, 709, 709, 710, 145, 711, 145, 145, 145, 145, respectively, in order of columns. FIG. 8C discloses SEQ ID NOs: 149, 712, 712, 713, 713, 129, 714, 715, 716, 152, 717, 718, 718, 153, 719, 720, 720, respectively, in order of columns.

FIG. 10A discloses SEQ ID NOs: 613-630, 614, 631-635, 614, 631, and 632, from top to bottom, left to right, respectively, in order of appearance. FIG. 10B discloses SEQ ID NOs: 636-638, 617, and 639-643, respectively, in order of appearance.

FIG. 11A discloses SEQ ID NOs: 644-648, 638, 649-654, 625-627, 655, 628, 656-662, and 657-659, from top to bottom, left to right, respectively, in order of appearance. FIG. 11B discloses SEQ ID NOs: 663-665, 646, and 666-670, respectively in order of appearance.

FIG. 13A discloses SEQ ID NOs: 671-685, respectively, in order of appearance. FIG. 13B discloses SEQ ID NOs: 686-691, respectively, in order of appearance.

FIG. 14 discloses SEQ ID NOs: 693-694, respectively, in order of appearance.

FIG. 16B summarizes the editing efficiencies of MG TadA candidates and demonstrates that MG68-3, and MG68-4 drove base edits of adenine.

FIG. 19 shows 28 MG68-4 variants designed for improvements of MG68-4-nMG34-1 base editing activity (SEQ ID NOs: 448-475). 12 residues were selected for targeted mutagenesis to improve editing of the enzymes.

BRIEF DESCRIPTION OF THE SEQUENCE LISTING

Figure 1:
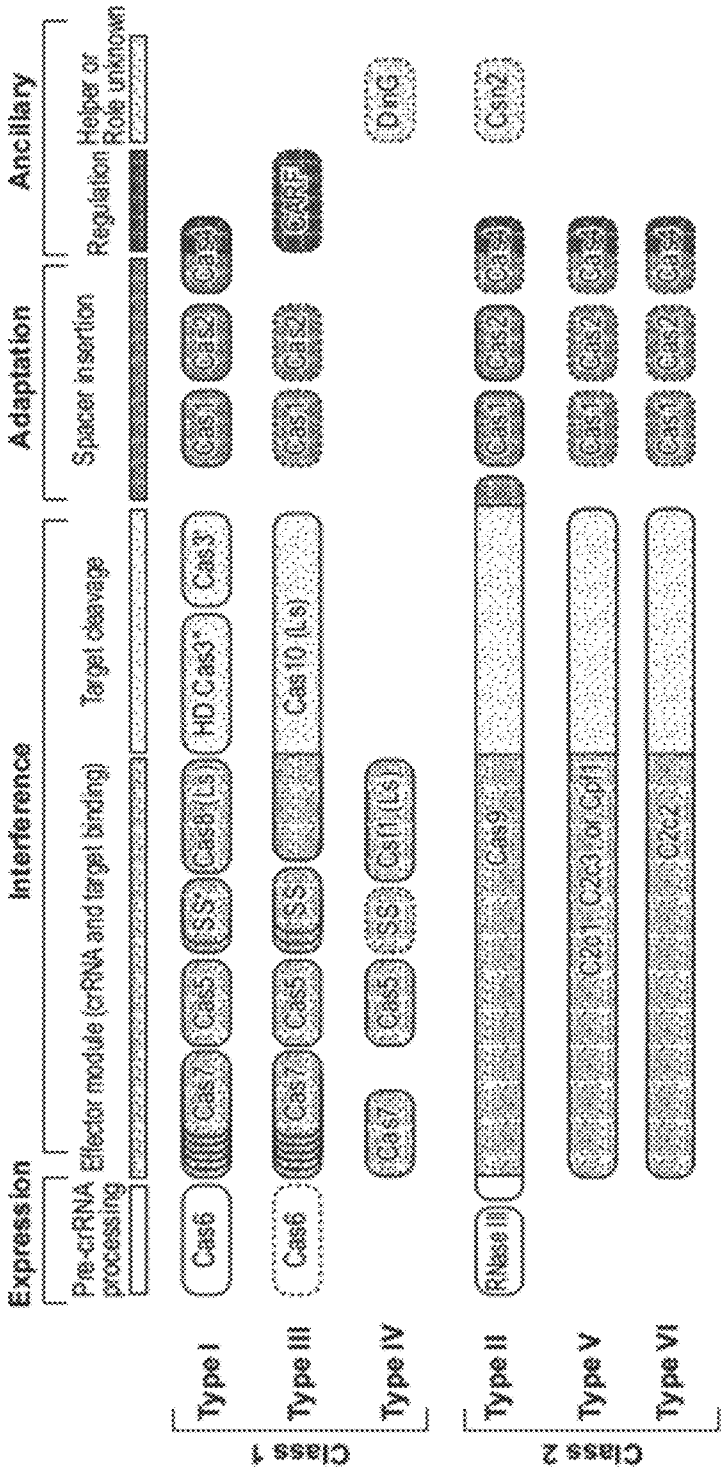
FIG. 1 depicts typical organizations of CRISPR/Cas loci of different classes and types.

The Sequence Listing filed herewith provides exemplary polynucleotide and polypeptide sequences for use in methods, compositions and systems according to the disclosure. Below are exemplary descriptions of sequences therein.

SEQ ID NOs: 1-47 show the full-length peptide sequences of MG66 deaminases suitable for the engineered nucleic acid editing systems described herein.

SEQ ID NOs: 48-49 show the full-length peptide sequences of MG67 deaminases suitable for the engineered nucleic acid editing systems described herein.

SEQ ID NOs: 50-51 show the full-length peptide sequences of MG68 deaminases suitable for the engineered nucleic acid editing systems described herein.

SEQ ID NOs: 52-56 show the sequences of uracil DNA glycosylase inhibitors suitable for the engineered nucleic acid editing systems described herein.

SEQ ID NOs: 57-66 show the sequences of reference deaminases.

SEQ ID NO: 67 shows the sequence of a reference uracil DNA glycosylase inhibitor.

SEQ ID NO: 68 shows the sequence of an adenine base editor.

SEQ ID NO: 69 shows the sequence of a cytosine base editor.

SEQ ID NOs: 70-78 show the full-length peptide sequences of MG nickases suitable for the engineered nucleic acid editing systems described herein.

SEQ ID NOs: 79-87 shows the protospacer and PAM used in in vitro nickase assays described herein.

SEQ ID NOs: 88-96 show the peptide sequences of single guide RNA used in in vitro nickase assays described herein.

SEQ ID NOs: 97-156 show the sequences of spacers when targeting *E. coli* lacZ.

SEQ ID NOs: 157-176 show the sequences of primers when conducting site directed mutagenesis.

SEQ ID NOs: 177-178 show the sequences of primers for lacZ sequencing.

SEQ ID NOs: 179-342 show the sequences of primers used during amplification.

SEQ ID NOs: 343-345 show the sequences of primers for lacZ sequencing.

SEQ ID NOs: 346-359 show the sequences of primers used during amplification.

SEQ ID NOs: 360-368 show protospacer adjacent motifs suitable for the engineered nucleic acid editing systems described herein.

SEQ ID NOs: 369-384 show nuclear localization sequences (NLS's) suitable for the engineered nucleic acid editing systems described herein.

SEQ ID NOs: 385-443 show the full-length peptide sequences of MG68 deaminases suitable for the engineered nucleic acid editing systems described herein.

SEQ ID NOs: 444-447 show the full-length peptide sequences of MG121 deaminases suitable for the engineered nucleic acid editing systems described herein.

SEQ ID NOs: 448-475 show the full-length peptide sequences of MG68 deaminases suitable for the engineered nucleic acid editing systems described herein.

SEQ ID NOs: 476 and 477 show sequences of adenine base editors.

SEQ ID NOs: 478-482 show sequences of cytosine base editors.

SEQ ID NOs: 483-487 show the sequences of plasmids suitable for encoding the engineered nucleic acid editing systems described herein.

SEQ ID NOs: 488 and 489 show the sgRNA scaffold sequences for MG15-1 and MG34-1.

SEQ ID NOs: 490-522 show the sequences of spacers used to target genomic loci in *E. coli* and HEK293T cells.

SEQ ID NOs: 523-585 show the sequences of primers used during amplification and Sanger sequencing.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The practice of some methods disclosed herein employ, unless otherwise indicated, techniques of immunology, biochemistry, chemistry, molecular biology, microbiology, cell biology, genomics and recombinant DNA. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)) (which is entirely incorporated by reference herein).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

As used herein, a "cell" generally refers to a biological cell. A cell may be the basic structural, functional and/or biological unit of a living organism. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be a synthetically made, sometimes termed an artificial cell).

The term "nucleotide," as used herein, generally refers to a base-sugar-phosphate combination. A nucleotide may comprise a synthetic nucleotide. A nucleotide may comprise a synthetic nucleotide analog. Nucleotides may be monomeric units of a nucleic acid sequence (e.g., deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives may include, for example, [αS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled, such as using moieties comprising optically detectable moieties (e.g., fluorophores). Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl) aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to generally refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure and may perform any function. A polynucleotide may comprise one or more analogs (e.g., altered backbone, sugar, or nucleobase). If present, modifications to the nucleotide structure may be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

The terms "transfection" or "transfected" generally refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The terms "peptide," "polypeptide," and "protein" are used interchangeably herein to generally refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer may be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids may include natural amino acids and non-natural amino acids, which have been chemically modified to include a group or a chemical moiety not naturally present on the amino acid. Amino acid analogues may refer to amino acid derivatives. The term "amino acid" includes both D-amino acids and L-amino acids.

As used herein, the "non-native" can generally refer to a nucleic acid or polypeptide sequence that is not found in a native nucleic acid or protein. Non-native may refer to affinity tags. Non-native may refer to fusions. Non-native may refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that may also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide.

The term "promoter", as used herein, generally refers to the regulatory DNA region which controls transcription or expression of a gene and which may be located adjacent to or overlapping a nucleotide or region of nucleotides at which RNA transcription is initiated. A promoter may contain specific DNA sequences which bind protein factors, often referred to as transcription factors, which facilitate binding of RNA polymerase to the DNA leading to gene transcription. A 'basal promoter', also referred to as a 'core promoter', may generally refer to a promoter that contains all the basic necessary elements to promote transcriptional expression of an operably linked polynucleotide. Eukaryotic basal promoters typically, though not necessarily, contain a TATA-box and/or a CAAT box.

The term "expression", as used herein, generally refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof generally refer to juxtaposition of genetic elements, e.g., a promoter, an enhancer, a polyadenylation sequence, etc., wherein the elements are in a relationship permitting them to operate in the expected manner. For instance, a regulatory element, which may comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein, generally refers to a macromolecule or association of macromolecules that comprises or associates with a polynucleotide and which may be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target.

As used herein, "an expression cassette" and "a nucleic acid cassette" are used interchangeably generally to refer to a combination of nucleic acid sequences or elements that are expressed together or are operably linked for expression. In some cases, an expression cassette refers to the combination of regulatory elements and a gene or genes to which they are operably linked for expression.

A "functional fragment" of a DNA or protein sequence generally refers to a fragment that retains a biological activity (either functional or structural) that is substantially similar to a biological activity of the full-length DNA or protein sequence. A biological activity of a DNA sequence may be its ability to influence expression in a manner known to be attributed to the full-length sequence.

As used herein, an "engineered" object generally indicates that the object has been modified by human intervention. According to non-limiting examples: a nucleic acid may be modified by changing its sequence to a sequence that does not occur in nature; a nucleic acid may be modified by ligating it to a nucleic acid that it does not associate with in nature such that the ligated product possesses a function not present in the original nucleic acid; an engineered nucleic acid may synthesized in vitro with a sequence that does not exist in nature; a protein may be modified by changing its amino acid sequence to a sequence that does not exist in nature; an engineered protein may acquire a new function or property. An "engineered" system comprises at least one engineered component.

As used herein, "synthetic" and "artificial" are used interchangeably to refer to a protein or a domain thereof that has low sequence identity (e.g., less than 50% sequence identity, less than 25% sequence identity, less than 10% sequence identity, less than 5% sequence identity, less than 1% sequence identity) to a naturally occurring human protein. For example, VPR and VP64 domains are synthetic transactivation domains.

The term "tracrRNA" or "tracr sequence", as used herein, can generally refer to a nucleic acid with at least about 5%, 10%, 20%, 30%, 40%, 50%, 60%, 70%, 80%, 90%, 95%, or 100% sequence identity and/or sequence similarity to a wild type exemplary tracrRNA sequence (e.g., a tracrRNA from *S. pyogenes S. aureus*, etc.). tracrRNA can refer to a nucleic acid with at most about 5%, 10%, 20%, 30%, 40%, 50%, 60%, 70%, 80%, 90%, or 100% sequence identity and/or sequence similarity to a wild type exemplary tracrRNA sequence (e.g., a tracrRNA from *S. pyogenes S. aureus*, etc.). tracrRNA may refer to a modified form of a tracrRNA that can comprise a nucleotide change such as a deletion, insertion, or substitution, variant, mutation, or chimera. A tracrRNA may refer to a nucleic acid that can be at least about 60% identical to a wild type exemplary tracrRNA (e.g., a tracrRNA from *S. pyogenes S. aureus*, etc.) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from *S. pyogenes S. aureus*, etc.) sequence over a stretch of at least 6 contiguous nucleotides. Type II tracrRNA sequences can be predicted on a genome sequence by identifying regions with complementarity to part of the repeat sequence in an adjacent CRISPR array.

As used herein, a "guide nucleic acid" can generally refer to a nucleic acid that may hybridize to another nucleic acid. A guide nucleic acid may be RNA. A guide nucleic acid may be DNA. The guide nucleic acid may be programmed to bind to a sequence of nucleic acid site-specifically. The nucleic acid to be targeted, or the target nucleic acid, may comprise nucleotides. The guide nucleic acid may comprise nucleotides. A portion of the target nucleic acid may be complementary to a portion of the guide nucleic acid. The strand of a double-stranded target polynucleotide that is complementary to and hybridizes with the guide nucleic acid may be called the complementary strand. The strand of the double-stranded target polynucleotide that is complementary to the complementary strand, and therefore may not be complementary to the guide nucleic acid may be called noncomplementary strand. A guide nucleic acid may comprise a polynucleotide chain and can be called a "single guide nucleic acid." A guide nucleic acid may comprise two polynucleotide chains and may be called a "double guide nucleic acid." If not otherwise specified, the term "guide nucleic acid" may be inclusive, referring to both single guide nucleic acids and double guide nucleic acids. A guide nucleic acid may comprise a segment that can be referred to as a "nucleic acid-targeting segment" or a "nucleic acid-targeting sequence." A nucleic acid-targeting segment may comprise a sub-segment that may be referred to as a "protein binding segment" or "protein binding sequence" or "Cas protein binding segment".

The term "sequence identity" or "percent identity" in the context of two or more nucleic acids or polypeptide sequences, generally refers to two (e.g., in a pairwise alignment) or more (e.g., in a multiple sequence alignment) sequences that are the same or have a specified percentage of amino acid residues or nucleotides that are the same, when compared and aligned for maximum correspondence over a local or global comparison window, as measured using a sequence comparison algorithm. Suitable sequence comparison algorithms for polypeptide sequences include, e.g., BLASTP using parameters of a wordlength (W) of 3, an expectation (E) of 10, and the BLOSUM62 scoring matrix setting gap costs at existence of 11, extension of 1, and using a conditional compositional score matrix adjustment for polypeptide sequences longer than 30 residues; BLASTP using parameters of a wordlength (W) of 2, an expectation (E) of 1000000, and the PAM30 scoring matrix setting gap costs at 9 to open gaps and 1 to extend gaps for sequences of less than 30 residues (these are the default parameters for BLASTP in the BLAST suite available at blast.ncbi.nlm-.nih.gov); CLUSTALW with parameters of; the Smith-Waterman homology search algorithm with parameters of a match of 2, a mismatch of −1, and a gap of −1; MUSCLE with default parameters; MAFFT with parameters retree of 2 and maxiterations of 1000; Novafold with default parameters; HMMER hmmalign with default parameters.

As used herein, the term "RuvC_III domain" generally refers to a third discontinuous segment of a RuvC endonuclease domain (the RuvC nuclease domain being comprised of three discontiguous segments, RuvC_I, RuvC_II, and RuvC_III). A RuvC domain or segments thereof can generally be identified by alignment to known domain sequences, structural alignment to proteins with annotated domains, or by comparison to Hidden Markov Models (HMMs) built based on known domain sequences (e.g., Pfam HMM PF18541 for RuvC_III).

As used herein, the term "HNH domain" generally refers to an endonuclease domain having characteristic histidine and asparagine residues. An HNH domain can generally be identified by alignment to known domain sequences, structural alignment to proteins with annotated domains, or by comparison to Hidden Markov Models (HMMs) built based on known domain sequences (e.g., Pfam HMM PF01844 for domain HNH).

As used herein, the term "base editor" generally refers to an enzyme that catalyzes the conversion of one target base or base pair into another (e.g. A:T to G:C, C:G to T:A) without requiring the creation and repair of a double-strand break. In some embodiments, the base editor is a deaminase.

As used herein, the term "deaminase" generally refers to a protein or enzyme that catalyzes a deamination reaction. In some embodiments, the deaminase is an adenosine deaminase, which catalyzes the hydrolytic deamination of adenine or adenosine (e.g., an engineered adenosine deaminase that deaminates adenosine in DNA). In some embodiments, the deaminase or deaminase domain is a cytidine (or cytosine) deaminase, catalyzing the hydrolytic deamination of cytidine (or cytosine) or deoxycytidine to uridine (or uracil) or deoxyuridine, respectively. In some embodiments, the deaminase or deaminase domain is a cytidine (or cytosine) deaminase domain, catalyzing the hydrolytic deamination of cytosine (or cytosine) to uracil (or uridine). In some embodiments, the deaminase or deaminase domain is a naturally-occurring deaminase from an organism, such as a human, chimpanzee, gorilla, monkey, cow, dog, rat, mouse, or bacterium (e.g. *E. coli*). In some embodiments, the deaminase or deaminase domain is a variant of a naturally-occurring deaminase from an organism that does not occur in nature.

The term "optimally aligned" in the context of two or more nucleic acids or polypeptide sequences, generally refers to two (e.g., in a pairwise alignment) or more (e.g., in a multiple sequence alignment) sequences that have been aligned to maximal correspondence of amino acids residues or nucleotides, for example, as determined by the alignment producing a highest or "optimized" percent identity score.

Included in the current disclosure are variants of any of the enzymes described herein with one or more conservative amino acid substitutions. Such conservative substitutions can be made in the amino acid sequence of a polypeptide without disrupting the three-dimensional structure or function of the polypeptide. Conservative substitutions can be accomplished by substituting amino acids with similar hydrophobicity, polarity, and R chain length for one another. Additionally, or alternatively, by comparing aligned sequences of homologous proteins from different species, conservative substitutions can be identified by locating amino acid residues that have been mutated between species (e.g., non-conserved residues) without altering the basic functions of the encoded proteins. Such conservatively substituted variants may include variants with at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99% identity to any one of the endonuclease protein sequences described herein. In some embodiments, such conservatively substituted variants are functional variants. Such functional variants can encompass sequences with substitutions such that the activity of one or more critical active site residues or guide RNA binding residues of the endonuclease are not disrupted.

Also included in the current disclosure are variants of any of the enzymes described herein with substitution of one or more catalytic residues to decrease or eliminate activity of the enzyme (e.g. decreased-activity variants). In some embodiments, a decreased activity variant as a protein described herein comprises a disrupting substitution of at least one, at least two, or all three catalytic residues. In some embodiments, any of the endonucleases described herein can comprise a nickase mutation. In some embodiments, any of the endonucleases described herein can comprise a RuvC domain lacking nuclease activity. In some embodiments, any of the endonucleases described herein can be configured to cleave one strand of a double-stranded target deoxyribonucleic acid. In some embodiments, any of the endonucleases described herein can comprise can be configured to lack endonuclease activity or be catalytically dead.

Conservative substitution tables providing functionally similar amino acids are available from a variety of references (see, for e.g., Creighton, Proteins: Structures and Molecular Properties (W H Freeman & Co.; 2nd edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine(S), Threonine (T); and
8) Cysteine (C), Methionine (M)

Overview

The discovery of new Cas enzymes with unique functionality and structure may offer the potential to further disrupt deoxyribonucleic acid (DNA) editing technologies, improving speed, specificity, functionality, and ease of use. Relative to the predicted prevalence of Clustered Regularly Interspaced Short Palindromic Repeats (CRISPR) systems in microbes and the sheer diversity of microbial species, comparatively few functionally characterized CRISPR/Cas enzymes exist in the literature. This is partly because a huge number of microbial species may not be readily cultivated in laboratory conditions. Metagenomic sequencing from natural environmental niches that represent large numbers of microbial species may offer the potential to drastically increase the number of new CRISPR/Cas systems known and speed the discovery of new oligonucleotide editing functionalities. A recent example of the fruitfulness of such an approach is demonstrated by the 2016 discovery of CasX/CasY CRISPR systems from metagenomic analysis of natural microbial communities.

CRISPR/Cas systems are RNA-directed nuclease complexes that have been described to function as an adaptive immune system in microbes. In their natural context, CRISPR/Cas systems occur in CRISPR (clustered regularly interspaced short palindromic repeats) operons or loci, which generally comprise two parts: (i) an array of short repetitive sequences (30-40 bp) separated by equally short spacer sequences, which encode the RNA-based targeting element; and (ii) ORFs encoding the Cas encoding the nuclease polypeptide directed by the RNA-based targeting element alongside accessory proteins/enzymes. Efficient nuclease targeting of a particular target nucleic acid sequence generally requires both (i) complementary hybridization between the first 6-8 nucleic acids of the target (the target seed) and the crRNA guide; and (ii) the presence of a protospacer-adjacent motif (PAM) sequence within a defined vicinity of the target seed (the PAM usually being a sequence not commonly represented within the host genome). Depending on the exact function and organization of the system, CRISPR-Cas systems are commonly organized into 2 classes, 5 types and 16 subtypes based on shared functional characteristics and evolutionary similarity (see FIG. 1).

Class I CRISPR-Cas systems have large, multisubunit effector complexes, and comprise Types I, III, and IV.

Type I CRISPR-Cas systems are considered of moderate complexity in terms of components. In Type I CRISPR-Cas systems, the array of RNA-targeting elements is transcribed as a long precursor crRNA (pre-crRNA) that is processed at repeat elements to liberate short, mature crRNAs that direct the nuclease complex to nucleic acid targets when they are followed by a suitable short consensus sequence called a protospacer-adjacent motif (PAM). This processing occurs via an endoribonuclease subunit (Cas6) of a large endonuclease complex called Cascade, which also comprises a nuclease (Cas3) protein component of the crRNA-directed nuclease complex. Cas I nucleases function primarily as DNA nucleases.

Type III CRISPR systems may be characterized by the presence of a central nuclease, known as Cas10, alongside a repeat-associated mysterious protein (RAMP) that comprises Csm or Cmr protein subunits. Like in Type I systems, the mature crRNA is processed from a pre-crRNA using a Cas6-like enzyme. Unlike type I and II systems, type III systems appear to target and cleave DNA-RNA duplexes (such as DNA strands being used as templates for an RNA polymerase).

Type IV CRISPR-Cas systems possess an effector complex that consists of a highly reduced large subunit nuclease (csf1), two genes for RAMP proteins of the Cas5 (csf3) and Cas7 (csf2) groups, and, in some cases, a gene for a predicted small subunit; such systems are commonly found on endogenous plasmids.

Class II CRISPR-Cas systems generally have single-polypeptide multidomain nuclease effectors, and comprise Types II, V and VI.

Type II CRISPR-Cas systems are considered the simplest in terms of components. In Type II CRISPR-Cas systems, the processing of the CRISPR array into mature crRNAs does not require the presence of a special endonuclease subunit, but rather a small trans-encoded crRNA (tracrRNA) with a region complementary to the array repeat sequence; the tracrRNA interacts with both its corresponding effector nuclease (e.g. Cas9) and the repeat sequence to form a precursor dsRNA structure, which is cleaved by endogenous RNAse III to generate a mature effector enzyme loaded with both tracrRNA and crRNA. Cas II nucleases are known as DNA nucleases. Type 2 effectors generally exhibit a structure consisting of a RuvC-like endonuclease domain that adopts the RNase H fold with an unrelated HNH nuclease domain inserted within the folds of the RuvC-like nuclease domain. The RuvC-like domain is responsible for the cleavage of the target (e.g., crRNA complementary) DNA strand, while the HNH domain is responsible for cleavage of the displaced DNA strand.

Type V CRISPR-Cas systems are characterized by a nuclease effector (e.g. Cas12) structure similar to that of Type II effectors, comprising a RuvC-like domain. Similar to Type II, most (but not all) Type V CRISPR systems use a tracrRNA to process pre-crRNAs into mature crRNAs; however, unlike Type II systems which requires RNAse III to cleave the pre-crRNA into multiple crRNAs, type V systems are capable of using the effector nuclease itself to cleave pre-crRNAs. Like Type-II CRISPR-Cas systems, Type V CRISPR-Cas systems are again known as DNA nucleases. Unlike Type II CRISPR-Cas systems, some Type V enzymes (e.g., Cas12a) appear to have a robust single-stranded nonspecific deoxyribonuclease activity that is activated by the first crRNA directed cleavage of a double-stranded target sequence.

Type VI CRIPSR-Cas systems have RNA-guided RNA endonucleases. Instead of RuvC-like domains, the single polypeptide effector of Type VI systems (e.g. Cas13) comprises two HEPN ribonuclease domains. Differing from both Type II and V systems, Type VI systems also appear to not need a tracrRNA for processing of pre-crRNA into crRNA. Similar to type V systems, however, some Type VI systems (e.g., C2C2) appear to possess robust single-stranded nonspecific nuclease (ribonuclease) activity activated by the first crRNA directed cleavage of a target RNA.

Because of their simpler architecture, Class II CRISPR-Cas have been most widely adopted for engineering and development as designer nuclease/genome editing applications.

One of the early adaptations of such a system for in vitro use can be found in Jinek et al. (Science. 2012 Aug. 17; 337 (6096):816-21, which is entirely incorporated herein by reference). The Jinek study first described a system that involved (i) recombinantly-expressed, purified full-length Cas9 (e.g., a Class II, Type II Cas enzyme) isolated from *S. pyogenes* SF370, (ii) purified mature ~42 nt crRNA bearing a ~20 nt 5' sequence complementary to the target DNA sequence to be cleaved followed by a 3' tracr-binding sequence (the whole crRNA being in vitro transcribed from a synthetic DNA template carrying a T7 promoter sequence); (iii) purified tracrRNA in vitro transcribed from a synthetic DNA template carrying a T7 promoter sequence, and (iv) $Mg^{2+}$. Jinek later described an improved, engineered system wherein the crRNA of (ii) is joined to the 5' end of (iii) by a linker (e.g., GAAA) to form a single fused synthetic guide RNA (sgRNA) capable of directing Cas9 to a target by itself.

Mali et al. (Science. 2013 Feb. 15; 339 (6121): 823-826), which is entirely incorporated herein by reference, later adapted this system for use in mammalian cells by providing DNA vectors encoding (i) an ORF encoding codon-optimized Cas9 (e.g., a Class II, Type II Cas enzyme) under a suitable mammalian promoter with a C-terminal nuclear localization sequence (e.g., SV40 NLS) and a suitable polyadenylation signal (e.g., TK pA signal); and (ii) an ORF encoding an sgRNA (having a 5' sequence beginning with G followed by 20 nt of a complementary targeting nucleic acid sequence joined to a 3' tracr-binding sequence, a linker, and the tracrRNA sequence) under a suitable Polymerase III promoter (e.g., the U6 promoter).

Base Editing

Base editing is the conversion of one target base or base pair into another (e.g. A:T to G:C, C:G to T:A) without requiring the creation and repair of a double-strand break. The base editing may be achieved with the help of DNA and RNA base editors that allow the introduction of point mutations at specific sites, in either DNA or RNA. Generally, DNA base editors may comprise a fusion of a catalytically inactive nuclease and a catalytically active base-modification enzyme that acts only on single-stranded DNAs (ssDNAs). RNA base editors may comprise of similar, RNA-specific enzymes. Base editing may increase the efficiency of gene modification, while reducing the off-target and random mutations in the DNA.

DNA base editors are engineered ribonucleoprotein complexes that act as tools for single base substitution in cells and organism. They may be created by fusing an engineered base-modification enzyme and a catalytically deficient Cas variant that cannot cut dsDNA, but it is able to unfold the dsDNA in a protospacer adjacent motif (PAM) sequence-dependent manner, such that a guide RNA can find its complementary target to indicate a ssDNA scission site. The guide RNA anneals to the complementary DNA, displacing a fragment of ssDNA and directing the Cas 'scissors' to the base modification site. The cellular repair machinery will repair the nicked non-edited strand using information from the complementary edited template.

So far, two types of DNA editors, cytosine base (CBEs) and adenine base editors (ABEs) have been developed. They were shown to efficiently and precisely edit point mutations in DNA with minimal off-target DNA editing (see Nat Biotechnol. 2017; 35:435-437, Nat Biotechnol. 2017; 35:438-440 and Nat Biotechnol. 2017; 35:475-480, each of which is entirely incorporated herein by reference). However, recent findings indicate that off-target modifications are present in DNA, and that many off-target modifications are also introduced into RNA by DNA base editors.

MG Base Editors

In some aspects, the present disclosure provides for an engineered nucleic acid editing system, comprising: (a) an endonuclease comprising a RuvC domain and an HNH domain, wherein the endonuclease is derived from an uncultivated microorganism, wherein the endonuclease is a class 2, type II Cas endonuclease, and wherein the endonuclease is configured to be deficient in nuclease activity; (b) a base editor coupled to the endonuclease; and (c) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease. In some embodiments, the endonuclease comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof. In some cases, the RuvC domain lacks nuclease activity. In some cases, the endonuclease comprises a nickase mutation. In some cases, the endonuclease is configured to cleave one strand of a double-stranded target deoxyribonucleic acid. In some cases the ribonucleic acid sequence configured to bind to the endonuclease comprises a tracr sequence.

In some aspects, the present disclosure provides for an engineered nucleic acid editing system comprising: (a) an endonuclease having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof, wherein the endonuclease is configured to be deficient in nuclease activity; a base editor coupled to the endonuclease; and an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease. In some cases the ribonucleic acid sequence configured to bind to the endonuclease comprises a tracr sequence. In some cases, the RuvC domain lacks nuclease activity. In some cases, the endonuclease comprises a nickase mutation. In some cases, the endonuclease is configured to cleave one strand of a double-stranded target deoxyribonucleic acid.

In some aspects, the present disclosure provides for an engineered nucleic acid editing system comprising: (a) an endonuclease configured to bind to a protospacer adjacent motif (PAM) sequence comprising any one of SEQ ID NOs: 360-368 or 598, wherein the endonuclease is a class 2, type II Cas endonuclease, and the endonuclease is configured to be deficient in nuclease activity; and (b) a base editor coupled to the endonuclease; and (c) an engineered guide ribonucleic acid structure configured to form a complex with the endonuclease comprising: (i) a guide ribonucleic acid sequence configured to hybridize to a target deoxyribonucleic acid sequence; and (ii) a ribonucleic acid sequence configured to bind to the endonuclease. In some cases, the ribonucleic acid sequence configured to bind to the endonuclease comprises a tracr sequence. In some cases, the endonuclease comprises a nickase mutation. In some cases, the RuvC domain lacks nuclease activity. In some cases, the endonuclease is configured to cleave one strand of a double-stranded target deoxyribonucleic acid.

In some embodiments, the endonuclease is derived from an uncultivated microorganism. In some embodiments, the endonuclease has less than 80% identity to a Cas9 endonuclease. In some embodiments, the endonuclease further comprises an HNH domain. In some embodiments, the tracr ribonucleic acid sequence comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to about 60 to 90 consecutive nucleotides selected from any one of SEQ ID NOs: 88-96 or 488-489 or a variant thereof. In some embodiments, the tracr ribonucleic acid sequence comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity non-degenerate nucleotides of any one of SEQ ID NOs: 88-96 or 488-489 or a variant thereof.

In some aspects, the present disclosure provides an engineered nucleic acid editing system comprising, (a) an engineered guide ribonucleic acid structure comprising: (i) a guide ribonucleic acid sequence configured to hybridize to a target deoxyribonucleic acid sequence; and (ii) a tracr ribonucleic acid sequence configured to bind to an endonuclease, wherein the tracr ribonucleic acid sequence comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity non-degenerate nucleotides of any one of SEQ ID NOs: 88-96 or 488-489 or a variant thereof; and a class 2, type II Cas endonuclease configured to bind to the engineered guide ribonucleic acid.

In some embodiments, the endonuclease is configured to bind to a protospacer adjacent motif (PAM) sequence comprising any one of SEQ ID NOs: 360, 362, or 368. In some embodiments, the base editor comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-51, 57-66, 385-443, 444-475, or 594-595 or a variant thereof. In some embodiments, the base editor is an adenine deaminase. In some embodiments, the adenosine deaminase comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NOs: 50-51, 57, 385-443, 448-475, or 595 or a variant thereof. In some embodiments, the base editor is a cytosine deaminase. In some embodiments, the cytosine deaminase comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-49, 444-447, 594, or 58-66 or a variant thereof.

In some embodiments, the engineered nucleic acid editing system further comprises a uracil DNA glycosylase inhibitor. In some embodiments, the uracil DNA glycosylase inhibitor comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 52-56 or SEQ ID NO: 67 or a variant thereof.

In some embodiments, the engineered guide ribonucleic acid structure comprises at least two ribonucleic acid polynucleotides. In some embodiments, the engineered guide ribonucleic acid structure comprises one ribonucleic acid polynucleotide comprising the guide ribonucleic acid sequence and the tracr ribonucleic acid sequence. In some embodiments, the guide ribonucleic acid sequence is complementary to a prokaryotic, bacterial, archaeal, eukaryotic, fungal, plant, mammalian, or human genomic sequence. In some embodiments, the guide ribonucleic acid sequence is 15-24 nucleotides in length. In some embodiments, the endonuclease comprises one or more nuclear localization sequences (NLSs) proximal to an N- or C-terminus of the endonuclease.

The NLS can comprise any of the sequences in Table 1 below, or a combination thereof:

TABLE 1

Example NLS Sequences that can be used with Cas Effectors According to the Disclosure

| Source | NLS amino acid sequence | SEQ ID NO: |
|---|---|---|
| SV40 | PKKKRKV | 369 |
| nucleoplasmin bipartite NLS | KRPAATKKAGQAKKKK | 370 |
| c-myc NLS | PAAKRVKLD | 371 |
| c-myc NLS | RQRRNELKRSP | 372 |
| hRNPA1 M9 NLS | NQSSNFGPMKGGNFGGRSSGPYGGGGQYFAKPRNQGGY | 373 |
| Importin-alpha IBB domain | RMRIZFKNKGKDTAELRRRRVEVSVELRKAKKDEQILKRRNV | 374 |
| Myoma T protein | VSRKRPRP | 375 |
| Myoma T protein | PPKKARED | 376 |
| p53 | PQPKKKPL | 377 |
| mouse c-abl IV | SALIKKKKKMAP | 378 |
| influenza virus NS1 | DRLRR | 379 |
| influenza virus NS1 | PKQKKRK | 380 |
| Hepatitis virus delta antigen | RKLKKKIKKL | 381 |
| mouse Mx1 protein | REKKKFLKRR | 382 |
| human poly(ADP-ribose) polymerase | KRKGDEVDGVDEVAKKKSKK | 383 |
| steroid hormone receptor (human) glucocorticoid | RKCLQAGMNLEARKTKK | 384 |

In some embodiments, the endonuclease is covalently coupled directly to the base editor or covalently coupled to the base editor through a linker. In some embodiments, linkers joining any of the enzymes or domains described herein can comprise one or multiple copies of a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SGGSSGGSSGSETPGTSESATPESSGGSSGGS, SGSETPGTSESATPESA, GSGGS, SGSETPGTSESATPES, SGGSS, or GAAA, or any other linker sequence described herein. In some embodiments, a polypeptide comprises the endonuclease and the base editor. In some embodiments, the endonuclease is configured to cleave one strand of a double-stranded target deoxyribonucleic acid. In some embodiments, the endonuclease comprises a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof. In some embodiments, the system further comprises a source of $Mg^{2+}$.

In some embodiments, the endonuclease comprises a sequence at least 70%, at least 80%, or at least 90% identical to SEQ ID NO: 70 or a variant thereof; the guide RNA structure comprises a sequence at least 70%, at least 80%, or at least 90% identical to at least one of SEQ ID NO: 88; and the endonuclease is configured to bind to a PAM comprising SEQ ID NO: 360.

In some embodiments, the endonuclease comprises a sequence at least 70%, at least 80%, or at least 90% identical to SEQ ID NO: 71 or a variant thereof; the guide RNA structure comprises a sequence at least 70%, at least 80%, or at least 90% identical to at least one of SEQ ID NO: 89; and the endonuclease is configured to bind to a PAM comprising SEQ ID NO: 361.

In some embodiments, the endonuclease comprises a sequence at least 70%, at least 80%, or at least 90% identical to SEQ ID NO: 73 or a variant thereof; the guide RNA structure comprises a sequence at least 70%, at least 80%, or at least 90% identical to at least one of SEQ ID NO: 91; and the endonuclease is configured to bind to a PAM comprising SEQ ID NO: 363.

In some embodiments, the endonuclease comprises a sequence at least 70%, at least 80%, or at least 90% identical to SEQ ID NO: 75 or a variant thereof; the guide RNA structure comprises a sequence at least 70%, at least 80%, or at least 90% identical to at least one of SEQ ID NO: 93; and the endonuclease is configured to bind to a PAM comprising SEQ ID NO: 365.

In some embodiments, the endonuclease comprises a sequence at least 70%, at least 80%, or at least 90% identical to SEQ ID NO: 76 or a variant thereof; the guide RNA structure comprises a sequence at least 70%, at least 80%, or at least 90% identical to at least one of SEQ ID NO: 94; and the endonuclease is configured to bind to a PAM comprising SEQ ID NO: 366.

In some embodiments, the endonuclease comprises a sequence at least 70%, at least 80%, or at least 90% identical to SEQ ID NO: 77 or a variant thereof; the guide RNA structure comprises a sequence at least 70%, at least 80%, or at least 90% identical to at least one of SEQ ID NO: 95; and the endonuclease is configured to bind to a PAM comprising SEQ ID NO: 367.

In some embodiments, the endonuclease comprises a sequence at least 70%, at least 80%, or at least 90% identical to SEQ ID NO: 78 or a variant thereof; the guide RNA structure comprises a sequence at least 70%, at least 80%, or at least 90% identical to at least one of SEQ ID NO: 96; and the endonuclease is configured to bind to a PAM comprising SEQ ID NO: 368.

In some embodiments, the base editor comprises an adenine deaminase. In some embodiments, the adenine deaminase comprises SEQ ID NO: 57 or a variant thereof. In some embodiments, the base editor comprises a cytosine deaminase. In some embodiments, the cytosine deaminase comprises SEQ ID NO: 58 or a variant thereof. In some embodiments, the engineered nucleic acid editing system described herein further comprises a uracil DNA glycosylation inhibitor. In some embodiments, the uracil DNA glycosylation inhibitor comprises SEQ ID NO: 67 or a variant thereof.

In some embodiments, the sequence identity is determined by a BLASTP, CLUSTALW, MUSCLE, MAFFT, or Smith-Waterman homology search algorithm. In some embodiments, the sequence identity is determined by said BLASTP homology search algorithm using parameters of a wordlength (W) of 3, an expectation (E) of 10, and a BLOSUM62 scoring matrix setting gap costs at existence of 11, extension of 1, and using a conditional compositional score matrix adjustment.

In some aspects, the present disclosure provides a nucleic acid comprising an engineered nucleic acid sequence optimized for expression in an organism, wherein the nucleic acid encodes a class 2, type II Cas endonuclease coupled to a base editor, and wherein the endonuclease is derived from an uncultivated microorganism.

In some aspects, the present disclosure provides a nucleic acid comprising an engineered nucleic acid sequence optimized for expression in an organism, wherein the nucleic acid encodes an endonuclease having at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof coupled to a base editor. In some embodiments, the endonuclease comprises a sequence encoding one or more nuclear localization sequences (NLSs) proximal to an N- or C-terminus of said endonuclease. In some embodiments, the organism is prokaryotic, bacterial, eukaryotic, fungal, plant, mammalian, rodent, or human.

In some aspects, the present disclosure provides a vector comprising a nucleic acid sequence encoding a class 2, type II Cas endonuclease coupled to a base editor, wherein said endonuclease is derived from an uncultivated microorganism. In some embodiments, the vector comprises the nucleic acid described herein. In some embodiments, the vector further comprises a nucleic acid encoding an engineered guide ribonucleic acid structure configured to form a complex with the endonuclease comprising: a guide ribonucleic acid sequence configured to hybridize to a target deoxyribonucleic acid sequence; and a tracr ribonucleic acid sequence configured to binding to the endonuclease. In some embodiments, the vector is a plasmid, a minicircle, a CELiD, an adeno-associated virus (AAV) derived virion, or a lentivirus. In some aspects, the present disclosure provides a cell comprising the vector described herein. In some aspects, the present disclosure provides a method of manufacturing an endonuclease, comprising cultivating the cell described herein.

In some aspects, the present disclosure provides a method for modifying a double-stranded deoxyribonucleic acid polynucleotide comprising contacting the double-stranded deoxyribonucleic acid polynucleotide with a complex comprising: an endonuclease comprising a RuvC domain and an HINH domain, wherein the endonuclease is derived from an uncultivated microorganism, wherein the endonuclease is a class 2, type II Cas endonuclease, and wherein the RuvC domain lacks nuclease activity; a base editor coupled to the endonuclease; and an engineered guide ribonucleic acid structure configured to bind to the endonuclease and the double-stranded deoxyribonucleic acid polynucleotide; wherein the double-stranded deoxyribonucleic acid polynucleotide comprises a protospacer adjacent motif (PAM).

In some embodiments, the endonuclease comprising a RuvC domain and an HNH domain is covalently coupled directly to the base editor or covalently coupled to the base editor through a linker. In some embodiments, the endonuclease comprising a RuvC domain and an HNH domain comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof.

In some aspects, the present disclosure provides a method for modifying a double-stranded deoxyribonucleic acid polynucleotide, comprising contacting the double-stranded deoxyribonucleic acid polynucleotide with a complex comprising: a class 2, type II Cas endonuclease, a base editor coupled to the endonuclease, and an engineered guide ribonucleic acid structure configured to bind to the endonuclease and the double-stranded deoxyribonucleic acid polynucleotide; wherein the double-stranded deoxyribonucleic acid polynucleotide comprises a protospacer adjacent motif (PAM); and wherein the PAM comprises a sequence selected from the group consisting of SEQ ID NOs: 360-368 or 598 or a variant thereof.

In some embodiments, the class 2, type II Cas endonuclease is covalently coupled to the base editor or coupled to the base editor through a linker. In some embodiments, the base editor comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from SEQ ID NOs: 1-51, 57-66, 385-443, 444-475, or 594-595 or a variant thereof. In some embodiments, the base editor comprises an adenine deaminase; the double-stranded deoxyribonucleic acid polynucleotide comprises an adenine; and modifying the double-stranded deoxyribonucleic acid polypeptide comprises converting the adenine to guanine. In some embodiments, the adenine deaminase comprises a sequence with at least 95% identity to SEQ ID NO: 57 or a variant thereof.

In some embodiments, the base editor comprises a cytosine deaminase; the double-stranded deoxyribonucleic acid polynucleotide comprises a cytosine; and modifying the double-stranded deoxyribonucleic acid polypeptide comprises converting the cytosine to uracil. In some embodiments, the cytosine deaminase comprises a sequence with at least 95% identity to SEQ ID NO: 58 or a variant thereof. In some embodiments, the cytosine deaminase comprises a sequence with at least 95% identity to any one of SEQ ID NOs: 59-66 or a variant thereof.

In some embodiments, the complex further comprises a uracil DNA glycosylase inhibitor. In some embodiments, the uracil DNA glycosylase inhibitor comprises a sequence with at least 70%, 80%, 90% or 95% identity to any one of SEQ ID NOs: 52-56 or SEQ ID NO: 67 or a variant thereof. In some embodiments, the double-stranded deoxyribonucleic acid polynucleotide comprises a first strand comprising a sequence complementary to a sequence of the engineered guide ribonucleic acid structure and a second strand comprising said PAM. In some embodiments, the PAM is directly adjacent to the 3' end of the sequence complementary to the sequence of the engineered guide ribonucleic acid structure.

In some embodiments, the class 2, type II Cas endonuclease is not a Cas9 endonuclease, a Cas 14 endonuclease, a Cas 12a endonuclease, a Cas12b endonuclease, a Cas 12c endonuclease, a Cas 12d endonuclease, a Cas12e endonuclease, a Cas13a endonuclease, a Cas13b endonuclease, a Cas 13c endonuclease, or a Cas 13d endonuclease. In some embodiments, the class 2, type II Cas endonuclease is derived from an uncultivated microorganism. In some embodiments, the double-stranded deoxyribonucleic acid polynucleotide is a eukaryotic, plant, fungal, mammalian, rodent, or human double-stranded deoxyribonucleic acid polynucleotide.

In some aspects, the present disclosure provides a method of modifying a target nucleic acid locus, said method comprising delivering to said target nucleic acid locus the engineered nucleic acid editing system described herein, wherein the endonuclease is configured to form a complex with the engineered guide ribonucleic acid structure, and wherein the complex is configured such that upon binding of the complex to the target nucleic acid locus, the complex modifies a nucleotide of the target nucleic locus.

In some embodiments, the engineered nucleic acid editing system comprises an adenine deaminase, the nucleotide is an adenine, and modifying the target nucleic acid locus comprises converting the adenine to a guanine. In some embodiments, the engineered nucleic acid editing system comprises a cytidine deaminase and a uracil DNA glycosylase inhibitor, the nucleotide is a cytosine and modifying the target nucleic acid locus comprises converting the adenine to a uracil. In some embodiments, the target nucleic acid locus comprises genomic DNA, viral DNA, or bacterial DNA. In some embodiments, the target nucleic acid locus is in vitro. In some embodiments, the target nucleic acid locus is within a cell. In some embodiments, the cell is a prokaryotic cell, a bacterial cell, a eukaryotic cell, a fungal cell, a plant cell, an animal cell, a mammalian cell, a rodent cell, a primate cell, or a human cell. In some embodiments, the cell is within an animal.

In some embodiments, the cell is within a cochlea. In some embodiments, the cell is within an embryo. In some embodiments, the embryo is a two-cell embryo. In some embodiments, the embryo is a mouse embryo. In some embodiments, delivering the engineered nucleic acid editing system to the target nucleic acid locus comprises delivering the nucleic acid described herein or the vector described herein. In some embodiments, delivering the engineered nucleic acid editing system to the target nucleic acid locus comprises delivering a nucleic acid comprising an open reading frame encoding the endonuclease.

In some embodiments, the nucleic acid comprises a promoter to which the open reading frame encoding the endonuclease is operably linked. In some embodiments, delivering the engineered nucleic acid editing system to said target nucleic acid locus comprises delivering a capped mRNA containing the open reading frame encoding the endonuclease. In some embodiments, delivering the engineered nucleic acid editing system to the target nucleic acid locus comprises delivering a translated polypeptide. In some embodiments, delivering the engineered nucleic acid editing system to the target nucleic acid locus comprises delivering a deoxyribonucleic acid (DNA) encoding the engineered guide ribonucleic acid structure operably linked to a ribonucleic acid (RNA) pol III promoter.

In some aspects, the present disclosure provides an engineered nucleic acid editing polypeptide, comprising: an endonuclease comprising a RuvC domain and an HNH domain, wherein the endonuclease is derived from an uncultivated microorganism, wherein the endonuclease is a class 2, type II Cas endonuclease, and wherein the endonuclease is configured to be deficient in nuclease activity. In some embodiments, the endonuclease comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof.

In some aspects, the present disclosure provides an engineered nucleic acid editing polypeptide, comprising: an endonuclease having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof, wherein the endonuclease is configured to be deficient in nuclease activity; and a base editor coupled to the endonuclease.

In some aspects, the present disclosure provides an engineered nucleic acid editing polypeptide, comprising: an endonuclease configured to bind to a protospacer adjacent motif (PAM) sequence comprising any one of SEQ ID NOs: 360-368 or 598, wherein the endonuclease is a class 2, type II Cas endonuclease, and wherein the endonuclease is configured to be deficient in nuclease activity; and a base editor coupled to the endonuclease.

In some embodiments, the endonuclease is derived from an uncultivated microorganism. In some embodiments, the endonuclease has less than 80% identity to a Cas9 endonuclease. In some embodiments, the endonuclease further comprises an HNH domain. In some embodiments, the ribonucleic acid sequence configured to bind the endonuclease comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to about 60 to 90 consecutive nucleotides selected from any one of SEQ ID NOs: 88-96 or 488-489 or a variant thereof. In some embodiments, the ribonucleic acid sequence configured to bind the endonuclease comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to non-degenerate nucleotides of any one of SEQ ID NOs: 88-96 or 488-489 or a variant thereof. In some embodiments, the base editor comprises a sequence with at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 70-78 or 597 or a variant thereof. In some embodiments, the base editor is an adenine deaminase. In some embodiments, the adenosine deaminase comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 50-51, 57, 385-443, 448-475, or 595 or a variant thereof. In some embodiments, the base editor is a cytosine deaminase. In some embodiments, the cytosine deaminase comprises a sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any one of SEQ ID NOs: 1-49, 444-447, 594, or 58-66 or a variant thereof.

Systems of the present disclosure may be used for various applications, such as, for example, nucleic acid editing (e.g., gene editing), binding to a nucleic acid molecule (e.g., sequence-specific binding). Such systems may be used, for example, for addressing (e.g., removing or replacing) a genetically inherited mutation that may cause a disease in a subject, inactivating a gene in order to ascertain its function in a cell, as a diagnostic tool to detect disease-causing genetic elements (e.g. via cleavage of reverse-transcribed viral RNA or an amplified DNA sequence encoding a disease-causing mutation), as deactivated enzymes in combination with a probe to target and detect a specific nucleotide sequence (e.g. sequence encoding antibiotic resistance int bacteria), to render viruses inactive or incapable of infecting host cells by targeting viral genomes, to add genes or amend metabolic pathways to engineer organisms to produce valuable small molecules, macromolecules, or secondary metabolites, to establish a gene drive element for evolutionary selection, to detect cell perturbations by foreign small molecules and nucleotides as a biosensor.

TABLE 2

Sequence Listing of Protein and Nucleic Acid Sequences Referred to Herein

| Category | SEQ ID NO: | Description | Type | Organism | Other Information | Sequence |
|---|---|---|---|---|---|---|
| Cytosine Deaminase | 594 | CMP/dCMP-type deaminase domain-containing protein (uniprot | protein | Cebus imitator | unknown | MEASPASRPRPLMGPR TFTENFTNNPEVFGRH QTYLCYEVKCQGPDG TRDLMTEQRDFLCNQ ARNLLSGFDGRHAER CFLDRVPSWRLDPAQ TYRVTCFISWSPCFSC |

TABLE 2-continued

Sequence Listing of Protein and Nucleic Acid Sequences Referred to Herein

| Category | SEQ ID NO: | Description | Type | Organism | Other Information | Sequence |
|---|---|---|---|---|---|---|
| | | accession A0A2K5RDN7) | | | | AREVAEFLQENPHVN LRIFAARIYDCRPRYEE GLQMLQNAGAQVSIM TSEEFRHCWDTFVDH QGHPFQPWEGLDEHS QALSRRLQAILQGNR WMILSL |
| Adenosine Deaminase | 595 | TadA* (ABE8.17m) | protein | unknown | unknown | MSEVEFSHEYWMRHA LTLAKRARDEREVPV GAVLVLNNRVIGEGW NRAIGLHDPTAHAEIM ALRQGGLVMQNYRLI DATLYSTFEPCVMCA GAMIHSRIGRVVFGVR NAKTGAAGSLMDVLH YPGMNHR VEITEGILA DECAALLCYFFRMPR RVFNAQKKAQSSTD |
| MG34 active effectors | 596 | MG34-1 effector | protein | unknown | uncultivated organism | MERELVLGIDYGGKY TGLAVVDRRHNQVLY ANRLKMRDDVAGILK DRRKQRGIRRTAQTK KKRLRELKNYLKSIGY NESTATFETVYSLAHK RGYDYADMPEEKTSE EIEAMDVEERKQWEK EKQEWEETKRNSRHR KEVVKDVHKAMIEGR ATEEQIKRVERIFNKQ YRPKRFNNRILTKCKV EDCGVNTPLRKNVRD LLIENIVRFFPIEQSEKD NLKDAVLDKNRREEV KSFFRKHKTDEHIRKQ VYDIADNKLSGRTVFC KEHILEHTEHSKEERK VFRLAPSLKTKIENVL AVIKDEILPKFTVNKV VMESNNFDIAAKTQG KKRLAKEEYGKGPRE GKETRKEALLRETDG RCIYCGKSIDISNAHD DHIFPRKAGGLNIFAN LVACCAVCNENKKGR TPLESGISPKPEIIAFMK NDLKKKILEDARNINT VDFNKYMSHASIGWR YMRDRLRESAGNKKL PIERQSGIYTAYFRRW WGFKKERGNTLHHAL DAVILASRKGYSDDGL VDMTLKPKYNKGGEF DPEKHLPEPIEFKMDK GSRGSALHDRNPLSYK KGIITRRFMVTEIECGK EDDVISETYREKLKEA FKRFDTKKGKCLTDK EAKEAGFCIKKNELV MSLKCSIKGTGPGQMI RINNNVFKTNVHNVG VDVYLDEKGKKKAYE RKNPRLSKHFIEPPPQP NGRVSFTLKRRDMVT VEGEDAIYRIKKLGTS PTIEAVVGSDGKTRTV SATKLTKANSAE |
| nickase | 597 | MG34-1 (D10A) | protein | unknown | uncultivated organism | MERELVLGIAYGGKY TGLAVVDRRHNQVLY ANRLKMRDDVAGILK DRRKQRGIRRTAQTK KKRLRELKNYLKSIGY |

TABLE 2-continued

Sequence Listing of Protein and Nucleic Acid Sequences Referred to Herein

| Category | SEQ ID NO: | Description | Type | Organism | Other Information | Sequence |
|---|---|---|---|---|---|---|
| | | | | | | NESTATFETVYSLAHK RGYDYADMPEEKTSE EIEAMDVEERKQWEK EKQEWEETKRNSRHR KEVVKDVHKAMIEGR ATEEQIKRVERIFNKQ YRPKRFNNRILTKCKV EDCGVNTPLRKNVRD LLIENIVRFFPIEQSEKD NLKDAVLDKNRREEV KSFFRKHKTDEHIRKQ VYDIADNKLSGRTVFC KEHILEHTEHSKEERK VFRLAPSLKTKIENVL AVIKDEILPKFTVNKV VMESNNFDIAAKTQG KKRLAKEEYGKGPRE GKETRKEALLRETDG RCIYCGKSIDISNAHD DHIFPRKAGGLNIFAN LVACCAVCNENKKGR TPLESGISPKPEIIAFMK NDLKKKILEDARNINT VDFNKYMSHASIGWR YMRDRLRESAGNKKL PIERQSGIYTAYFRRW WGFKKERGNTLHHAL DAVILASRKGYSDDGL VDMTLKPKYNKGGEF DPEKHLPEPIEFKMDK GSRGSALHDRNPLSYK KGIITRRFMVTEIECGK EDDVISETYREKLKEA FKRFDTKKGKCLTDK EAKEAGFCIKKNELV MSLKCSIKGTGPGQMI RINNNVFKTNVHNVG VDVYLDEKGKKKAYE RKNPRLSKHFIEPPPQP NGRVSFTLKRRDMVT VEGEDAIYRIKKLGTS PTIEAVVGSDGKTRTV SATKLTKANSAE |
| PAM | 598 | MG34-1 PAM | nucleotide | unknown | unknown | NGG |

EXAMPLES

Example 1.—Plasmid Construction for Base Editors

To create base editing enzymes that utilize CRISPR functionality to target their base editing, Cas effector enzymes were fused in various configurations to the exemplary deaminases described herein. This process involved a first stage of constructing vectors suitable for generating the fusion enzymes. Two entry plasmid vectors, MGA, and MGC, were first constructed.

Figure 3:
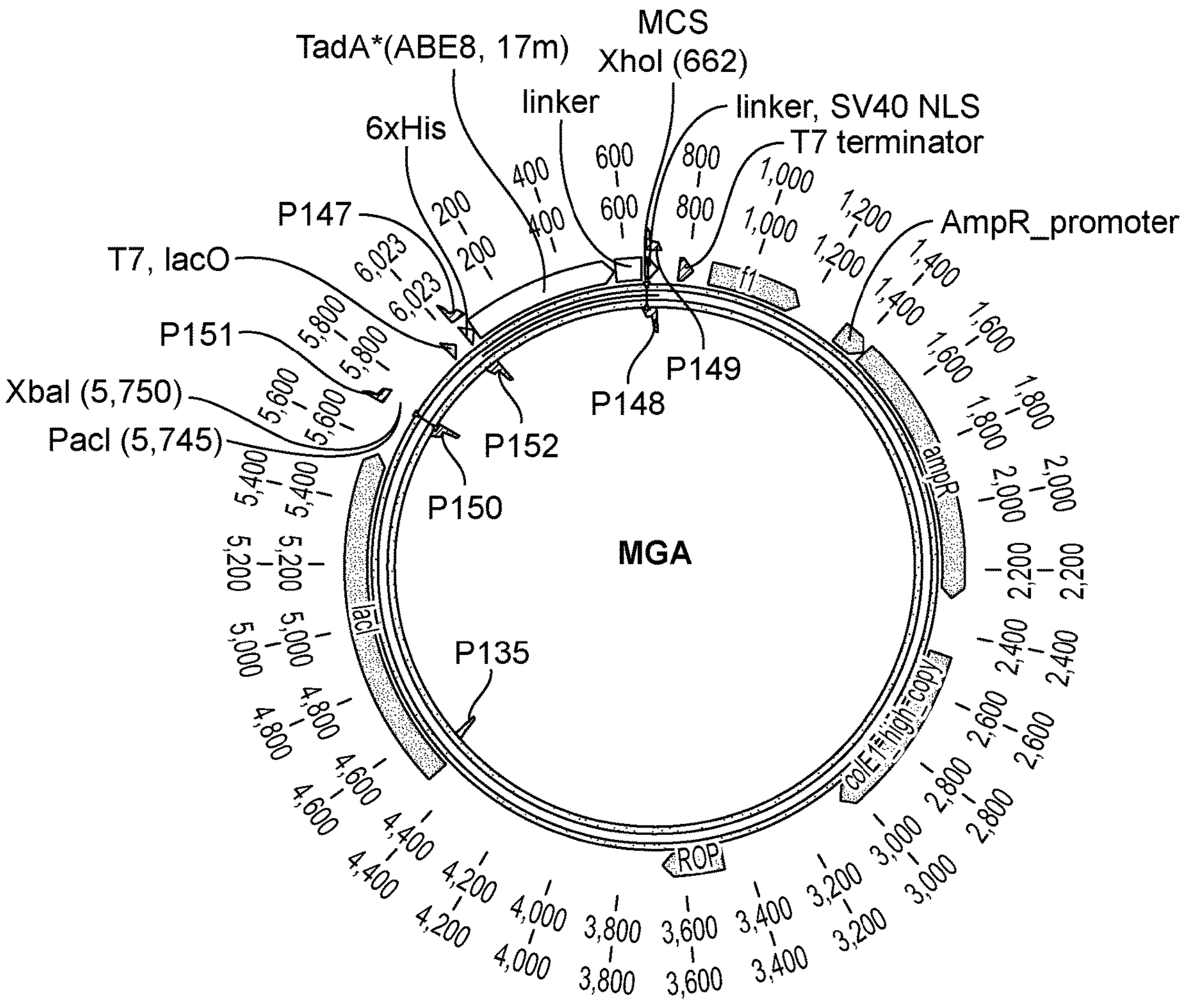
FIG. 3 shows plasmid maps for systems described herein. MGA contains TadA*(from ABE8.17m)-SV40 NLS and MGC contains APOBEC1 (from BE3) linked to a uracil glycosylase inhibitor and an SV40 NLS.
Figure 3:
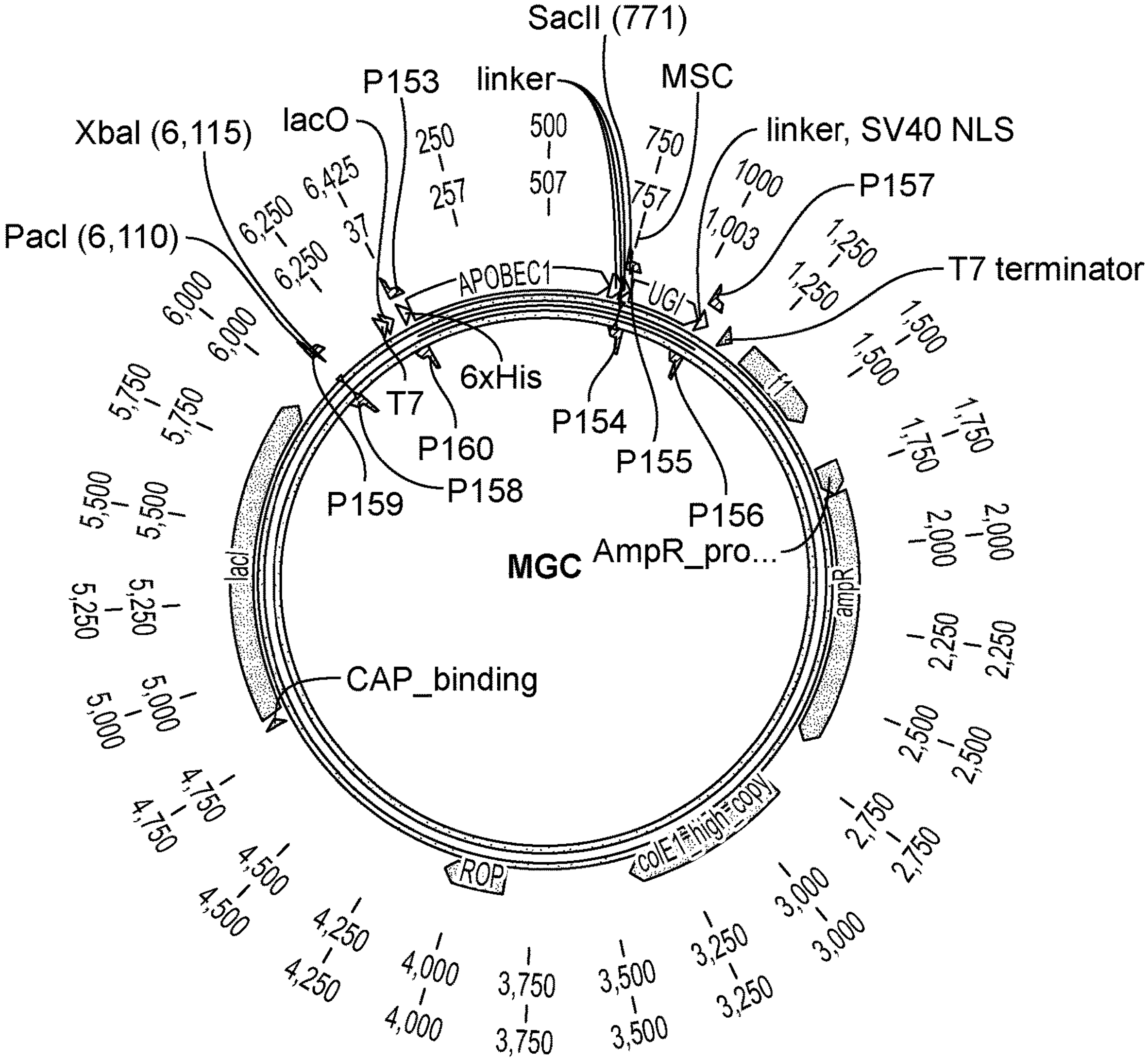

To construct the MGA (Metagenomi adenine base editor) entry plasmid containing T7 promoter-His tag-TadA* (ABE8.17m)-SV40 NLS, three DNA fragments were amplified from pAL6. To construct the MGC (Metagenomi cytosine base editor) entry plasmid containing T7 promoter-His tag-APOBEC1 (BE3)-UGI-SV40 NLS, APOBEC1 and UGI-SV40 NLS were amplified from pAL9 and two pieces of vector backbones were amplified from pAL6 (see FIG. 3).

To introduce mutations into the effectors, source plasmids containing MG1-4, MG1-6, MG3-6, MG3-7, MG3-8, MG4-5, MG14-1, MG15-1, or MG18-1 effector gene sequences were amplified by Q5 DNA polymerase with forward primers incorporating appropriate mutations and reverse primers. The linear DNA fragments were then phosphorylated and ligated. The DNA templates were digested with DpnI using KLD Enzyme Mix (New England Biolabs) per the manufacturer's instructions.

Figure 2:
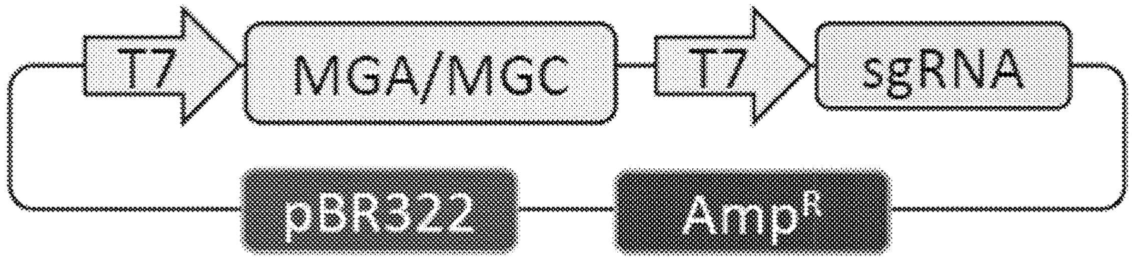
FIG. 2 shows the structure of a base editor plasmid containing a T7 promoter driving expression of the systems described herein.

To generate the pMGA and pMGC expression plasmids, genes were amplified from plasmids carrying mutated effectors and cloned into MGA and MGC entry plasmids via XhoI and SacII sites, respectively. To clone sgRNA expression cassettes comprising T7 promoter-sgRNA-bidirectional terminator into BE expression plasmids, one set of primers (P366 as the forward primer) was used to amplify a T7 promoter-spacer sequence while another set of primers (P367 as the reverse primer) was used to amplify spacer sequence-sgRNA scaffold-bidirectional terminator, in which pTCM plasmids were used as templates (see FIG. 2). The two fragments were assembled into pMGA and pMGC via XbaI sites, resulting pMGA-sgRNA and pMGC-sgRNA, respectively.

TABLE 3

| Summary of constructs made for ABE screening systems described herein | | |
|---|---|---|
| # | Application | Candidate |
| 1 | ABE | MGA1-4-sgRNA1 |
| 2 | | MGA1-4-sgRNA2 |
| 3 | | MGA1-4-sgRNA3 |
| 4 | | MGA1-6-sgRNA1 |
| 5 | | MGA1-6-sgRNA2 |
| 6 | | MGA1-6-sgRNA3 |
| 7 | | MGA3-6-sgRNA1 |
| 8 | | MGA3-6-sgRNA2 |
| 9 | | MGA3-6-sgRNA3 |
| 10 | | MGA3-7-sgRNA1 |
| 11 | | MGA3-7-sgRNA2 |
| 12 | | MGA3-7-sgRNA3 |
| 13 | | MGA3-8-sgRNA1 |
| 14 | | MGA3-8-sgRNA2 |
| 15 | | MGA3-8-sgRNA3 |
| 16 | | MGA14-1-sgRNA1 |
| 17 | | MGA14-1-sgRNA2 |
| 18 | | MGA14-1-sgRNA3 |
| 19 | | MGA15-1-sgRNA1 |
| 20 | | MGA15-1-sgRNA2 |
| 21 | | MGA15-1-sgRNA3 |
| 22 | | MGA18-1-sgRNA1 |
| 23 | | MGA18-1-sgRNA2 |
| 24 | | MGA18-1-sgRNA3 |
| 25 | | ABE8.17m-sgRNA1 |
| 26 | | ABE8.17m-sgRNA2 |
| 27 | | ABE8.17m-sgRNA3 |
| 28 | CBE | MGC1-4-sgRNA1 |
| 29 | | MGC1-4-sgRNA2 |
| 30 | | MGC1-4-sgRNA3 |
| 31 | | MGC1-6-sgRNA1 |
| 32 | | MGC1-6-sgRNA2 |
| 33 | | MGC1-6-sgRNA3 |
| 34 | | MGC3-6-sgRNA1 |
| 35 | | MGC3-6-sgRNA2 |
| 36 | | MGC3-6-sgRNA3 |
| 37 | | MGC3-7-sgRNA1 |
| 38 | | MGC3-7-sgRNA2 |
| 39 | | MGC3-7-sgRNA3 |
| 40 | | MGC3-8-sgRNA1 |
| 41 | | MGC3-8-sgRNA2 |
| 42 | | MGC3-8-sgRNA3 |
| 43 | | MGC4-5-sgRNA1 |
| 44 | | MGC4-5-sgRNA2 |
| 45 | | MGC4-5-sgRNA3 |
| 46 | | MGC14-1-sgRNA1 |
| 47 | | MGC14-1-sgRNA2 |
| 48 | | MGC14-1-sgRNA3 |
| 49 | | MGC15-1-sgRNA1 |
| 50 | | MGC15-1-sgRNA2 |
| 51 | | MGC15-1-sgRNA3 |
| 52 | | MGC18-1-sgRNA1 |
| 53 | | MGC18-1-sgRNA2 |
| 54 | | MGC18-1-sgRNA3 |
| 55 | | BE3-sgRNA1 |
| 56 | | BE3-sgRNA2 |
| 57 | | BE3-sgRNA3 |

Figure 4:
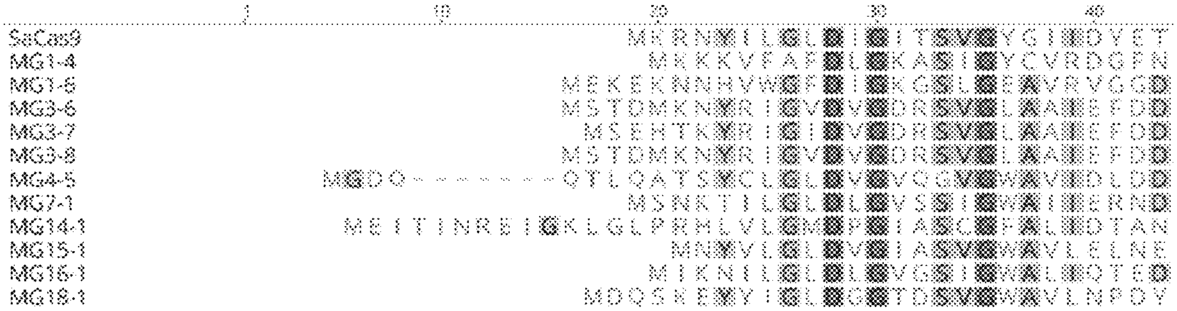
FIG. 4 shows predicted catalytic residues in the RuvCI domains of selected endonucleases described herein which are mutated to disrupt nuclease activity to generate nickase enzymes. SEQ ID NOs: 601-612, respectively, are shown in order of appearance.
Figure 5:
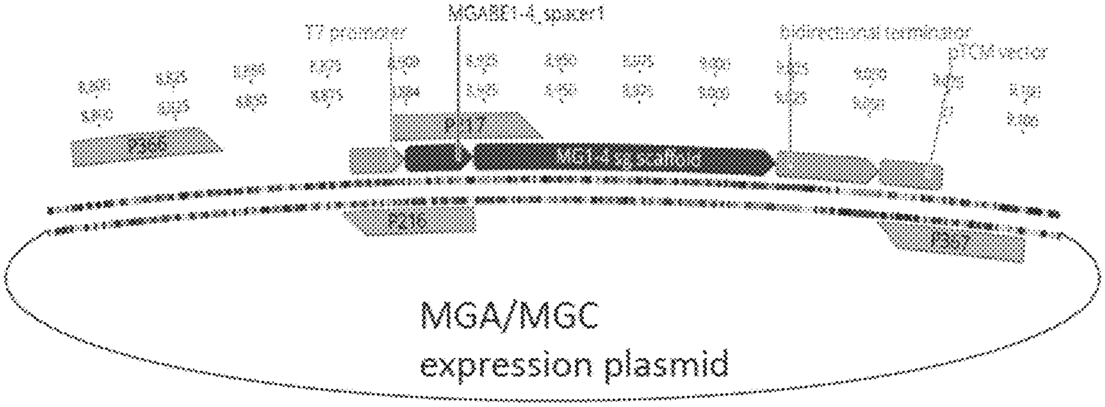
FIG. 5 depicts an exemplary method for cloning a single guide RNA expression cassette into the systems described herein. One fragment comprises a T7 promoter plus spacer. The other fragment comprises spacer plus single guide scaffold sequence plus bidirectional terminator. The fragments are assembled into expression plasmids, resulting in functional constructs that can simultaneously express sgRNAs and base editors.

All amplified DNA fragments were purified by QIAquick Gel Extraction Kit (Qiagen), assembled via NEBuilder HiFi DNA Assembly (New England Biolabs), and the resulting assemblies were propagated via Endura Electrocompetent cells (Lucergen) per the manufacturer's instructions (see FIGS. 4 & 5). The DNA sequences of all cloned genes were confirmed at ELIM BIOPHARM.

TABLE 4

| Conserved catalytic residues parsed out for selected systems described herein | | |
|---|---|---|
| Nickase Candidate | Length | Associated Full-length Protein Sequence |
| nMG1-4 (D9A) | 1025 | SEQ ID NO: 70 |
| nMG1-6 (D13A) | 1059 | SEQ ID NO: 71 |
| nMG3-6 (D13A) | 1134 | SEQ ID NO: 72 |
| nMG3-7 (D12A) | 1131 | SEQ ID NO: 73 |
| nMG3-8 (D13A) | 1132 | SEQ ID NO: 74 |
| nMG4-5 (D17A) | 1055 | SEQ ID NO: 75 |
| nMG14-1 (D23A) | 1003 | SEQ ID NO: 76 |
| nMG15-1 (D8A) | 1082 | SEQ ID NO: 77 |
| nMG18-1 (D12A) | 1348 | SEQ ID NO: 78 |

Example 2.—Protein Expression and Purification

Figure 7:
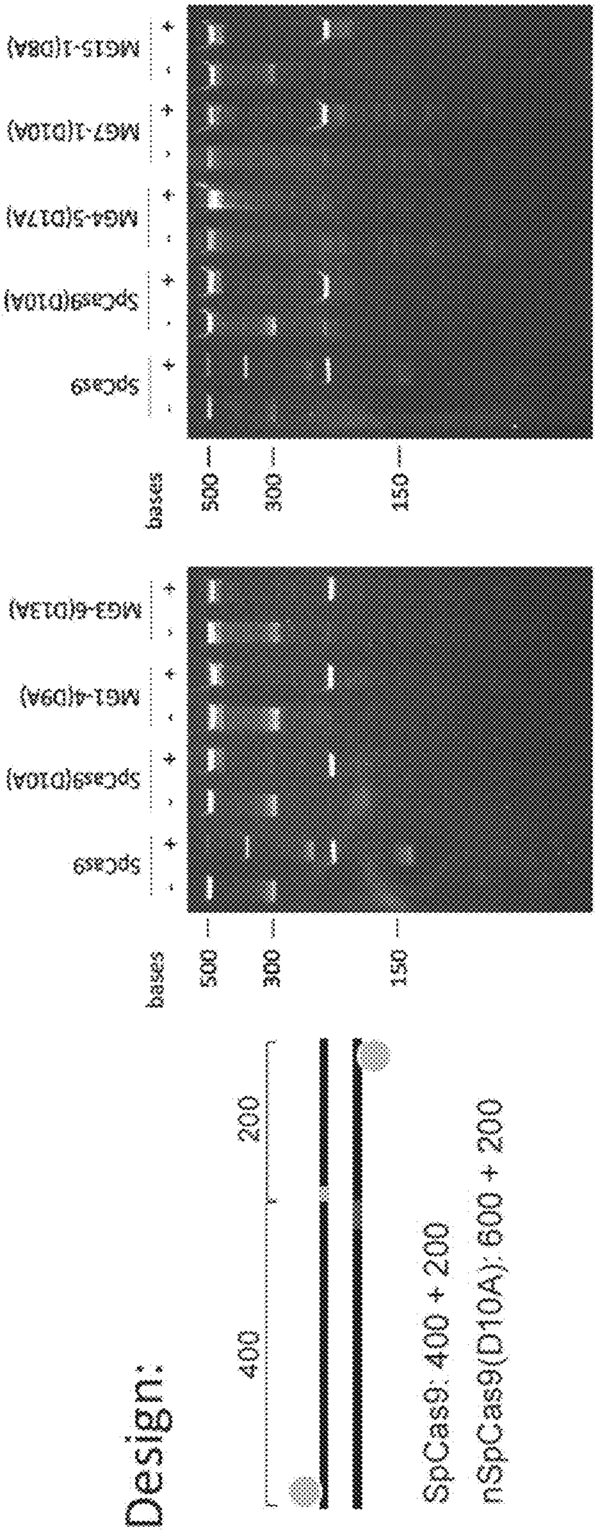
FIG. 7 shows the nickase activity of selected mutated effectors. 600 bp double-stranded DNA fragments labeled with a fluorophore (6-FAM) on both 5' ends were incubated with purified enzymes supplemented with their cognate sgRNAs. The reaction products were resolved on a 10% TBE-Urea denaturing gel. Double-stranded cleavage yields bands of 400 and 200 bases. Nickase activity yields bands of 600 and 200 bases.

The T7 promoter driven mutated effector genes in the pMGA and pMGC plasmids were expressed in *E. coli* BL21 (DE3) cells in Magic Media per manufacturer's instructions (Thermo) by transformation with each of the respective plasmids described in Example 1 above. After a 40 hour incubation at 16° C. the transformed cells were harvested, suspended in lysis buffer (HisTrap equilibration buffer: 20 mM Tris (Sigma T2319-100 ML), 300 mM sodium chloride (VWR VWRVE529-500 ML), 5% glycerol, 10 mM $MgCl_2$, with 10 mM imidazole (Sigma 68268-100 ML-F); pH 7.5) and EDTA-free protease inhibitor (Pierce), and frozen in the −80° C. freezer. The cells were then thawed on ice, sonicated, clarified, and filtered before affinity purification. The protein was applied to Cytiva 5 ml HisTrap FF column on the Akta Avant FPLC per the manufacturer's specifications and the protein was eluted in an isocratic elution of 20 mM Tris (Sigma T2319-100 ML), 300 mM sodium chloride (VWR VWRVE529-500 ML), 5% glycerol, 10 mM $MgCl_2$, with 250 mM imidazole (Sigma 68268-100 ML-F); pH 7.5. Eluted fractions containing the His-tagged effector proteins were concentrated and buffer exchanged into 50 mM Tris-HCl, 300 mM NaCl, 1 mM TCEP, 5% glycerol; pH 7.5. The protein concentration was determined by bicinchoninic acid assay (Thermo) and adjusted after determining the relative purity by SDS PAGE densitometry in Image Lab (Bio-Rad) (see FIG. 7).

Example 3.—In Vitro Nickase Assay 6-carboxyfluorescein (6-FAM) labeled primers P141 and P146 (SEQ ID NOs: 179 and 180) synthesized by IDT were used to amplify linear fragments of LacZ containing targeting sequences of effectors using Q5 DNA polymerase. DNA fragments containing the T7 promoter followed by sgRNAs containing 20-bp or 22-bp spacer sequences were transcribed in vitro using HiScribe T7 High Yield RNA Synthesis Kit (New England Biolabs) per manufacturer's instructions. Synthetic sgRNAs with the sequences corresponding to the named sgRNAs in the sequence listing were purified by Monarch RNA Cleanup Kit (New England Biolabs) according to the users manual and concentrations were measured by Nanodrop.

To determine DNA nickase activity, each of the purified mutated effectors was first supplemented with its cognate sgRNA. Reactions were initiated by adding the linear DNA substrate in a 15 μL reaction mixture containing 10 mM Tris pH 7.5, 10 mM $MgCl_2$, and 100 mM NaCl, 150 nM enzyme, 150 nM RNA, and 15 nM DNA. The reaction was incubated at 37° C. for 2h. Digested DNA was purified using AMPure XP SPRI paramagnetic beads (Beckman Coulter) and eluted with 6 μL TE buffer (10 mM Tris, 1 mM EDTA; pH 8.0). The nicked DNA was resolved on a 10% TBE-Urea denaturing gel (Biorad) and imaged by ChemiDoc (Bio-Rad) (see FIG. 7, which shows that the depicted enzymes display nickase activity by production of bands 600 and 200 bases versus 400 and 200 bases in the case of the wild-type enzyme). The results indicated that all the tested nickase mutants in FIG. 7 displayed their expected nickase activity instead of wild type cleavage activity with the exception of MG4-5 (D17A), which was inconclusive.

Example 4.—Base Editor Introduction into *E. coli*

Plasmids were transformed into Lucergen's electrocompetent BL21 (DE3) cells according to the manufacturer's instructions. After electroporation, cells were recovered with expression recovery media at 37° C. for 1 h and spread on LB plates containing 100 L/mg ampicillin and 0.1 mM IPTG. After overnight growth at 37° C., colonies were picked and lacZ gene was amplified by Q5 DNA polymerase (New England Biolabs) with primers P137 and P360. The resulting PCR products were purified and sequenced by Sanger sequencing at ELIM BIOPHARM. Base edits were determined by examining whether there exists C to T conversion or A to G conversion in the targeted protospacer regions for cytosine base editors or adenine base editors, respectively.

To evaluate editing efficiency in *E. coli*, plasmids were transformed into electrocompetent BL21 (DE3) (Lucergen) and the electroporated cells were recovered with expression recovery media at 37° C. for 1h. 10 μL of recovered cells were then inoculated into 990 μL SOB containing 100 μL/mg ampicillin and 0.1 mM IPTG in a 96-well deep well plate, and grown at 37° C. for 20h. 1 μL cells induced for base editor expression were used for amplification of the lacZ gene in a 20 μL PCR reaction (Q5 DNA polymerase) with primers P137 and P360. The resulting PCR products were purified and sequenced by Sanger sequencing at ELIM BIOPHARM. Quantification of editing efficiency was processed by Edit R as described in Example 12.

TABLE 5

The MG base editors described herein with associated PAM and deaminases

| Candidate | Type | PAM | Deaminase | Linker (Deaminase-Nickase) | Nickase | UGI | Linker (Nickase-UGI) |
|---|---|---|---|---|---|---|---|
| MGA1-4 | II | nRRR SEQ ID NO: 360 | TadA* (ABE8.17m) SEQ ID NO: 595 | SGGSSGGSSGSE TPGTSESATPESS GGSSGGS | nMG1-4 (D9A) SEQ ID NO: 70 | — | |
| MGA3-7 | II | nnRnYAY SEQ ID NO: 363 | TadA* (ABE8.17m) SEQ ID NO: 595 | SGGSSGGSSGSE TPGTSESATPESS GGSSGGS | nMG3-7 (D12A) SEQ ID NO: 73 | — | |
| MGA18-1 | II | nRWART SEQ ID NO: 368 | TadA* (ABE8.17m) SEQ ID NO: 595 | SGGSSGGSSGSE TPGTSESATPESS GGSSGGS | nMG18-1 (D12A) SEQ ID NO: 78 | — | |
| MGC1-6 | II | nnRRAY SEQ ID NO: 361 | APOBEC1 (BE3) SEQ ID NO: 58 | SGSETPGTSESAT PESA | nMG1-6 (D13A) SEQ ID NO: 71 | UGI (BE3) SEQ ID NO: 67 | GSGGS |
| MGC3-7 | II | nnRnYAY SEQ ID NO: 363 | APOBEC1 (BE3) SEQ ID NO: 58 | SGSETPGTSESAT PESA | nMG3-7 (D12A) SEQ ID NO: 73 | UGI (BE3) SEQ ID NO: 67 | GSGGS |
| MGC4-5 | II | nRCCV SEQ ID NO: 365 | APOBEC1 (BE3) SEQ ID NO: 58 | SGSETPGTSESAT PESA | nMG4-5 (D17A) SEQ ID NO: 74 | UGI (BE3) SEQ ID NO: 67 | GSGGS |
| MGC14-1 | II | nRnnGRKA SEQ ID NO: 366 | APOBEC1 (BE3) SEQ ID NO: 58 | SGSETPGTSESAT PESA | nMG14-1 (D23A) SEQ ID NO: 76 | UGI (BE3) SEQ ID NO: 67 | GSGGS |
| MGC15-1 | II | nnnnC SEQ ID NO: 367 | APOBEC1 (BE3) SEQ ID NO: 58 | SGSETPGTSESAT PESA | nMG15-1 (D8A) SEQ ID NO: 77 | UGI (BE3) SEQ ID NO: 67 | GSGGS |
| MGC18-1 | II | nRWART SEQ ID NO 368 | APOBEC1 (BE3) SEQ ID NO: 58 | SGSETPGTSESAT PESA | nMG18-1 (D12A) SEQ ID NO: 78 | UGI (BE3) | GSGGS |

Example 5.—Protein Nucleofection and Amplicon Seq in Mammalian Cells (Prophetic)

Nucleofection is conducted in mammalian cells (e.g. K-562, Neuro-2A or RAW264.7) according to the manufacturer's recommendations using a Lonza 4D nucleofector and the Lonza SF Cell Line 4D-Nucleofector X Kit S (cat. no. V4XC-2032). After formulating the SF nucleofection buffer, 200,000 cells are resuspended in 5 μl of buffer per nucleofection. In the remaining 15 μl of buffer per nucleofection, 20 μmol of chemically modified sgRNA from Synthego is combined with 18 μmol of base editor enzymes (e.g. ABE8e) and incubated for 5 min at room temperature to complex. Cells are added to the 20 μl nucleofection cuvettes, followed by protein solution, and the mixture is triturated to mix. Cells are nucleofected with program CM-130, immediately after which 80 μl of warmed media is added to each well for recovery. After 5 min, 25 μl from each sample is added to 250 μl of fresh media in a 48-well poly-d-lysine plate (Corning). Cells are then treated in the same way as lipofected cells above for genomic DNA extraction after three more days of culture.

Following Illumina barcoding, PCR products are pooled and purified by electrophoresis with a 2% agarose gel using a Monarch DNA Gel Extraction Kit (New England Biolabs), eluting with 30 μl H2O. DNA concentration is quantified with a Qubit dsDNA High Sensitivity Assay Kit (Thermo Fisher Scientific) and sequenced on an Illumina MiSeq instrument (paired-end read, R1: 250-280 cycles, R2: 0 cycles) according to the manufacturer's protocols.

Sequencing reads are demultiplexed using the MiSeq Reporter (Illumina) and FASTQ files are analyzed using CRISPResso2. Dual editing in individual alleles is analyzed by a Python script. Base editing values are representative of n=3 independent biological replicates collected by different researchers, with the mean±s.d. shown. Base editing values are reported as a percentage of the number of reads with adenine mutagenesis over the total aligned reads.

Example 6.—Plasmid Nucleofection and Whole Genome Seq in Mammalian Cells (Prophetic)

All plasmids are assembled by the uracil-specific excision reagent (USER) cloning method. Guide RNA plasmids for SpCas9, SaCas9 and all engineered variants are assembled. Plasmids for mammalian cell transfections are prepared using the ZymoPURE Plasmid Midiprep kit (Zymo Research Corporation). HEK293T cells (ATCC CRL-3216) are cultured in Dulbecco's modified Eagle's medium (Corning) supplemented with 10% fetal bovine serum (ThermoFisher Scientific) and maintained at 37° C. with 5% CO2.

HEK293T cells are seeded on 48-well poly-d-lysine plates (Corning) in the same culture medium. Cells are transfected 12-16 h after plating with 1.5 μl Lipofectamine 2000 (ThermoFisher Scientific) using 750 ng base editor plasmid, 250 ng guide RNA plasmid and 10 ng green fluorescent protein as a transfection control. Cells are cultured for 3 d with media exchanged following the first day, then washed with Å~1 PBS (ThermoFisher Scientific), followed by genomic DNA extraction by addition of 100 μl freshly prepared lysis buffer (10 mM Tris-HCl, pH 7.5, 0.05% SDS, 25 μg ml-1 proteinase K (ThermoFisher Scientific)) directly into each transfected well. The mixture is incubated at 37° C. for 1 h then heat inactivated at 80° C. for 30 min. Genomic DNA lysate is subsequently used immediately for high-throughput sequencing (HTS).

HTS of genomic DNA from HEK293T cells is performed. Following Illumina barcoding, PCR products are pooled and purified by electrophoresis with a 2% agarose gel using a Monarch DNA Gel Extraction Kit (NEB), eluting with 30 μl H2O. DNA concentration is quantified with Qubit dsDNA High Sensitivity Assay Kit (ThermoFisher Scientific) and sequenced on an Illumina MiSeq instrument (paired end read, R1: 250-280 cycles, R2: 0 cycles) according to the manufacturer's protocols.

Example 7.—Determining Editing Window (Prophetic)

To examine the editing window regions, the cytosine showing the highest C-T conversion frequency in a specified sgRNA is normalized to 1, and other cytosines at positions spanning from 30 nt upstream to 10 nt downstream of the PAM sequence (total 43 bp) of the same sgRNA are normalized subsequently. Then normalized C-T conversion frequencies are classified and compared according to their positions for all tested sgRNAs of a specified base editor. A comprehensive editing window (CEW) is defined to span positions with an average C-T conversion efficiency exceeding 0.6 after normalization.

To examine the substrate preference for each cytidine deaminase, C sites are initially classified according to their positions in sgRNA targeting regions and those positions containing at least one C site with ≥0.8 normalized C-T conversion frequency are included in subsequent analysis. Selected C sites are then compared depending on base types upstream or downstream of the edited cytosine (NC or CN). For cytidine deaminases showing efficient C-T conversion at both N-terminus and C-terminus of the endonuclease, the substrate preference is evaluated by integrating respective NT- and CT-CBEs together. For statistical analysis, one-way ANOVA is used and $p<0.05$ is considered as significant Example 8a.—Testing Off-Target Analysis with Whole Genome Sequencing and Transcriptomics in Mammalian Cells (Prophetic)

HEK293T cells are plated on 48-well poly-d-lysine-coated plates 16 to 20 h before lipofection at a density of 3.104 cells per well in DMEM+GlutaMAX medium (Thermo Fisher Scientific) without antibiotics. 750 ng nickase or base editor expression plasmid DNA is combined with 250 ng of sgRNA expression plasmid DNA in 15 μl Opti-MEM+GlutaMAX. This is combined with 10 μl of lipid mixture, comprising 1.5 μl Lipofectamine 2000 and 8.5 μl Opti-MEM+GlutaMAX per well. Cells are harvested 3 d after transfection and either DNA or RNA was harvested. For DNA analysis, cells are washed once in PBS, and then lysed in 100 μl QuickExtract Buffer (Lucigen) according to the manufacturer's instructions. For RNA harvest, the MagMAX mirVana Total RNA Isolation Kit (Thermo Fisher Scientific) is used with the KingFisher Flex.

Genomic DNA from mammalian cells is fragmented and adapter-ligated using the Nextera DNA Flex Library Prep Kit (Illumina) using 96-well plate Nextera indexing primers (Illumina), according to the manufacturer's instructions. Library size and concentration is confirmed by Fragment Analyzer (Agilent) and DNA is sent to Novogene for WGS using an Illumina HiSeq system.

All targeted NGS data is analyzed by performing four general steps: (1) alignment; (2) duplicate marking; (3) variant calling; and (4) background filtration of variants to remove artifacts and germline mutations. The mutation reference and alternate alleles are reported relative to the plus strand of the reference genome.

For whole Transcriptome sequencing, mRNA selection is performed using the NEBNext Poly(A) mRNA Magnetic Isolation Module (New England BioLabs). RNA library preparation is performed using NEBNext Ultra II RNA Library Prep Kit for Illumina (New England BioLabs). Based on the RNA input amount, a cycle number of 12 is used for the PCR enrichment of adapter-ligated DNA. NEBNext Sample Purification Beads (New England BioLabs) is used throughout for all of the size selection performed by this method. NEBNext Multiplex Oligos for Illumina (New England BioLabs) is used for the multiplex indexes in accordance with the PCR recipe outlined in the protocol. Prior to sequencing, samples are quality checked using the High Sensitivity D1000 ScreenTape on the 4200 TapeStation System (Agilent). The libraries are pooled and sequenced using a NovaSeq (Novogene). Targeted RNA sequencing is then performed. Complementary DNA is generated by PCR with reverse transcription (RT-PCR) from the isolated RNA using the SuperScript IV One-Step RT-PCR System with EZDnase (Thermo Fisher Scientific) according to the manufacturer's instructions.

The following program is used: 58° C. for 12 min; 98° C. for 2 min; followed by PCR cycles that varied by amplicon: for CTNNB1 and IP90; 32 cycles of (98° C. for 10 s; 60° C. for 10 sec; 72° C. for 30 sec). Following the combined RT-PCR, amplicons are barcoded and sequenced using an Illumina MiSeq sequencer as described above. The first 125 nucleotides in each amplicon, beginning at the first base after the end of the forward primer in each amplicon, are aligned to a reference sequence and used for analysis of maximum A-to-I frequencies in each amplicon. Off-target DNA sequencing is performed using primers, using a two-step PCR and barcoding method to prepare samples for sequencing using Illumina MiSeq sequencers as above.

Example 8b.—Analysis of Off-Target Edits by Whole Genome Sequencing and Transcriptomics (Prophetic)

Transfected cells prepared as in Example 8a are harvested after 3 days and the genomic DNA isolated using the Agencourt DNAdvance Genomic DNA Isolation Kit (Beckman Coulter) according to the manufacturer's instructions. On-target and off-target genomic regions of interest are amplified by PCR with flanking HTS primer pairs. PCR amplification is carried out with Phusion high-fidelity DNA polymerase (ThermoFisher) according to the manufacturer's instructions using 5 ng of genomic DNA as a template. Cycle numbers are determined separately for each primer pair as to ensure the reaction was stopped in the linear range of amplification (30, 28, 28, 28, 32, and 32 cycles for EMX1, FANCF, HEK293 site 2, HEK293 site 3, HEK293 site 4, and RNF2 primers, respectively). PCR products are purified using RapidTips (Diffinity Genomics). Purified DNA is amplified by PCR with primers containing sequencing adaptors. The products are gel-purified and quantified using the Quant-iT™ PicoGreen dsDNA Assay Kit (ThermoFisher) and KAPA Library Quantification Kit-Illumina (KAPA Biosystems). Samples are sequenced on an Illumina MiSeq as previously described.

Sequencing reads are automatically demultiplexed using MiSeq Reporter (Illumina), and individual FASTQ files are analyzed with a custom Matlab script. Each read is pairwise aligned to the appropriate reference sequence using the Smith-Waterman algorithm. Base calls with a Q-score below 31 are replaced with N's and are thus excluded in calculating nucleotide frequencies. This treatment yields an expected MiSeq base-calling error rate of approximately 1 in 1,000. Aligned sequences in which the read and reference sequence contained no gaps are stored in an alignment table from which base frequencies were tabulated for each locus. Indel frequencies were quantified with a custom Matlab script.

Sequencing reads are scanned for exact matches to two 10-bp sequences that flank both sides of a window in which indels might occur. If no exact matches were located, the read is excluded from analysis. If the length of this indel window exactly matched the reference sequence the read is classified as not containing an indel. If the indel window is two or more bases longer or shorter than the reference sequence, then the sequencing read is classified as an insertion or deletion, respectively.

Example 9.—Mouse Editing Experiments (Prophetic)

It is envisaged that a base editor consisting of a novel DNA targeting nuclease domain fused to a novel deaminase domain can be validated as a therapeutic candidate by testing in appropriate mouse models of disease.

One example of an appropriate model comprises mice that have been engineered to express the human PCSK9 protein, for example, as described by Herbert et al (10.1161/ATVBAHA.110.204040). The PCSK9 protein regulates LDL receptor (LDLR) levels and influences serum cholesterol levels. Mice expressing the human PCSK9 protein exhibit elevated levels of cholesterol and more rapid development of atherosclerosis. PCSK9 is a validated drug target for the reduction of lipid levels in people at increased risk of cardiovascular disease due abnormally high plasma lipid levels (doi.org/10.1038/s41569-018-0107-8). Reducing the levels of PCSK9 via genome editing is expected to permanently lower lipid levels for the life-time of the individual thus providing a life-long reduction in cardiovascular disease risk. One genome editing approach can involve targeting the coding sequence of the PCSK9 gene with the goal of editing a sequence to create a premature stop codon and thus prevent the translation of the PCSK9 mRNA into a functional protein. Targeting a region close to the 5' end of the coding sequence is useful in order to block translation of the majority of the protein. To create a stop codon (TGA, TAA, TAG) with high efficiency and specificity will require targeting a region of the PCSK9 coding sequence wherein the editing window will be placed over an appropriate sequence such that the highest frequency editing event results in a stop codon. Therefore, the availability of multiple base editing systems with a wide range of PAMs or a base editing system with a degenerate PAM is useful to access a larger number of potential target sites in the PCSK9 gene. In addition, additional editing systems wherein the frequency of off-target editing is low (e.g. in the range of 1% or less of the on-target editing events) are also useful to perform gene editing in this context.

The efficiency of base editing required for a therapeutic effect is in the range of 50% or higher in order to achieve a significant reduction in plasma lipid levels. An example of the use of a base editor to create a stop codon in the PCSK9 gene is that of Carreras et al (doi.org/10.1186/s12915-018-0624-2) in which between 10% and 34% of the PCSK9 alleles were edited to create a stop codon. While this level of editing was sufficient to result in a measurable reduction in plasma lipid levels in the mice, a higher editing efficiency will be required for therapeutic use in humans.

To identify a base-editing (BE) system and a guide that are optimal for introducing the stop codons in the PCSK9 gene, a screen may be performed in a mouse liver cell line such as Hepa1-6 cells. In silico screening may first be used to identify guides that target the PCSK9 gene with the various BE systems available. To select among the large number of possible guides an in-silico analysis may be performed to determine which guides have an editing window that encompasses a sequence that when edited may create a stop codon. Preference may then be given to those guides that are closer to the 5' end of the coding sequence. The resulting set of guides and BE proteins may be combined to form a ribonucleoprotein complex (RNP) and may be nucleofected into Hepa1-6 cells. After 72 h the efficiency of editing at the target site may be determined by NGS analysis. Based on these in vitro results the one or more BE/guide combinations that resulted in the highest frequency of stop codon formation may be selected for in vivo testing.

For application in a human therapeutic setting a safe and effective method of delivering the base editing components comprising the base editor and the guide RNA is required. In vivo delivery methods can be divided in to viral or non-viral methods. Among viral vectors the Adeno Associated Virus (AAV) is the virus of choice for clinical use due to its safety record, efficient delivery to multiple tissues and cell types and established manufacturing processes. The large size of base editors (BE) exceeds the packaging capacity of AAV which interferes with packaging in a single Adeno Associated Virus. While approaches that package BE into two AAV using split intein technology have been demonstrated to be successful in mice (doi.org/10.1038/s41551-019-0501-5), the need for 2 viruses complicates development and manufacture. An additional disadvantage of AAV is that while the virus does not have a mechanism for promoting integration into the genome of host cells, and most of the AAV genomes remain episomal, a fraction of the AAV genomes do become integrated at random double strand breaks that occur naturally in cells (Curr Opin Mol Ther. 2009 August; 11 (4): 442-447). This may lead to the persistence of gene sequences expressing the BE for the life-time of the organism. Moreover, AAV genomes persist as episomes inside the nucleus of transduced cells and can be maintained for years which may result in the long-term expression of BE in these cells and thus an increased risk of off-target effects because the risk of an off-target event occurring is a function of the time over which the editing enzyme is active. Adenovirus (Ad) such as Ad5 can efficiently deliver DNA payloads to the liver of mammals and can package up to 45 kb of DNA. However, adenoviruses are known to induce a strong immune response in mammals (dx.doi.org/10.1136/gut.48.5.733), including in patients which can result in serious adverse events including death (doi.org/10.1016/j.ymthe.2020.02.010).

Non-viral delivery vectors (reviewed in doi:10.1038/mt.2012.79) which include lipid nanoparticles and polymeric nanoparticles have several advantages compared to viral delivery vectors including lower immunogenicity and transient expression of the nucleic acid cargo. The transient expression elicited by non-viral delivery vectors is particularly suited to genome editing applications because it is expected to minimize off target events. In addition, non-viral delivery unlike viral vectors has the potential for repeat administration to achieve the therapeutic effect. There is also no theoretical limit to the size of the nucleic acid molecules that can be packaged in non-viral vectors, although in practice the packaging becomes less efficient as the size of the nucleic acid increases and the particles size may increase.

A BE may be delivered in vivo using a non-viral vector such as a lipid nanoparticle (LNP) by encapsulating a synthetic mRNA encoding the BE together with the guide RNA into the LNP. This can be performed using methodologies well known in the art, for example as described by Finn et al (DOI: 10.1016/j.celrep.2018.02.014) or Yin et al (doi:10.1038/nbt.3471). Typically, LNP deliver their cargo primarily to the hepatocytes of the liver, which is also a target organ/cell type when attempting to interfere with the expression of the PCSK9 gene. In order to demonstrate proof of concept for this approach we envisage that a BE comprised of a novel genome editing protein fused to a deaminase domain may be encoded in a synthetic mRNA and packaged in a LNP together with an appropriate guide RNA that targets the selected site in the PCSK9 gene of the mouse. In the case of mice that were engineered to express the human PCSK9 gene the guide may be designed to target only the human PCSK9 gene or both the human and mouse PCSK9 genes. Following injection of these LNP the editing efficiency at the on-target site in the genome of the liver cells may be analyzed by amplicon sequencing or other methods such as tracking of indels by decomposition (doi:10.1093/nar/gku936). The physiologic impact may be determined by measuring lipid levels in the blood of the mice, including total cholesterol and triglyceride levels using standard methods.

Another example of a disease that may be modeled in mice to evaluate a novel BE is Primary Hyperoxaluria type I. Primary Hyperoxaluria type I (PH1) is a rare autosomal recessive disease caused by defects in the AGXT gene that encodes the enzyme alanine-glyoxylate aminotransferase. This results in a defect in glyoxylate metabolism and the accumulation of the toxic metabolite oxalate. One approach to treating this disease is to reduce the expression of the enzyme glycolate oxidase (GO) that produces glyoxylate from glycolate and thereby reducing the amount of substrate (glyoxylate) available for the formation of oxalate. PH1 can be modeled in mice in which both copies of the AGXT gene have been knocked out (agxt−/− mice) resulting in a significant 3-fold increase in oxalate levels in the urine compared to wild type controls. The agxt−/− mice can therefore be used to assess the efficacy of a novel base editor designed to create a stop codon in the coding sequence of the endogenous mouse GO gene. To identify a BE system and a guide that is optimal for introducing stop codons in the GO gene, a screen may be performed in a mouse liver cell line such as Hepa1-6 cells. In silico screening may first be used to identify guides that target the GO gene with the various BE systems available. To select among the large number of possible guides an in-silico analysis may be performed to determine which guides have an editing window that encompasses a sequence that when edited may create a stop codon. Preference may then be given to those guides that are closer to the 5' end of the coding sequence. The resulting set of guides and BE proteins may be combined to form a ribonucleoprotein complex (RNP) and may be nucleofected in to Hepa1-6 cells. After 72 h, the efficiency of editing at the target site may be determined by NGS analysis. Based on these in vitro results the one or more BE/guide combinations that resulted in the highest frequency of stop codon formation may be selected for in vivo testing in mice.

The BE and guide may be delivered to the mice using an AAV virus with a split intein system to express the BE and a 3rd AAV to deliver the guide. Alternatively, an Adenovirus type 5 may be used to deliver the BE and guide in a single virus because of the >40 Kb packaging capacity of Adenovirus. Further, the BE may be delivered as a mRNA together with the guide RNA packaged in an appropriate LNP. After intravenous injection of the LNP into the agxt−/− mice the oxalate levels in the urine may be monitored over time to determine if oxalate levels were reduced which may indicate that the BE was active and had the expected therapeutic effect. To determine if the BE had introduced the stop codons, the appropriate region of the GO gene can be PCR amplified from the genomic DNA extracted from livers of treated and control mice. The resultant PCR product can be sequenced using Next Generation Sequencing to determine the frequency of the sequence changes.

Example 10.—Gene Discovery of New Deaminases

4 Tbp (tera base pairs) of proprietary and public assembled metagenomic sequencing data from diverse environments (soil, sediments, groundwater, thermophilic, human, and non-human microbiomes) were mined to discover novel deaminases. HMM profiles of known deaminases were built and searched against all predicted proteins using HMMER3 (hmmer.org) to identify deaminases from our databases. Predicted and reference (e.g., eukaryotic APOBEC1, bacterial TadA) deaminases were aligned with MAFFT and a phylogenetic tree was inferred using FastTree2. Novel families and subfamilies were defined by identifying clades composed of sequences disclosed herein. Candidates were selected based on the presence of critical catalytic residues indicative of enzymatic function (see e.g. SEQ ID NOs: 1-51, 385-386, 387-443, 444-447, or 488-475).

Example 11.—Plasmid Construction

DNA fragments of genes were synthesized at either Twist Bioscience or Integrated DNA Technologies (IDT). Plasmid DNA was amplified in Endura electrocompetent cells (Lucigen) and isolated by QIAprep Spin Miniprep Kit (Qiagen). Vector backbones were prepared by restriction enzyme digestion of plasmids. Inserts were amplified by Q5 High-Fidelity DNA polymerase (New England Biolabs) using primers ordered either from Elim BIOPHARM or IDT. Both vector backbones and inserts were purified by gel extraction using the Gel DNA Recovery Kit (Zymo Research). One or multiple DNA fragments were assembled into the vectors through NEBuilder HiFi DNA assembly (New England Biolabs) (SEQ ID NOs. 483-487).

Example 12.—Assessment of Base Edit Efficiency in *E. coli* by Sequencing 5 ng extracted DNA prepared as in Example 4 was used as the template and primers (P137 and P360) were used for PCR amplification, and the resulting products were submitted for Sanger sequencing at ELIM BIOPHARM. Primers used for sequencing are shown in Tables 6 and 7 (Seq ID NOs. 523-531).

TABLE 6

Primers used for base editing analysis of lacZ gene in *E. coli*

| Name | SEQ ID NO. | Description | Sequence (5' → 3') |
|---|---|---|---|
| P137 | 523 | Forward primer used to amplify lacZ | CCAGGCTTTACACTTTATGCT |
| P360 | 524 | Reverse primer used to amplify lacZ | CGAACATCCAAAAGTTTGTGTTTTT |
| P137 | 523 | Sanger sequencing primer of MGA1-4_site 1 | CCAGGCTTTACACTTTATGCT |
| P137 | 523 | Sanger sequencing primer of MGA1-4_site 2 | CCAGGCTTTACACTTTATGCT |
| P361 | 528 | Sanger sequencing primer of MGA1-4_site 3 | TGAGCGCATTTTTACGCGC |
| P361 | 528 | Sanger sequencing primer of MGA1-6_site 1 | TGAGCGCATTTTTACGCGC |
| P361 | 528 | Sanger sequencing primer of MGA1-6_site 2 | TGAGCGCATTTTTACGCGC |
| P361 | 528 | Sanger sequencing primer of MGA1-6_site 3 | TGAGCGCATTTTTACGCGC |
| P361 | 528 | Sanger sequencing primer of MGA3-6_site 1 | TGAGCGCATTTTTACGCGC |
| P363 | 529 | Sanger sequencing primer of MGA3-6_site 2 | GAAAACGGCAACCCGTGG |
| P360 | 524 | Sanger sequencing primer of MGA3-6_site 3 | CGAACATCCAAAAGTTTGTGTTTTT |
| P137 | 523 | Sanger sequencing primer of MGA3-7_site 1 | CCAGGCTTTACACTTTATGCT |
| P361 | 528 | Sanger sequencing primer of MGA3-7_site 2 | TGAGCGCATTTTTACGCGC |
| P361 | 528 | Sanger sequencing primer of MGA3-7_site 3 | TGAGCGCATTTTTACGCGC |
| P137 | 523 | Sanger sequencing primer of MGA3-8_site 1 | CCAGGCTTTACACTTTATGCT |

TABLE 6-continued

Primers used for base editing analysis of lacZ gene in *E. coli*

| Name | SEQ ID NO. | Description | Sequence (5' → 3') |
|---|---|---|---|
| P361 | 528 | Sanger sequencing primer of MGA3-8_site 2 | TGAGCGCATTTTTACGCGC |
| P363 | 529 | Sanger sequencing primer of MGA3-8_site 3 | GAAAACGGCAACCCGTGG |
| P139 | 526 | Sanger sequencing primer of MGA4-2_site 1 | GTATGTGGTGGATGAAGCC |
| P363 | 529 | Sanger sequencing primer of MGA4-2_site 2 | GAAAACGGCAACCCGTGG |
| P360 | 524 | Sanger sequencing primer of MGA4-2_site 3 | CGAACATCCAAAAGTTTGTGTTTTT |
| P361 | 528 | Sanger sequencing primer of MGA4-5_site 1 | TGAGCGCATTTTTACGCGC |
| P361 | 528 | Sanger sequencing primer of MGA4-5_site 2 | TGAGCGCATTTTTACGCGC |
| P461 | 530 | Sanger sequencing primer of MGA4-5_Site 3 | GGATTGAAAATGGTCTGCTG |
| P137 | 523 | Sanger sequencing primer of MGA7-1_site 1 | CCAGGCTTTACACTTTATGCT |
| P361 | 528 | Sanger sequencing primer of MGA7-1_site 2 | TGAGCGCATTTTTACGCGC |
| P461 | 530 | Sanger sequencing primer of MGA7-1_site 3 | GGATTGAAAATGGTCTGCTG |
| P139 | 526 | Sanger sequencing primer of MGA14-1_site 1 | GTATGTGGTGGATGAAGCC |
| P363 | 529 | Sanger sequencing primer of MGA14-1_site 2 | GAAAACGGCAACCCGTGG |
| P360 | 524 | Sanger sequencing primer of MGA14-1_site 3 | CGAACATCCAAAAGTTTGTGTTTTT |
| P137 | 523 | Sanger sequencing primer of MGA15-1_site 1 | CCAGGCTTTACACTTTATGCT |
| P361 | 528 | Sanger sequencing primer of MGA15-1_site 2 | TGAGCGCATTTTTACGCGC |
| P140 | 527 | Sanger sequencing primer of MGA15-1_site 3 | TTGTGGAGCGACATCCAG |
| P137 | 523 | Sanger sequencing primer of MGA16-1_site 1 | CCAGGCTTTACACTTTATGCT |
| P361 | 528 | Sanger sequencing primer of MGA16-1_site 2 | TGAGCGCATTTTTACGCGC |
| P361 | 528 | Sanger sequencing primer of MGA16-1_site 3 | TGAGCGCATTTTTACGCGC |
| P361 | 528 | Sanger sequencing primer of MGA18-1_site 1 | TGAGCGCATTTTTACGCGC |
| P363 | 529 | Sanger sequencing primer of MGA18-1_site 2 | GAAAACGGCAACCCGTGG |
| P462 | 531 | Sanger sequencing primer of MGA18-1_site 3 | ACTGCTGACGCCGCTGCG |
| P363 | 529 | Sanger sequencing primer of ABE8.17_site 1 | GAAAACGGCAACCCGTGG |
| P137 | 523 | Sanger sequencing primer of ABE8.17_site 2 | CCAGGCTTTACACTTTATGCT |

TABLE 6-continued

Primers used for base editing analysis of lacZ gene in *E. coli*

| Name | SEQ ID NO. | Description | Sequence (5' → 3') |
|---|---|---|---|
| P139 | 526 | Sanger sequencing primer of ABE8.17_site 3 | GTATGTGGTGGATGAAGCC |
| P137 | 523 | Sanger sequencing primer of MGC1-4_site 1 | CCAGGCTTTACACTTTATGCT |
| P137 | 523 | Sanger sequencing primer of MGC1-4_site 2 | CCAGGCTTTACACTTTATGCT |
| P361 | 528 | Sanger sequencing primer of MGC1-4_site 3 | TGAGCGCATTTTTACGCGC |
| P137 | 523 | Sanger sequencing primer of MGC1-6_site 1 | CCAGGCTTTACACTTTATGCT |
| P137 | 523 | Sanger sequencing primer of MGC1-6_site 2 | CCAGGCTTTACACTTTATGCT |
| P361 | 528 | Sanger sequencing primer of MGC1-6_site 3 | TGAGCGCATTTTTACGCGC |
| P138 | 525 | Sanger sequencing primer of MGC3-6_site 1 | CCGAAAGGCGCGGTGCCG |
| P361 | 528 | Sanger sequencing primer of MGC3-6_site 2 | TGAGCGCATTTTTACGCGC |
| P360 | 524 | Sanger sequencing primer of MGC3-6_site 3 | CGAACATCCAAAAGTTTGTGTTTTT |
| P137 | 523 | Sanger sequencing primer of MGC3-7_site 1 | CCAGGCTTTACACTTTATGCT |
| P137 | 523 | Sanger sequencing primer of MGC3-7_site 2 | CCAGGCTTTACACTTTATGCT |
| P137 | 523 | Sanger sequencing primer of MGC3-7_site 3 | CCAGGCTTTACACTTTATGCT |
| P137 | 523 | Sanger sequencing primer of MGC3-8_site 1 | CCAGGCTTTACACTTTATGCT |
| P361 | 528 | Sanger sequencing primer of MGC3-8_site 2 | TGAGCGCATTTTTACGCGC |
| P361 | 528 | Sanger sequencing primer of MGC3-8_site 3 | TGAGCGCATTTTTACGCGC |
| P361 | 528 | Sanger sequencing primer of MGC4-2_site 1 | TGAGCGCATTTTTACGCGC |
| P139 | 526 | Sanger sequencing primer of MGC4-2_site 2 | GTATGTGGTGGATGAAGCC |
| P363 | 529 | Sanger sequencing primer of MGC4-2_site 3 | GAAAACGGCAACCCGTGG |
| P137 | 523 | Sanger sequencing primer of MGC4-5_site 1 | CCAGGCTTTACACTTTATGCT |
| P361 | 528 | Sanger sequencing primer of MGC4-5_site 2 | TGAGCGCATTTTTACGCGC |
| P139 | 526 | Sanger sequencing primer of MGC4-5_site 3 | GTATGTGGTGGATGAAGCC |
| P361 | 528 | Sanger sequencing primer of MGC7-1_site 1 | TGAGCGCATTTTTACGCGC |
| P461 | 530 | Sanger sequencing primer of MGC7-1_site 2 | GGATTGAAAATGGTCTGCTG |
| P139 | 526 | Sanger sequencing primer of MGC7-1_site 3 | GTATGTGGTGGATGAAGCC |

TABLE 6-continued

Primers used for base editing analysis of lacZ gene in *E. coli*

| Name | SEQ ID NO. | Description | Sequence (5' → 3') |
|---|---|---|---|
| P137 | 523 | Sanger sequencing primer of MGC14-1_site 1 | CCAGGCTTTACACTTTATGCT |
| P139 | 526 | Sanger sequencing primer of MGC14-1_site 2 | GTATGTGGTGGATGAAGCC |
| P139 | 526 | Sanger sequencing primer of MGC14-1_site 3 | GTATGTGGTGGATGAAGCC |
| P361 | 528 | Sanger sequencing primer of MGC15-1_site 1 | TGAGCGCATTTTTACGCGC |
| P461 | 530 | Sanger sequencing primer of MGC15-1_site 2 | GGATTGAAAATGGTCTGCTG |
| P139 | 526 | Sanger sequencing primer of MGC15-1_site 3 | GTATGTGGTGGATGAAGCC |
| P137 | 523 | Sanger sequencing primer of MGC16-1_site 1 | CCAGGCTTTACACTTTATGCT |
| P137 | 523 | Sanger sequencing primer of MGC16-1_site 2 | CCAGGCTTTACACTTTATGCT |
| P361 | 528 | Sanger sequencing primer of MGC16-1_site 3 | TGAGCGCATTTTTACGCGC |
| P361 | 528 | Sanger sequencing primer of MGC18-1_site 1 | TGAGCGCATTTTTACGCGC |
| P139 | 526 | Sanger sequencing primer of MGC18-1_site 2 | GTATGTGGTGGATGAAGCC |
| P363 | 529 | Sanger sequencing primer of MGC18-1_site 3 | GAAAACGGCAACCCGTGG |
| P363 | 529 | Sanger sequencing primer of BE3_site 1 | GAAAACGGCAACCCGTGG |
| P360 | 524 | Sanger sequencing primer of BE3_site 2 | CGAACATCCAAAAGTTTGTGTTTTT |
| P137 | 523 | Sanger sequencing primer of BE3_site 3 | CCAGGCTTTACACTTTATGCT |

TABLE 7

Primers used for base editing analysis of the effect of uracil glycosylase inhibitor (UGI) in *E. coli*

| Name | SEQ ID NO. | Description | Sequence (5' → 3') |
|---|---|---|---|
| P137 | 523 | Forward primer used to amplify lacZ | CCAGGCTTTACACTTTATGCT |
| P360 | 524 | Reverse primer used to amplify lacZ | CGAACATCCAAAAGTTTGTGTTTTT |
| P461 | 530 | Sanger sequencing primer of lacZ site | GGATTGAAAATGGTCTGCTG |

Figure 8A:
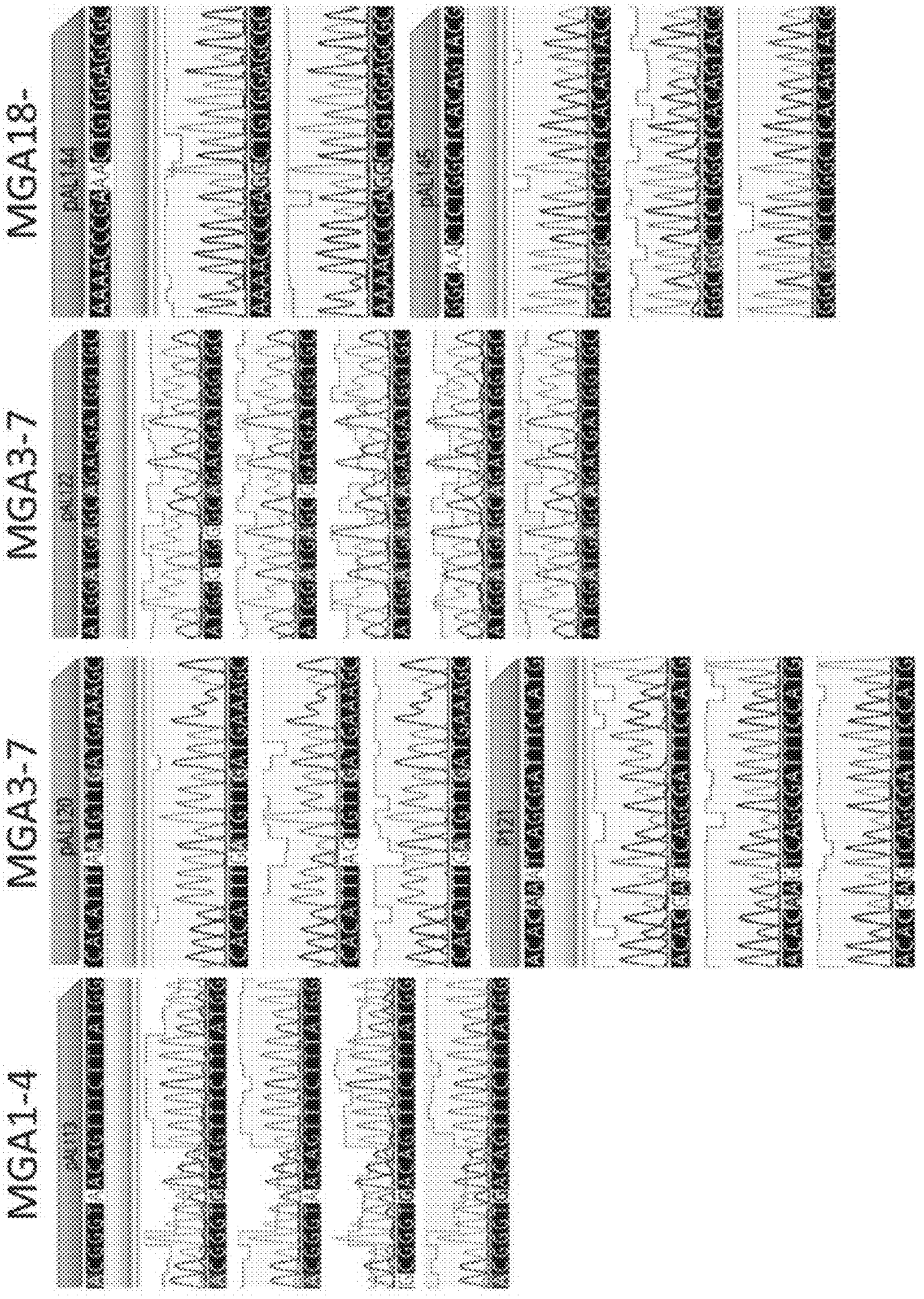
FIGS. 8A, 8B, and 8C show Sanger sequencing results demonstrating base edits by selected systems described herein.
Figure 8B:
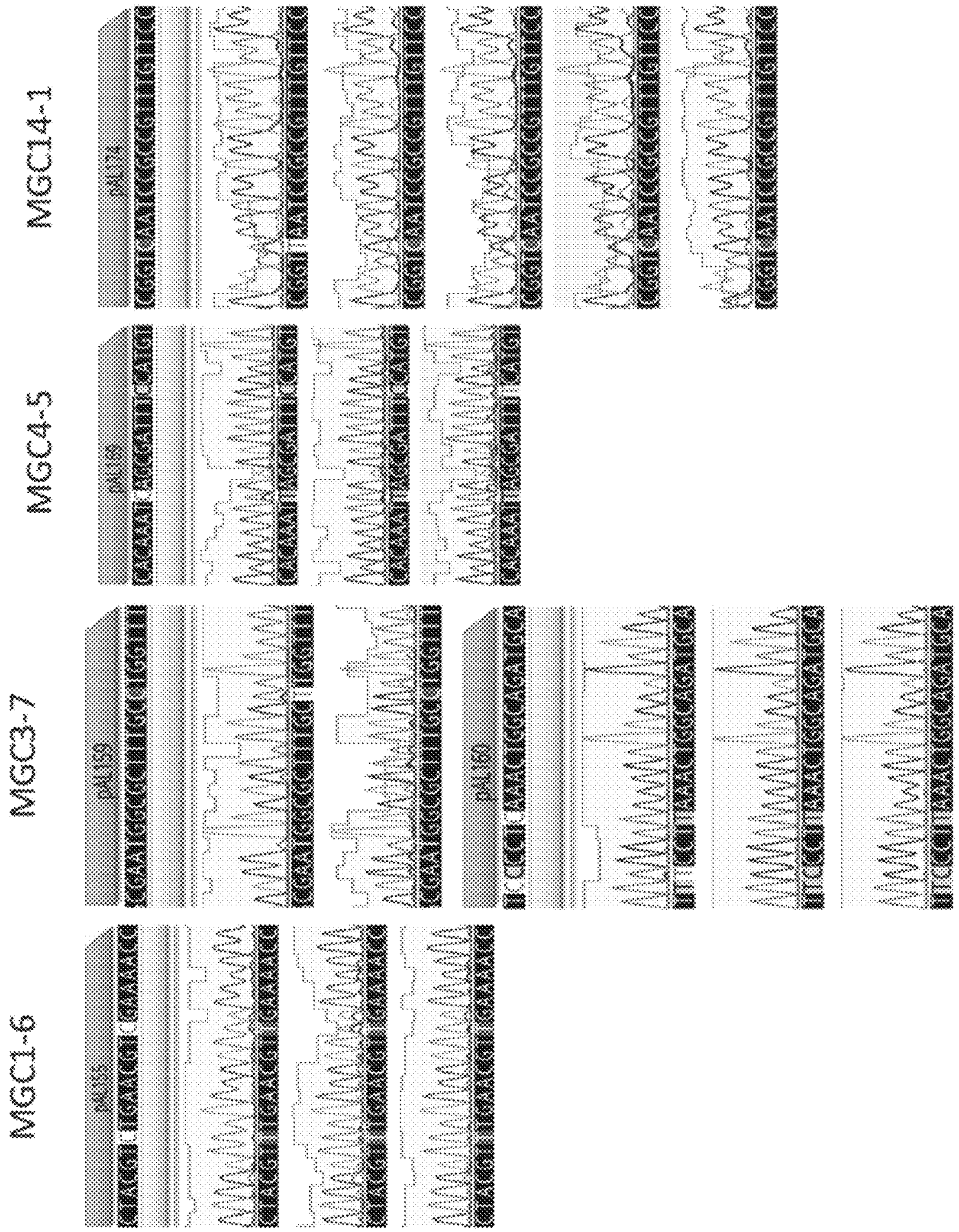
Figure 8C:
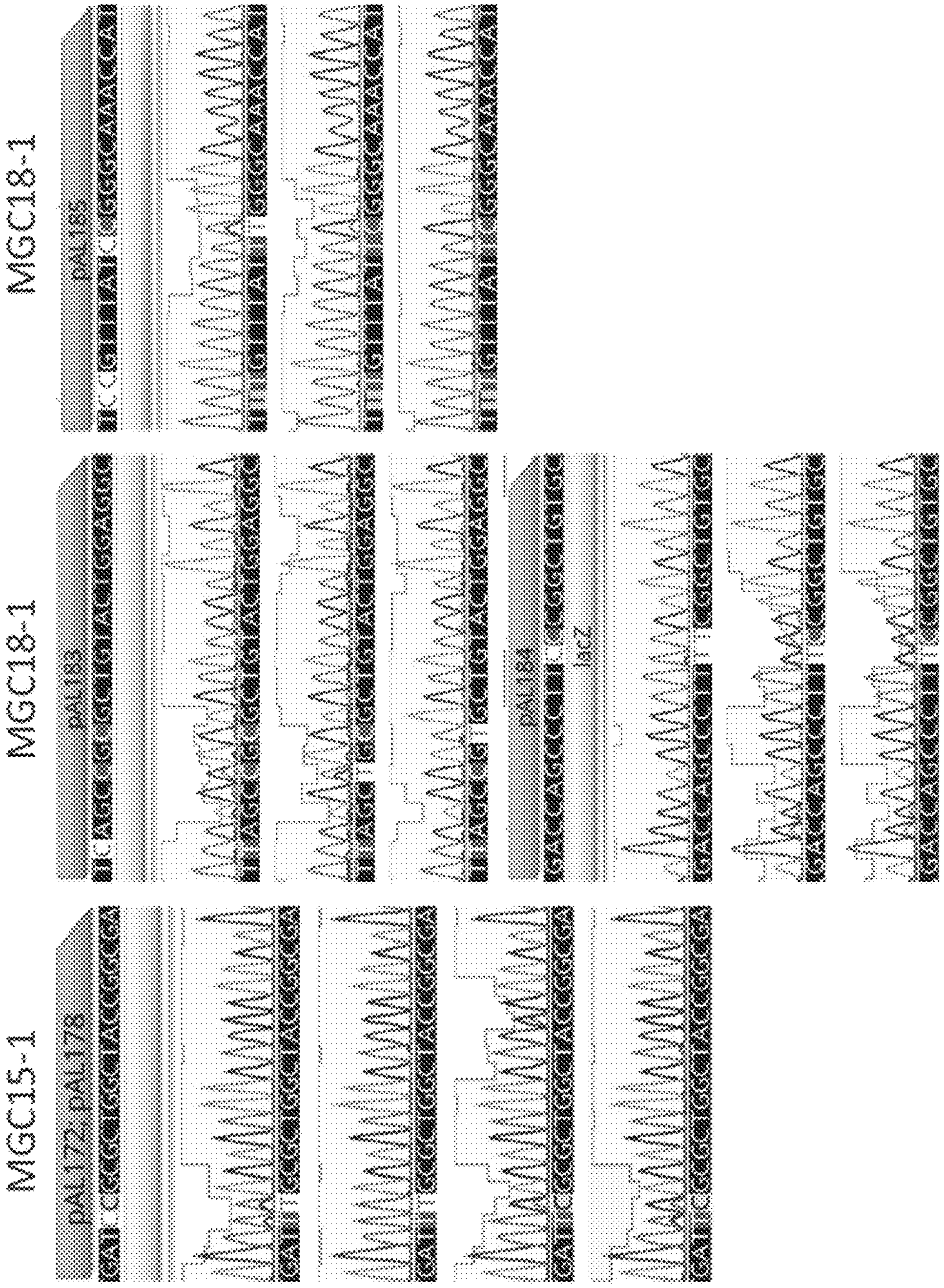
Figure 9:
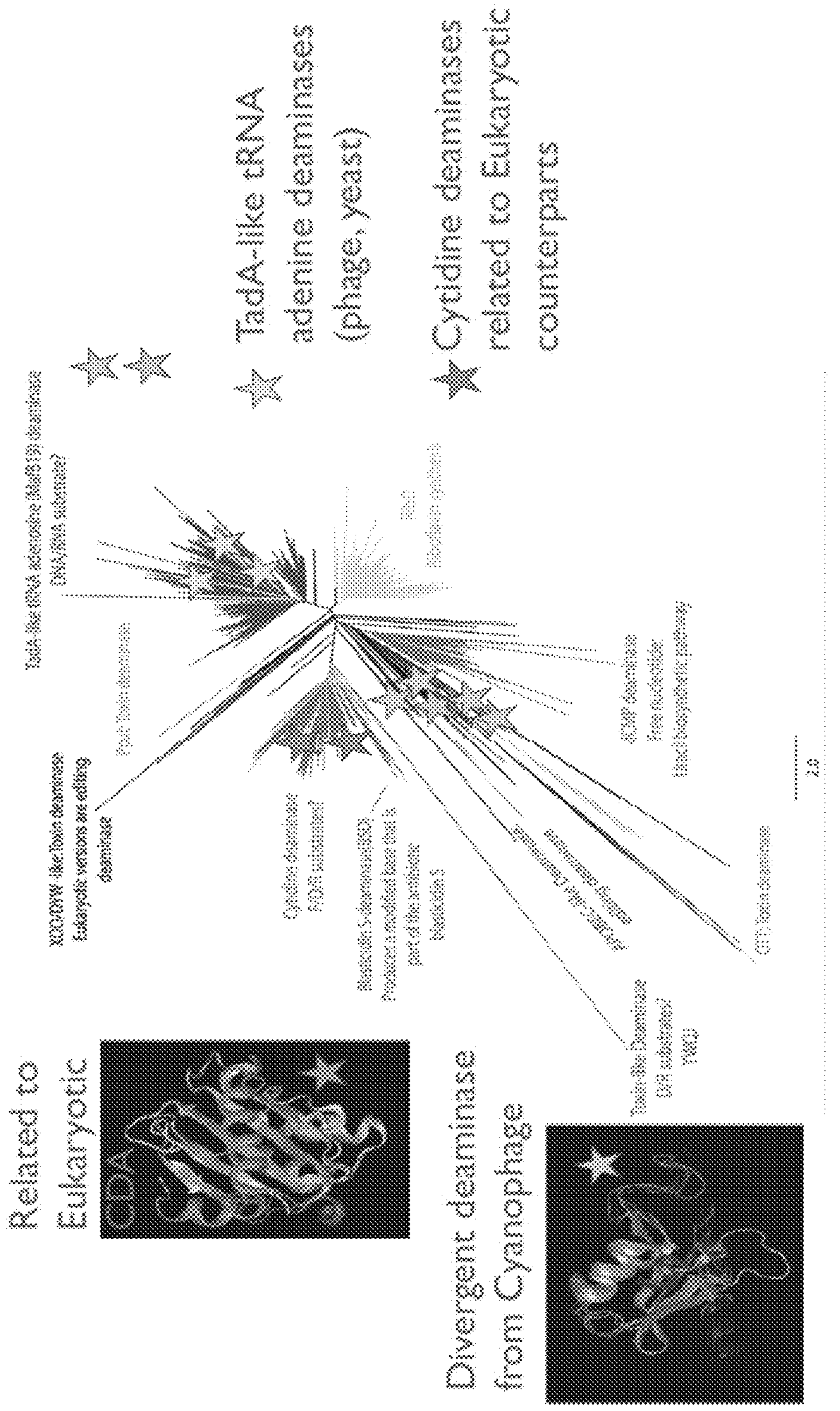
FIG. 9 shows how the systems described herein expand base-editing capabilities with the endonucleases and base editors described herein.

FIG. 8 shows example base edits by enzymes interrogated by this experiment, as assessed by Sanger sequencing.

Figure 10A:
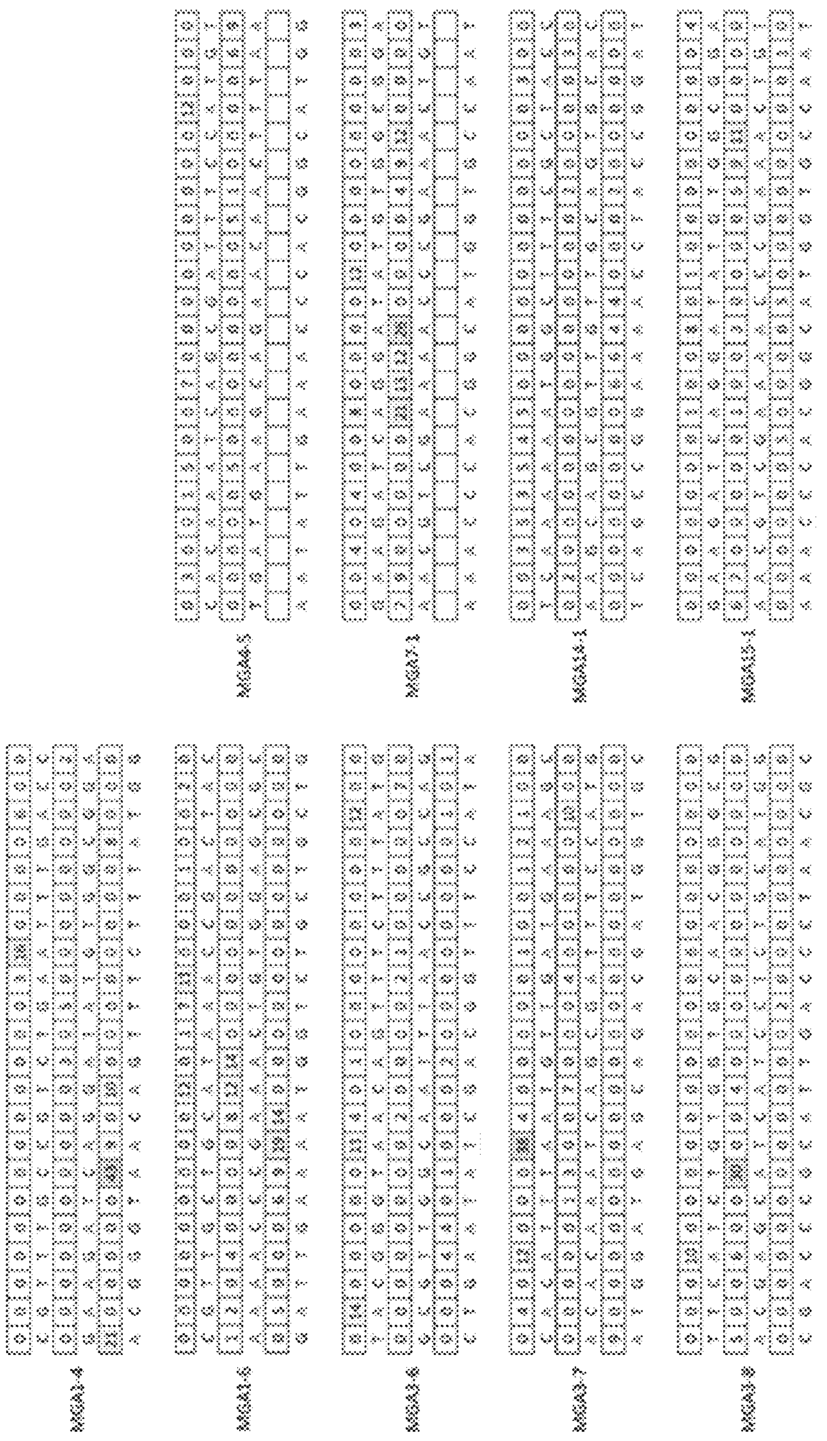
FIGS. 10A and 10B show base editing efficiencies of adenine base editors (ABEs) comprising TadA (ABE8.17m) and MG nickases. TadA is a tRNA adenine deaminase, and TadA (ABE8.17m) is an engineered variant of *E. coli* TadA. 12 MG nickases fused with TadA (ABE8.17m) were constructed and tested in *E. coli*. Three guides were designed to target lacZ. Numbers shown in boxes indicate percentages of A to G conversion quantified by Edit R. ABE8.17m was used as the positive control for the experiment.
Figure 10B:
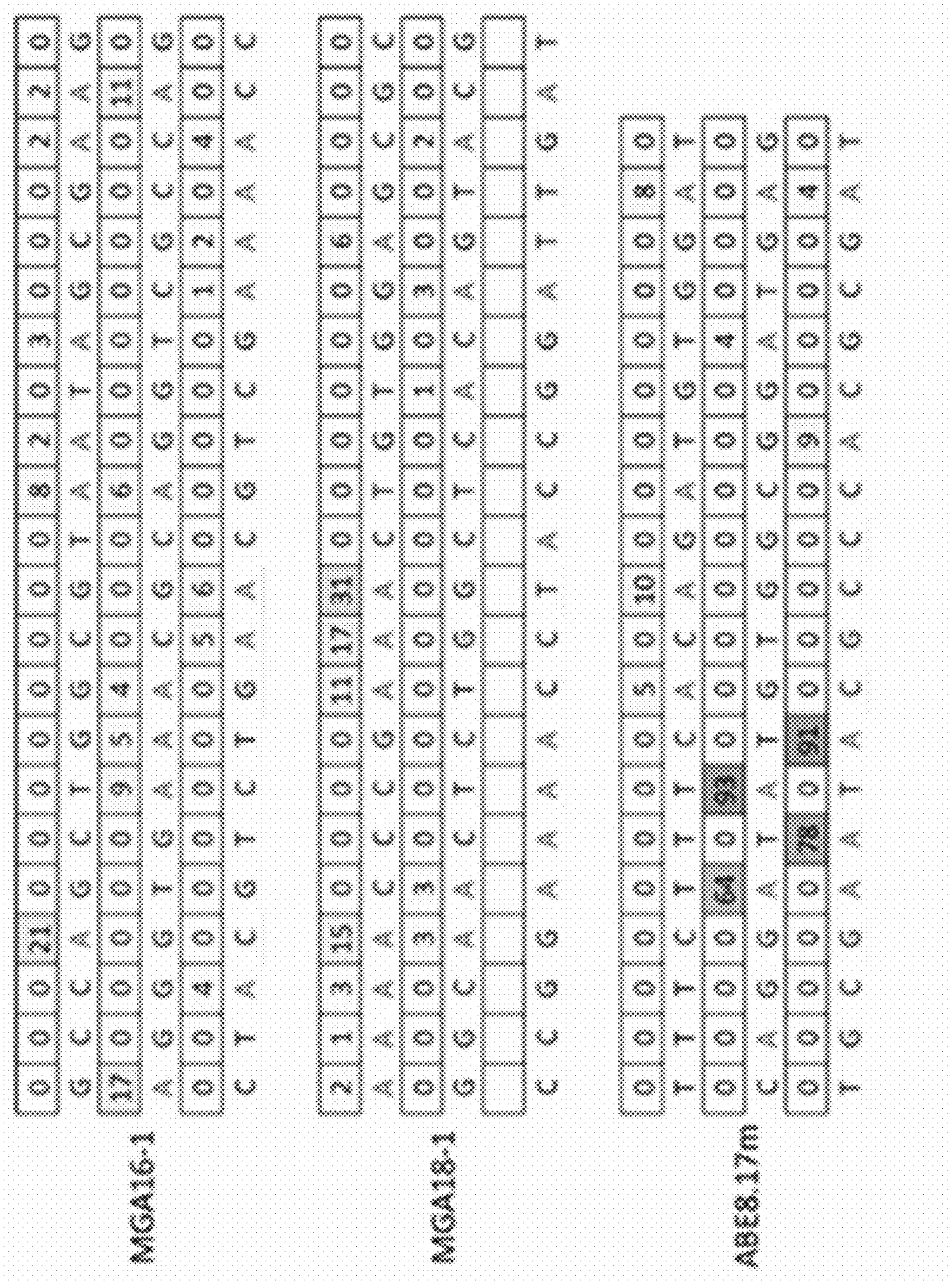

FIG. 10 shows base editing efficiencies of adenine base editors (ABEs) using TadA (ABE8.17m) (SEQ ID NO: 596) and MG nickases according to Table 3. TadA is a tRNA adenine deaminase; TadA (ABE8.17m) is an engineered variant of *E. coli* TadA. Twelve MG nickases fused with TadA (ABE8.17m) were constructed and tested in *E. coli*. Three guides were designed to target lacZ. Numbers shown in boxes indicate percentages of A to G conversion quantified by Edit R at each position. ABE8.17m was used as the positive control for the experiment.

Figure 11A:
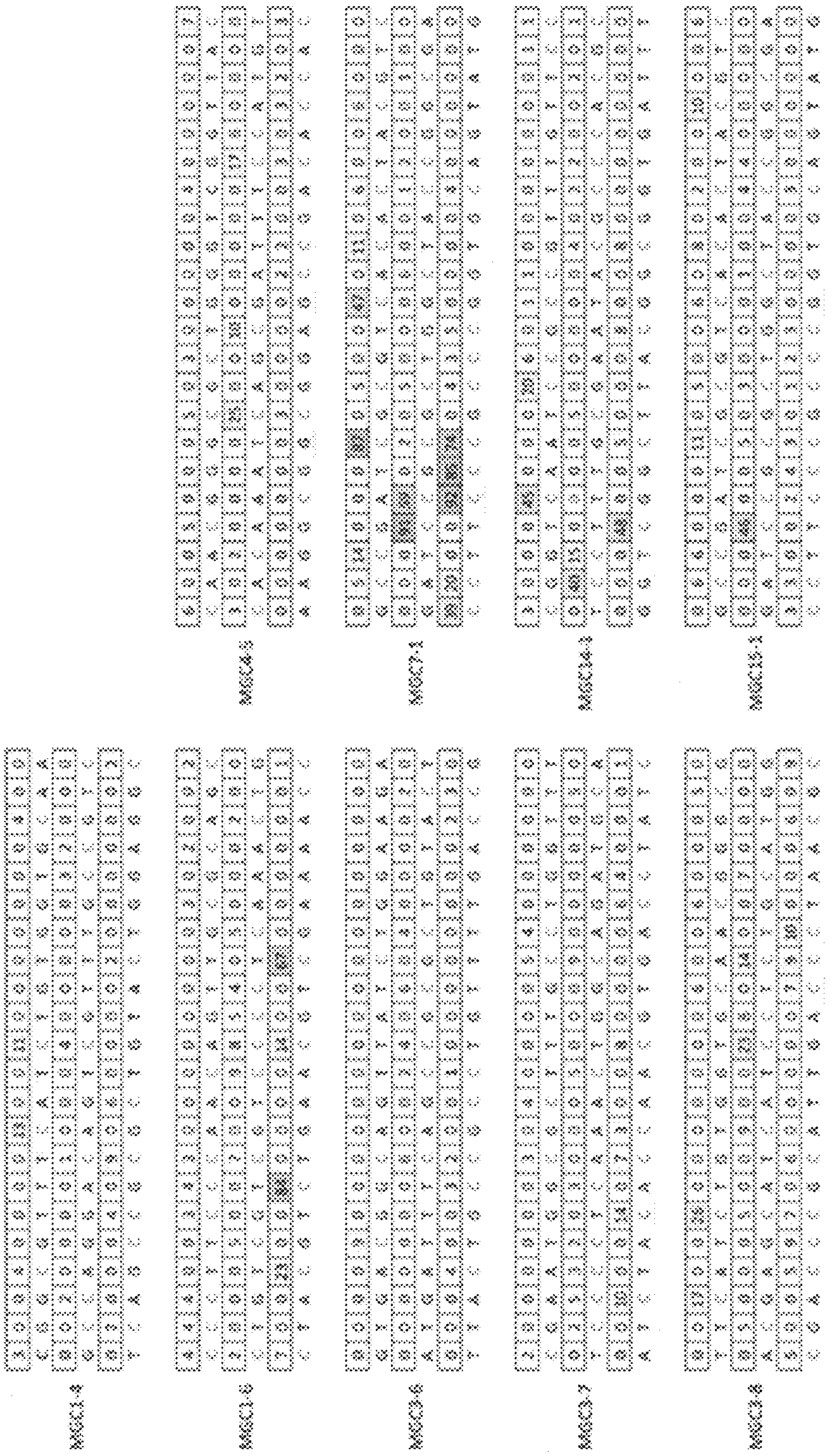
FIGS. 11A and 11B show base editing efficiencies of cytosine base editors (CBEs) comprising rat APOBEC1, MG nickases, and the uracil glycosylase inhibitor of *Bacillus subtilis* bacteriophage (UGI (PBS1)). APOBEC1 is a cytosine deaminase. 12 MG nickases fused to rAPOBEC1 on their N-terminus and UGI on their C-terminus were constructed and tested in *E. coli*. Three guides were designed to target lacZ. The numbers shown in boxes indicate percentages of C to T conversion quantified by Edit R. BE3 was used as the positive control in the experiment.
Figure 11B:

FIG. 11 shows base editing efficiencies of cytosine base editors (CBEs) comprising rat APOBEC1, MG nickases, and uracil glycosylase inhibitor of *Bacillus subtilis* bacteriophage (UGI (PBS1)). APOBEC1 is a cytosine deaminase. 12 MG nickases fused with rAPOBEC1 on N-terminus and UGI on C-terminus were constructed and tested in *E. coli*. Three guides were designed to target lacZ. Numbers shown in boxes indicate percentages of C to T conversion quantified by Edit R. BE3 was used as the positive control in the experiment.

Figure 12:
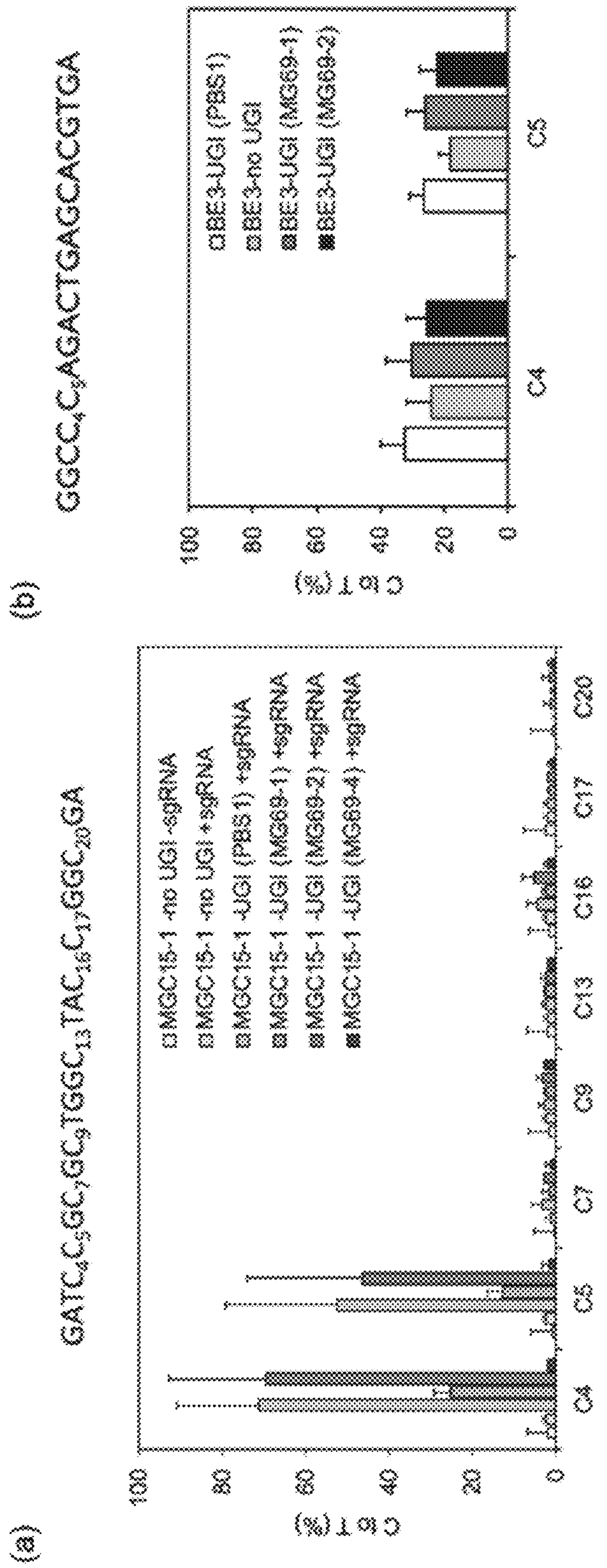
FIG. 12 shows effects of MG uracil glycosylase inhibitors (UGIs) on the base-editing activities of CBEs. Panel (a) depicts a graph showing base-editing activity of MGC15-1 and variants, which comprise an N-terminal APOBEC1, the MG15-1 nickase, and a C-terminal UGI. Three MG UGIs were tested for improvements of cytosine base editing activities in *E. coli*. Panel (b) is a graph showing base editing activity of BE3, which comprises an N-terminal rAPOBEC1, the SpCas9 nickase, and a C-terminal UGI. Two MG UGIs were tested for improvements of cytosine base editing activities in HEK293T cells. Editing efficiencies were quantified by Edit R. SEQ ID NOs: 149 and 495, respectively, are disclosed in order of appearance.

FIG. 12 shows effects of MG uracil glycosylase inhibitors (UGIs) on base editing activity when added to CBEs. (a) MGC15-1 comprises of N-terminal APOBEC1, MG15-1 nickase, and C-terminal UGI. Three MG UGIs were tested for improvements of cytosine base editing activities in *E. coli*. (b) BE3 comprises N-terminal rAPOBEC1, SpCas9 nickase, and C-terminal UGI. Two MG UGIs were tested for improvements of cytosine base editing activities in HEK293T cells. Editing efficiencies were quantified by Edit R.

Example 13.—Cell Culture, Transfections, Next Generation Sequencing, and Base Edit Analysis HEK293T cells were grown and passaged in Dulbecco's Modified Eagle's Medium plus GlutaMAX (Gibco) supplemented with 10% (v/v) fetal bovine serum (Gibco) at 37° C. with 5% $CO_2$. $5\times10^4$ cells were seeded on 96-well cell culture plates treated for cell attachment (Costar), grown for 20 to 24 h, and the spent media were refreshed with new media right before transfection. 200 ng expression plasmid and 1 μL lipofectamine 2000 (ThermoFisher Scientific) were used for transfection per well per manufacturer's instructions. Transfected cells were grown for 3 days, harvested, and gDNA was extracted with QuickExtract (Lucigen) per manufacturer's instructions. Targeted regions for base edits were amplified using Q5 High-Fidelity DNA polymerase (New England Biolabs) with primers listed in Tables 8 and 9 (SEQ ID NOs. 538-585) and extracted DNA as the templates.

TABLE 8

Primers used for base edit analysis of the effect of UGI in HEK293T

| Name | SEQ ID NO. | Description | Sequence (5' → 3') |
|---|---|---|---|
| P577 | 536 | Forward primer used to amplify the targeted region | GAGGCTGGAGAGGCCCGT |
| P578 | 537 | Reverse primer used to amplify the targeted region | GATTTTCATGCAGGTGCTGAAA |
| P577 | 536 | Sanger sequencing primer | GAGGCTGGAGAGGCCCGT |

TABLE 9a

Primers used to amplify targeted regions in HEK293T cells transfected with A0A2K5RND7-MG nickase-MG69-1

| Name | SEQ ID NO. | Description | Sequence (5' → 3') |
|---|---|---|---|
| P969 | 538 | Forward primer used to amplify A0A2K5RDN7-nSpCas9 (D10A)-MG69-1_site 1 | GCTCTTCCGATCTNNNNNAGGAG GAAGGGCCTGAGT |
| P970 | 539 | Reverse primer used to amplify A0A2K5RDN7-nSpCas9 (D10A)-MG69-1_site 1 | GCTCTTCCGATCTNNNNNTCTGC CCTCGTGGGTTTG |
| P971 | 540 | Forward primer used to amplify A0A2K5RDN7-nSpCas9 (D10A)-MG69-1_site 2 | GCTCTTCCGATCTNNNNNCTCTG GCCACTCCCTGGC |
| P972 | 541 | Reverse primer used to amplify A0A2K5RDN7-nSpCas9 (D10A)-MG69-1_site 2 | GCTCTTCCGATCTNNNNNGGCAG GCTCTCCGAGGAG |
| P973 | 542 | Forward primer used to amplify A0A2K5RDN7-nSpCas9 (D10A)-MG69-1_site 3 | GCTCTTCCGATCTNNNNNGGGAA TAATAAAAGTCTCTCTCTTAA |
| P974 | 543 | Reverse primer used to amplify A0A2K5RDN7-nSpCas9 (D10A)-MG69-1_site 3 | GCTCTTCCGATCTNNNNNCCCCC TCCACCAGTACCC |
| P975 | 544 | Forward primer used to amplify A0A2K5RDN7-nSpCas9 (D10A)-MG69-1_site 4 | GCTCTTCCGATCTNNNNNCCTGT CCTTGGAGAACCG |
| P976 | 545 | Reverse primer used to amplify A0A2K5RDN7-nSpCas9 (D10A)-MG69-1_site 4 | GCTCTTCCGATCTNNNNNGCAGG TGAACACAAGAGCT |

TABLE 9a-continued

Primers used to amplify targeted regions in HEK293T cells transfected with A0A2K5RND7-MG nickase-MG69-1

| Name | SEQ ID NO. | Description | Sequence (5' → 3') |
|---|---|---|---|
| P977 | 546 | Forward primer used to amplify A0A2K5RDN7-nSpCas9 (D10A)-MG69-1_site 5 | GCTCTTCCGATCTNNNNNGAAGG TGTGGTTCCAGAAC |
| P978 | 547 | Reverse primer used to amplify A0A2K5RDN7-nSpCas9 (D10A)-MG69-1_site 5 | GCTCTTCCGATCTNNNNNTCGAT GTCCTCCCCATTG |
| P979 | 548 | Forward primer used to amplify A0A2K5RDN7-nMG1-4 (D9A)-MG69-1_site 1 | GCTCTTCCGATCTNNNNNAAACA GGCTAGACATAGGGA |
| P980 | 549 | Reverse primer used to amplify A0A2K5RDN7-nMG1-4 (D9A)-MG69-1_site 1 | GCTCTTCCGATCTNNNNNGAAGC CACCAGAGTCTCTA |
| P981 | 550 | Forward primer used to amplify A0A2K5RDN7-nMG1-4 (D9A)-MG69-1_site 2 | GCTCTTCCGATCTNNNNNGCCGC CATTGACAGAGGG |
| P982 | 551 | Reverse primer used to amplify A0A2K5RDN7-nMG1-4 (D9A)-MG69-1_site 2 | GCTCTTCCGATCTNNNNNGCATC AAAACAAAAGGGAGATTG |
| P983 | 552 | Forward primer used to amplify A0A2K5RDN7-nMG1-4 (D9A)-MG69-1_site 3 | GCTCTTCCGATCTNNNNNCCTCT GCCCACCTCACTT |
| P984 | 553 | Reverse primer used to amplify A0A2K5RDN7-nMG1-4 (D9A)-MG69-1_site 3 | GCTCTTCCGATCTNNNNNGCCAT GTGGGTTAATCTGG |
| P985 | 554 | Forward primer used to amplify A0A2K5RDN7-nMG1-4 (D9A)-MG69-1_site 4 | GCTCTTCCGATCTNNNNNCCGGA CGCACCTACCCAT |
| P986 | 555 | Reverse primer used to amplify A0A2K5RDN7-nMG1-4 (D9A)-MG69-1_site 4 | GCTCTTCCGATCTNNNNNCTAGA TGGGAATGGATGGG |
| P987 | 556 | Forward primer used to amplify A0A2K5RDN7-nMG3-6 (D13A)-MG69-1_site 1 | GCTCTTCCGATCTNNNNNAACCA CAAACCCACGAGG |
| P988 | 557 | Reverse primer used to amplify A0A2K5RDN7-nMG3-6 (D13A)-MG69-1_site 1 | GCTCTTCCGATCTNNNNNTCAAT GGCGGCCCCGGGC |
| P989 | 558 | Forward primer used to amplify A0A2K5RDN7-nMG3-6 (D13A)-MG69-1_site 2 | GCTCTTCCGATCTNNNNNAGTGA TCCCCAGTGTCCC |
| P990 | 559 | Reverse primer used to amplify A0A2K5RDN7-nMG3-6 (D13A)-MG69-1_site 2 | GCTCTTCCGATCTNNNNNGCCCT GAACGCGTTTGCT |
| P991 | 560 | Forward primer used to amplify A0A2K5RDN7-nMG3-6 (D13A)-MG69-1_site 3 | GCTCTTCCGATCTNNNNNTGGGA ATAATAAAAGTCTCTCTCT |
| P992 | 561 | Reverse primer used to amplify A0A2K5RDN7-nMG3-6 (D13A)-MG69-1_site 3 | GCTCTTCCGATCTNNNNNCCCCT CCACCAGTACCCC |
| P993 | 562 | Forward primer used to amplify A0A2K5RDN7-nMG3-6 (D13A)-MG69-1_site 4 | GCTCTTCCGATCTNNNNNCAGGG CCTCCTCAGCCCA |
| P994 | 563 | Reverse primer used to amplify A0A2K5RDN7-nMG3-6 (D13A)-MG69-1_site 4 | GCTCTTCCGATCTNNNNNGTCTG GATGTCGTAAGGGAA |

TABLE 9a-continued

Primers used to amplify targeted regions in HEK293T cells transfected with A0A2K5RND7-MG nickase-MG69-1

| Name | SEQ ID NO. | Description | Sequence (5' → 3') |
|---|---|---|---|
| P995 | 564 | Forward primer used to amplify A0A2K5RDN7-nMG3-6 (D13A)-MG69-1_site 5 | GCTCTTCCGATCTNNNNNGGGGTGTAACTCAGAATGTTTT |
| P996 | 565 | Reverse primer used to amplify A0A2K5RDN7-nMG3-6 (D13A)-MG69-1_site 5 | GCTCTTCCGATCTNNNNNGGGAGTGAGACTCAGAGA |
| P997 | 566 | Forward primer used to amplify A0A2K5RDN7-nMG3-6 (D13A)-MG69-1_site 6 | GCTCTTCCGATCTNNNNNGCAAAGAGGGAAATGAGATCA |
| P998 | 567 | Reverse primer used to amplify A0A2K5RDN7-nMG3-6 (D13A)-MG69-1_site 6 | GCTCTTCCGATCTNNNNNGTGACACATTTGTTTGAGAATCA |
| P999 | 568 | Forward primer used to amplify A0A2K5RDN7-nMG3-6 (D13A)-MG69-1_site 7 | GCTCTTCCGATCTNNNNNCTTTATCCCCGCACAGAG |
| P1000 | 569 | Reverse primer used to amplify A0A2K5RDN7-nMG3-6 (D13A)-MG69-1_site 7 | GCTCTTCCGATCTNNNNNCTTGGCCCATGGGAAATC |
| P1001 | 570 | Forward primer used to amplify A0A2K5RDN7-nMG4-2 (D28A)-MG69-1_site 1 | GCTCTTCCGATCTNNNNNGTCCCATCCCAACACCCC |
| P1002 | 571 | Reverse primer used to amplify A0A2K5RDN7-nMG4-2 (D28A)-MG69-1_site 1 | GCTCTTCCGATCTNNNNNTGGGCATGTGTGCTCCCA |
| P1003 | 572 | Forward primer used to amplify A0A2K5RDN7-nMG4-2 (D28A)-MG69-1_site 2 | GCTCTTCCGATCTNNNNNCTATGGGAATAATAAAAGTCTCTC |
| P1004 | 573 | Reverse primer used to amplify A0A2K5RDN7-nMG4-2 (D28A)-MG69-1_site 2 | GCTCTTCCGATCTNNNNNCTCCACCAGTACCCCACC |
| P1005 | 574 | Forward primer used to amplify A0A2K5RDN7-nMG4-2 (D28A)-MG69-1_site 3 | GCTCTTCCGATCTNNNNNGGACCCTGGTCTCTACCT |
| P1006 | 575 | Reverse primer used to amplify A0A2K5RDN7-nMG4-2 (D28A)-MG69-1_site 3 | GCTCTTCCGATCTNNNNNCCTCTCCCATTGAACTACC |
| P1007 | 576 | Forward primer used to amplify A0A2K5RDN7-nMG4-2 (D28A)-MG69-1_site 4 | GCTCTTCCGATCTNNNNNCCCCAGTGACTCAGGGCC |
| P1008 | 577 | Reverse primer used to amplify A0A2K5RDN7-nMG4-2 (D28A)-MG69-1_site 4 | GCTCTTCCGATCTNNNNNTCGTAAGGGAAAGACTTAGGAA |
| P1009 | 578 | Forward primer used to amplify A0A2K5RDN7-nMG18-1 (D12A)-MG69-1_site 1 | GCTCTTCCGATCTNNNNNTCTCCCTTTTGTTTTGATGCATTT |
| P1010 | 579 | Reverse primer used to amplify A0A2K5RDN7-nMG18-1 (D12A)-MG69-1_site 1 | GCTCTTCCGATCTNNNNNCCACCCCAGGCTCTGGGG |
| P1011 | 580 | Forward primer used to amplify A0A2K5RDN7-nMG18-1 (D12A)-MG69-1_site 2 | GCTCTTCCGATCTNNNNNCCTTTTGTTTTGATGCATTTCTGTTT |
| P1012 | 581 | Reverse primer used to amplify A0A2K5RDN7-nMG18-1 (D12A)-MG69-1_site 2 | GCTCTTCCGATCTNNNNNAATCTACCACCCCAGGCT |

TABLE 9a-continued

Primers used to amplify targeted regions in HEK293T cells transfected with A0A2K5RND7-MG nickase-MG69-1

| Name | SEQ ID NO. | Description | Sequence (5' → 3') |
|---|---|---|---|
| P1013 | 582 | Forward primer used to amplify A0A2K5RDN7-nMG18-1 (D12A)-MG69-1_site 3 | GCTCTTCCGATCTNNNNNATCCC CAGTGTCCCCCTT |
| P1014 | 583 | Reverse primer used to amplify A0A2K5RDN7-nMG18-1 (D12A)-MG69-1_site 3 | GCTCTTCCGATCTNNNNNCCAGG CCCTGAACGCGTT |
| P1015 | 584 | Forward primer used to amplify A0A2K5RDN7-nMG18-1 (D12A)-MG69-1_site 4 | GCTCTTCCGATCTNNNNNAGGCC AGGCCTGCGGGGG |
| P1016 | 585 | Reverse primer used to amplify A0A2K5RDN7-nMG18-1 (D12A)-MG69-1_site 4 | GCTCTTCCGATCTNNNNNCCAAA AACTCCCAAATTAGCAAA |

PCR products were purified using the HighPrep PCR Clean-up System (MAGBIO) per manufacturer's instructions. The effect of uracil glycosylase inhibitor (UGI) on control. Three independent experiments were performed on different days. Abbreviations: R, repeat; NEG, negative control.

TABLE 9b

Protein Domains used in constructs in Example 13

| Candidate | Type | PAM | Deaminase | Linker (Deaminase-Nickase) | Nickase | UGI | Linker (Nickase-UGI) |
|---|---|---|---|---|---|---|---|
| A0A2K5RDN7-nMG3-6-MG69-1 | II | nnRGGnT SEQ ID NO: 362 | A0A2K5RDN7 SEQ ID NO: 594 | SGSETPGT SESATPES | nMG3-6 (D13A) SEQ ID NO: 71 | MG69-1 SEQ ID NO: 52 | SGGSS |
| A0A2K5RDN7-nMG1-4-MG69-1 | II | nRRR SEQ ID NO: 360 | A0A2K5RDN7 SEQ ID NO: 594 | SGSETPGT SESATPES | nMG1-4 SEQ ID NO:70 | MG69-1 SEQ ID NO: 52 | SGGSS |
| A0A2K5RDN7-nMG18-1-MG69-1 | II | nRWART SEQ ID NO: 368 | A0A2K5RDN7 SEQ ID NO: 594 | SGSETPGT SESATPES | nMG18-1 SEQ ID NO: 78 | MG69-1 SEQ ID NO: 52 | SGGSS |

base editing of candidate enzymes was analyzed by submitting PCR products to Elim BIOPHARM for Sanger sequencing, and the efficiency was quantified by Edit R. To analyze base editing of A0A2K5RND7-MG nickase-MG69-1, adapters used for next generation sequencing (NGS) were appended to PCR products by subsequent PCR reactions using KAPA HiFi HotStart Ready Mix PCR Kit (Roche) and primers compatible with TruSeq DNA Library Prep Kits (illumina). DNA concentrations of the resulting products were quantified by TapeStation (Agilent), and samples were pooled together to prepare the library for NGS analysis. The resulting library was quantified by qPCR with Aria Realtime PCR System (Agilent) and high through sequencing was performed with an Illumina Miseq instrument per manufacturer's instructions. Sequencing data was analyzed for base edits by Cripresso2.

Figure 13A:
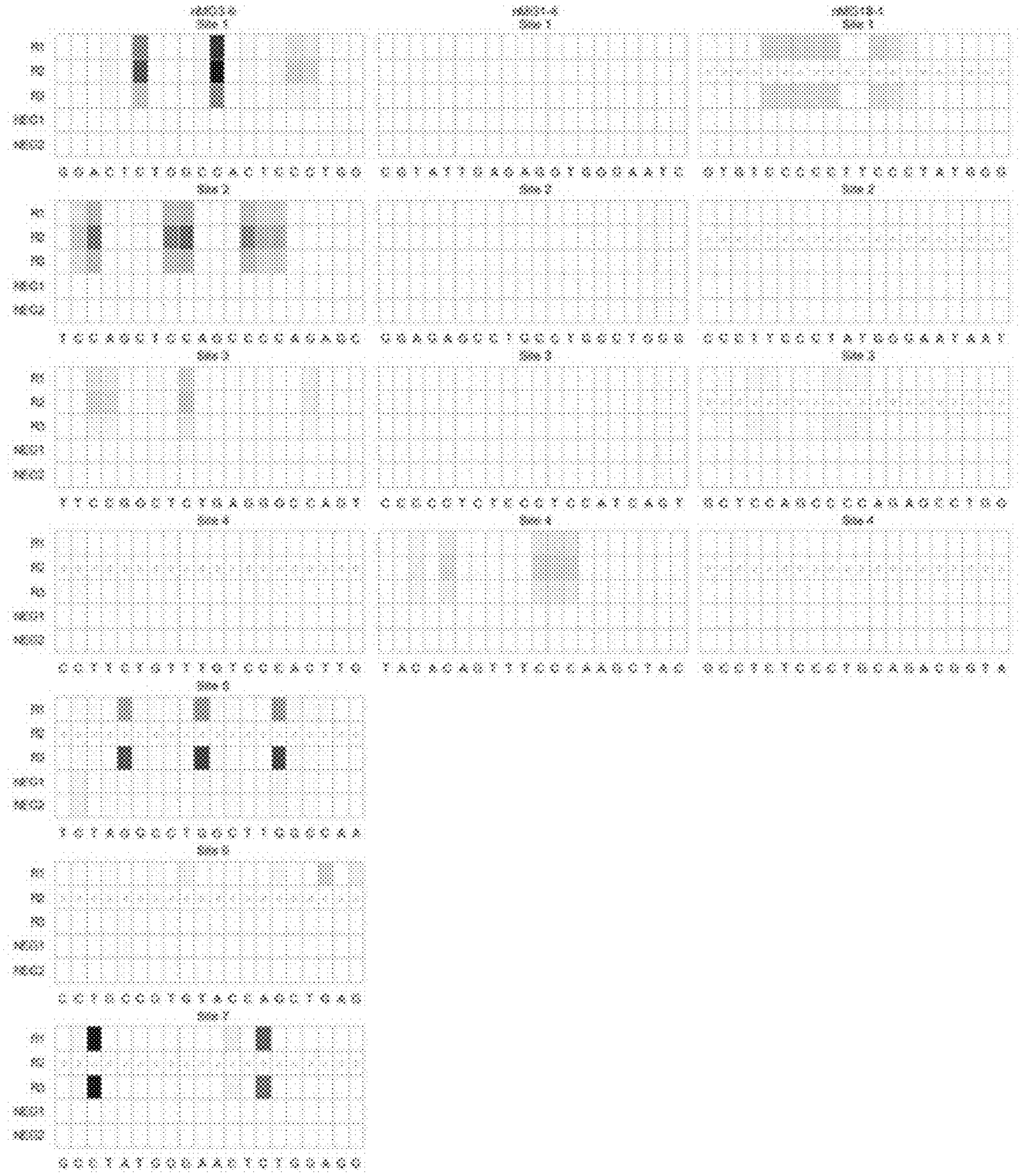
FIGS. 13A and 13B depict maps of edited sites showing editing efficiencies of cytosine base editors comprising A0A2K5RDN7, an MG nickases, and an MG UGI. The constructs comprise an N-terminal A0A2K5RDN7, an MG nickases, and a C-terminal MG69-1. For simplicity, only the identities of MG nickases are shown in the figure. BE3 was used as the positive control for base editing. An empty vector was used for the negative control. Three independent experiments were performed on different days. Abbreviations: R, repeat; NEG, negative control.
Figure 13B:
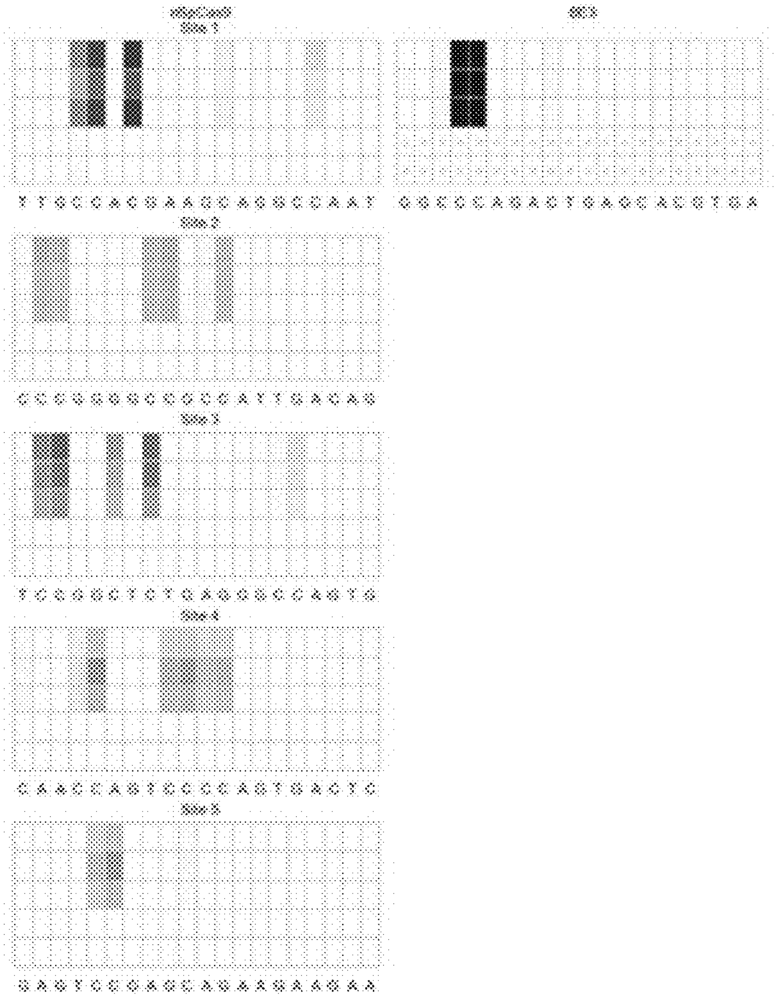

FIG. 13 shows maps of sites targeted by base editors showing base editing efficiencies of cytosine base editors comprising CMP/dCMP-type deaminase domain-containing protein (uniprot accession A0A2K5RDN7), MG nickases, and MG UGI. The constructs comprise N-terminal A0A2K5RDN7, MG nickases, and C-terminal MG69-1. For simplicity, only the identities of MG nickases are shown in the figure. BE3 (APOBEC1) was used as a positive control for base editing. An empty vector was used for the negative

Example 14.—Positive Selection of Base Editor Mutants in *E. coli*

Figure 14:
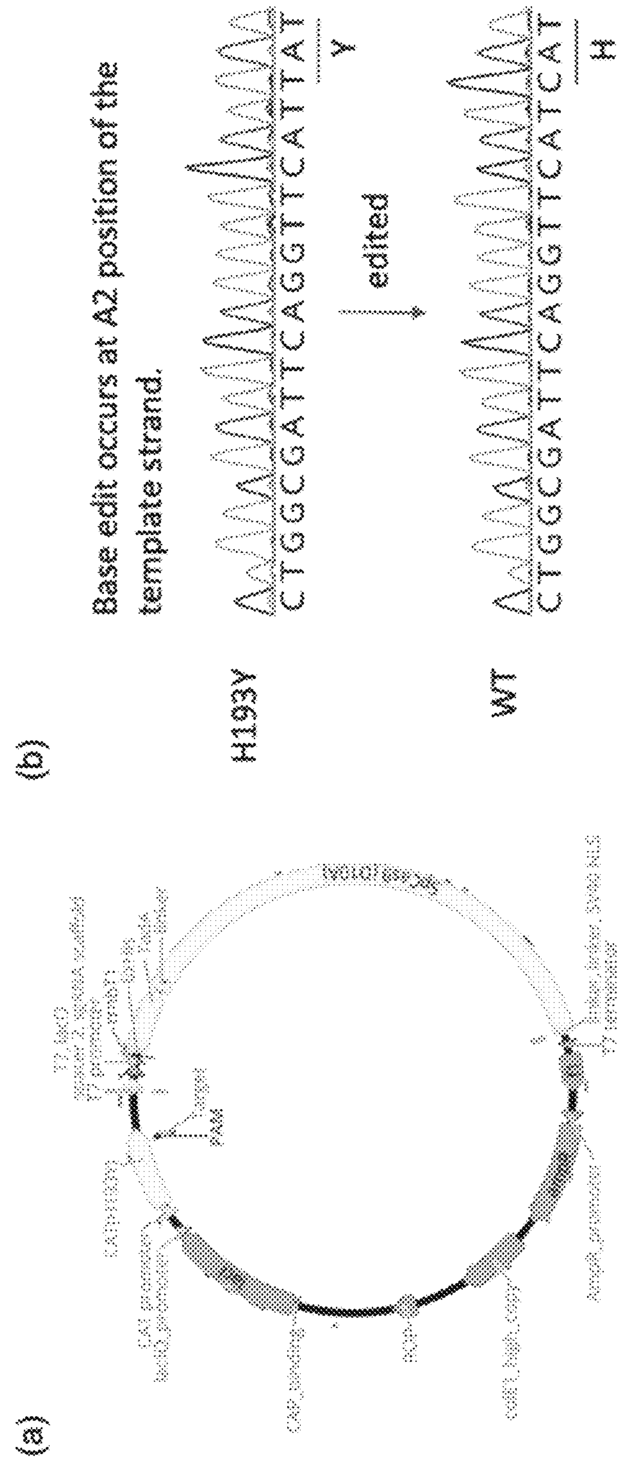
FIG. 14 shows a positive selection method for TadA characterization in *E. coli*. Panel (a) shows a map of one plasmid system used for TadA selection. The vector comprises CAT (H193Y), a sgRNA expression cassette targeting CAT, and an ABE expression cassette. In this figure, N-terminal TadA from *E. coli* and a C-terminal SpCas9 (D10A) from *Streptococcus pyogenes* are shown. Panel (b) shows sequencing traces demonstrating that when introduced/transformed into *E. coli* cells, the A2 position of CAT (H193Y)'s template strand is edited, reverting the H193Y mutant to wild type and restoring its activity. Abbreviations: CAT, chloramphenicol acetyltransferase.

FIG. 14 shows a positive selection method for TadA characterization in *E. coli*. Panel (a) shows a map of one plasmid system used for TadA selection. The vector comprises CAT (H193Y), a sgRNA expression cassette targeting CAT, and an ABE expression cassette. In this figure, N-terminal TadA from *E. coli* and a C-terminal SpCas9 (D10A) from *Streptococcus pyogenes* are shown. Panel (b) shows sequencing traces demonstrating that when introduced/transformed into *E. coli* cells, the A2 position of CAT (H193Y)'s template strand is edited, reverting the H193Y mutant to wild type and restoring its activity. Abbreviations: CAT, chloramphenicol acetyltransferase.

1 μL of plasmid solution with a concentration of 10 ng/μL was transformed into 25 μL BL21 (DE3) electrocompetent cells (Lucigen), recovered with 975 μL expression recovery medium at 37° C. for 1 h. 50 μL of the resulting cells were spread on a LB agar plate containing 100 μg/mL carbenicillin, 0.1 mM IPTG, and appropriate amount of chloramphenicol. The plate was incubated at 37° C. until colonies were pickable. Colony PCR were used to amplify the genomic region containing base edits, and the resulting products were submitted for Sanger sequencing at ELIM BIOPHARM. Primers used for PCR and sequencing are listed in Table 10 (SEQ ID NOs. 532-537).

TABLE 10

Primers used for base edit analysis of CAT (H193Y)

| Name | SEQ ID NO. | Description | Sequence (5' → 3') |
|---|---|---|---|
| P570 | 532 | Forward primer used to amplify CAT (H193Y) of CAT (H193Y)-sgRNA-MG68-4 variant-nSpCas9 (D10A) | CCGCCGCCGCAAGGAATGGTTTAATTAATTTGATCGGCACGTAAGAGG |
| P1050 | 534 | Forward primer used to amplify CAT (H193Y) of CAT (H193Y)-sgRNA-MG68-4 variant-nMG34-1 (D10A) | AAGGAATGGTTTAATTAATTCTAGATTAATTAATTTGATCGGCACGTAAG |
| P571 | 533 | Reverse primer used to amplify CAT (H193Y) of CAT (H193Y)-sgRNA-MG68-4 variant-nSpCas9 | GGACTGTTGGGCGCCATCTCCTTGCATGCTTCACTTATTCAGGCGTAGCA |
| P571 | 535 | Sanger sequencing primer of CAT (H193Y) | GGACTGTTGGGCGCCATCTCCTTGCATGCTTCACTTATTCAGGCGTAGCA |

Figure 15:
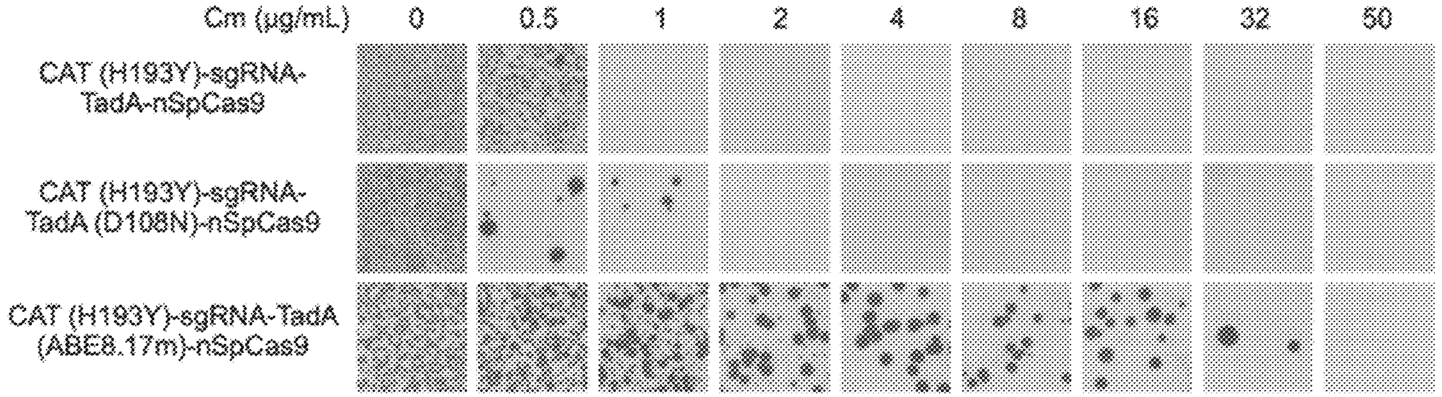
FIG. 15 shows mutations caused by TadA enable high tolerance of chloramphenicol (Cm). Panel (a) shows photographs of growth plates where different concentrations of chloramphenicol were used to select for antibiotics resistance of *E. coli*. In this example, wild type and two variants of TadA from *E. coli* (EcTadA) were tested. Panel (b) shows a results summary table demonstrating that ABEs carrying mutated TadA show higher editing efficiencies than the wild type. In these experiments, colonies were picked from the plates with greater than or equal to 0.5 μg/mL Cm. For simplicity, only identities of deaminases are shown in the table.

FIG. 15 shows mutations caused by TadA enable high tolerance of chloramphenicol (Cm). Panel (a) shows photographs of growth plates where different concentrations of chloramphenicol were used to select for antibiotics resistance of *E. coli*. In this example, wild type and two variants of TadA from *E. coli* (EcTadA) were tested. Panel (b) shows a results summary table demonstrating that ABEs carrying mutated TadA show higher editing efficiencies than the wild type. In these experiments, colonies were picked from the plates with greater than or equal to 0.5 µg/mL Cm. For simplicity, only identities of deaminases are shown in the table, but effectors (SpCas9) and construct organization are shown in the figures above.

Figure 16A:
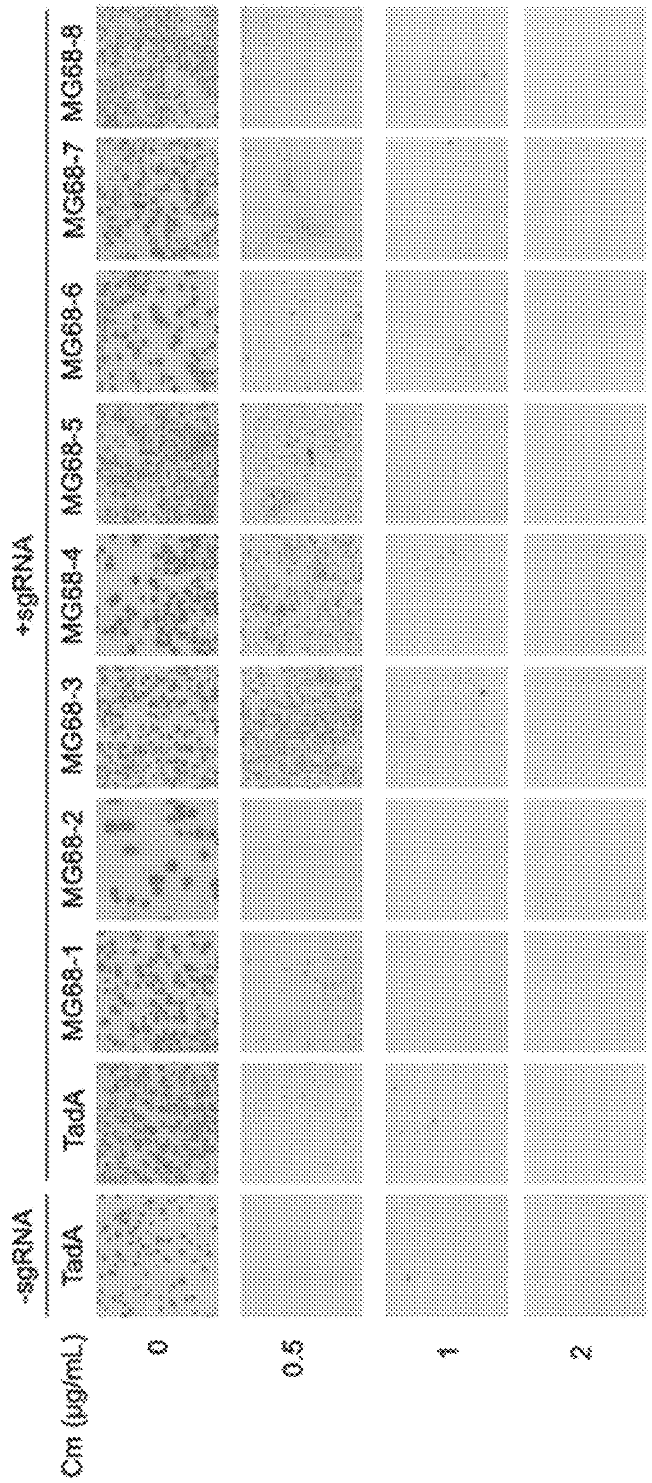
FIG. 16A shows photographs of growth plates to investigate MG TadA activity in positive selection. 8 MG68 TadA candidates were tested against 0 to 2 μg/mL of chloramphenicol (ABEs comprised N-terminal TadA variants and C-terminal SpCas9 (D10A) nickase). For simplicity, only identities of deaminases are shown. In this experiment, colonies were picked from the plates with greater than or equal to 0.5 μg/mL Cm.

FIG. 16 shows investigation of MG TadA activity in positive selection. Panel (a) shows photographs of growth plates from an experiment where 8 MG68 TadA candidates were tested against 0 to 2 µg/mL of chloramphenicol (ABEs comprised N-terminal TadA variants and C-terminal SpCas9 (D10A) nickase). For simplicity, only identities of deaminases are shown. Panel (b) shows a summary table depicting editing efficiencies of MG TadA candidates. Panel (b) demonstrates that MG68-3 and MG68-4 drove base edits of adenine. In this experiment, colonies were picked from the plates with greater than or equal to 0.5 µg/mL Cm.

Figure 17:
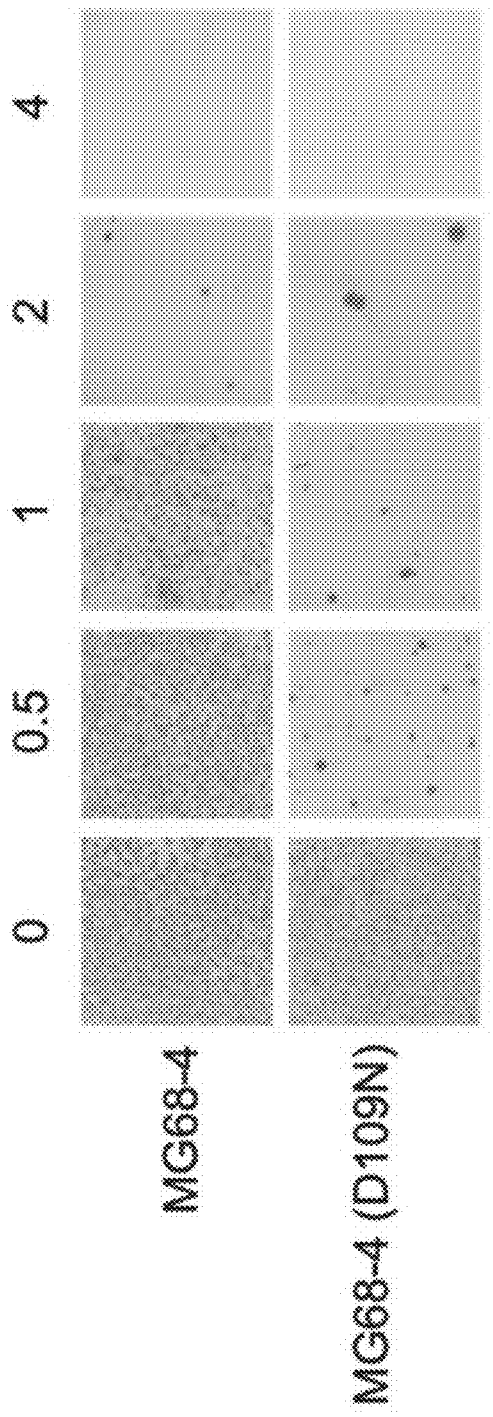
FIG. 17 shows an improvement of base editing efficiency of MG68-4_nSpCas9 via D109N mutation on MG68-4. Panel (a) shows photographs of growth plates where wild type MG68-4 and its variant were tested against 0 to 4 μg/mL of chloramphenicol. For simplicity, only identities of deaminases are shown. Adenine base editors in this experiment are comprise N-terminal TadA variants and C-terminal SpCas9 (D10A) nickase. Panel (b) shows a summary table depicting editing efficiencies of MG TadA candidates. Panel (b) demonstrates that MG68-4 and MG68-4 (D109N) showed base edits of adenine, with the D109N mutant showing increased activity. In this experiment, colonies were picked from the plates with greater than or equal to 0.5 μg/mL Cm.

FIG. 17 shows an improvement of base editing efficiency of MG68-4_nSpCas9 via D109N mutation on MG68-4. Panel (a) shows photographs of growth plates where wild type MG68-4 and its variant were tested against 0 to 4 µg/mL of chloramphenicol. For simplicity, only identities of deaminases are shown. Adenine base editors in this experiment comprise N-terminal TadA variants and C-terminal SpCas9 (D10A) nickase. Panel (b) shows a summary table depicting editing efficiencies of MG TadA candidates. Panel (b) demonstrates that MG68-4 and MG68-4 (D109N) showed base edits of adenine, with the D109N mutant showing increased activity. In this experiment, colonies were picked from the plates with greater than or equal to 0.5 µg/mL Cm.

Figure 18:
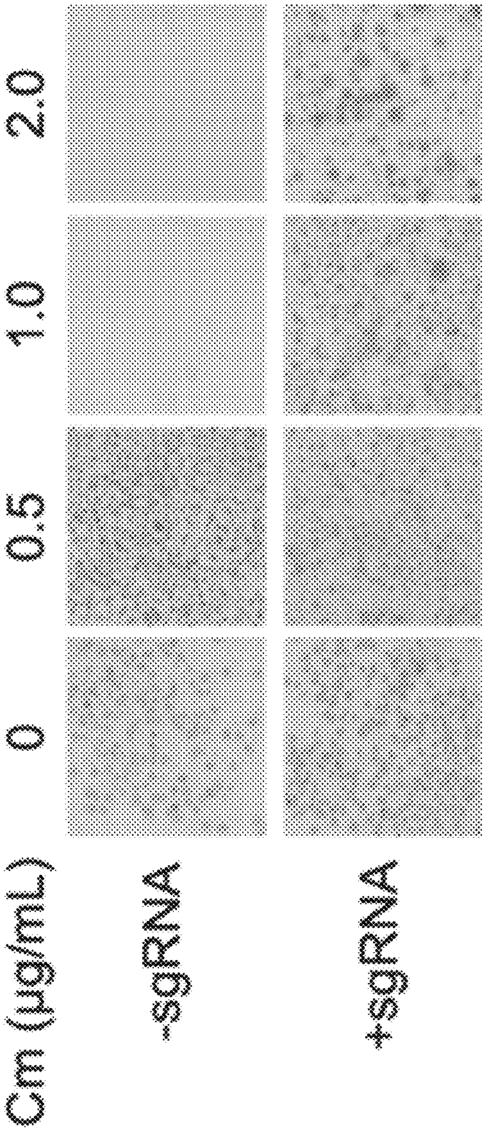
FIG. 18 shows base editing of MG68-4 (D109N)_nMG34-1. Panel (a) shows photographs of growth plates of an experiment where an ABE comprising N-terminal MG68-4 (D109N) and C-terminal SpCas9 (D10A) nickase was tested against 0 to 2 μg/mL of chloramphenicol. Panel (b) shows a summary table depicting editing efficiencies with and without sgRNA. In this experiment, colonies were picked from the plates with greater than or equal to 1 μg/mL Cm.

FIG. 18 shows base editing of MG68-4 (D109N)_nMG34-1. Panel (a) shows photographs of growth plates of an experiment where an ABE comprising N-terminal MG68-4 (D109N) and C-terminal SpCas9 (D10A) nickase was tested against 0 to 2 µg/mL of chloramphenicol. Panel (b) shows a summary table depicting editing efficiencies with and without sgRNA. In this experiment, colonies were picked from the plates with greater than or equal to 1 µg/mL Cm.

FIG. 19 shows 28 MG68-4 variants designed for improvements of MG68-4-nMG34-1 base editing activity. 12 residues were selected for targeted mutagenesis to improve editing of the enzymes.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for modifying a nucleic acid molecule, the method comprising contacting said nucleic acid molecule with an engineered complex comprising a base editor, wherein said base editor comprises the amino acid sequence of SEQ ID NO: 386.

2. The method of claim 1, wherein said nucleic acid molecule comprises an adenine, wherein modifying said nucleic acid molecule comprises converting said adenine to guanine.

3. The method of claim 1, wherein said engineered complex further comprises an endonuclease comprising a RuvC domain and an HNH domain and wherein said endonuclease is a class 2, type II Cas endonuclease.

4. The method of claim 3, wherein said endonuclease comprising said RuvC domain and said HNH domain is covalently coupled directly to said base editor or covalently coupled to said base editor through a linker.

5. The method of claim 3, wherein said endonuclease comprises the sequence of SEQ ID NO: 597.

6. The method of claim 5, wherein said endonuclease is configured to bind a protospacer adjacent motif (PAM) sequence comprising NGG.

7. The method of claim 5, wherein said engineered complex further comprises an engineered guide ribonucleic acid structure configured to bind to said endonuclease and said nucleic acid molecule, wherein said engineered guide ribonucleic acid structure comprises the sequence of SEQ ID NO: 489.

8. The method of claim 3, wherein said endonuclease cleaves one strand of said nucleic acid molecule.

9. The method of claim 3, wherein said endonuclease or said base editor comprises one or more nuclear localization sequences (NLSs).

10. The method of claim 1, wherein said engineered complex further comprises a uracil deoxyribonucleic acid glycosylase inhibitor.

11. The method of claim 10, wherein said uracil deoxyribonucleic acid glycosylase inhibitor comprises a sequence of any one of SEQ ID NOs: 52-56 or SEQ ID NO: 67.

12. The method of claim 1, wherein said nucleic acid molecule is a eukaryotic, plant, fungal, mammalian, rodent, or human nucleic acid molecule.

13. The method of claim 1, wherein said nucleic acid molecule encodes a PCSK9 gene.

14. The method of claim 1, wherein said nucleic acid molecule encodes an AGXT gene.

* * * * *

SEQUENCE LISTING

```
Sequence total quantity: 720
SEQ ID NO: 1            moltype = AA  length = 186
FEATURE                 Location/Qualifiers
REGION                  1..186
                        note = Description of Unknown: uncultivated organism
REGION                  1..186
```

```
                      note = Category: MG66 putative cytidine deaminase
REGION                1..186
                      note = Description: MG66-2 deaminase
source                1..186
                      mol_type = protein
                      organism = unidentified
SEQUENCE: 1
MARVLGLDPG FATCGYALVD LTRKDGAPFV DVRSLGTLRT AKADKKRKVL AADDNLRRAQ  60
ELIRALYPLA SNAQAIVAES MSFPRNSAAA AKMAMCWGIV ATLAEMNDLP IVQATPKEIK  120
IAVAGVGTAT KEDVAAAVCA KCGRQFSEEL LAQGLPKGMH EHAYDAVASV LACLNSDVLR  180
AIRRAG                                                           186

SEQ ID NO: 2          moltype = AA  length = 164
FEATURE               Location/Qualifiers
REGION                1..164
                      note = Description of Unknown: uncultivated organism
REGION                1..164
                      note = Category: MG66 putative cytidine deaminase
REGION                1..164
                      note = Description: MG66-3 deaminase
source                1..164
                      mol_type = protein
                      organism = unidentified
SEQUENCE: 2
MDRLSLHQYA IALAWVAATR SEDPYTRVGC VALSEQGNVL ATAYNGLKPK ATFGPEFWNN  60
RESRLPFMVH AEMNLVSLTK RNEVHTVAIN ILPCPTCAAF LATHGVQQVV YSEVYHRDKG  120
TVGLTVLREY GVEIHHLPYY RVRPVFLDMD EAHRKVRSEQ RTAA                 164

SEQ ID NO: 3          moltype = AA  length = 135
FEATURE               Location/Qualifiers
REGION                1..135
                      note = Description of Unknown: uncultivated organism
REGION                1..135
                      note = Category: MG66 putative cytidine deaminase
REGION                1..135
                      note = Description: MG66-4 deaminase
source                1..135
                      mol_type = protein
                      organism = unidentified
SEQUENCE: 3
MREYIQAARD EAAKSRCDRA HVGCVIVDRA TGHVVSSAFN ETPHGLEPCD TGGHRIVDNH  60
CVNTVHAERN AIRKMTEHGS EYTLYVTHYP CQGCAHLIAS CPEIVEVVYL GDYNNSSEAT  120
ALLSGLSKGV HHGEE                                                 135

SEQ ID NO: 4          moltype = AA  length = 160
FEATURE               Location/Qualifiers
REGION                1..160
                      note = Description of Unknown: uncultivated organism
REGION                1..160
                      note = Category: MG66 putative cytidine deaminase
REGION                1..160
                      note = Description: MG66-5 deaminase
source                1..160
                      mol_type = protein
                      organism = unidentified
SEQUENCE: 4
MSNTQSLHTT FMHILFEFSK LSHCVSKQVA AMAVKDGRII STGINGTAPG YTNCDDIFNK  60
SDFNRELHHQ FSNTYEIHAE MNMILYAAKN GISLDGATLY CSMLPCWNCI KHISVTGIKH  120
IIYAKRYDML SLEDEKNIYY YCKKLGITIQ QFDPDTLGSF                      160

SEQ ID NO: 5          moltype = AA  length = 124
FEATURE               Location/Qualifiers
REGION                1..124
                      note = Description of Unknown: uncultivated organism
REGION                1..124
                      note = Category: MG66 putative cytidine deaminase
REGION                1..124
                      note = Description: MG66-6 deaminase
source                1..124
                      mol_type = protein
                      organism = unidentified
SEQUENCE: 5
MTSGILKLAL EEAESSTYRF RVGAVVFKGS RILASGHNGI RSSRIHPLHK NYNNALHAEQ  60
DAILNVKDWS TLKGCSILVV KVSKTKGTIS MAKPCPMCQQ LLRHVGIKTM YFSNENGEII  120
SEKL                                                             124

SEQ ID NO: 6          moltype = AA  length = 132
FEATURE               Location/Qualifiers
REGION                1..132
```

```
                       note = Description of Unknown: uncultivated organism
REGION                 1..132
                       note = Category: MG66 putative cytidine deaminase
REGION                 1..132
                       note = Description: MG66-7 deaminase
source                 1..132
                       mol_type = protein
                       organism = unidentified
SEQUENCE: 6
MTKREIAYFN AAKAVSSLSD HKYKMGCVIV NKHRIISSGF NSETKCHRIQ AELDMNEYKM  60
HSSGKVHAET SALLSLRHID LSKASIFIYR ELKDGTKALA RPCPCCQKLI RKAGIKHVYY  120
TGNNSLIYEE FI                                                     132

SEQ ID NO: 7           moltype = AA  length = 142
FEATURE                Location/Qualifiers
REGION                 1..142
                       note = Description of Unknown: uncultivated organism
REGION                 1..142
                       note = Category: MG66 putative cytidine deaminase
REGION                 1..142
                       note = Description: MG66-8 deaminase
source                 1..142
                       mol_type = protein
                       organism = unidentified
SEQUENCE: 7
AAGDFVQVRE YIKAARDEAA KSRCDRAHVG CVIVDRVTGR VVSRAFNETP HGLEPCDTGG  60
HRMIDGHCVN TVHAERNAIR KMKEHESEYT LYVTHYPCQG CAHLIASCPE IVEVVYLGDY  120
RNSKEATALL MGLSKGVHRG EE                                          142

SEQ ID NO: 8           moltype = AA  length = 82
FEATURE                Location/Qualifiers
REGION                 1..82
                       note = Description of Unknown: uncultivated organism
REGION                 1..82
                       note = Category: MG66 putative cytidine deaminase
REGION                 1..82
                       note = Description: MG66-9 deaminase
source                 1..82
                       mol_type = protein
                       organism = unidentified
SEQUENCE: 8
HRIVDNHCVN TVHAERNAIR KMKEHGSEYT LYVTHYPCQG CAHLISSCPE IVEVVYLGDY  60
RNSSEATALL SGLSKGVHRG EE                                          82

SEQ ID NO: 9           moltype = AA  length = 115
FEATURE                Location/Qualifiers
REGION                 1..115
                       note = Description of Unknown: uncultivated organism
REGION                 1..115
                       note = Category: MG66 putative cytidine deaminase
REGION                 1..115
                       note = Description: MG66-10 deaminase
source                 1..115
                       mol_type = protein
                       organism = unidentified
SEQUENCE: 9
HVGCVIVDHA TGQVVSSAFN ETPPGLEPCD TGGHRIVDDH CVNTVHAERG AIRKMAEHGS  60
EYTLYVTHYP CRGCAHLISS CPEIVEVVYL GDYNNSSEAT DLLMSLSKGV HRAEE       115

SEQ ID NO: 10          moltype = AA  length = 186
FEATURE                Location/Qualifiers
REGION                 1..186
                       note = Description of Unknown: uncultivated organism
REGION                 1..186
                       note = Category: MG66 putative cytidine deaminase
REGION                 1..186
                       note = Description: MG66-11 deaminase
source                 1..186
                       mol_type = protein
                       organism = unidentified
SEQUENCE: 10
MARVLGLDPG FATCGYALVD LTRKDGAPFV DVRSLGTLRT AKADKKRKVL AADDNLRRAQ  60
ELIRALYPLA SNAQAIVAES MSFPRNSAAA AKMAMCWGIV ATLAEMNDLP IVQATPKEIK  120
IAVAGVGTAT KEDVAAAVCA KCGRQFSEEL LAQGLPKGMH EHAYDAVASV LACLNSDVLR  180
AIRRAG                                                            186

SEQ ID NO: 11          moltype = AA  length = 232
FEATURE                Location/Qualifiers
REGION                 1..232
```

```
                      note = Description of Unknown: uncultivated organism
REGION                1..232
                      note = Category: MG66 putative cytidine deaminase
REGION                1..232
                      note = Description: MG66-12 deaminase
source                1..232
                      mol_type = protein
                      organism = unidentified
SEQUENCE: 11
MDNLPKYEYL NVLDPERTGI SETWLSYFMN IARVIATKSK DPSTKVGAVA VDTNTKRILA  60
TGYNGFPAGV KERPERWERP VKYSYIVHSE ANIVASAARF GINLTGSTLF VTLHPCVDCA  120
KIVASAGFKN VIYIDTEIKA QVGREWITLL QHSKNIFEES RIGLYACREV PAKKKEEPKL  180
YKTYKGTVET TTELNNKRDK QLGDLVFVKS RNTLYEWNGV IWTVIGEYQH LL          232

SEQ ID NO: 12         moltype = AA  length = 113
FEATURE               Location/Qualifiers
REGION                1..113
                      note = Description of Unknown: uncultivated organism
REGION                1..113
                      note = Category: MG66 putative cytidine deaminase
REGION                1..113
                      note = Description: MG66-13 deaminase
source                1..113
                      mol_type = protein
                      organism = unidentified
SEQUENCE: 12
MDNLPKYEYL NVLDPERTRI SETWLSYFMN IARVIATKSK DPSTKVGAVA VDTNTKRILA  60
TGYNGFPAGV KERPERWERP VKYSYIVHSE ANIVASAARF GINLTGSTLF VTL         113

SEQ ID NO: 13         moltype = AA  length = 232
FEATURE               Location/Qualifiers
REGION                1..232
                      note = Description of Unknown: uncultivated organism
REGION                1..232
                      note = Category: MG66 putative cytidine deaminase
REGION                1..232
                      note = Description: MG66-14 deaminase
source                1..232
                      mol_type = protein
                      organism = unidentified
SEQUENCE: 13
MDNLPKYEYL NVLDPERTRI SETWLSYFMN IARVIATKSK DPSTKVGAVA VDTNTKRILA  60
TGYNGFPAGV KERPERWERP VKYSYIVHSE ANIVASAARF GINLTGSTLF VTLHPCVDCA  120
KIVASAGFKN VIYIDTEIKP QVGREWITLL QHSKNIFEES RIGLYACREV PAKKKEEPKL  180
YKTFKGTVET TVELNNKRDK QLGDLVFVKS RNTLYEWNGV IWTVIGEYQH LL          232

SEQ ID NO: 14         moltype = AA  length = 164
FEATURE               Location/Qualifiers
REGION                1..164
                      note = Description of Unknown: uncultivated organism
REGION                1..164
                      note = Category: MG66 putative cytidine deaminase
REGION                1..164
                      note = Description: MG66-15 deaminase
source                1..164
                      mol_type = protein
                      organism = unidentified
SEQUENCE: 14
MDRLSLHQYA IALAWVAATR SEDPYTRVGC VALSEQGNVL ATAYNGLKPK ATFGPEFWNN  60
RESRLPFMVH AEMNLVSLTK RNEVHTVAIN ILPCPTCAAF LATHGVQQVV YSEVYHRDKG  120
TVGLTVLREY GVEIHHLPYY RVRPVFLDMD EAHRKVRSEQ RTAA                  164

SEQ ID NO: 15         moltype = AA  length = 50
FEATURE               Location/Qualifiers
REGION                1..50
                      note = Description of Unknown: uncultivated organism
REGION                1..50
                      note = Category: MG66 putative cytidine deaminase
REGION                1..50
                      note = Description: MG66-18 deaminase
source                1..50
                      mol_type = protein
                      organism = unidentified
SEQUENCE: 15
MKQYIQAARD EAAKSRCDRA HVGCVIVDRA TGQVVSRAFN ETPHGLEPCD             50

SEQ ID NO: 16         moltype = AA  length = 135
FEATURE               Location/Qualifiers
REGION                1..135
```

```
                      note = Description of Unknown: uncultivated organism
REGION                1..135
                      note = Category: MG66 putative cytidine deaminase
REGION                1..135
                      note = Description: MG66-19 deaminase
source                1..135
                      mol_type = protein
                      organism = unidentified
SEQUENCE: 16
MKQYIQAARD EAAKSRCDRA HVGCVIVDRA TGQVVSRAFN ETPHGLEPCD TGGHRIVDNH  60
CVNTVHAERN AIRKMKEHGS EYTLYVTHYP CQGCAHLISS CPEIVEVVYL GDYRNSSEAT  120
ALLSGLSKGV HRGEE                                                   135

SEQ ID NO: 17         moltype = AA  length = 135
FEATURE               Location/Qualifiers
REGION                1..135
                      note = Description of Unknown: uncultivated organism
REGION                1..135
                      note = Category: MG66 putative cytidine deaminase
REGION                1..135
                      note = Description: MG66-20 deaminase
source                1..135
                      mol_type = protein
                      organism = unidentified
SEQUENCE: 17
MKQYIQAARD EAAKSRCDRA HVGCVIVDRA TGQVVSRAFN ETPHGLEPCD TGGHRIVDNH  60
CVNTVHAERN AIRQMKEHGS EYTLYVTHYP CQGCAHLISS CPEIIEVVYI GDYNNSSEAT  120
ALLSGLSKGV HRGEE                                                   135

SEQ ID NO: 18         moltype = AA  length = 204
FEATURE               Location/Qualifiers
REGION                1..204
                      note = Description of Unknown: uncultivated organism
REGION                1..204
                      note = Category: MG66 putative cytidine deaminase
REGION                1..204
                      note = Description: MG66-21 deaminase
source                1..204
                      mol_type = protein
                      organism = unidentified
SEQUENCE: 18
MNIARVIATK SKDPSTKVGA VAVDTNTKRI LATGYNGFPA GVKERPERWE RPVKYSYIVH  60
SEANIVASAA RFGINLTGST LFVTLHPCVD CAKIVASAGF KNVIYIDTEI KPQVGREWIT  120
LLQHSKNIFE ESRIGLYACR EVPAKKKEEP KLYKTFKGTV ETTVELNNKR DKQLGDLIFV  180
RSRNTLYEWN GVIWTVIGEY QHLL                                         204

SEQ ID NO: 19         moltype = AA  length = 142
FEATURE               Location/Qualifiers
REGION                1..142
                      note = Description of Unknown: uncultivated organism
REGION                1..142
                      note = Category: MG66 putative cytidine deaminase
REGION                1..142
                      note = Description: MG66-22 deaminase
source                1..142
                      mol_type = protein
                      organism = unidentified
SEQUENCE: 19
MREFIKAARD EAAKSRCDRA HVGCVIVDRA TGRVVSRAFN ETPHGLEPCD TGGHRMIDGH  60
CVNTVHAERG AIRKMQSHDS EYTLYVTHYP CQGCAHLIAS CPDIVEVVYL GDYRNSNEAT  120
ALLMGLSKGV HHAEEDCSSS PA                                           142

SEQ ID NO: 20         moltype = AA  length = 142
FEATURE               Location/Qualifiers
REGION                1..142
                      note = Description of Unknown: uncultivated organism
REGION                1..142
                      note = Category: MG66 putative cytidine deaminase
REGION                1..142
                      note = Description: MG66-23 deaminase
source                1..142
                      mol_type = protein
                      organism = unidentified
SEQUENCE: 20
MREFIKAARD EAAKSRCDRA HVGCVIVDRA TGRVVSRAFN ETPHGLEPCD TGGHRMIDGH  60
CVNTVHAERG AIRKMQSHDS EYTLYVTHYP CQGCAHLIAS CPEIVEVVYL GDYRNSNEAT  120
ALLMGLSKGV HHAEEDCSSS PA                                           142

SEQ ID NO: 21         moltype = AA  length = 142
```

```
FEATURE                 Location/Qualifiers
REGION                  1..142
                        note = Description of Unknown: uncultivated organism
REGION                  1..142
                        note = Category: MG66 putative cytidine deaminase
REGION                  1..142
                        note = Description: MG66-24 deaminase
source                  1..142
                        mol_type = protein
                        organism = unidentified
SEQUENCE: 21
MREFIKAARD EAAKSRCDRA HVGCVIVDRA TGRVVSRAFN ETPHGLEPCD TGGHRMIDGH  60
CVNTVHAERG AIRKMQTHDS EYTLYVTHYP CQGCAHLIAS CPEIVEVVYL GDYRNSNEAT  120
ALLMGLSKGV HHAEEDCSSS PA                                           142

SEQ ID NO: 22           moltype = AA  length = 142
FEATURE                 Location/Qualifiers
REGION                  1..142
                        note = Description of Unknown: uncultivated organism
REGION                  1..142
                        note = Category: MG66 putative cytidine deaminase
REGION                  1..142
                        note = Description: MG66-25 deaminase
source                  1..142
                        mol_type = protein
                        organism = unidentified
SEQUENCE: 22
MREFIKAARD EAAKSRCDRA HVGCVIVDRA TGRVVSRAFN ETPHGLEPCD TGGHRMIDGH  60
CVNTVHAERG AIRKMTSHDS EYTLYVTHYP CQGCAHLIAS CPEIVEVVYL GDYRNSNEAT  120
ALLMGLSKGV HHAEEDCSSS PA                                           142

SEQ ID NO: 23           moltype = AA  length = 136
FEATURE                 Location/Qualifiers
REGION                  1..136
                        note = Description of Unknown: uncultivated organism
REGION                  1..136
                        note = Category: MG66 putative cytidine deaminase
REGION                  1..136
                        note = Description: MG66-26 deaminase
source                  1..136
                        mol_type = protein
                        organism = unidentified
SEQUENCE: 23
MRELGIKAAR DEAKKSRCDR AHVGCVIIDR ASGQVVSRAF NETPPTLEPC DTGGHRMVDG  60
HCVNTVHAER GAIRKMAEHG SEYTLYVTHY PCRGCAHLIS SCPEIVEVVY LGDYNNSSEA  120
TALLMSLSKG VHRVKG                                                  136

SEQ ID NO: 24           moltype = AA  length = 135
FEATURE                 Location/Qualifiers
REGION                  1..135
                        note = Description of Unknown: uncultivated organism
REGION                  1..135
                        note = Category: MG66 putative cytidine deaminase
REGION                  1..135
                        note = Description: MG66-27 deaminase
source                  1..135
                        mol_type = protein
                        organism = unidentified
SEQUENCE: 24
MREYIKAARD EAAKSRCDRA HVGCVIVDHA TGQVVSRAFN ETPHGLEPCD TGGHRIVDNH  60
CVNTVHAERN AIRKMKEHGS EYTLYVTHYP CRGCAHLIST CPEIVEVVYL GDYNNSSEAT  120
ALLEGLSKGV HRGEE                                                   135

SEQ ID NO: 25           moltype = AA  length = 135
FEATURE                 Location/Qualifiers
REGION                  1..135
                        note = Description of Unknown: uncultivated organism
REGION                  1..135
                        note = Category: MG66 putative cytidine deaminase
REGION                  1..135
                        note = Description: MG66-28 deaminase
source                  1..135
                        mol_type = protein
                        organism = unidentified
SEQUENCE: 25
MREYIKAARD EAAKSRCDRA HVGCVIVDRA TEQVVSRAFN ETPNGLEPCD TGGHRIVDDH  60
CVNTVHAERN AIRKMREHGS EYTLYVTHYP CQGCAHLISS CPEIVEVVYL GDYNNSSEAT  120
ALLSGLSKGV HRGEE                                                   135
```

```
SEQ ID NO: 26          moltype = AA  length = 36
FEATURE                Location/Qualifiers
REGION                 1..36
                       note = Description of Unknown: uncultivated organism
REGION                 1..36
                       note = Category: MG66 putative cytidine deaminase
REGION                 1..36
                       note = Description: MG66-29 deaminase
source                 1..36
                       mol_type = protein
                       organism = unidentified
SEQUENCE: 26
MREYIKAARD EAAKSRCDRA HVGCVIVDRA TGQVVS                            36

SEQ ID NO: 27          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-30 deaminase
source                 1..135
                       mol_type = protein
                       organism = unidentified
SEQUENCE: 27
MREYIKAARD EAAKSRCDRA HVGCVIVDRA TGQVVSGAFN ETPHGLEPCD TGGHRIVDGH  60
CVNTVHAERN AIRKMKEHGS EYTLYVTHYP CRGCAHLISS CPEIVEVVYL GDYNNSSEAT  120
ALLSGLSKGV HRGEE                                                   135

SEQ ID NO: 28          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-31 deaminase
source                 1..135
                       mol_type = protein
                       organism = unidentified
SEQUENCE: 28
MREYIKAARD EAAKSRCDRA HVGCVIVDRA TGQVVSRAFN ETPHGLEPCD TGGHRIVDNH  60
CVNTVHAERN AIRKMKEHGS EYTLYVTHYP CQGCAHLISS CPEIVEVVYL GDYRNSSEAT  120
ALLSGLSKGV HRGEE                                                   135

SEQ ID NO: 29          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-32 deaminase
source                 1..135
                       mol_type = protein
                       organism = unidentified
SEQUENCE: 29
MREYIKAARD EAAKSRCDRA HVGCVIVDRA TGQVVSRAFN ETPHGLEPCD TGGHRIVDNH  60
CVNTVHAERN AIRKMTDHGS EYTLYVTHYP CQGCAHLISS CPEIVEVVYL GDYNNSSEAT  120
ALLSGLSKGV HRGEE                                                   135

SEQ ID NO: 30          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-33 deaminase
source                 1..135
                       mol_type = protein
                       organism = unidentified
SEQUENCE: 30
MREYIKAARD EAAKSRCDRA HVGCVIVDRA TGQVVSRAFN ETPHGLEPCD TGGHRMVDDH  60
CVNTIHAERN AIRQMKEHGS EYTLYVTHYP CRGCAHFIST CPEIVEVVYL GDYRNSSEAT  120
ALLSGLSKGV HRGEE                                                   135

SEQ ID NO: 31          moltype = AA  length = 40
```

```
FEATURE                Location/Qualifiers
REGION                 1..40
                       note = Description of Unknown: uncultivated organism
REGION                 1..40
                       note = Category: MG66 putative cytidine deaminase
REGION                 1..40
                       note = Description: MG66-34 deaminase
source                 1..40
                       mol_type = protein
                       organism = unidentified
SEQUENCE: 31
MREYIKAARD EAAKSRCDRA HVGCVIVDRA TGQVVSSAFN                         40

SEQ ID NO: 32          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-35 deaminase
source                 1..135
                       mol_type = protein
                       organism = unidentified
SEQUENCE: 32
MREYIKAARD EAAKSRCDRA HVGCVIVDRA TGQVVSSAFN ETPHGLEPCD TGGHRIVDNH  60
CVNTVHAERN AIRQMTDHGS EYTLYVTHYP CQGCAHLIAS CPEIVEVVYL GDYNNSSEAT  120
ALLSGLSKGV HRGEE                                                   135

SEQ ID NO: 33          moltype = AA  length = 142
FEATURE                Location/Qualifiers
REGION                 1..142
                       note = Description of Unknown: uncultivated organism
REGION                 1..142
                       note = Category: MG66 putative cytidine deaminase
REGION                 1..142
                       note = Description: MG66-36 deaminase
source                 1..142
                       mol_type = protein
                       organism = unidentified
SEQUENCE: 33
MREYIKAARD EAAKSRCDRA HVGCVIVDRA TGRVVSRAFN ETPHGLEPCD TGGHRMIDGH  60
CVNTVHAERN AIRKMPSHDS EYTLYVTHYP CQGCAHLIAS CPDIVEVVYL GDYRNSEEAT  120
ALLMGLSKGI HCAEEDRSSS PA                                           142

SEQ ID NO: 34          moltype = AA  length = 142
FEATURE                Location/Qualifiers
REGION                 1..142
                       note = Description of Unknown: uncultivated organism
REGION                 1..142
                       note = Category: MG66 putative cytidine deaminase
REGION                 1..142
                       note = Description: MG66-37 deaminase
source                 1..142
                       mol_type = protein
                       organism = unidentified
SEQUENCE: 34
MREYIKAARD EAAKSRCDRA HVGCVIVDRA TGRVVSRAFN ETPHGLEPCD TGGHRMIDGH  60
CVNTVHAERN AIRKMPSHDS EYTLYVTHYP CQGCAHLIAS CPDIVEVVYL GDYRNSEEAT  120
ALLMGLSKGV HCAEEDRSSS PA                                           142

SEQ ID NO: 35          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-38 deaminase
source                 1..135
                       mol_type = protein
                       organism = unidentified
SEQUENCE: 35
MREYIKAARD EAKKSRCDRA HVGCVIVDRA SGQVVSSAFN ETPPGLEPCD TGGHRMVDDH  60
CVNTVHAERG AILKMAEHGS EYTLYVTHYP CRGCAHLISS CPEIVEVVYL GDYNNSSEAT  120
TLLMSLSKGV HHVEG                                                   135

SEQ ID NO: 36          moltype = AA  length = 135
FEATURE                Location/Qualifiers
```

```
REGION                 1..135
                       note = Description of Unknown: uncultivated organism
REGION                 1..135
                       note = Category: MG66 putative cytidine deaminase
REGION                 1..135
                       note = Description: MG66-39 deaminase
source                 1..135
                       mol_type = protein
                       organism = unidentified
SEQUENCE: 36
MREYIKAARD EAKKSRCDRA HVGCVIVDRA TGQVVSKGFN ETPPGLEPCD TGGHHIVDNH  60
CVNTVHAERS AIRKMTEHGS EYTLYVTHYP CRGCAHLITS CPEIMEVVYL GDYNNSSEAT  120
ELLMGLSKGV HHVEG                                                   135

SEQ ID NO: 37          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-40 deaminase
source                 1..135
                       mol_type = protein
                       organism = unidentified
SEQUENCE: 37
MREYIKAARD EAKKSRCDRA HVGCVIVDRA TGRVVSRAFN ETPHGLEPCD TGGHRIVDDH  60
CVNTVHAERN AIRRMVEHGS EYTLYVTHYP CQGCAHLISS CPEIVEVVYL GDYNNSSEAT  120
ALLSGLSKGV HRGEE                                                   135

SEQ ID NO: 38          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-41 deaminase
source                 1..135
                       mol_type = protein
                       organism = unidentified
SEQUENCE: 38
MREYIQAARD EAKKSRCDRA HVGCVIVDRA SGQVVSSAFN ETPPGLEPCD TGGHRMVDGH  60
CVNTVHAERG AIRKMAEHGS EYTLYVTHYP CRGCAHLISS CPEIMEVVYL GDYNNSSEAT  120
TLLMGLSKGV HHVEE                                                   135

SEQ ID NO: 39          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-42 deaminase
source                 1..135
                       mol_type = protein
                       organism = unidentified
SEQUENCE: 39
MREYIQAARD EAKKSRCDRA HVGCVIVDRA TGRVVSSAFN ETPPGLEPCD TGGHRMVDGH  60
CVNTVHAERG AIRKMAEHGS EYTLYVTHYP CRGCGHLISS CPEIVEVVYL GDYNNSSEAT  120
ALLMGLSKGV HHVEE                                                   135

SEQ ID NO: 40          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-43 deaminase
source                 1..135
                       mol_type = protein
                       organism = unidentified
SEQUENCE: 40
MREYIQAARD EASKSRCDRA HVGCVIVDRA TGQVVSRAFN ETPHGLEPCD TGGHRIVDNH  60
CVNTIHAERN AIRKMPTHDS EYTLYVTHYP CQGCAHLISS CPEIVEVVYL GDYRNSSEAT  120
ALLSGLSKGV HRGEE                                                   135

SEQ ID NO: 41          moltype = AA  length = 135
```

```
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-44 deaminase
source                 1..135
                       mol_type = protein
                       organism = unidentified
SEQUENCE: 41
MREYIRAARD EAAKSRCDRA HVGCVIVDRA TGQVVSRAFN ETPHGLEPCD TGGHRIVDNH  60
CVNTVHAERN AIRKMTEHGS EYTLYVTHYP CQGCAHLISS CPEIVEVVYL GDYNNSSEAT  120
ALLEGLSKGV HRGEE                                                   135

SEQ ID NO: 42          moltype = AA  length = 135
FEATURE                Location/Qualifiers
REGION                 1..135
                       note = Description of Unknown: uncultivated organism
REGION                 1..135
                       note = Category: MG66 putative cytidine deaminase
REGION                 1..135
                       note = Description: MG66-45 deaminase
source                 1..135
                       mol_type = protein
                       organism = unidentified
SEQUENCE: 42
MREYIRAARD EAAKSRCDRA HVGCVIVDRA TSRVVSRAFN ETPHGLDPCD TGGHRMIDGH  60
CVNTVHAERN AIRKMPSHDS EYTLYVTHYP CQGCAHLIAS CPDIVEVVYL GDYRNSKEAT  120
ALLMGLSKGI HHAEE                                                   135

SEQ ID NO: 43          moltype = AA  length = 151
FEATURE                Location/Qualifiers
REGION                 1..151
                       note = Description of Unknown: uncultivated organism
REGION                 1..151
                       note = Category: MG66 putative cytidine deaminase
REGION                 1..151
                       note = Description: MG66-46 deaminase
source                 1..151
                       mol_type = protein
                       organism = unidentified
SEQUENCE: 43
MRVRPDWDTY FMRIAKVVAQ RSHDEDTQVG CVIVSPDKRI LSTGYNGFPP GFPDGKLPRT  60
RPGKYPYIVH SEINAIVSAL NRDLRGATLY CRFTPCKDCV KAIITAGITR IVYEETYARD  120
NTDAAVVFEM LEMGGVEIVK HLEHEHEADS D                                 151

SEQ ID NO: 44          moltype = AA  length = 159
FEATURE                Location/Qualifiers
REGION                 1..159
                       note = Description of Unknown: uncultivated organism
REGION                 1..159
                       note = Category: MG66 putative cytidine deaminase
REGION                 1..159
                       note = Description: MG66-47 deaminase
source                 1..159
                       mol_type = protein
                       organism = unidentified
SEQUENCE: 44
MSNTQSLHTT FMHILFEFSK LSHCVSKQVA AMAVKDGRII STGINGTAPG YTNCDDIFNK  60
SDFDRELHHQ FSNTYEIHAE MNMILYAAKN GISLDGATLY CSMLPCWNCI KHISVTGIKH  120
IIYAKRYDML SLEDEKNIYY YCKKLGITIQ QFDPDTLGS                         159

SEQ ID NO: 45          moltype = AA  length = 160
FEATURE                Location/Qualifiers
REGION                 1..160
                       note = Description of Unknown: uncultivated organism
REGION                 1..160
                       note = Category: MG66 putative cytidine deaminase
REGION                 1..160
                       note = Description: MG66-48 deaminase
source                 1..160
                       mol_type = protein
                       organism = unidentified
SEQUENCE: 45
MSNTQSLHTT FMHILFEFSK LSHCVSKQVA AMAVKDGRII STGINGTAPG YTNCDDIFNK  60
SDFDRELHHQ FSNTYEIHAE MNMILYAAKN GISLDGATLY CSMLPCWNCI KHISVTGIKH  120
IIYAKRYDML SLEDEKNIYY YCKKLGITIQ QFDPDTLGSF                        160
```

```
SEQ ID NO: 46          moltype = AA  length = 124
FEATURE                Location/Qualifiers
REGION                 1..124
                       note = Description of Unknown: uncultivated organism
REGION                 1..124
                       note = Category: MG66 putative cytidine deaminase
REGION                 1..124
                       note = Description: MG66-49 deaminase
source                 1..124
                       mol_type = protein
                       organism = unidentified
SEQUENCE: 46
MTSGILKLAL EEAESSTYRF RVGAVVFKGS RILASGHNGI RSSRIHPLHK NYNNALHAEQ  60
DAILNVKDWS TLKGCSILVV KVSKTKGTIS MAKPCPMCQQ LLRHVGIKTM YFSNENGEII  120
SEKL                                                               124

SEQ ID NO: 47          moltype = AA  length = 80
FEATURE                Location/Qualifiers
REGION                 1..80
                       note = Description of Unknown: uncultivated organism
REGION                 1..80
                       note = Category: MG66 putative cytidine deaminase
REGION                 1..80
                       note = Description: MG66-50 deaminase
source                 1..80
                       mol_type = protein
                       organism = unidentified
SEQUENCE: 47
MVDGHCVNTV HAERGAIRKM TEHGSEYTLY VTHYPCRGCA HLISSCPEIV EVVYLGDYNN  60
SSEATALLMG LSKGVHHVEG                                              80

SEQ ID NO: 48          moltype = AA  length = 150
FEATURE                Location/Qualifiers
REGION                 1..150
                       note = Description of Unknown: uncultivated organism
REGION                 1..150
                       note = Category: MG67 putative cytidine deaminase
REGION                 1..150
                       note = Description: MG67-2 deaminase
source                 1..150
                       mol_type = protein
                       organism = unidentified
SEQUENCE: 48
MTACKDKPVC NVAQADATLL STCLRLLQTA HEIKQNAYAP YSGFQVGAAV LAKNGSIITG  60
VNVENGSLGL TICAERTALS KAVSEGYRPG DFVAIAVAAS ADGFSPCGAC REVINEFGQN  120
MLVVFEYQDE VVVAPLKTLL AYNFVKGKPS                                   150

SEQ ID NO: 49          moltype = AA  length = 62
FEATURE                Location/Qualifiers
REGION                 1..62
                       note = Description of Unknown: uncultivated organism
REGION                 1..62
                       note = Category: MG67 putative cytdidine deaminase
REGION                 1..62
                       note = Description: MG67-4 deaminase
source                 1..62
                       mol_type = protein
                       organism = unidentified
SEQUENCE: 49
MAYRPGDFVA IAIAASSPDF SPCGACREVI NEFGDDMAVI FEIKGETVVS QLKEHLPYNF  60
KM                                                                 62

SEQ ID NO: 50          moltype = AA  length = 250
FEATURE                Location/Qualifiers
REGION                 1..250
                       note = Description of Unknown: uncultivated organism
REGION                 1..250
                       note = Category: MG68 putative adenosine deaminase
                        (TadA-like)
REGION                 1..250
                       note = Description: MG68-1 deaminase
source                 1..250
                       mol_type = protein
                       organism = unidentified
SEQUENCE: 50
MQHVKHMRTA VRLARYALDH DETPVACIFV HTPTGQVMAY GMNDTNKSLT GVAHAEFMGI  60
DQIKAMLGSR GVVDVFKDIT LYVTVEPCIM CASALKQLGI GKVVFGCGNE RFGGNGTVLS  120
VNHDTCTLVP KNNSAAGYES IPGILRKEAI MLLRYFYVRQ NERAPKPRSK SDRVLDKNTF  180
PPMEWSKYLN EEAFIETFGD DYKTCFANKV DLSSNSVDWD LIDSHQDNII QELEEQCKMF  240
```

```
RFNVHKKSKV                                                        250

SEQ ID NO: 51          moltype = AA  length = 239
FEATURE                Location/Qualifiers
REGION                 1..239
                       note = Description of Unknown: uncultivated organism
REGION                 1..239
                       note = Category: MG68 putative adenosine deaminase
                        (TadA-like)
REGION                 1..239
                       note = Description: MG68-2 deaminase
source                 1..239
                       mol_type = protein
                       organism = unidentified
SEQUENCE: 51
MLLNKRSYGH FYFIALMTEF SKWDEYYMKL ALMEAEKALN SNEVPIGCVF VKSDTEVEIP  60
PLPSRYSKDE FHSSVIASGR NFTNENYNAT HHAEIMALTD LISCLECNCK KIDNMGEPCK  120
PTFSKDTECP QCNFNLKNVT LYVTIEPCIM CISALMELQV SRIVFGANND KFGGCGGTLT  180
NVPEILKDTC SKDFEEIKIE RGLYREEAVI LLRKFYLIQN PKAPNPKKKA KRTLNLIVD   239

SEQ ID NO: 52          moltype = AA  length = 87
FEATURE                Location/Qualifiers
REGION                 1..87
                       note = Description of Unknown: uncultivated organism
REGION                 1..87
                       note = Category: MG69 UGI
REGION                 1..87
                       note = Description: MG69-1 deaminase
source                 1..87
                       mol_type = protein
                       organism = unidentified
SEQUENCE: 52
MSKTIKDLEE FAAEKLGYDI VFQESISMEP QEVEHLITTD EKSVLVNSTY DDNKEITISM  60
ISTPHPEYRP IALIIQDMEG EVQRKEL                                     87

SEQ ID NO: 53          moltype = AA  length = 88
FEATURE                Location/Qualifiers
REGION                 1..88
                       note = Description of Unknown: uncultivated organism
REGION                 1..88
                       note = Category: MG69 UGI
REGION                 1..88
                       note = Description: MG69-2 deaminase
source                 1..88
                       mol_type = protein
                       organism = unidentified
SEQUENCE: 53
MSKTIKDLEE FAAEKLGYDI VFQESISMEP QEVEHLITTD EKSVLVNSTY DDDKEITISV  60
ISTPHPEYRP IALVIQDMEG EVQRKELY                                    88

SEQ ID NO: 54          moltype = AA  length = 84
FEATURE                Location/Qualifiers
REGION                 1..84
                       note = Description of Unknown: uncultivated organism
REGION                 1..84
                       note = Category: MG69 UGI
REGION                 1..84
                       note = Description: MG69-3 deaminase
source                 1..84
                       mol_type = protein
                       organism = unidentified
SEQUENCE: 54
MTNLSDIIEK ETGKQLVIQE SILMLPEEVE EVIGNKPESD ILVHTAYDES TDENVMLLTS  60
DAPEYKPWAL VIQDSNGENK IKML                                        84

SEQ ID NO: 55          moltype = AA  length = 67
FEATURE                Location/Qualifiers
REGION                 1..67
                       note = Description of Unknown: uncultivated organism
REGION                 1..67
                       note = Category: MG69 UGI
REGION                 1..67
                       note = Description: MG69-4 deaminase
source                 1..67
                       mol_type = protein
                       organism = unidentified
SEQUENCE: 55
MIVRVTYNVE QEVEISNKFN KDVDIMKPEE YDDYIDDLMF ALNEKLPEYA EISCVINDNT  60
GEVLFEG                                                           67
```

```
SEQ ID NO: 56           moltype = AA  length = 35
FEATURE                 Location/Qualifiers
REGION                  1..35
                        note = Description of Unknown: uncultivated organism
REGION                  1..35
                        note = Category: MG69 UGI
REGION                  1..35
                        note = Description: MG69-5 deaminase
source                  1..35
                        mol_type = protein
                        organism = unidentified
SEQUENCE: 56
MSKTIKDLEE FAAEKLGYDI VFQESISMEP QEVEH                              35

SEQ ID NO: 57           moltype = AA  length = 167
FEATURE                 Location/Qualifiers
REGION                  1..167
                        note = Category: reference deaminase
REGION                  1..167
                        note = Description: P68398 TADA tRNA specific adenosine
                         deaminase
source                  1..167
                        mol_type = protein
                        organism = Escherichia coli
SEQUENCE: 57
MSEVEFSHEY WMRHALTLAK RAWDEREVPV GAVLVHNNRV IGEGWNRPIG RHDPTAHAEI  60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTD                 167

SEQ ID NO: 58           moltype = AA  length = 229
FEATURE                 Location/Qualifiers
REGION                  1..229
                        note = Category: reference deaminase
REGION                  1..229
                        note = Description: P38483 APOBEC 1 C U editing deaminase
source                  1..229
                        mol_type = protein
                        organism = Rattus norvegicus
SEQUENCE: 58
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLK               229

SEQ ID NO: 59           moltype = AA  length = 251
FEATURE                 Location/Qualifiers
REGION                  1..251
                        note = Category: reference deaminase
REGION                  1..251
                        note = Description: Aicda XM 004869540 cytidine deaminase
source                  1..251
                        mol_type = protein
                        organism = Heterocephalus glaber
SEQUENCE: 59
MAVGSKPKAA LVGPHWERER IWCFLCSTGL GTQQTGQTSR WLRPAATQDP VSPPRSLLMK  60
QRKFLYHFKN VRWAKGRHET YLCYVVKRRD SATSFSLDFG YLRNKSGCHV ELLFLRYISD  120
WDLDPGRCYR VTWFTSWSPC YDCARHVADF LRGNPNLSLR IFTARLYFCE DRKAEPEGLR  180
RLHRAGVQIA IMTFKDYFYC WNTFVENHER TFKAWEGLHE NSVRLSRQLR RILLPLYEVD  240
DLRDAFRTLG L                                                        251

SEQ ID NO: 60           moltype = AA  length = 224
FEATURE                 Location/Qualifiers
REGION                  1..224
                        note = Category: reference deaminase
REGION                  1..224
                        note = Description: PmCDA1 L1 AVN88313.1 cytidine deaminase
source                  1..224
                        mol_type = protein
                        organism = Petromyzon marinus
SEQUENCE: 60
MAGYECVRVS EKLDFDTFEF QFENLHYATE RHRTYVIFDV KPQSAGGRSR RLWGYIINNP  60
NVCHAELILM SMIDRHLESN PGVYAMTWYM SWSPCANCSS KLNPWLKNLL EEQGHTLTMH  120
FSRIYDRDRE GDHRGLRGLK HVSNSFRMGV VGRAEVKECL AEYVEASRRT LTWLDTTESM  180
AAKMRRKLFC ILVRCAGMRE SGIPLHLFTL QTPLLSGRVV WWRV                    224

SEQ ID NO: 61           moltype = AA  length = 208
FEATURE                 Location/Qualifiers
REGION                  1..208
```

```
                          note = Category: reference deaminase
REGION                    1..208
                          note = Description: PmCDA1 ABO15149.1 cytosine deaminase
source                    1..208
                          mol_type = protein
                          organism = Petromyzon marinus
SEQUENCE: 61
MTDAEYVRIH EKLDIYTFKK QFFNNKKSVS HRCYVLFELK RRGERRACFW GYAVNKPQSG  60
TERGIHAEIF SIRKVEEYLR DNPGQFTINW YSSWSPCADC AEKILEWYNQ ELRGNGHTLK  120
IWACKLYYEK NARNQIGLWN LRDNGVGLNV MVSEHYQCCR KIFIQSSHNQ LNENRWLEKT  180
LKRAEKRRSE LSIMIQVKIL HTTKSPAV                                     208

SEQ ID NO: 62             moltype = AA  length = 199
FEATURE                   Location/Qualifiers
REGION                    1..199
                          note = Category: reference deaminase
REGION                    1..199
                          note = Description: NP 663745.1 DNA dC- dU-editing
                           deaminase APOBEC-3A isoform a
source                    1..199
                          mol_type = protein
                          organism = Homo sapiens
SEQUENCE: 62
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 63             moltype = AA  length = 198
FEATURE                   Location/Qualifiers
REGION                    1..198
                          note = Category: reference deaminase
REGION                    1..198
                          note = Description: Q9GZX7.1 AICDA Single-stranded DNA
                           cytosine deaminase (Activation-induced cytidine deaminase,
                           Cytidine aminohydrolase)
source                    1..198
                          mol_type = protein
                          organism = Homo sapiens
SEQUENCE: 63
MDSLLMNRRK FLYQFKNVRW AKGRRETYLC YVVKRRDSAT SFSLDFGYLR NKNGCHVELL  60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                                198

SEQ ID NO: 64             moltype = AA  length = 197
FEATURE                   Location/Qualifiers
REGION                    1..197
                          note = Category: reference deaminase
REGION                    1..197
                          note = Description: LpCDA1L1 3 AVN88320.1 cytidine deaminase
source                    1..197
                          mol_type = protein
                          organism = Lampetra planeri
SEQUENCE: 64
MAGDENVRVS EKLHFNTFEF EFENLHYAEG RGQTYVIFDV KPQSEGGRGE RLWGYVRNKP  60
LGDHAEVILM SKINDHLETH QDNYTMTWYM SWSPCGKCSS ELVPWLQNLL KKQHKLTMHF  120
SRIYDKDRAV DHRGLCDLQH VVSNGFQMGV MGQTEVDTCL AEYVEASGCP PLKWLHMTDS  180
NATQMQDKLS SILMNRF                                                 197

SEQ ID NO: 65             moltype = AA  length = 198
FEATURE                   Location/Qualifiers
REGION                    1..198
                          note = Category: reference deaminase
REGION                    1..198
                          note = Description: LpCDA1L1 1 AVN88319.1 cytidine deaminase
source                    1..198
                          mol_type = protein
                          organism = Lampetra planeri
SEQUENCE: 65
MAGDENVRVS KKLDFNTFEF EFENLHYAEG RGRTYVIFDV KPQSEGGRGE RLWGYVRNNP  60
LDDHAEVILM SKINDHLETH QGNYTMTWYM SWSPCGNCSS ELVPWLQNLL EEQQHTLTMY  120
FSRIYDKDRA VDHRGLCDLQ HVVSNGFQMG VMGQTEVDTC LAEYVEASGC PPLKWLHMTD  180
SNATQTQDKL SSILMNRF                                                198

SEQ ID NO: 66             moltype = DNA  length = 642
FEATURE                   Location/Qualifiers
misc_feature              1..642
                          note = Category: reference deaminase
```

```
misc_feature          1..642
                      note = Description: ljCDA1 cytidine deaminase
source                1..642
                      mol_type = other DNA
                      organism = Lampetra planeri
SEQUENCE: 66
gccaacgccg agtacgtgcg cgtgggcgag aagctggaca gctgcacctt ccgcacccag  60
ttcctgaact accgccgcag ccgcagccgc cgctgctgcg tgatcttcga gctgaagcgc  120
cagaacagcc gcgtgcgctt ctggggctac gccatgaaca agccctggag caacgccgac  180
gtgggcatcc acgccgagtt cttctgcatc aagaaggtga agaagtacct gcgcaagaac  240
cccggcatct acaccatcaa ctggtacagc agctggagcc cctgcgccaa ctgcgccgag  300
aagatcctga actggtacaa caagaagctg atgggcaagg gccacaccct gaagatttgg  360
gcctgcaagc tgtacttcga gaacatcaag cgcaaccaga tcggcctgtg gaacctgcgc  420
aacaacggcg tgggcctggc catcatgctg ggcgagcact accagtggtg ctggaacaac  480
tacatccaga ccctgggccg caacctgaac gagaacaagt ggctgaaaaa gaccagcaac  540
cgcgcccgca cccgccgcag cgagctgagc atcatgatcc acgtgaagcg cctgcacacc  600
gcccgcctgc tgctgttcaa gcgcctgtgc ggctggttca gc                    642

SEQ ID NO: 67         moltype = AA  length = 84
FEATURE               Location/Qualifiers
REGION                1..84
                      note = Description of Unknown: Bacillus phage PBS2 sequence
REGION                1..84
                      note = Category: reference UGI
REGION                1..84
                      note = Description: P14739 UNGI BPPB2 (UGI)
source                1..84
                      mol_type = protein
                      organism = unidentified
SEQUENCE: 67
MTNLSDIIEK ETGKQLVIQE SILMLPEEVE EVIGNKPESD ILVHTAYDES TDENVMLLTS  60
DAPEYKPWAL VIQDSNGENK IKML                                        84

SEQ ID NO: 68         moltype = AA  length = 1245
FEATURE               Location/Qualifiers
REGION                1..1245
                      note = Description of Artificial Sequence: Synthetic
                       polypeptide
REGION                1..1245
                      note = Category: adenine base editor
REGION                1..1245
                      note = Description: linker-His tag-adenine
                       deaminse-linker-nickase -linker-SV40 NLS
source                1..1245
                      mol_type = protein
                      organism = synthetic construct
SEQUENCE: 68
MGSSHHHHHH SEVEFSHEYW MRHALTLAKR ARDEREVPVG AVLVLNNRVI GEGWNRAIGL  60
HDPTAHAEIM ALRQGGLVMQ NYRLIDATLY STFEPCVMCA GAMIHSRIGR VVFGVRNAKT  120
GAAGSLMDVL HYPGMNHRVE ITEGILADEC AALLCYFFRM PRRVFNAQKK AQSSTDSGGS  180
SGGSSGSETP GTSESATPES SGGSSGGSMK KKVFAFALGK ASIGYCVRDG FNINEANSII  240
IDKDHAETMS LRDRRRIKKT LDAHHAREEY FNKVWSGVGL NILDKNNNNF KKEFPSKNED  300
VIYTSCLLRI ALLQNQKLEE WQIYKALYNA FQRRGYDVNI AWKSVQTDDD KENIERMKKY  360
TCENDIELII SDEYKYPCYY DALRLGLWNE DEPTKLNRSI PQHNSNKVRT TEYVAPRELV  420
EKELKQLWLN AQLQLPQLNS ISAEEFLYGE YKIPYGSCVQ KEFKQYRGTK KDWQGVLCQK  480
IPRFDNRIIA KCKLLPKRNV CKANTIENVS FVLLMKLKNL RFTVISGEKL RLSPVQIKQI  540
YENWLEKVED TYNKDLEKAE KLGKENPEKR LNITITRQEI EKIIGEKIID KIEPMKADIS  600
GRSSFCRRAC QIMNKIILDG ELYPQNVDIS EFVDRDNAKN GITEEEIQSM LSKIGDWNNL  660
YIPDNREENA QNASNSRIKT DIMLGNITNP IVRNRLQIFR DLLLNLAEKY GTPDEVIFEF  720
VRDGADNSLY GSKKAQDTER FMKQQEKENE QIINELKDAG LYVNGQNHAN ATYFLMHKLL  780
KSQGGKCIYS GQNISPSNYD ECEIDHIYPR TLGGNDALYN KVVCYRRENQ DKKGRTPYEW  840
LSPDSDKWAN YVNRLNKIKK QLGKKKFELL TSKPEDCEKL IESYNGLAET SHIARVAQQM  900
TAFIFGWGLQ IQGESRRIFV NNGSSTCAIR KRYGLNKLLG DNLKKNRSND KHHALDAICI  960
SFSRDFKYDK EIKKDIIKGF NPEIVKNAID KIMPYPYAND KPFKGNTKPL ETIYGLRTYG  1020
DKSYITQRVE LNSIDKKATK IKSIIDETIK NDLLNKLKEN PTEQEWKLML QNYIHPKKQT  1080
KVKKVMISVS EGEITKDSNN RERMGEFVDF GTKGTQHQFK HSKRHKGQIL YFNEKGVVEV  1140
MPVYSNIKTT DVKDKLQNMG CKLYNKGQMF YSGCLVDIPK PFKAGSKEYP AGRYQIKTIR  1200
SDKVAELEDA CGNKISTNVK YLVPAEFKKV ESKGSGGSPK KKRKV                 1245

SEQ ID NO: 69         moltype = AA  length = 1380
FEATURE               Location/Qualifiers
REGION                1..1380
                      note = Description of Artificial Sequence: Synthetic
                       polypeptide
REGION                1..1380
                      note = Category: cytosine base editor
REGION                1..1380
                      note = Description: linker-His tag-cytidine
                       deaminase-linker-nickase -linker-uracil glycosylase
```

```
                         inhibitor-linker-SV40 NLS
source                  1..1380
                        mol_type = protein
                        organism = synthetic construct
SEQUENCE: 69
MGSSHHHHHH MSSETGPVAV DPTLRRRIEP HEFEVFFDPR ELRKETCLLY EINWGGRHSI  60
WRHTSQNTNK HVEVNFIEKF TTERYFCPNT RCSITWFLSW SPCGECSRAI TEFLSRYPHV  120
TLFIYIARLY HHADPRNRQG LRDLISSGVT IQIMTEQESG YCWRNFVNYS PSNEAHWPRY  180
PHLWVRLYVL ELYCIILGLP PCLNILRRKQ PQLTFFTIAL QSCHYQRLPP HILWATGLKS  240
GSETPGTSES ATPESAMKKK VFAFALGKAS IGYCVRDGFN INEANSIIID KDHAETMSLR  300
DRRRIKKTLD AHHAREEYFN KVWSGVGLNI LDKNNNNFKK EFPSKNEDVI YTSCLLRIAL  360
LQNQKLEEWQ IYKALYNAFQ RRGYDVNIAW KSVQTDDDKE NIERMKKYTC ENDIELIISD  420
EYKYPCYYDA LRLGLWNEDE PTKLNRSIPQ HNSNKVRTTE YVAPRELVEK ELKQLWLNAQ  480
LQLPQLNSIS AEEFLYGEYK IPYGSCVQKE FKQYRGTKKD WQGVLCQKIP RFDNRIIAKC  540
KLLPKRNVCK ANTIENVSFV LLMKLKNLRF TVISGEKLRL SPVQIKQIYE NWLEKVEDTY  600
NKDLEKAEKL GKENPEKRLN ITITRQEIEK IIGEKIIDKI EPMKADISGR SSFCRRACQI  660
MNKIILDGEL YPQNVDISEF VDRDNAKNGI TEEEIQSMLS KIGDWNNLYI PDNREENAQN  720
ASNSRIKTDI MLGNITNPIV RNRLQIFRDL LLNLAEKYGT PDEVIFEFVR DGADNSLYGS  780
KKAQDTERFM KQQEKENEQI INELKDAGLY VNGQNHANAT YFLMHKLLKS QGGKCIYSGQ  840
NISPSNYDEC EIDHIYPRTL GGNDALYNKV VCYRRENQDK KGRTPYEWLS PDSDKWANYV  900
NRLNKIKKQL GKKKFELLTS KPEDCEKLIE SYNGLAETSH IARVAQQMTA FIFGWGLQIQ  960
GESRRIFVNN GSSTCAIRKR YGLNKLLGDN LKKNRSNDKH HALDAICISF SRDFKYDKEI  1020
KKDIIKGFNP EIVKNAIDKI MPYPYANDKP FKGNTKPLET IYGLRTYGDK SYITQRVELN  1080
SIDKKATKIK SIIDETIKND LLNKLKENPT EQEWKLMLQN YIHPKKQTKV KKVMISVSEG  1140
EITKDSNNRE RMGEFVDFGT KGTQHQFKHS KRHKGQILYF NEKGVVEVMP VYSNIKTTDV  1200
KDKLQNMGCK LYNKGQMFYS GCLVDIPKPF KAGSKEYPAG RYQIKTIRSD KVAELEDACG  1260
NKISTNVKYL VPAEFKKVES KGSGGSTNLS DIIEKETGKQ LVIQESILML PEEVEEVIGN  1320
KPESDILVHT AYDESTDENV MLLTSDAPEY KPWALVIQDS NGENKIKMLS GGSPKKKRKV  1380

SEQ ID NO: 70           moltype = AA  length = 1025
FEATURE                 Location/Qualifiers
REGION                  1..1025
                        note = Description of Artificial Sequence: Synthetic
                         polypeptide
REGION                  1..1025
                        note = Category: nickase
REGION                  1..1025
                        note = Description: nMG1-4 (D9A) nickase
source                  1..1025
                        mol_type = protein
                        organism = synthetic construct
SEQUENCE: 70
MKKKVFAFAL GKASIGYCVR DGFNINEANS IIIDKDHAET MSLRDRRRIK KTLDAHHARE  60
EYFNKVWSGV GLNILDKNNN NFKKEFPSKN EDVIYTSCLL RIALLQNQKL EEWQIYKALY  120
NAFQRRGYDV NIAWKSVQTD DDKENIERMK KYTCENDIEL IISDEYKYPC YYDALRLGLW  180
NEDEPTKLNR SIPQHNSNKV RTTEYVAPRE LVEKELKQLW LNAQLQLPQL NSISAEEFLY  240
GEYKIPYGSC VQKEFKQYRG TKKDWQGVLC QKIPRFDNRI IAKCKLLPKR NVCKANTIEN  300
VSFVLLMKLK NLRFTVISGE KLRLSPVQIK QIYENWLEKV EDTYNKDLEK AEKLGKENPE  360
KRLNITITRQ EIEKIIGEKI IDKIEPMKAD ISGRSSFCRR ACQIMNKIIL DGELYPQNVD  420
ISEFVDRDNA KNGITEEEIQ SMLSKIGDWN NLYIPDNREE NAQNASNSRI KTDIMLGNIT  480
NPIVRNRLQI FRDLLLNLAE KYGTPDEVIF EFVRDGADNS LYGSKKAQDT ERFMKQQEKE  540
NEQIINELKD AGLYVNGQNH ANATYFLMHK LLKSQGGKCI YSGQNISPSN YDECEIDHIY  600
PRTLGGNDAL YNKVVCYRRE NQDKKGRTPY EWLSPDSDKW ANYVNRLNKI KKQLGKKKFE  660
LLTSKPEDCE KLIESYNGLA ETSHIARVAQ QMTAFIFGWG LQIQGESRRI FVNNGSSTCA  720
IRKRYGLNKL LGDNLKKNRS NDKHHALDAI CISFSRDFKY DKEIKKDIIK GFNPEIVKNA  780
IDKIMPYPYA NDKPFKGNTK PLETIYGLRT YGDKSYITQR VELNSIDKKA TKIKSIIDET  840
IKNDLLNKLK ENPTEQEWKL MLQNYIHPKK QTKVKKVMIS VSEGEITKDS NNRERMGEFV  900
DFGTKGTQHQ FKHSKRHKGQ ILYFNEKGVV EVMPVYSNIK TTDVKDKLQN MGCKLYNKGQ  960
MFYSGCLVDI PKPFKAGSKE YPAGRYQIKT IRSDKVAELE DACGNKISTN VKYLVPAEFK  1020
KVESK                                                            1025

SEQ ID NO: 71           moltype = AA  length = 1059
FEATURE                 Location/Qualifiers
REGION                  1..1059
                        note = Description of Artificial Sequence: Synthetic
                         polypeptide
REGION                  1..1059
                        note = Category: nickase
REGION                  1..1059
                        note = Description: nMG1-6 (D13A) nickase
source                  1..1059
                        mol_type = protein
                        organism = synthetic construct
SEQUENCE: 71
MEKEKNNHVW GFAIGKGSLG EAVRVGGDFK HIASVLLDPE FGEIKTAALA RRQMRTRKAH  60
KAREKWLEEC LDGTGVEILK RREVGIVDGQ WRLISKGDER LEREFPPNGE EVCYNSIALR  120
CKLLLGEKLE GWQVFKALNS AIQKRGYDEN IPWGEAEEKS SKKDEDDYAQ KLSQYEREKS  180
ELFESFADGE KYDFPCFFKA YKMGLWSPEN PRRVEVRIDC RAQKAKSYVV ARKYVEREFE  240
CLVEAAAKFF PKLKGRAKFI LYGVSETPYA SYYGNMRKKF GLKRGAESDW TALGQKVPRF  300
```

```
DNRIIDKCRL IPRMNVCKIR PLNEARNEKD LLYYEVTLAL KLLNLRFFRN SNIEQLTFEE  360
FKKAFEIASG AKYKMTKTAM KKFLKSISAT ALGDDYAEIE PPKESGRASF SRPAMDILKE  420
LIFSGMPPRE FYGRKIPEIS NTDKNKGVVA SDLDFIKLMG DCPWGGIFIP DVQTYQFANA  480
AFPNPDAQIN KLIGSQNNPI VRHRLTFFFE RIKFLESKYG VPDKVVLEFV RDDFMGEKEK  540
KEMRIAMKKR AEEKMMIAKD LDEHGFKGGN LLLKMELYRK QNGICLYTGD ALPLSELATL  600
EIEHIVPRSR GGPDAQYNYV ITREKTNKLK GDKTPYEWLS SDAKEWASYT DRVNACAKAL  660
GKKRCRLLLE KDAEELVEKY TALAETAHIA KLAQKIVCMH FGFQFGGLSG TKRVFTVPGA  720
LTSRIRKFYG LDRILHNAAA ESENLSFEEF LKFSEDLEKK NRKNKKHHAL DAMCLCFAPT  780
GVDSRRAKLG EILPEKLRSE KAAREFFKSY LDKIMPVDVA PKKPRLEDGI YSKRIIGGKA  840
CMVKRNNLVD LAYKSGLKPV FDIPTLIKLV DKKEKGIINP QIRKMIGEFA ATNPDESAWR  900
KWCEEVRLPS KSGLGARVLR VLVYYGEADE YKDLSKDGCG AYRKGDGHKG QVVWESVDGK  960
YYVEPVYVHA SKAGVMAALN ANPKKKRICG MFNSHCTVDV GDVYNDRGDF ILPAGRYMVN  1020
TILTTGRCVL TNADGEKRNP ININYLMRAG MRRVELSEL                       1059

SEQ ID NO: 72          moltype = AA  length = 1134
FEATURE                Location/Qualifiers
REGION                 1..1134
                       note = Description of Artificial Sequence: Synthetic
                        polypeptide
REGION                 1..1134
                       note = Category: nickase
REGION                 1..1134
                       note = Description: nMG3-6 (D13A) nickase
source                 1..1134
                       mol_type = protein
                       organism = synthetic construct
SEQUENCE: 72
MSTDMKNYRI GVAVGDRSVG LAAIEFDDDG LPIQKLALVT FRHDGGLDPT KNKTPMSRKE  60
TRGIARRTMR MNRERKRRLR NLDNVLENLG YSVPEGPEPE TYEAWTSRAL LASIKLASAD  120
ELNEHLVRAV RHMARHRGWA NPWWSLDQLE KASQEPSETF EIILARAREL FGEKVPANPT  180
LGMLGALAAN NEVLLRPRDE KKRKTGYVRG TPLMFAQVRQ GDQLAELRRI CEVQGIEDQY  240
EALRLGVFDH KHPYVPKERV GKDPLNPSTN RTIRASLEFQ EFRILDSVAN LRVRIGSRAK  300
RELTEAEYDA AVEFLMDYAD KEQPSWADVA EKIGVPGNRL VAPVLEDVQQ KTAPYDRSSA  360
AFEKAMGKKT EARQWWESTD DDQLRSLLIA FLVDATNDTE EAAAEAGLSE LYKSWPAEER  420
EALSNIDFEK GRVAYSQETL SKLSEYMHEY RVGLHEARKA VFGVDDTWRP PLDKLEEPTG  480
QPAVDRVLTI LRRFVLDCER QWGRPRAITV EHTRTGLMGP TQRQKILNEQ KKNRADNERI  540
RDELRESGVD NPSRAEVRRH LIVQEQECQC LYCGTMITTT TSELDHIVPR AGGGSSRREN  600
LAAVCRACNA KKKRELFYAW AGPVKSQETI ERVRQLKAFK DSKKAKMFKN QIRRLNQTEA  660
DEPIDERSLA STSYAAVAVR ERLEQHFNEG LALDDKSRVV LDVYAGAVTR ESRRAGGIDE  720
RILLRGERDK NRFDVRHHAV DAAVMTLLNR SVALTLEQRS QLRRTFYEQG LDKLDRNQLK  780
PEEDWRDFTG LAPASQEKFL EWRKAATILG DLLAEAIEDD SIAVVSPLRL RPQNGSVHLE  840
TISAVKKQTL GSDWPADAVK RIVDPEIYLA MKDALGKLKE LPEDSARSLE LPDGRFVEAD  900
DEVLFFPENA ASILTPRGVA EIGGSIHHAR LYGWLTKKGE LKVGMLRVYG AEFPWLMRES  960
GSRNVLSMPI HRGSQSFRDM QDTTRKAVES GEAVEFAWIT QNDELEFDPD DYIAHGGKDE  1020
LRQFLGFMPE CRWRVDGFKK NYQIRIRPAM LSREQLPSDI QRRLESKTLT KNESLLLKAL  1080
DTGLVVAIGG LLPLETLKVI RRNNLGFPRW RGNGNLPTSF EVRSSALRAL GVEG        1134

SEQ ID NO: 73          moltype = AA  length = 1131
FEATURE                Location/Qualifiers
REGION                 1..1131
                       note = Description of Artificial Sequence: Synthetic
                        polypeptide
REGION                 1..1131
                       note = Category: nickase
REGION                 1..1131
                       note = Description: nMG3-7 (D12A) nickase
source                 1..1131
                       mol_type = protein
                       organism = synthetic construct
SEQUENCE: 73
MSEHTKYRIG IAVGDRSVGL AAIEFDDDGF PLSNLAMVTY RHDGGLDPTT NKSPKSRKET  60
RGVALRTMRM RRRKKSRLKD LDKTLRALGY VVPACEEPQT YEAWKSRALL ATTKVEGAQE  120
LGEHLVRAVR HMARHRGWRN PWWTFNQLEI ASTAPSDTFA KIRERAEKEW PGVVPEEATL  180
GMIGALAASN NVLLRPRTYR KDQPRHSKKL NVLGQEPILV DKVRQEDLLA ELRTICKKQD  240
IEDQYEKLAQ AVFEQTRPYV PLDRVGKDPL QPNKSRASRA SLEFQRFRIL DAVAHLRVRV  300
GASDRRALTD EEHDKAVHFL MGYSKKDVPT WGDVADEIGV EPAHLIAPVI DDVRLNKAPY  360
DRSSTEFEQK MKKKTRARQW WDEANLESRS QLILLVSDPT DETMRLAEVS GLYEVFESWP  420
DEEKEALEGL KVESGRAAYS TDTLNKLSDH MRLKRIDLHE ARKIAFGVDD MWHPPLDRID  480
EPTGQPTVDR VLTIVRRFIF DCERAWGCPE NVVIEHARTG LMGPAQRADV LNEIAKNRKK  540
NDKIREDLRA GGINNPTRAD IRRNAIVQDQ ESQCLYCGAT IGVSYSELDH IVPRAGGGSS  600
RRENLAAVCR ACNDSKKDTP FAVWAKNTSR PVTLEGTIQR LRELKAFKRP KDRRMVDLII  660
RRLKQTEKDD PIDERSLAST SYAATAIRER IEQYFNEKAE KLDLAKVHID VYSGSLTRES  720
RRAGGIDKMV LLRGQSDKNR FDVRHHAIDA AVLTLLNRSV AVTLEQRRLI KQQREYSLEK  780
SRRERDNVWR DFMGLGPAAQ EKFAKWKKTA YVLADIIKEA ISNDAIPVVS PLRLRPQNGS  840
VHLDTVDAVL ERTIGDAWTV DQVHRIVNPQ IYLAFAGYLG NQKALDPDSS RVLALNDGRK  900
LTAEDVIYVF PEKAASILTP RGVVKIGESV HHVRLYAWKN RKGKAEVGML RVFGAEFPWL  960
MRESGVKDVL RVPIHTGSQS YRDLSFTVRK NIEKGEAAEI GWLTQNEELE FNPESYLQEG  1020
GKDKLAKFLA FLPETRWRVD GFPMPDKLRI RPALLSREEI PEGVFRTEEQ SLLEEALTKG  1080
LIIATKGLLS LPDVKVLRRN NLGIPRWRGG SYRPVSLDIQ RAALAALDEQ E           1131
```

```
SEQ ID NO: 74          moltype = AA  length = 1132
FEATURE                Location/Qualifiers
REGION                 1..1132
                       note = Description of Artificial Sequence: Synthetic
                        polypeptide
REGION                 1..1132
                       note = Category: nickase
REGION                 1..1132
                       note = Description: nMG3-8 (D13A) nickase
source                 1..1132
                       mol_type = protein
                       organism = synthetic construct
SEQUENCE: 74
MSTDMKNYRI GVAVGDRSVG LAAIEFDDAG FPIQKLALVT FRHDGGLDPT DNPKSRKETR  60
GEARRRMRMT RRRKQRLRDL DKVLENLGYT VPEGPEPETY EAWTSRALLA SIKLASADEL  120
NEHLVRAVRH IARHRGWVNP WWSLDQLERA SQEPSETFEI ILARARELFG ERVPANPTLG  180
MLGALAANNE VLLRPRAEKK KKTGYVRGTP LLAAQVRQID QVAELRRICE VQGIEEQYET  240
LRNAIFAHKV AYVPTERVGK DPLAPSKNRT IRASLEFQEF RILDSVANLR VRTDSRAKRE  300
LTEGEYDAAV EFLMGYTAKE QPSWADVAEE IGVPGNRLIA PVLEDVQQKT APFDRSSAAF  360
EKAMSKRTEA RQWWEANDDD QLRSLFIMFL ADATNDTEEA AAVAGLPELY MSWPAEEREA  420
LSNIDFEKGR VAYSHETLSK LSEYMHEHRV GLHEARKAVF GVDDTWRPPL AKLEEPTGQP  480
TVDRVLTILR RFVLDCERQW GRPRAITVEH ARIGLVGPAQ RQNILKEQED NRKNNECIRD  540
ELRKSGVENP SRTEVRRHLV VQDQESQCLY CGAVIRTDTS ELDHIVPRAG GGSSRRENLA  600
AVCRYCNSKK DRTLFYDWAG SVRLQETIDR VRQLKAFKDS KKAKMFKNQI RRLRQTEADE  660
PIDERSLAST SYAAVAVRER LEQHFNEGLA PDDKNRVVLD VYAGSVTRES RRAGGIDERI  720
LLRGERDKNR FDVRHHAIDA AVMTLLNRSV ALTLEQRSQL RRAFYEQGLD KLDRDQLKPE  780
EDWRNFIGLS LASQEKFLEW KKVTTVLGDL LAEAIEDDSI AVVSPLRLRP QNGRVHKDTI  840
AAVKKQTLGS AWSADAVKRI VDPEIYLAMK DALGKSKVLP EDSARTLELS DGRYLEADDE  900
VLFFPKNAAS ILTPRGVAEI GGSIHHARLY SWLTKKGELK IGMLRVYGAE FPWLMRESGS  960
HDVLRMPIHP GSQSFRDMQD TTRKAVESSE AVEFAWITQN DELEFEPEDY IAHGGKDELR  1020
QFLEFMPECR WRVDGFKKNY QIRIRPAMLS REQLPSDIQR RLESKTLTEN ESLLLKALDT  1080
GLVVAIGGLL PLGTLKVIRR NNLGFPRWRG NGNLPTSFEV RSSALRALGV EG          1132

SEQ ID NO: 75          moltype = AA  length = 1055
FEATURE                Location/Qualifiers
REGION                 1..1055
                       note = Description of Artificial Sequence: Synthetic
                        polypeptide
REGION                 1..1055
                       note = Category: nickase
REGION                 1..1055
                       note = Description: nMG4-5 (D17A) nickase
source                 1..1055
                       mol_type = protein
                       organism = synthetic construct
SEQUENCE: 75
MGDQQTLQAT SYCLGLAVGV QGVGWAVIDL DDQGQPLGVR RTGVRCFDSG VGSETEFEKG  60
VDEPPSTKRR QARQQRRQLW RRAQRQRRVF RALQEAGLLP PGPPTPVSRD KILRTLDADL  120
AIQFGSLEDR IAAHLLPYRL RALALDTPLP PYALGRAFYH LAQRRGFLSN KKALKEEKEA  180
GEVKKGIAEL QEEMNRAGAR ALGEYFSSLD PEQRRIRNRW TARQMYLDEF DRVWEAQSRY  240
HPRLTDELKT KVRRAIFFQR PLKSQKGLIG RCELEPRHRR APLASLLAQR FRYWQKINDL  300
EVIQPDGVVR PLSPEERHKL AHFLETQAEA TFARIRKLLD LKKPKGSQED FAFNLERGGE  360
KRILGNRTAA KMAAVLGQRW AAMDDEDKRR LVNEILSFEK EAPLARRLVR AWNLDEPTAA  420
QLAALDFEPG YAALSARAIR KLLPLMQREG MRFATARKQV YGDHLLGTRA YDALPPVAKA  480
IPSLRNPAVC RALTEVRKVV NALVRAYGKP AMVRIELARD MKRGRKQRKE TWQAMRENER  540
CRLDARKLLQ DHGIQEPRPA DILKVLLAEE CNWECPYTGK AISMDALIGS QPQFDVEHII  600
PFSRSLDNSF LNKTLCYHEE NRNVKQNRTP FEAYGGDEQR WHEILQRVRR FRGSAAESKL  660
RKFQLRQLPA DFTNRHLNDT RYASRLAADY LALLYGGRVD ANGRQRVQVG TGATTGFLRD  720
EWGLNAILGD NDEKERADHR HHAIDAVVIA LTGPGTVQAL TRAALRAKEL GRRLFVPLDP  780
PWADRDSFLR DVRASVEAIT VSYRVDRKVS GQLHEESNYS KPHMTVDNKG NLVEHRHIRK  840
PLKDMSVEEV EAIVDDRVRK LVQEKLRQLG QEPKKAFADE ANHPYFTTAD GRLVPIHKAR  900
IRKTVATITV GPPQCPRHVA PGLNHHIEIL AVRDPAGAVT HWEGELVSLF EAARRVKAGE  960
PVVRRNHGPN KDFLFSLAKG EYVEMELQPG KRQLFRVTVI SAKQIEFRLH HDARPTMLLR  1020
KTPGARVIRS PGSLFKAKAR KVAVDPLGNV FPAND                          1055

SEQ ID NO: 76          moltype = AA  length = 1003
FEATURE                Location/Qualifiers
REGION                 1..1003
                       note = Description of Artificial Sequence: Synthetic
                        polypeptide
REGION                 1..1003
                       note = Category: nickase
REGION                 1..1003
                       note = Description: nMG14-1 (D23A) nickase
source                 1..1003
                       mol_type = protein
                       organism = synthetic construct
SEQUENCE: 76
```

```
MEITINREIG KLGLPRHLVL GMAPGIASCG FALIDTANHE ILDLGVRLFD SPTHPKTGQS  60
LAVIRRGFRS TRRNIDRTQA RLKHCLQVLK AYGLIPQDAT KEYFHTTKGD KQPLKLRVDG  120
LDRLLNDREW ALVLYSLCKR RGYIPHGEGN QDKSSEGGKV LSALAANKEA IAETSCRTVG  180
EWLAQQPQSR NRGGNYDKYV THAQLIEETH ILFDAQRSFG SKYASPEFEA AYIEVCDWER  240
SRKDFDRRTY DLVGHCSYFP TEKRAARCTL TSELVSAYGA LGNITIIHEN GTSRALSATE  300
RDECIAILFS CEPIRGNKDC AVKFGALRKA LDLSSGDYFK GVPAADEKTR EVYKPKGWRV  360
LRNTLNAANP ILLQRLRDDR DLADAVMEAV AYSSALPVLQ EQLQGLPLSE AEIEALCRLP  420
YSSKALNGYG NRSKKALDML LDCLEEPEVL NLTQAENDCG LLGLRIAGAQ LERSDRLMPY  480
ETWIERTGRT NNNPVVIRSM SQMRKVVNAI CRKWGVPNEI HVELDRELRL PQRAKDEIAK  540
ANKKNEKNRE RIAGQIAELR GCTADEVTGK QIEKYRLWEE QEYFDLYTGA KIEVDRLISD  600
DTYTQIDHIL PFSRTGENSR NNKVLVLAKS NQDKREQTPY EWMSHDGAPS WDAFERRVQE  660
NQKLSRRKKN FLLEKDLDTK EGEFLARSFT DTAYMSREVC AYLADCLLFP DDGAKAHVVP  720
TTGRATAWLR RRWGLNFGSN GEKDRSDDRH HATDACVIAA CSPSLVIKTA RINQETHWSI  780
TRGMNETQRR DAIMKALESV MPWETFANEV RAAHDFVVPT RFVPRKGKGE LFEQTVYRYA  840
GVNAQGKDIA RKASSDKDIV MGNAVVSADE KSVIKVSEML CLRLWHDPEA KKGQGAWYAD  900
PVYKADIPAL KDGTYVPRIA KAHTGRKAWK PVPESAMAKP PLEIYFGDLV QIGDFIGRFS  960
GYNINNANWS FTDRLTRLNL SCPTVGQLNN DLSPVVIRES PIK                   1003

SEQ ID NO: 77          moltype = AA  length = 1082
FEATURE                Location/Qualifiers
REGION                 1..1082
                       note = Description of Artificial Sequence: Synthetic
                        polypeptide
REGION                 1..1082
                       note = Category: nickase
REGION                 1..1082
                       note = Description: nMG15-1 (D8A) nickase
source                 1..1082
                       mol_type = protein
                       organism = synthetic construct
SEQUENCE: 77
MNYVLGLAVG IASVGWAVLE LNEEDNPIRI EGLGARIFDK AEVPKTGASL AAPRRMSRGI  60
RRVIRRRRFR LQRVRSYLKK HNILPAEKVD HLYDVPSAID IYELRKRALT EKVTAEEWAR  120
LLIFFAKHRG FKSNRKKASG DADEGEMLKA IAANAEILKN YRTVGEMLCD NEKFRKRKRN  180
RDGAYNFTVS RAMLMEEIHT LFEIQRNLGQ KFADEKLEEE YVILFAAQRK FDEGPGENSP  240
YAGNQIEKMI GSCTLEGKKE KRAPKASYAF MAFNLWQKIN HLKVNRRGSE RFLTEEERRR  300
IADLAWKKEK LTYGSLRKVL SLDPEDRFVG LRYDLKKGKA ENLEEPVSEA EKRSFSWVKD  360
YHSIRKALDK VEKNRILKLS HEQLDTIATA FSVYKNEETI EKYLEEGGIG KADGEALLER  420
LSGFSKFGHL SLKACYKLLP FLEKGEVYSR ACELAGYDFS KSSLENIDDI PNPVVKRSIS  480
QTLKVINAII LRYGNPVEVH IELARELARS FRDRKMEKG  MQENQAKNEK IRQRLISEFG  540
VLRPKGMDIV KFKLCEEQNG ECAYSQKHFD MEKLLKDPSY AEVDHIIPYS RSFDDSYNNK  600
VLVLTKENRE KRNRIPMEYL ADAPERKNRF IHWVKSTIRN SRKRENLLRT DYTATTENEW  660
KRRNLQDTQY ISKYLYNYLR HHLVLAKGYT ERKRRIIPVN GAVTAYFRKR LGINKIRENG  720
DLHHAVDAVI IACATQGIVN KVSRYSKSRE LWDYEVDMET GEVLQKKNKN TKDVFPEPWL  780
NFRYELEQKV RVRPLDIPET ADITEMEEPF VSHMPNRKIH GPAHKETIRS GRLKEEGYTI  840
SKTALIDLKL TEDKEEIKGY YNKESDRLLY EALKKQLQRY GGKAKEAFKE PFHKPKADGT  900
PGPIVNKVKI MEKSTMLIPV NGGKGLASNG NMVRIDVFRA EEKGKKKYYF IPVYVADTVK  960
EELPNRAVLA HKPYEAWKIM KEENFIFSLY PNDLIFVDAG KEIPFKAALK GSTLDPEKKA  1020
SRFLMYYKGA DIATGSISGV NHDETYKARG VGIQSLREIK KCCIDVLGNI SFASKEKRQT  1080
FR                                                                1082

SEQ ID NO: 78          moltype = AA  length = 1348
FEATURE                Location/Qualifiers
REGION                 1..1348
                       note = Description of Artificial Sequence: Synthetic
                        polypeptide
REGION                 1..1348
                       note = Category: nickase
REGION                 1..1348
                       note = Description: nMG18-1 (D12A) nickase
source                 1..1348
                       mol_type = protein
                       organism = synthetic construct
SEQUENCE: 78
MDQSKEYYIG LAGGTDSVGW AVLNPDYTVV KKRGKSLWGV RLFESGQTAA ERRLARSARR  60
RTDRKKWRLK LLKELFAEEV AACDPAFFAR LAESRYWEDD KKVDGADTLF HDADFTDKDY  120
HRQFPTIYHL RRHLMCCTEK PDIRLLYLAV AHMIKNRGHF LNEGQDLNQV RRFDDVWQNL  180
CAAVSDVLGI ELAVENGAKA AEVLTSSVKI KEKTKQLESV LGEGESEADR SVCKALAGLL  240
AGAKVSAVDL FNGDEALKEC GKFSLAEKSI EELEPDLGDA LGEERFSLLQ YAYAAYNWAV  300
FARLLPEGKT ISEVKTEEYE AYKADLRALK QLVKQYASDQ YYRVFRSAKI KGNYASYVGK  360
TNCGNEKSNP ESCKPEEFFA FLKKELKPLW SQNIPAAASL AAKLESGTLL RRQRSGENAA  420
IPYQAHLQEL QIILKNMQQF YPFLQKADEN GFTPAYKIEK LLTFRIPYYV GPLNDAHKEK  480
GFCWIVKKAD VPVLPWNFDQ VVDENACEDA FIGRMSATCT YLVGENVLPQ NSPLYCRFMV  540
LNELNNLRIR SEKITPALKQ AIFTQLFCAG KGGKVTQKKL LDFLHSQGID ANKQDISGID  600
GDFKASMAPA VKLQSIFTEP LPPEILERLA FALTVSGESH KMLQNRIRAI LPNADNAVIR  660
KVCALKFTGW GRLSQKLLTE IYDVDQTTGE CRSLMDLLWS TNNNLMQLLS GDFTFAAGID  720
AYNAAQNGTE NIFDYDHLVK DLYVSPSVKR GLWQTLLLVK EVRKIMGCDP ARVFIEMARG  780
VSPEQKNKRT VSRKDQLLAL YKACKEDARD WCGELEALPE DKLRSDKLYL YYTQMGRCMY  840
SGEPIRLDDL MHDTANQLYD IDHIYPQSKT KDDSLTNRVL VKRQLNAIKS NDYPLPQTMR  900
```

-continued

```
QTALWKALLE KGLISKQKYL RLTRTTPFTE EELAGFINRQ LVETRQSTKA AAHLLEQLLP  960
NTEVVYVKAG LAADFRQEFG FVKCRDANDF HHAKDAYLNA VVGNVYHEKF TKNPLRFVRS  1020
GQEYSLNLSA LFQNWNIYKG GRVIWQKGED GSLETVRARM AKNDPMVTRY CTEGRGALYD  1080
LQPMKKSKGQ LPLKSSDERL QHIDRYGGYN KLAGAYFTLA AYYKKGKRVK SIESVPLYLA  1140
AKLQRDPAAL QQYLADQLGT DRVEILVPEI KLGTLFKWNG YPMTLSGRTG PQLLFRNAAE  1200
LRTNAEQEQY IKKMSRYLEK CKGRKEPLPI RPAYDKLTPE ENLQLYDAFT QWLTSGIYAK  1260
RLSLQGKFLL EKRDAFAALS PEAQVRQLME ILHLFQCNPV AANLSELGGA AHAGILLASK  1320
NIDGKVPVSI VHQSVTGYFT QEVCLNDL                                   1348

SEQ ID NO: 79          moltype = DNA  length = 37
FEATURE                Location/Qualifiers
misc_feature           1..37
                       note = Description of Artificial Sequence: Synthetic
                        oligonucleotide
misc_feature           1..37
                       note = Category: target sequence
misc_feature           1..37
                       note = Description: nMG1-4 (D9A) protospacer and PAM for in
                        vitro nickase assay
source                 1..37
                       mol_type = other DNA
                       organism = synthetic construct
SEQUENCE: 79
ccgtgagcca ccacgtcgca agcctcgacc aggaagg                          37

SEQ ID NO: 80          moltype = DNA  length = 38
FEATURE                Location/Qualifiers
misc_feature           1..38
                       note = Description of Artificial Sequence: Synthetic
                        oligonucleotide
misc_feature           1..38
                       note = Category: target sequence
misc_feature           1..38
                       note = Description: nMG1-6 (D13A) protospacer and PAM for
                        in vitro nickase assay
source                 1..38
                       mol_type = other DNA
                       organism = synthetic construct
SEQUENCE: 80
tccgtgagcc accacgtcgc aagcctcgac tagaacgg                         38

SEQ ID NO: 81          moltype = DNA  length = 32
FEATURE                Location/Qualifiers
misc_feature           1..32
                       note = Description of Artificial Sequence: Synthetic
                        oligonucleotide
misc_feature           1..32
                       note = Category: target sequence
misc_feature           1..32
                       note = Description: nMG3-6 (D13A) protospacer and PAM for
                        in vitro nickase assay
source                 1..32
                       mol_type = other DNA
                       organism = synthetic construct
SEQUENCE: 81
agccaccacg tcgcaagcct cgacgtgggt ta                               32

SEQ ID NO: 82          moltype = DNA  length = 31
FEATURE                Location/Qualifiers
misc_feature           1..31
                       note = Description of Artificial Sequence: Synthetic
                        oligonucleotide
misc_feature           1..31
                       note = Category: target sequence
misc_feature           1..31
                       note = Description: nMG3-7 (D12A) protospacer and PAM for
                        in vitro nickase assay
source                 1..31
                       mol_type = other DNA
                       organism = synthetic construct
SEQUENCE: 82
agccaccacg tcgcaagcct cgacgtgtta c                                31

SEQ ID NO: 83          moltype = DNA  length = 32
FEATURE                Location/Qualifiers
misc_feature           1..32
                       note = Description of Artificial Sequence: Synthetic
                        oligonucleotide
misc_feature           1..32
```

```
                        note = Category: target sequence
misc_feature            1..32
                        note = Description: nMG3-8 (D13A) protospacer and PAM for
                         in vitro nickase assay
source                  1..32
                        mol_type = other DNA
                        organism = synthetic construct
SEQUENCE: 83
agccaccacg tcgcaagcct cgacgtgggt ta                              32

SEQ ID NO: 84           moltype = DNA  length = 29
FEATURE                 Location/Qualifiers
misc_feature            1..29
                        note = Description of Artificial Sequence: Synthetic
                         oligonucleotide
misc_feature            1..29
                        note = Category: target sequence
misc_feature            1..29
                        note = Description: nMG4-5 (D17A) protospacer and PAM for
                         in vitro nickase assay
source                  1..29
                        mol_type = other DNA
                        organism = synthetic construct
SEQUENCE: 84
agccaccacg tcgcaagcct cgacggcca                                  29

SEQ ID NO: 85           moltype = DNA  length = 40
FEATURE                 Location/Qualifiers
misc_feature            1..40
                        note = Description of Artificial Sequence: Synthetic
                         oligonucleotide
misc_feature            1..40
                        note = Category: target sequence
misc_feature            1..40
                        note = Description: nMG14-1 (D23A) protospacer and PAM for
                         in vitro nickase assay
source                  1..40
                        mol_type = other DNA
                        organism = synthetic construct
SEQUENCE: 85
tccgtgagcc accacgtcgc aagcctcgac ggcggggacg                      40

SEQ ID NO: 86           moltype = DNA  length = 37
FEATURE                 Location/Qualifiers
misc_feature            1..37
                        note = Description of Artificial Sequence: Synthetic
                         oligonucleotide
misc_feature            1..37
                        note = Category: target sequence
misc_feature            1..37
                        note = Description: nMG15-1 (D8A) protospacer and PAM for
                         in vitro nickase assay
source                  1..37
                        mol_type = other DNA
                        organism = synthetic construct
SEQUENCE: 86
ccgtgagcca ccacgtcgca agcctcgact ggacctg                         37

SEQ ID NO: 87           moltype = DNA  length = 32
FEATURE                 Location/Qualifiers
misc_feature            1..32
                        note = Description of Artificial Sequence: Synthetic
                         oligonucleotide
misc_feature            1..32
                        note = Category: target sequence
misc_feature            1..32
                        note = Description: nMG18-1 (D12A) protospacer and PAM for
                         in vitro nickase assay
source                  1..32
                        mol_type = other DNA
                        organism = synthetic construct
SEQUENCE: 87
agccaccacg tcgcaagcct cgaccgtaat tg                              32

SEQ ID NO: 88           moltype = DNA  length = 121
FEATURE                 Location/Qualifiers
misc_feature            1..121
                        note = Description of Artificial Sequence: Synthetic
                         polynucleotide
```

```
misc_feature           1..121
                       note = Category: single guide RNA
misc_feature           1..121
                       note = Description: nMG1-4 (D9A) single guide RNA for in
                        vitro nickase assay
source                 1..121
                       mol_type = other DNA
                       organism = synthetic construct
SEQUENCE: 88
ccaccacgtc gcaagcctcg acgttttgat ttactcgaaa gagtccaatc ataattgacc  60
ggagaataat tgattcctct acaatgtacg aataaattca ttctctaaac cttaaaaatt  120
t                                                                  121

SEQ ID NO: 89          moltype = DNA  length = 99
FEATURE                Location/Qualifiers
misc_feature           1..99
                       note = Description of Artificial Sequence: Synthetic
                        oligonucleotide
misc_feature           1..99
                       note = Category: single guide RNA
misc_feature           1..99
                       note = Description: nMG1-6 (D13A) single guide RNA for in
                        vitro nickase assay
source                 1..99
                       mol_type = other DNA
                       organism = synthetic construct
SEQUENCE: 89
ccaccacgtc gcaagcctcg acgttttgac ttgaaaaagt cttaactgat tttgccgaat  60
ttcaagctct gcattgcacc ttggcattcg gcatatttt                         99

SEQ ID NO: 90          moltype = DNA  length = 110
FEATURE                Location/Qualifiers
misc_feature           1..110
                       note = Description of Artificial Sequence: Synthetic
                        polynucleotide
misc_feature           1..110
                       note = Category: single guide RNA
misc_feature           1..110
                       note = Description: nMG3-6 (D13A) single guide RNA for in
                        vitro nickase assay
source                 1..110
                       mol_type = other DNA
                       organism = synthetic construct
SEQUENCE: 90
ccaccacgtc gcaagcctcg acgttgagaa tcgaaagatt cttaataagg catccttccg  60
atgctgactt ctcaccgtcc gttttccaat aggagcgggc ggtatgtttt             110

SEQ ID NO: 91          moltype = DNA  length = 113
FEATURE                Location/Qualifiers
misc_feature           1..113
                       note = Description of Artificial Sequence: Synthetic
                        polynucleotide
misc_feature           1..113
                       note = Category: single guide RNA
misc_feature           1..113
                       note = Description: nMG3-7 (D12A) single guide RNA for in
                        vitro nickase assay
source                 1..113
                       mol_type = other DNA
                       organism = synthetic construct
SEQUENCE: 91
ccaccacgtc gcaagcctcg acgttgggaa ccgaaaggtt cccaataagg cgcatcttgg  60
cgctgacttc tcaccgtcct cttgctgctt agcagagggc ggtatgtttt ttt         113

SEQ ID NO: 92          moltype = DNA  length = 118
FEATURE                Location/Qualifiers
misc_feature           1..118
                       note = Description of Artificial Sequence: Synthetic
                        polynucleotide
misc_feature           1..118
                       note = Category: single guide RNA
misc_feature           1..118
                       note = Description: nMG3-8 (D13A) single guide RNA for in
                        vitro nickase assay
source                 1..118
                       mol_type = other DNA
                       organism = synthetic construct
SEQUENCE: 92
ccaccacgtc gcaagcctcg acgttgagaa tctttcgaaa gaaagattct taataaggca  60
```

```
tccttccgat gctgacttct caccgtccgg ctcctcttag gaacgggcgg tatgtttt    118

SEQ ID NO: 93          moltype = DNA  length = 124
FEATURE                Location/Qualifiers
misc_feature           1..124
                       note = Description of Artificial Sequence: Synthetic
                        polynucleotide
misc_feature           1..124
                       note = Category: single guide RNA
misc_feature           1..124
                       note = Description: nMG4-5 (D17A) single guide RNA for in
                        vitro nickase assay
source                 1..124
                       mol_type = other DNA
                       organism = synthetic construct
SEQUENCE: 93
ccaccacgtc gcaagcctcg acgctgtggc ttgcggggga aaccccttgt cacagtaagg  60
gactttcgtt cgcgaaaggc aacctcgcca gcatcgctgg gcgaggacca gggcaaggcg  120
attt                                                                124

SEQ ID NO: 94          moltype = DNA  length = 118
FEATURE                Location/Qualifiers
misc_feature           1..118
                       note = Description of Artificial Sequence: Synthetic
                        polynucleotide
misc_feature           1..118
                       note = Category: single guide RNA
misc_feature           1..118
                       note = Description: nMG14-1 (D23A) single guide RNA for in
                        vitro nickase assay
source                 1..118
                       mol_type = other DNA
                       organism = synthetic construct
SEQUENCE: 94
ccaccacgtc gcaagcctcg acgtcttgag cgaaagctcc agacaagggg agccacttaa  60
gtggcttacc cgtaaagtaa cccccgttca atcttcggat tgggcggggc gaactttt    118

SEQ ID NO: 95          moltype = DNA  length = 118
FEATURE                Location/Qualifiers
misc_feature           1..118
                       note = Description of Artificial Sequence: Synthetic
                        polynucleotide
misc_feature           1..118
                       note = Category: single guide RNA
misc_feature           1..118
                       note = Description: nMG15-1 (D8A) single guide RNA for in
                        vitro nickase assay
source                 1..118
                       mol_type = other DNA
                       organism = synthetic construct
SEQUENCE: 95
ccaccacgtc gcaagcctcg acgttgtaat tccctagaaa taggttatta caataaggtc  60
caacaggagt gttggtaccg taaagctcta acggcaccca cgggtgccgt tatctttt    118

SEQ ID NO: 96          moltype = DNA  length = 101
FEATURE                Location/Qualifiers
misc_feature           1..101
                       note = Description of Artificial Sequence: Synthetic
                        polynucleotide
misc_feature           1..101
                       note = Category: single guide RNA
misc_feature           1..101
                       note = Description: nMG18-1 (D12A) single guide RNA for in
                        vitro nickase assay
source                 1..101
                       mol_type = other DNA
                       organism = synthetic construct
SEQUENCE: 96
ccaccacgtc gcaagcctcg acgtttgaga gtagtgaaaa ctacgagttc aaatacaatt  60
ttttcaaatt gccctatagg gccctcacag tgtgagattt t                      101

SEQ ID NO: 97          moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
```

```
                        note = Description: MGA1-4 sgRNA spacer 1 (targeting E.
                         coli lacZ)
source                  1..22
                        mol_type = other DNA
                        organism = synthetic construct
SEQUENCE: 97
cgtttgccgt ctgaatttga cc                                              22

SEQ ID NO: 98           moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA1-4 sgRNA spacer 2 (targeting E.
                         coli lacZ)
source                  1..22
                        mol_type = other DNA
                        organism = synthetic construct
SEQUENCE: 98
gaagatcagg atatgtggcg ga                                              22

SEQ ID NO: 99           moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA1-4 sgRNA spacer 3 (targeting E.
                         coli lacZ)
source                  1..22
                        mol_type = other DNA
                        organism = synthetic construct
SEQUENCE: 99
acgggtaaca gtttctttat gg                                              22

SEQ ID NO: 100          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA1-6 sgRNA spacer 1 (targeting E.
                         coli lacZ)
source                  1..22
                        mol_type = other DNA
                        organism = synthetic construct
SEQUENCE: 100
cgttgctgca taaaccgact ac                                              22

SEQ ID NO: 101          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA1-6 sgRNA spacer 2 (targeting E.
                         coli lacZ)
source                  1..22
                        mol_type = other DNA
                        organism = synthetic construct
SEQUENCE: 101
aaaacccgaa actgtggagc gc                                              22

SEQ ID NO: 102          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
```

```
misc_feature           1..22
                       note = Description: MGA1-6 sgRNA spacer 3 (targeting E.
                        coli lacZ)
source                 1..22
                       mol_type = other DNA
                       organism = synthetic construct
SEQUENCE: 102
gattgaaaat ggtctgctgc tg                                           22

SEQ ID NO: 103         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGA3-6 sgRNA spacer 1 (targeting E.
                        coli lacZ)
source                 1..22
                       mol_type = other DNA
                       organism = synthetic construct
SEQUENCE: 103
tacgggtaac agtttcttta tg                                           22

SEQ ID NO: 104         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGA3-6 sgRNA spacer 2 (targeting E.
                        coli lacZ)
source                 1..22
                       mol_type = other DNA
                       organism = synthetic construct
SEQUENCE: 104
gcgttggcaa tttaaccgcc ag                                           22

SEQ ID NO: 105         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGA3-6 sgRNA spacer 3 (targeting E.
                        coli lacZ)
source                 1..22
                       mol_type = other DNA
                       organism = synthetic construct
SEQUENCE: 105
ctgaatatcg acggtttcca ta                                           22

SEQ ID NO: 106         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGA3-7 sgRNA spacer 1 (targeting E.
                        coli lacZ)
source                 1..22
                       mol_type = other DNA
                       organism = synthetic construct
SEQUENCE: 106
cacatttaat gttgatgaaa gc                                           22

SEQ ID NO: 107         moltype = DNA  length = 22
FEATURE                Location/Qualifiers
misc_feature           1..22
                       note = Description of Artificial Sequence: Synthetic
                        oligonucleotide
misc_feature           1..22
```

```
                        note = Category: spacer
misc_feature            1..22
                        note = Description: MGA3-7 sgRNA spacer 2 (targeting E.
                         coli lacZ)
source                  1..22
                        mol_type = other DNA
                        organism = synthetic construct
SEQUENCE: 107
acacaaatca gcgatttcca tg                                             22

SEQ ID NO: 108          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA3-7 sgRNA spacer 3 (targeting E.
                         coli lacZ)
source                  1..22
                        mol_type = other DNA
                        organism = synthetic construct
SEQUENCE: 108
atggatgagc agacgatggt gc                                             22

SEQ ID NO: 109          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA3-8 sgRNA spacer 1 (targeting E.
                         coli lacZ)
source                  1..22
                        mol_type = other DNA
                        organism = synthetic construct
SEQUENCE: 109
ttcatctgtg gtgcaacggg cg                                             22

SEQ ID NO: 110          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA3-8 sgRNA spacer 2 (targeting E.
                         coli lacZ)
source                  1..22
                        mol_type = other DNA
                        organism = synthetic construct
SEQUENCE: 110
acgagcatca tcctctgcat gg                                             22

SEQ ID NO: 111          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA3-8 sgRNA spacer 3 (targeting E.
                         coli lacZ)
source                  1..22
                        mol_type = other DNA
                        organism = synthetic construct
SEQUENCE: 111
cgacccgcat tgaccctaac gc                                             22

SEQ ID NO: 112          moltype = DNA  length = 22
FEATURE                 Location/Qualifiers
misc_feature            1..22
                        note = Description of Artificial Sequence: Synthetic
                         oligonucleotide
```

```
misc_feature          1..22
                      note = Category: spacer
misc_feature          1..22
                      note = Description: MGA4-5 sgRNA spacer 1 (targeting E.
                       coli lacZ)
source                1..22
                      mol_type = other DNA
                      organism = synthetic construct
SEQUENCE: 112
cacaaatcag cgatttccat gt                                            22

SEQ ID NO: 113        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGA4-5 sgRNA spacer 2 (targeting E.
                       coli lacZ)
source                1..22
                      mol_type = other DNA
                      organism = synthetic construct
SEQUENCE: 113
tgatgaagca gaacaacttt aa                                            22

SEQ ID NO: 114        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGA4-5 sgRNA spacer 3 (targeting E.
                       coli lacZ)
source                1..22
                      mol_type = other DNA
                      organism = synthetic construct
SEQUENCE: 114
aatattgaaa cccacggcat gg                                            22

SEQ ID NO: 115        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGA14-1 sgRNA spacer 1 (targeting E.
                       coli lacZ)
source                1..22
                      mol_type = other DNA
                      organism = synthetic construct
SEQUENCE: 115
tcaaaaaatg gctttcgcta cc                                            22

SEQ ID NO: 116        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGA14-1 sgRNA spacer 2 (targeting E.
                       coli lacZ)
source                1..22
                      mol_type = other DNA
                      organism = synthetic construct
SEQUENCE: 116
aagcagcgtt gttgcagtgc ac                                            22

SEQ ID NO: 117        moltype = DNA  length = 22
FEATURE               Location/Qualifiers
misc_feature          1..22
                      note = Description of Artificial Sequence: Synthetic
```

```
                         oligonucleotide
misc_feature            1..22
                        note = Category: spacer
misc_feature            1..22
                        note = Description: MGA14-1 sgRNA spacer 3 (targeting E.
                         coli lacZ)
source                  1..22
                        mol_type = other DNA
                        organism = synthetic construct
SEQUENCE: 117
tcagccggaa aacctaccgg at                                            22

SEQ ID NO: 118          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA15-1 sgRNA spacer 1 (targeting E.
                         coli lacZ)
source                  1..22
                        mol_type = other DNA
                        organism = synthetic construct
SEQUENCE: 118
gaagatcagg atatgtggcg ga                                            22

SEQ ID NO: 119          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA15-1 sgRNA spacer 2 (targeting E.
                         coli lacZ)
source                  1..22
                        mol_type = other DNA
                        organism = synthetic construct
SEQUENCE: 119
aacgtcgaaa acccgaaact gt                                            22

SEQ ID NO: 120          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA15-1 sgRNA spacer 3 (targeting E.
                         coli lacZ)
source                  1..22
                        mol_type = other DNA
                        organism = synthetic construct
SEQUENCE: 120
aaacccacgg catggtgcca at                                            22

SEQ ID NO: 121          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA18-1 sgRNA spacer 1 (targeting E.
                         coli lacZ)
source                  1..22
                        mol_type = other DNA
                        organism = synthetic construct
SEQUENCE: 121
aaaacccgaa actgtggagc gc                                            22

SEQ ID NO: 122          moltype = DNA  length = 22
FEATURE                 Location/Qualifiers
misc_feature            1..22
```

```
                        note = Description of Artificial Sequence: Synthetic
                         oligonucleotide
misc_feature            1..22
                        note = Category: spacer
misc_feature            1..22
                        note = Description: MGA18-1 sgRNA spacer 2 (targeting E.
                         coli lacZ)
source                  1..22
                        mol_type = other DNA
                        organism = synthetic construct
SEQUENCE: 122
ggcaactctg gctcacagta cg                                            22

SEQ ID NO: 123          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGA18-1 sgRNA spacer 3 (targeting E.
                         coli lacZ)
source                  1..22
                        mol_type = other DNA
                        organism = synthetic construct
SEQUENCE: 123
ccggaaaacc taccggattg at                                            22

SEQ ID NO: 124          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: ABE8.17m sgRNA spacer 1 (targeting E.
                         coli lacZ)
source                  1..20
                        mol_type = other DNA
                        organism = synthetic construct
SEQUENCE: 124
tttctttcac agatgtggat                                               20

SEQ ID NO: 125          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: ABE8.17m sgRNA spacer 2 (targeting E.
                         coli lacZ)
source                  1..20
                        mol_type = other DNA
                        organism = synthetic construct
SEQUENCE: 125
caggatatgt ggcggatgag                                               20

SEQ ID NO: 126          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: ABE8.17m sgRNA spacer 3 (targeting E.
                         coli lacZ)
source                  1..20
                        mol_type = other DNA
                        organism = synthetic construct
SEQUENCE: 126
tgcgaatacg cccacgcgat                                               20

SEQ ID NO: 127          moltype = DNA  length = 22
FEATURE                 Location/Qualifiers
```

```
misc_feature          1..22
                      note = Description of Artificial Sequence: Synthetic
                       oligonucleotide
misc_feature          1..22
                      note = Category: spacer
misc_feature          1..22
                      note = Description: MGC1-4 sgRNA spacer 1 (targeting E.
                       coli lacZ)
source                1..22
                      mol_type = other DNA
                      organism = synthetic construct
SEQUENCE: 127
cggcgtttca tctgtggtgc aa                                           22

SEQ ID NO: 128        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGC1-4 sgRNA spacer 2 (targeting E.
                       coli lacZ)
source                1..22
                      mol_type = other DNA
                      organism = synthetic construct
SEQUENCE: 128
gccaggacag tcgtttgccg tc                                           22

SEQ ID NO: 129        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGC1-4 sgRNA spacer 3 (targeting E.
                       coli lacZ)
source                1..22
                      mol_type = other DNA
                      organism = synthetic construct
SEQUENCE: 129
tcagccgcgc tgtactggag gc                                           22

SEQ ID NO: 130        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGC1-6 sgRNA spacer 1 (targeting E.
                       coli lacZ)
source                1..22
                      mol_type = other DNA
                      organism = synthetic construct
SEQUENCE: 130
cccttcccaa cagttgcgca gc                                           22

SEQ ID NO: 131        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: MGC1-6 sgRNA spacer 2 (targeting E.
                       coli lacZ)
source                1..22
                      mol_type = other DNA
                      organism = synthetic construct
SEQUENCE: 131
ctgtcgtcgt cccctcaaac tg                                           22

SEQ ID NO: 132        moltype = DNA  length = 22
```

```
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC1-6 sgRNA spacer 3 (targeting E.
                        coli lacZ)
source                 1..22
                       mol_type = other DNA
                       organism = synthetic construct
SEQUENCE: 132
ctacgtctga acgtcgaaaa cc                                           22

SEQ ID NO: 133         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-6 sgRNA spacer 1 (targeting E.
                        coli lacZ)
source                 1..22
                       mol_type = other DNA
                       organism = synthetic construct
SEQUENCE: 133
gtgacggcag ttatctggaa ga                                           22

SEQ ID NO: 134         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-6 sgRNA spacer 2 (targeting E.
                        coli lacZ)
source                 1..22
                       mol_type = other DNA
                       organism = synthetic construct
SEQUENCE: 134
atgatttcag ccgcgctgta ct                                           22

SEQ ID NO: 135         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-6 sgRNA spacer 3 (targeting E.
                        coli lacZ)
source                 1..22
                       mol_type = other DNA
                       organism = synthetic construct
SEQUENCE: 135
ttactgccgc ctgttttgac cg                                           22

SEQ ID NO: 136         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-7 sgRNA spacer 1 (targeting E.
                        coli lacZ)
source                 1..22
                       mol_type = other DNA
                       organism = synthetic construct
SEQUENCE: 136
cgaatggcgc tttgcctggt tt                                           22
```

```
SEQ ID NO: 137         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-7 sgRNA spacer 2 (targeting E.
                        coli lacZ)
source                 1..22
                       mol_type = other DNA
                       organism = synthetic construct
SEQUENCE: 137
tcccctcaaa ctggcagatg ca                                           22

SEQ ID NO: 138         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-7 sgRNA spacer 3 (targeting E.
                        coli lacZ)
source                 1..22
                       mol_type = other DNA
                       organism = synthetic construct
SEQUENCE: 138
atctacacca acgtgaccta tc                                           22

SEQ ID NO: 139         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-8 sgRNA spacer 1 (targeting E.
                        coli lacZ)
source                 1..22
                       mol_type = other DNA
                       organism = synthetic construct
SEQUENCE: 139
ttcatctgtg gtgcaacggg cg                                           22

SEQ ID NO: 140         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-8 sgRNA spacer 2 (targeting E.
                        coli lacZ)
source                 1..22
                       mol_type = other DNA
                       organism = synthetic construct
SEQUENCE: 140
acgagcatca tcctctgcat gg                                           22

SEQ ID NO: 141         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC3-8 sgRNA spacer 3 (targeting E.
                        coli lacZ)
source                 1..22
                       mol_type = other DNA
                       organism = synthetic construct
SEQUENCE: 141
cgacccgcat tgaccctaac gc                                           22
```

```
SEQ ID NO: 142          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGC4-5 sgRNA spacer 1 (targeting E.
                         coli lacZ)
source                  1..22
                        mol_type = other DNA
                        organism = synthetic construct
SEQUENCE: 142
caacgggcgc tgggtcggtt ac                                           22

SEQ ID NO: 143          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGC4-5 sgRNA spacer 2 (targeting E.
                         coli lacZ)
source                  1..22
                        mol_type = other DNA
                        organism = synthetic construct
SEQUENCE: 143
cacaaatcag cgatttccat gt                                           22

SEQ ID NO: 144          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGC4-5 sgRNA spacer 3 (targeting E.
                         coli lacZ)
source                  1..22
                        mol_type = other DNA
                        organism = synthetic construct
SEQUENCE: 144
aaggcggcgg agccgacacc ac                                           22

SEQ ID NO: 145          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGC14-1 sgRNA spacer 1 (targeting E.
                         coli lacZ)
source                  1..22
                        mol_type = other DNA
                        organism = synthetic construct
SEQUENCE: 145
cggtcaatcc gccgtttgtt cc                                           22

SEQ ID NO: 146          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: MGC14-1 sgRNA spacer 2 (targeting E.
                         coli lacZ)
source                  1..22
                        mol_type = other DNA
                        organism = synthetic construct
SEQUENCE: 146
```

```
tcctttgcga atacgcccac gc                                            22

SEQ ID NO: 147         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC14-1 sgRNA spacer 3 (targeting E.
                        coli lacZ)
source                 1..22
                       mol_type = other DNA
                       organism = synthetic construct
SEQUENCE: 147
ggtcggctta cggcggtgat tt                                            22

SEQ ID NO: 148         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC15-1 sgRNA spacer 1 (targeting E.
                        coli lacZ)
source                 1..22
                       mol_type = other DNA
                       organism = synthetic construct
SEQUENCE: 148
gccgatcgcg tcacactacg tc                                            22

SEQ ID NO: 149         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC15-1 sgRNA spacer 2 (targeting E.
                        coli lacZ)
source                 1..22
                       mol_type = other DNA
                       organism = synthetic construct
SEQUENCE: 149
gatccgcgct ggctaccggc ga                                            22

SEQ ID NO: 150         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC15-1 sgRNA spacer 3 (targeting E.
                        coli lacZ)
source                 1..22
                       mol_type = other DNA
                       organism = synthetic construct
SEQUENCE: 150
ccttcccgcc cggtgcagta tg                                            22

SEQ ID NO: 151         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC18-1 sgRNA spacer 1 (targeting E.
                        coli lacZ)
source                 1..22
                       mol_type = other DNA
                       organism = synthetic construct
```

```
SEQUENCE: 151
tcagccgcgc tgtactggag gc                                            22

SEQ ID NO: 152         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC18-1 sgRNA spacer 2 (targeting E.
                        coli lacZ)
source                 1..22
                       mol_type = other DNA
                       organism = synthetic construct
SEQUENCE: 152
gaccagccct tcccggctgt gc                                            22

SEQ ID NO: 153         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: MGC18-1 sgRNA spacer 3 (targeting E.
                        coli lacZ)
source                 1..22
                       mol_type = other DNA
                       organism = synthetic construct
SEQUENCE: 153
tccgtttatc cgggcaaacc at                                            22

SEQ ID NO: 154         moltype = DNA  length = 20
FEATURE                Location/Qualifiers
misc_feature           1..20
                       note = Description of Artificial Sequence: Synthetic
                        oligonucleotide
misc_feature           1..20
                       note = Category: spacer
misc_feature           1..20
                       note = Description: BE3 sgRNA spacer 1 (targeting E. coli
                        lacZ)
source                 1..20
                       mol_type = other DNA
                       organism = synthetic construct
SEQUENCE: 154
cctctggatg tcgctccaca                                               20

SEQ ID NO: 155         moltype = DNA  length = 20
FEATURE                Location/Qualifiers
misc_feature           1..20
                       note = Description of Artificial Sequence: Synthetic
                        oligonucleotide
misc_feature           1..20
                       note = Category: spacer
misc_feature           1..20
                       note = Description: BE3 sgRNA spacer 2 (targeting E. coli
                        lacZ)
source                 1..20
                       mol_type = other DNA
                       organism = synthetic construct
SEQUENCE: 155
gggacgcgcg aattgaatta                                               20

SEQ ID NO: 156         moltype = DNA  length = 20
FEATURE                Location/Qualifiers
misc_feature           1..20
                       note = Description of Artificial Sequence: Synthetic
                        oligonucleotide
misc_feature           1..20
                       note = Category: spacer
misc_feature           1..20
                       note = Description: BE3 sgRNA spacer 3 (targeting E. coli
                        lacZ)
source                 1..20
                       mol_type = other DNA
```

```
                        organism = synthetic construct
SEQUENCE: 156
cgttttacaa cgtcgtgact                                            20

SEQ ID NO: 157          moltype = DNA  length = 40
FEATURE                 Location/Qualifiers
misc_feature            1..40
                        note = Description of Artificial Sequence: Synthetic primer
misc_feature            1..40
                        note = Category: primer
misc_feature            1..40
                        note = Description: Site-directed mutagenesis of MG1-4 (D9A)
source                  1..40
                        mol_type = other DNA
                        organism = synthetic construct
SEQUENCE: 157
tgaaaaagaa agttttcgca tttgcgcttg gtaaagcaag                      40

SEQ ID NO: 158          moltype = DNA  length = 27
FEATURE                 Location/Qualifiers
misc_feature            1..27
                        note = Description of Artificial Sequence: Synthetic primer
misc_feature            1..27
                        note = Category: primer
misc_feature            1..27
                        note = Description: Site-directed mutagenesis of MG1-4 (D9A)
source                  1..27
                        mol_type = other DNA
                        organism = synthetic construct
SEQUENCE: 158
tggtatatct ccttcttaaa gttaaac                                    27

SEQ ID NO: 159          moltype = DNA  length = 35
FEATURE                 Location/Qualifiers
misc_feature            1..35
                        note = Description of Artificial Sequence: Synthetic primer
misc_feature            1..35
                        note = Category: primer
misc_feature            1..35
                        note = Description: Site-directed mutagenesis of MG1-6
                         (D13A)
source                  1..35
                        mol_type = other DNA
                        organism = synthetic construct
SEQUENCE: 159
accatgtttg gggctttgcg attggcaaag ggtct                           35

SEQ ID NO: 160          moltype = DNA  length = 25
FEATURE                 Location/Qualifiers
misc_feature            1..25
                        note = Description of Artificial Sequence: Synthetic primer
misc_feature            1..25
                        note = Category: primer
misc_feature            1..25
                        note = Description: Site-directed mutagenesis of MG1-6
                         (D13A)
source                  1..25
                        mol_type = other DNA
                        organism = synthetic construct
SEQUENCE: 160
tgttcttttc tttctccatg gtata                                      25

SEQ ID NO: 161          moltype = DNA  length = 35
FEATURE                 Location/Qualifiers
misc_feature            1..35
                        note = Description of Artificial Sequence: Synthetic primer
misc_feature            1..35
                        note = Category: primer
misc_feature            1..35
                        note = Description: Site-directed mutagenesis of MG3-6
                         (D13A)
source                  1..35
                        mol_type = other DNA
                        organism = synthetic construct
SEQUENCE: 161
attatcgcat tggcgtggcg gtcggggatc gcagc                           35

SEQ ID NO: 162          moltype = DNA  length = 21
FEATURE                 Location/Qualifiers
```

```
misc_feature           1..21
                       note = Description of Artificial Sequence: Synthetic primer
misc_feature           1..21
                       note = Category: primer
misc_feature           1..21
                       note = Description: Site-directed mutagenesis of MG3-6
                        (D13A)
source                 1..21
                       mol_type = other DNA
                       organism = synthetic construct
SEQUENCE: 162
tcttcatatc ggttgacatg g                                            21

SEQ ID NO: 163         moltype = DNA  length = 35
FEATURE                Location/Qualifiers
misc_feature           1..35
                       note = Description of Artificial Sequence: Synthetic primer
misc_feature           1..35
                       note = Category: primer
misc_feature           1..35
                       note = Description: Site-directed mutagenesis of MG3-7
                        (D12A)
source                 1..35
                       mol_type = other DNA
                       organism = synthetic construct
SEQUENCE: 163
agtaccgcat tggcatcgcg gtgggcgatc gctcg                             35

SEQ ID NO: 164         moltype = DNA  length = 22
FEATURE                Location/Qualifiers
misc_feature           1..22
                       note = Description of Artificial Sequence: Synthetic primer
misc_feature           1..22
                       note = Category: primer
misc_feature           1..22
                       note = Description: Site-directed mutagenesis of MG3-7
                        (D12A)
source                 1..22
                       mol_type = other DNA
                       organism = synthetic construct
SEQUENCE: 164
tagtatgttc gctcatggta ta                                           22

SEQ ID NO: 165         moltype = DNA  length = 35
FEATURE                Location/Qualifiers
misc_feature           1..35
                       note = Description of Artificial Sequence: Synthetic primer
misc_feature           1..35
                       note = Category: primer
misc_feature           1..35
                       note = Description: Site-directed mutagenesis of MG3-8
                        (D13A)
source                 1..35
                       mol_type = other DNA
                       organism = synthetic construct
SEQUENCE: 165
attaccgcat tggcgtggcg gtaggtgatc gtagt                             35

SEQ ID NO: 166         moltype = DNA  length = 21
FEATURE                Location/Qualifiers
misc_feature           1..21
                       note = Description of Artificial Sequence: Synthetic primer
misc_feature           1..21
                       note = Category: primer
misc_feature           1..21
                       note = Description: Site-directed mutagenesis of MG3-8
                        (D13A)
source                 1..21
                       mol_type = other DNA
                       organism = synthetic construct
SEQUENCE: 166
tcttcatatc agtgctcatg g                                            21

SEQ ID NO: 167         moltype = DNA  length = 35
FEATURE                Location/Qualifiers
misc_feature           1..35
                       note = Description of Artificial Sequence: Synthetic primer
misc_feature           1..35
                       note = Category: primer
```

```
misc_feature           1..35
                       note = Description: Site-directed mutagenesis of MG4-5
                        (D17A)
source                 1..35
                       mol_type = other DNA
                       organism = synthetic construct
SEQUENCE: 167
gctactgctt gggcctggcg gtaggtgtgc aagga                              35

SEQ ID NO: 168         moltype = DNA  length = 18
FEATURE                Location/Qualifiers
misc_feature           1..18
                       note = Description of Artificial Sequence: Synthetic primer
misc_feature           1..18
                       note = Category: primer
misc_feature           1..18
                       note = Description: Site-directed mutagenesis of MG4-5
                        (D17A)
source                 1..18
                       mol_type = other DNA
                       organism = synthetic construct
SEQUENCE: 168
tggtcgcctg cagggtct                                                 18

SEQ ID NO: 169         moltype = DNA  length = 35
FEATURE                Location/Qualifiers
misc_feature           1..35
                       note = Description of Artificial Sequence: Synthetic primer
misc_feature           1..35
                       note = Category: primer
misc_feature           1..35
                       note = Description: Site-directed mutagenesis of MG14-1
                        (D23A)
source                 1..35
                       mol_type = other DNA
                       organism = synthetic construct
SEQUENCE: 169
acctggttct gggtatggcg ccgggcatcg cctca                              35

SEQ ID NO: 170         moltype = DNA  length = 18
FEATURE                Location/Qualifiers
misc_feature           1..18
                       note = Description of Artificial Sequence: Synthetic primer
misc_feature           1..18
                       note = Category: primer
misc_feature           1..18
                       note = Description: Site-directed mutagenesis of MG14-1
                        (D23A)
source                 1..18
                       mol_type = other DNA
                       organism = synthetic construct
SEQUENCE: 170
ggcgaggcaa gcctaatt                                                 18

SEQ ID NO: 171         moltype = DNA  length = 35
FEATURE                Location/Qualifiers
misc_feature           1..35
                       note = Description of Artificial Sequence: Synthetic primer
misc_feature           1..35
                       note = Category: primer
misc_feature           1..35
                       note = Description: Site-directed mutagenesis of MG15-1
                        (D8A)
source                 1..35
                       mol_type = other DNA
                       organism = synthetic construct
SEQUENCE: 171
actatgtgct cggcctggcg gtcggtattg cttca                              35

SEQ ID NO: 172         moltype = DNA  length = 25
FEATURE                Location/Qualifiers
misc_feature           1..25
                       note = Description of Artificial Sequence: Synthetic primer
misc_feature           1..25
                       note = Category: primer
misc_feature           1..25
                       note = Description: Site-directed mutagenesis of MG15-1
                        (D8A)
source                 1..25
```

```
                        mol_type = other DNA
                        organism = synthetic construct
SEQUENCE: 172
tcatggtata tctccttctt aaagt                              25

SEQ ID NO: 173          moltype = DNA  length = 40
FEATURE                 Location/Qualifiers
misc_feature            1..40
                        note = Description of Artificial Sequence: Synthetic primer
misc_feature            1..40
                        note = Category: primer
misc_feature            1..40
                        note = Description: Site-directed mutagenesis of MG18-1
                         (D12A)
source                  1..40
                        mol_type = other DNA
                        organism = synthetic construct
SEQUENCE: 173
taaagagtac tacattggtc tggcgggtgg tacggactcg              40

SEQ ID NO: 174          moltype = DNA  length = 21
FEATURE                 Location/Qualifiers
misc_feature            1..21
                        note = Description of Artificial Sequence: Synthetic primer
misc_feature            1..21
                        note = Category: primer
misc_feature            1..21
                        note = Description: Site-directed mutagenesis of MG18-1
                         (D12A)
source                  1..21
                        mol_type = other DNA
                        organism = synthetic construct
SEQUENCE: 174
ctctggtcca tggtatatct c                                  21

SEQ ID NO: 175          moltype = DNA  length = 42
FEATURE                 Location/Qualifiers
misc_feature            1..42
                        note = Description of Artificial Sequence: Synthetic primer
misc_feature            1..42
                        note = Category: primer
misc_feature            1..42
                        note = Description: Site-directed mutagenesis of SpCas9
                         (D10A)
source                  1..42
                        mol_type = other DNA
                        organism = synthetic construct
SEQUENCE: 175
gataagaaat actcaatagg actggcgatt ggcacaaata gc           42

SEQ ID NO: 176          moltype = DNA  length = 25
FEATURE                 Location/Qualifiers
misc_feature            1..25
                        note = Description of Artificial Sequence: Synthetic primer
misc_feature            1..25
                        note = Category: primer
misc_feature            1..25
                        note = Description: Site-directed mutagenesis of SpCas9
                         (D10A)
source                  1..25
                        mol_type = other DNA
                        organism = synthetic construct
SEQUENCE: 176
catggtatat ctccttctta aagtt                              25

SEQ ID NO: 177          moltype = DNA  length = 21
FEATURE                 Location/Qualifiers
misc_feature            1..21
                        note = Description of Artificial Sequence: Synthetic primer
misc_feature            1..21
                        note = Category: primer
misc_feature            1..21
                        note = Description: For lacZ sequencing
source                  1..21
                        mol_type = other DNA
                        organism = synthetic construct
SEQUENCE: 177
ccaggcttta cactttatgc t                                  21
```

```
SEQ ID NO: 178         moltype = DNA  length = 19
FEATURE                Location/Qualifiers
misc_feature           1..19
                       note = Description of Artificial Sequence: Synthetic primer
misc_feature           1..19
                       note = Category: primer
misc_feature           1..19
                       note = Description: For lacZ sequencing
source                 1..19
                       mol_type = other DNA
                       organism = synthetic construct
SEQUENCE: 178
gtatgtggtg gatgaagcc                                               19

SEQ ID NO: 179         moltype = DNA  length = 18
FEATURE                Location/Qualifiers
misc_feature           1..18
                       note = Description of Artificial Sequence: Synthetic primer
misc_feature           1..18
                       note = Category: primer
misc_feature           1..18
                       note = Description: Amplify the fragment for nickase assay
source                 1..18
                       mol_type = other DNA
                       organism = synthetic construct
SEQUENCE: 179
agcttccagg gggaaacg                                                18

SEQ ID NO: 180         moltype = DNA  length = 26
FEATURE                Location/Qualifiers
misc_feature           1..26
                       note = Description of Artificial Sequence: Synthetic primer
misc_feature           1..26
                       note = Category: primer
misc_feature           1..26
                       note = Description: Amplify the fragment for nickase assay
source                 1..26
                       mol_type = other DNA
                       organism = synthetic construct
SEQUENCE: 180
attaacctat aaaaataggc gtatca                                       26

SEQ ID NO: 181         moltype = DNA  length = 60
FEATURE                Location/Qualifiers
misc_feature           1..60
                       note = Description of Artificial Sequence: Synthetic primer
misc_feature           1..60
                       note = Category: primer
misc_feature           1..60
                       note = Description: Amplify T7 promoter-His tag-adenine
                        deaminase for MGA entry plasmid
source                 1..60
                       mol_type = other DNA
                       organism = synthetic construct
SEQUENCE: 181
gatataccat gggcagcagt catcatcatc accatcactc cgaggttgaa tttagtcatg  60

SEQ ID NO: 182         moltype = DNA  length = 60
FEATURE                Location/Qualifiers
misc_feature           1..60
                       note = Description of Artificial Sequence: Synthetic primer
misc_feature           1..60
                       note = Category: primer
misc_feature           1..60
                       note = Description: Amplify T7 promoter-His tag-adenine
                        deaminase for MGA entry plasmid
source                 1..60
                       mol_type = other DNA
                       organism = synthetic construct
SEQUENCE: 182
agactttcct cttcttcttg ggagacccgc cagagcctcg aggacccacc agagctgcct  60

SEQ ID NO: 183         moltype = DNA  length = 55
FEATURE                Location/Qualifiers
misc_feature           1..55
                       note = Description of Artificial Sequence: Synthetic primer
misc_feature           1..55
                       note = Category: primer
misc_feature           1..55
```

```
                         note = Description: Amplify SV40 NLS-vector backbone for
                          MGA entry plasmid
source                   1..55
                         mol_type = other DNA
                         organism = synthetic construct
SEQUENCE: 183
tctggcgggt ctcccaagaa gaagaggaaa gtctaagatc cggctgctaa caaag       55

SEQ ID NO: 184           moltype = DNA  length = 45
FEATURE                  Location/Qualifiers
misc_feature             1..45
                         note = Description of Artificial Sequence: Synthetic primer
misc_feature             1..45
                         note = Category: primer
misc_feature             1..45
                         note = Description: Amplify SV40 NLS-vector backbone for
                          MGA entry plasmid
source                   1..45
                         mol_type = other DNA
                         organism = synthetic construct
SEQUENCE: 184
ctccttgcat gctctagaat taattaaacc attccttgcg gcggc                  45

SEQ ID NO: 185           moltype = DNA  length = 48
FEATURE                  Location/Qualifiers
misc_feature             1..48
                         note = Description of Artificial Sequence: Synthetic primer
misc_feature             1..48
                         note = Category: primer
misc_feature             1..48
                         note = Description: Amplify vector backbone for MGA entry
                          plasmid
source                   1..48
                         mol_type = other DNA
                         organism = synthetic construct
SEQUENCE: 185
aggaatggtt taattaattc tagagcatgc aaggagatgg cgcccaac               48

SEQ ID NO: 186           moltype = DNA  length = 56
FEATURE                  Location/Qualifiers
misc_feature             1..56
                         note = Description of Artificial Sequence: Synthetic primer
misc_feature             1..56
                         note = Category: primer
misc_feature             1..56
                         note = Description: Amplify vector backbone for MGA entry
                          plasmid
source                   1..56
                         mol_type = other DNA
                         organism = synthetic construct
SEQUENCE: 186
gtgatggtga tgatgatgac tgctgcccat ggtatatctc cttcttaaag ttaaac      56

SEQ ID NO: 187           moltype = DNA  length = 60
FEATURE                  Location/Qualifiers
misc_feature             1..60
                         note = Description of Artificial Sequence: Synthetic primer
misc_feature             1..60
                         note = Category: primer
misc_feature             1..60
                         note = Description: Amplify T7 promoter-His-tag-cytosine
                          deaminase for MGC entry plasmid
source                   1..60
                         mol_type = other DNA
                         organism = synthetic construct
SEQUENCE: 187
aggagatata ccatgggcag cagtcatcat catcaccatc acatgtcgtc tgagaccggg  60

SEQ ID NO: 188           moltype = DNA  length = 60
FEATURE                  Location/Qualifiers
misc_feature             1..60
                         note = Description of Artificial Sequence: Synthetic primer
misc_feature             1..60
                         note = Category: primer
misc_feature             1..60
                         note = Description: Amplify T7 promoter-His-tag-cytosine
                          deaminase for MGC entry plasmid
source                   1..60
                         mol_type = other DNA
```

```
                         organism = synthetic construct
SEQUENCE: 188
taatatctga aagattggta gaaccaccag acccgcggca gattcaggtg tcgcactttc  60

SEQ ID NO: 189           moltype = DNA  length = 44
FEATURE                  Location/Qualifiers
misc_feature             1..44
                         note = Description of Artificial Sequence: Synthetic primer
misc_feature             1..44
                         note = Category: primer
misc_feature             1..44
                         note = Description: Amplify UGI-SV40 NLS for MGC entry
                          plasmid
source                   1..44
                         mol_type = other DNA
                         organism = synthetic construct
SEQUENCE: 189
cgacacctga atctgccgcg ggtctggtgg ttctaccaat cttt                    44

SEQ ID NO: 190           moltype = DNA  length = 60
FEATURE                  Location/Qualifiers
misc_feature             1..60
                         note = Description of Artificial Sequence: Synthetic primer
misc_feature             1..60
                         note = Category: primer
misc_feature             1..60
                         note = Description: Amplify UGI-SV40 NLS for MGC entry
                          plasmid
source                   1..60
                         mol_type = other DNA
                         organism = synthetic construct
SEQUENCE: 190
ttagactttc ctcttcttct tgggagaacc accagaaagc attttgatct tgttttcgcc  60

SEQ ID NO: 191           moltype = DNA  length = 54
FEATURE                  Location/Qualifiers
misc_feature             1..54
                         note = Description of Artificial Sequence: Synthetic primer
misc_feature             1..54
                         note = Category: primer
misc_feature             1..54
                         note = Description: Amplify SV40 NLS-vector backbone for
                          MGC entry plasmid
source                   1..54
                         mol_type = other DNA
                         organism = synthetic construct
SEQUENCE: 191
ctggtggttc tcccaagaag aagaggaaag tctaagatcc ggctgctaac aaag        54

SEQ ID NO: 192           moltype = DNA  length = 45
FEATURE                  Location/Qualifiers
misc_feature             1..45
                         note = Description of Artificial Sequence: Synthetic primer
misc_feature             1..45
                         note = Category: primer
misc_feature             1..45
                         note = Description: Amplify SV40 NLS-vector backbone for
                          MGC entry plasmid
source                   1..45
                         mol_type = other DNA
                         organism = synthetic construct
SEQUENCE: 192
ctccttgcat gctctagaat taattaacca ttccttgcgg cggcg                  45

SEQ ID NO: 193           moltype = DNA  length = 48
FEATURE                  Location/Qualifiers
misc_feature             1..48
                         note = Description of Artificial Sequence: Synthetic primer
misc_feature             1..48
                         note = Category: primer
misc_feature             1..48
                         note = Description: Amplify vector backbone for MGC entry
                          plasmid
source                   1..48
                         mol_type = other DNA
                         organism = synthetic construct
SEQUENCE: 193
aggaatggtt aattaattct agagcatgca aggagatggc gcccaaca               48
```

```
SEQ ID NO: 194          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify vector backbone for MGC entry
                         plasmid
source                  1..50
                        mol_type = other DNA
                        organism = synthetic construct
SEQUENCE: 194
gtgatgatga tgactgctgc ccatggtata tctccttctt aaagttaaac             50

SEQ ID NO: 195          moltype = DNA  length = 55
FEATURE                 Location/Qualifiers
misc_feature            1..55
                        note = Description of Artificial Sequence: Synthetic primer
misc_feature            1..55
                        note = Category: primer
misc_feature            1..55
                        note = Description: Amplify nMG1-4 (D9A) for pMGA
                         expression plasmid
source                  1..55
                        mol_type = other DNA
                        organism = synthetic construct
SEQUENCE: 195
aaagtagtgg aggcagctct ggtgggtcca tgaaaaagaa agttttcgca tttgc       55

SEQ ID NO: 196          moltype = DNA  length = 55
FEATURE                 Location/Qualifiers
misc_feature            1..55
                        note = Description of Artificial Sequence: Synthetic primer
misc_feature            1..55
                        note = Category: primer
misc_feature            1..55
                        note = Description: Amplify nMG1-4 (D9A) for pMGA
                         expression plasmid
source                  1..55
                        mol_type = other DNA
                        organism = synthetic construct
SEQUENCE: 196
ctcttcttct tgggagaccc gccagagcct ttgctttcga cttttttaaa ttcgg       55

SEQ ID NO: 197          moltype = DNA  length = 54
FEATURE                 Location/Qualifiers
misc_feature            1..54
                        note = Description of Artificial Sequence: Synthetic primer
misc_feature            1..54
                        note = Category: primer
misc_feature            1..54
                        note = Description: Amplify nMG1-6 (D13A) for pMGA
                         expression plasmid
source                  1..54
                        mol_type = other DNA
                        organism = synthetic construct
SEQUENCE: 197
gaaagtagtg gaggcagctc tggtgggtcc atggagaaag aaaagaacaa ccat        54

SEQ ID NO: 198          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify nMG1-6 (D13A) for pMGA
                         expression plasmid
source                  1..50
                        mol_type = other DNA
                        organism = synthetic construct
SEQUENCE: 198
cctcttcttc ttgggagacc cgccagagcc cagttcactt aactcgacgc             50

SEQ ID NO: 199          moltype = DNA  length = 55
FEATURE                 Location/Qualifiers
misc_feature            1..55
                        note = Description of Artificial Sequence: Synthetic primer
```

```
misc_feature           1..55
                       note = Category: primer
misc_feature           1..55
                       note = Description: Amplify nMG3-6 (D13A) for pMGA
                        expression plasmid
source                 1..55
                       mol_type = other DNA
                       organism = synthetic construct
SEQUENCE: 199
gaaagtagtg gaggcagctc tggtgggtcc atgtcaaccg atatgaagaa ttatc       55

SEQ ID NO: 200         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify nMG3-6 (D13A) for pMGA
                        expression plasmid
source                 1..48
                       mol_type = other DNA
                       organism = synthetic construct
SEQUENCE: 200
cctcttcttc ttgggagacc cgccagagcc cccctctact ccaagcgc               48

SEQ ID NO: 201         moltype = DNA  length = 52
FEATURE                Location/Qualifiers
misc_feature           1..52
                       note = Description of Artificial Sequence: Synthetic primer
misc_feature           1..52
                       note = Category: primer
misc_feature           1..52
                       note = Description: Amplify nMG3-7 (D12A) for pMGA
                        expression plasmid
source                 1..52
                       mol_type = other DNA
                       organism = synthetic construct
SEQUENCE: 201
gaaagtagtg gaggcagctc tggtgggtcc atgagcgaac atactaagta cc          52

SEQ ID NO: 202         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify nMG3-7 (D12A) for pMGA
                        expression plasmid
source                 1..50
                       mol_type = other DNA
                       organism = synthetic construct
SEQUENCE: 202
cctcttcttc ttgggagacc cgccagagcc ttcttgttca tcaagggctg             50

SEQ ID NO: 203         moltype = DNA  length = 54
FEATURE                Location/Qualifiers
misc_feature           1..54
                       note = Description of Artificial Sequence: Synthetic primer
misc_feature           1..54
                       note = Category: primer
misc_feature           1..54
                       note = Description: Amplify nMG3-8 (D13A) for pMGA
                        expression plasmid
source                 1..54
                       mol_type = other DNA
                       organism = synthetic construct
SEQUENCE: 203
gaaagtagtg gaggcagctc tggtgggtcc atgagcactg atatgaagaa ttac        54

SEQ ID NO: 204         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify nMG3-8 (D13A) for pMGA
```

```
                         expression plasmid
source                  1..48
                        mol_type = other DNA
                        organism = synthetic construct
SEQUENCE: 204
cctcttcttc ttgggagacc cgccagagcc accctcgacg cctaacgc              48

SEQ ID NO: 205          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG4-5 (D17A) for pMGA
                         expression plasmid
source                  1..48
                        mol_type = other DNA
                        organism = synthetic construct
SEQUENCE: 205
gaaagtagtg gaggcagctc tggtgggtcc atgggagatc agcagacc              48

SEQ ID NO: 206          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG4-5 (D17A) for pMGA
                         expression plasmid
source                  1..48
                        mol_type = other DNA
                        organism = synthetic construct
SEQUENCE: 206
cctcttcttc ttgggagacc cgccagagcc atcgttcgcg ggaaacac              48

SEQ ID NO: 207          moltype = DNA  length = 55
FEATURE                 Location/Qualifiers
misc_feature            1..55
                        note = Description of Artificial Sequence: Synthetic primer
misc_feature            1..55
                        note = Category: primer
misc_feature            1..55
                        note = Description: Amplify nMG14-1 (D23A) for pMGA
                         expression plasmid
source                  1..55
                        mol_type = other DNA
                        organism = synthetic construct
SEQUENCE: 207
gaaagtagtg gaggcagctc tggtgggtcc atggaaatta caattaaccg tgaga       55

SEQ ID NO: 208          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG14-1 (D23A) for pMGA
                         expression plasmid
source                  1..48
                        mol_type = other DNA
                        organism = synthetic construct
SEQUENCE: 208
cctcttcttc ttgggagacc cgccagagcc cttaatcggg ctctcacg              48

SEQ ID NO: 209          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify nMG15-1 (D8A) for pMGA
                         expression plasmid
source                  1..49
                        mol_type = other DNA
                        organism = synthetic construct
```

```
SEQUENCE: 209
gaaagtagtg gaggcagctc tggtgggtcc atgaactatg tgctcggcc              49

SEQ ID NO: 210         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify nMG15-1 (D8A) for pMGA
                        expression plasmid
source                 1..48
                       mol_type = other DNA
                       organism = synthetic construct
SEQUENCE: 210
cctcttcttc ttgggagacc cgccagagcc acggaacgtt tggcgctt               48

SEQ ID NO: 211         moltype = DNA  length = 52
FEATURE                Location/Qualifiers
misc_feature           1..52
                       note = Description of Artificial Sequence: Synthetic primer
misc_feature           1..52
                       note = Category: primer
misc_feature           1..52
                       note = Description: Amplify nMG18-1 (D12A) for pMGA
                        expression plasmid
source                 1..52
                       mol_type = other DNA
                       organism = synthetic construct
SEQUENCE: 211
gaaagtagtg gaggcagctc tggtgggtcc atggaccaga gtaaagagta ct          52

SEQ ID NO: 212         moltype = DNA  length = 54
FEATURE                Location/Qualifiers
misc_feature           1..54
                       note = Description of Artificial Sequence: Synthetic primer
misc_feature           1..54
                       note = Category: primer
misc_feature           1..54
                       note = Description: Amplify nMG18-1 (D12A) for pMGA
                        expression plasmid
source                 1..54
                       mol_type = other DNA
                       organism = synthetic construct
SEQUENCE: 212
cctcttcttc ttgggagacc cgccagagcc cagatcattt aaacacacct cttg        54

SEQ ID NO: 213         moltype = DNA  length = 55
FEATURE                Location/Qualifiers
misc_feature           1..55
                       note = Description of Artificial Sequence: Synthetic primer
misc_feature           1..55
                       note = Category: primer
misc_feature           1..55
                       note = Description: Amplify SpCas9 (D10A) for pMGA
                        expression plasmid
source                 1..55
                       mol_type = other DNA
                       organism = synthetic construct
SEQUENCE: 213
gaaagtagtg gaggcagctc tggtgggtcc atggataaga aatactcaat aggac       55

SEQ ID NO: 214         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify SpCas9 (D10A) for pMGA
                        expression plasmid
source                 1..48
                       mol_type = other DNA
                       organism = synthetic construct
SEQUENCE: 214
cctcttcttc ttgggagacc cgccagagcc gtcacctccc agctgact               48

SEQ ID NO: 215         moltype = DNA  length = 56
```

```
FEATURE                 Location/Qualifiers
misc_feature            1..56
                        note = Description of Artificial Sequence: Synthetic primer
misc_feature            1..56
                        note = Category: primer
misc_feature            1..56
                        note = Description: Amplify nMG1-4 (D9A) for pMGC
                         expression plasmid
source                  1..56
                        mol_type = other DNA
                        organism = synthetic construct
SEQUENCE: 215
acatccgaaa gtgcgacacc tgaatctgcc atgaaaaaga aagttttcgc atttgc      56

SEQ ID NO: 216          moltype = DNA  length = 56
FEATURE                 Location/Qualifiers
misc_feature            1..56
                        note = Description of Artificial Sequence: Synthetic primer
misc_feature            1..56
                        note = Category: primer
misc_feature            1..56
                        note = Description: Amplify nMG1-4 (D9A) for pMGC
                         expression plasmid
source                  1..56
                        mol_type = other DNA
                        organism = synthetic construct
SEQUENCE: 216
atctgaaaga ttggtagaac caccagaccc tttgctttcg actttttttaa attcgg      56

SEQ ID NO: 217          moltype = DNA  length = 54
FEATURE                 Location/Qualifiers
misc_feature            1..54
                        note = Description of Artificial Sequence: Synthetic primer
misc_feature            1..54
                        note = Category: primer
misc_feature            1..54
                        note = Description: Amplify nMG1-6 (D13A) for pMGC
                         expression plasmid
source                  1..54
                        mol_type = other DNA
                        organism = synthetic construct
SEQUENCE: 217
acatccgaaa gtgcgacacc tgaatctgcc atggagaaag aaaagaacaa ccat        54

SEQ ID NO: 218          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify nMG1-6 (D13A) for pMGC
                         expression plasmid
source                  1..50
                        mol_type = other DNA
                        organism = synthetic construct
SEQUENCE: 218
atctgaaaga ttggtagaac caccagaccc cagttcactt aactcgacgc             50

SEQ ID NO: 219          moltype = DNA  length = 54
FEATURE                 Location/Qualifiers
misc_feature            1..54
                        note = Description of Artificial Sequence: Synthetic primer
misc_feature            1..54
                        note = Category: primer
misc_feature            1..54
                        note = Description: Amplify nMG3-6 (D13A) for pMGC
                         expression plasmid
source                  1..54
                        mol_type = other DNA
                        organism = synthetic construct
SEQUENCE: 219
catccgaaag tgcgacacct gaatctgcca tgtcaaccga tatgaagaat tatc        54

SEQ ID NO: 220          moltype = DNA  length = 48
FEATURE                 Location/Qualifiers
misc_feature            1..48
                        note = Description of Artificial Sequence: Synthetic primer
misc_feature            1..48
```

```
                        note = Category: primer
misc_feature            1..48
                        note = Description: Amplify nMG3-6 (D13A) for pMGC
                         expression plasmid
source                  1..48
                        mol_type = other DNA
                        organism = synthetic construct
SEQUENCE: 220
atctgaaaga ttggtagaac caccagaccc cccctctact ccaagcgc               48

SEQ ID NO: 221          moltype = DNA  length = 52
FEATURE                 Location/Qualifiers
misc_feature            1..52
                        note = Description of Artificial Sequence: Synthetic primer
misc_feature            1..52
                        note = Category: primer
misc_feature            1..52
                        note = Description: Amplify nMG3-7 (D12A) for pMGC
                         expression plasmid
source                  1..52
                        mol_type = other DNA
                        organism = synthetic construct
SEQUENCE: 221
acatccgaaa gtgcgacacc tgaatctgcc atgagcgaac atactaagta cc          52

SEQ ID NO: 222          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify nMG3-7 (D12A) for pMGC
                         expression plasmid
source                  1..50
                        mol_type = other DNA
                        organism = synthetic construct
SEQUENCE: 222
atctgaaaga ttggtagaac caccagaccc ttcttgttca tcaagggctg             50

SEQ ID NO: 223          moltype = DNA  length = 54
FEATURE                 Location/Qualifiers
misc_feature            1..54
                        note = Description of Artificial Sequence: Synthetic primer
misc_feature            1..54
                        note = Category: primer
misc_feature            1..54
                        note = Description: Amplify nMG3-8 (D13A) for pMGC
                         expression plasmid
source                  1..54
                        mol_type = other DNA
                        organism = synthetic construct
SEQUENCE: 223
acatccgaaa gtgcgacacc tgaatctgcc atgagcactg atatgaagaa ttac        54

SEQ ID NO: 224          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG3-8 (D13A) for pMGC
                         expression plasmid
source                  1..48
                        mol_type = other DNA
                        organism = synthetic construct
SEQUENCE: 224
atctgaaaga ttggtagaac caccagaccc accctcgacg cctaacgc               48

SEQ ID NO: 225          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG4-5 (D17A) for pMGC
                         expression plasmid
```

```
source                  1..48
                        mol_type = other DNA
                        organism = synthetic construct
SEQUENCE: 225
acatccgaaa gtgcgacacc tgaatctgcc atgggagatc agcagacc               48

SEQ ID NO: 226          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG4-5 (D17A) for pMGC
                         expression plasmid
source                  1..48
                        mol_type = other DNA
                        organism = synthetic construct
SEQUENCE: 226
atctgaaaga ttggtagaac caccagaccc atcgttcgcg ggaaacac               48

SEQ ID NO: 227          moltype = DNA  length = 54
FEATURE                 Location/Qualifiers
misc_feature            1..54
                        note = Description of Artificial Sequence: Synthetic primer
misc_feature            1..54
                        note = Category: primer
misc_feature            1..54
                        note = Description: Amplify nMG14-1 (D23A) for pMGC
                         expression plasmid
source                  1..54
                        mol_type = other DNA
                        organism = synthetic construct
SEQUENCE: 227
acatccgaaa gtgcgacacc tgaatctgcc atggaaatta caattaaccg tgag        54

SEQ ID NO: 228          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify nMG14-1 (D23A) for pMGC
                         expression plasmid
source                  1..49
                        mol_type = other DNA
                        organism = synthetic construct
SEQUENCE: 228
atctgaaaga ttggtagaac caccagaccc cttaatcggg ctctcacga              49

SEQ ID NO: 229          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify nMG15-1 (D8A) for pMGC
                         expression plasmid
source                  1..49
                        mol_type = other DNA
                        organism = synthetic construct
SEQUENCE: 229
acatccgaaa gtgcgacacc tgaatctgcc atgaactatg tgctcggcc              49

SEQ ID NO: 230          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify nMG15-1 (D8A) for pMGC
                         expression plasmid
source                  1..48
                        mol_type = other DNA
                        organism = synthetic construct
SEQUENCE: 230
```

-continued

```
atctgaaaga ttggtagaac caccagaccc acggaacgtt tggcgctt              48

SEQ ID NO: 231         moltype = DNA  length = 49
FEATURE                Location/Qualifiers
misc_feature           1..49
                       note = Description of Artificial Sequence: Synthetic primer
misc_feature           1..49
                       note = Category: primer
misc_feature           1..49
                       note = Description: Amplify nMG18-1 (D12A) for pMGC
                        expression plasmid
source                 1..49
                       mol_type = other DNA
                       organism = synthetic construct
SEQUENCE: 231
atccgaaagt gcgacacctg aatctgccat ggaccagagt aaagagtac             49

SEQ ID NO: 232         moltype = DNA  length = 55
FEATURE                Location/Qualifiers
misc_feature           1..55
                       note = Description of Artificial Sequence: Synthetic primer
misc_feature           1..55
                       note = Category: primer
misc_feature           1..55
                       note = Description: Amplify nMG18-1 (D12A) for pMGC
                        expression plasmid
source                 1..55
                       mol_type = other DNA
                       organism = synthetic construct
SEQUENCE: 232
tatctgaaag attggtagaa ccaccagacc ccagatcatt taaacacacc tcttg       55

SEQ ID NO: 233         moltype = DNA  length = 55
FEATURE                Location/Qualifiers
misc_feature           1..55
                       note = Description of Artificial Sequence: Synthetic primer
misc_feature           1..55
                       note = Category: primer
misc_feature           1..55
                       note = Description: Amplify SpCas9 (D10A) for pMGC
                        expression plasmid
source                 1..55
                       mol_type = other DNA
                       organism = synthetic construct
SEQUENCE: 233
acatccgaaa gtgcgacacc tgaatctgcc atggataaga aatactcaat aggac       55

SEQ ID NO: 234         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify SpCas9 (D10A) for pMGC
                        expression plasmid
source                 1..48
                       mol_type = other DNA
                       organism = synthetic construct
SEQUENCE: 234
atctgaaaga ttggtagaac caccagaccc gtcacctccc agctgact              48

SEQ ID NO: 235         moltype = DNA  length = 44
FEATURE                Location/Qualifiers
misc_feature           1..44
                       note = Description of Artificial Sequence: Synthetic primer
misc_feature           1..44
                       note = Category: primer
misc_feature           1..44
                       note = Description: Amplify MGA1-4_sgRNA spacer 1
source                 1..44
                       mol_type = other DNA
                       organism = synthetic construct
SEQUENCE: 235
ggtcaaattc agacggcaaa cgctatagtg agtcgtatta aggt                  44

SEQ ID NO: 236         moltype = DNA  length = 50
FEATURE                Location/Qualifiers
misc_feature           1..50
```

```
                         note = Description of Artificial Sequence: Synthetic primer
misc_feature             1..50
                         note = Category: primer
misc_feature             1..50
                         note = Description: Amplify MGA1-4_sgRNA spacer 1
source                   1..50
                         mol_type = other DNA
                         organism = synthetic construct
SEQUENCE: 236
tatagcgttt gccgtctgaa tttgaccgtt ttgatttact cgaaagagtc              50

SEQ ID NO: 237           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGA1-4_sgRNA spacer 2
source                   1..50
                         mol_type = other DNA
                         organism = synthetic construct
SEQUENCE: 237
caaaactccg ccacatatcc tgatcttcct atagtgagtc gtattaaggt              50

SEQ ID NO: 238           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGA1-4_sgRNA spacer 2
source                   1..50
                         mol_type = other DNA
                         organism = synthetic construct
SEQUENCE: 238
tataggaaga tcaggatatg tggcggagtt ttgatttact cgaaagagtc              50

SEQ ID NO: 239           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGA1-4_sgRNA spacer 3
source                   1..50
                         mol_type = other DNA
                         organism = synthetic construct
SEQUENCE: 239
caaaacccat aaagaaactg ttacccgtct atagtgagtc gtattaaggt              50

SEQ ID NO: 240           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGA1-4_sgRNA spacer 3
source                   1..50
                         mol_type = other DNA
                         organism = synthetic construct
SEQUENCE: 240
tatagacggg taacagtttc tttatgggtt ttgatttact cgaaagagtc              50

SEQ ID NO: 241           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGA1-6_sgRNA spacer 1
source                   1..50
                         mol_type = other DNA
                         organism = synthetic construct
SEQUENCE: 241
```

```
caaaacgtag tcggtttatg cagcaacgct atagtgagtc gtattaaggt            50

SEQ ID NO: 242         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA1-6_sgRNA spacer 1
source                 1..50
                       mol_type = other DNA
                       organism = synthetic construct
SEQUENCE: 242
tagcgttgct gcataaaccg actacgtttt gacttgaaaa agtcttaact            50

SEQ ID NO: 243         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA1-6_sgRNA spacer 2
source                 1..50
                       mol_type = other DNA
                       organism = synthetic construct
SEQUENCE: 243
caaaacgcgc tccacagttt cgggttttct atagtgagtc gtattaaggt            50

SEQ ID NO: 244         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA1-6_sgRNA spacer 2
source                 1..50
                       mol_type = other DNA
                       organism = synthetic construct
SEQUENCE: 244
tagaaaaccc gaaactgtgg agcgcgtttt gacttgaaaa agtcttaact            50

SEQ ID NO: 245         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA1-6_sgRNA spacer 3
source                 1..50
                       mol_type = other DNA
                       organism = synthetic construct
SEQUENCE: 245
caaaaccagc agcagaccat tttcaatcct atagtgagtc gtattaaggt            50

SEQ ID NO: 246         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA1-6_sgRNA spacer 3
source                 1..50
                       mol_type = other DNA
                       organism = synthetic construct
SEQUENCE: 246
taggattgaa aatggtctgc tgctggtttt gacttgaaaa agtcttaact            50

SEQ ID NO: 247         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
```

```
                        note = Description: Amplify MGA3-6_sgRNA spacer 1
source                  1..50
                        mol_type = other DNA
                        organism = synthetic construct
SEQUENCE: 247
ctcaaccata aagaaactgt tacccgtact atagtgagtc gtattaaggt            50

SEQ ID NO: 248          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-6_sgRNA spacer 1
source                  1..50
                        mol_type = other DNA
                        organism = synthetic construct
SEQUENCE: 248
atagtacggg taacagtttc tttatggttg agaatcgaaa gattcttaat            50

SEQ ID NO: 249          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-6_sgRNA spacer 2
source                  1..50
                        mol_type = other DNA
                        organism = synthetic construct
SEQUENCE: 249
ctcaacctgg cggttaaatt gccaacgcct atagtgagtc gtattaaggt            50

SEQ ID NO: 250          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-6_sgRNA spacer 2
source                  1..50
                        mol_type = other DNA
                        organism = synthetic construct
SEQUENCE: 250
taggcgttgg caatttaacc gccaggttga gaatcgaaag attcttaata            50

SEQ ID NO: 251          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-6_sgRNA spacer 3
source                  1..50
                        mol_type = other DNA
                        organism = synthetic construct
SEQUENCE: 251
ctcaactatg gaaaccgtcg atattcagct atagtgagtc gtattaaggt            50

SEQ ID NO: 252          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-6_sgRNA spacer 3
source                  1..50
                        mol_type = other DNA
                        organism = synthetic construct
SEQUENCE: 252
tagctgaata tcgacggttt ccatagttga gaatcgaaag attcttaata            50

SEQ ID NO: 253          moltype = DNA  length = 50
FEATURE                 Location/Qualifiers
```

```
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 1
source                1..50
                      mol_type = other DNA
                      organism = synthetic construct
SEQUENCE: 253
cccaacgctt tcatcaacat taaatgtgct atagtgagtc gtattaaggt            50

SEQ ID NO: 254        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 1
source                1..50
                      mol_type = other DNA
                      organism = synthetic construct
SEQUENCE: 254
tcactatagc acatttaatg ttgatgaaag cgttgggaac cgaaaggttc            50

SEQ ID NO: 255        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 2
source                1..50
                      mol_type = other DNA
                      organism = synthetic construct
SEQUENCE: 255
cccaaccatg gaaatcgctg atttgtgtct atagtgagtc gtattaaggt            50

SEQ ID NO: 256        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 2
source                1..50
                      mol_type = other DNA
                      organism = synthetic construct
SEQUENCE: 256
tcactataga cacaaatcag cgatttccat ggttgggaac cgaaaggttc            50

SEQ ID NO: 257        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 3
source                1..50
                      mol_type = other DNA
                      organism = synthetic construct
SEQUENCE: 257
cccaacgcac catcgtctgc tcatccatct atagtgagtc gtattaaggt            50

SEQ ID NO: 258        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA3-7_sgRNA spacer 3
source                1..50
                      mol_type = other DNA
                      organism = synthetic construct
```

```
SEQUENCE: 258
tcactataga tggatgagca gacgatggtg cgttgggaac cgaaaggttc            50

SEQ ID NO: 259         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA4-5_sgRNA spacer 1
source                 1..50
                       mol_type = other DNA
                       organism = synthetic construct
SEQUENCE: 259
cacagcacat ggaaatcgct gatttgtgct atagtgagtc gtattaaggt            50

SEQ ID NO: 260         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify MGA4-5_sgRNA spacer 1
source                 1..48
                       mol_type = other DNA
                       organism = synthetic construct
SEQUENCE: 260
cactatagca caaatcagcg atttccatgt gctgtggctt gcggggga              48

SEQ ID NO: 261         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA4-5_sgRNA spacer 2
source                 1..50
                       mol_type = other DNA
                       organism = synthetic construct
SEQUENCE: 261
cacagcttaa agttgttctg cttcatcact atagtgagtc gtattaaggt            50

SEQ ID NO: 262         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify MGA4-5_sgRNA spacer 2
source                 1..48
                       mol_type = other DNA
                       organism = synthetic construct
SEQUENCE: 262
cactatagtg atgaagcaga acaactttaa gctgtggctt gcggggga              48

SEQ ID NO: 263         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA4-5_sgRNA spacer 3
source                 1..50
                       mol_type = other DNA
                       organism = synthetic construct
SEQUENCE: 263
cacagcccat gccgtgggtt tcaatattct atagtgagtc gtattaaggt            50

SEQ ID NO: 264         moltype = DNA  length = 48
FEATURE                Location/Qualifiers
misc_feature           1..48
                       note = Description of Artificial Sequence: Synthetic primer
misc_feature           1..48
                       note = Category: primer
```

```
misc_feature          1..48
                      note = Description: Amplify MGA4-5_sgRNA spacer 3
source                1..48
                      mol_type = other DNA
                      organism = synthetic construct
SEQUENCE: 264
cactatagaa tattgaaacc cacggcatgg gctgtggctt gcggggga              48

SEQ ID NO: 265        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA14-1_sgRNA spacer 1
source                1..50
                      mol_type = other DNA
                      organism = synthetic construct
SEQUENCE: 265
caagacggta gcgaaagcca ttttttgact atagtgagtc gtattaaggt            50

SEQ ID NO: 266        moltype = DNA  length = 48
FEATURE               Location/Qualifiers
misc_feature          1..48
                      note = Description of Artificial Sequence: Synthetic primer
misc_feature          1..48
                      note = Category: primer
misc_feature          1..48
                      note = Description: Amplify MGA14-1_sgRNA spacer 1
source                1..48
                      mol_type = other DNA
                      organism = synthetic construct
SEQUENCE: 266
cactatagtc aaaaaatggc tttcgctacc gtcttgagcg aaagctcc              48

SEQ ID NO: 267        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA14-1_sgRNA spacer 2
source                1..50
                      mol_type = other DNA
                      organism = synthetic construct
SEQUENCE: 267
caagacgtgc actgcaacaa cgctgcttct atagtgagtc gtattaaggt            50

SEQ ID NO: 268        moltype = DNA  length = 48
FEATURE               Location/Qualifiers
misc_feature          1..48
                      note = Description of Artificial Sequence: Synthetic primer
misc_feature          1..48
                      note = Category: primer
misc_feature          1..48
                      note = Description: Amplify MGA14-1_sgRNA spacer 2
source                1..48
                      mol_type = other DNA
                      organism = synthetic construct
SEQUENCE: 268
cactatagaa gcagcgttgt tgcagtgcac gtcttgagcg aaagctcc              48

SEQ ID NO: 269        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGA14-1_sgRNA spacer 3
source                1..50
                      mol_type = other DNA
                      organism = synthetic construct
SEQUENCE: 269
caagacatcc ggtaggtttt ccggctgact atagtgagtc gtattaaggt            50

SEQ ID NO: 270        moltype = DNA  length = 48
```

```
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify MGA14-1_sgRNA spacer 3
source                 1..48
                       mol_type = other DNA
                       organism = synthetic construct
SEQUENCE: 270
cactatagtc agccggaaaa cctaccggat gtcttgagcg aaagctcc              48

SEQ ID NO: 271         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA15-1_sgRNA spacer 1
source                 1..50
                       mol_type = other DNA
                       organism = synthetic construct
SEQUENCE: 271
tacaactccg ccacatatcc tgatcttcct atagtgagtc gtattaaggt            50

SEQ ID NO: 272         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA15-1_sgRNA spacer 1
source                 1..50
                       mol_type = other DNA
                       organism = synthetic construct
SEQUENCE: 272
tataggaaga tcaggatatg tggcggagtt gtaattccct agaaataggt            50

SEQ ID NO: 273         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA15-1_sgRNA spacer 2
source                 1..50
                       mol_type = other DNA
                       organism = synthetic construct
SEQUENCE: 273
tacaacacag tttcgggttt tcgacgttct atagtgagtc gtattaaggt            50

SEQ ID NO: 274         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA15-1_sgRNA spacer 2
source                 1..50
                       mol_type = other DNA
                       organism = synthetic construct
SEQUENCE: 274
tatagaacgt cgaaaacccg aaactgtgtt gtaattccct agaaataggt            50

SEQ ID NO: 275         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA15-1_sgRNA spacer 3
source                 1..50
                       mol_type = other DNA
```

```
                        organism = synthetic construct
SEQUENCE: 275
tacaacattg gcaccatgcc gtgggtttct atagtgagtc gtattaaggt             50

SEQ ID NO: 276          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA15-1_sgRNA spacer 3
source                  1..50
                        mol_type = other DNA
                        organism = synthetic construct
SEQUENCE: 276
tatagaaacc cacggcatgg tgccaatgtt gtaattccct agaaataggt             50

SEQ ID NO: 277          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA18-1_sgRNA spacer 1
source                  1..50
                        mol_type = other DNA
                        organism = synthetic construct
SEQUENCE: 277
tcaaacgcgc tccacagttt cgggttttct atagtgagtc gtattaaggt             50

SEQ ID NO: 278          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA18-1_sgRNA spacer 1
source                  1..50
                        mol_type = other DNA
                        organism = synthetic construct
SEQUENCE: 278
tatagaaaac ccgaaactgt ggagcgcgtt tgagagtagt gaaaactacg             50

SEQ ID NO: 279          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA18-1_sgRNA spacer 2
source                  1..50
                        mol_type = other DNA
                        organism = synthetic construct
SEQUENCE: 279
tcaaaccgta ctgtgagcca gagttgccct atagtgagtc gtattaaggt             50

SEQ ID NO: 280          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA18-1_sgRNA spacer 2
source                  1..50
                        mol_type = other DNA
                        organism = synthetic construct
SEQUENCE: 280
tatagggcaa ctctggctca cagtacggtt tgagagtagt gaaaactacg             50

SEQ ID NO: 281          moltype = DNA  length = 50
FEATURE                 Location/Qualifiers
misc_feature            1..50
                        note = Description of Artificial Sequence: Synthetic primer
misc_feature            1..50
```

```
                          note = Category: primer
misc_feature              1..50
                          note = Description: Amplify MGA18-1_sgRNA spacer 3
source                    1..50
                          mol_type = other DNA
                          organism = synthetic construct
SEQUENCE: 281
tcaaacatca atccggtagg ttttccggct atagtgagtc gtattaaggt             50

SEQ ID NO: 282            moltype = DNA  length = 50
FEATURE                   Location/Qualifiers
misc_feature              1..50
                          note = Description of Artificial Sequence: Synthetic primer
misc_feature              1..50
                          note = Category: primer
misc_feature              1..50
                          note = Description: Amplify MGA18-1_sgRNA spacer 3
source                    1..50
                          mol_type = other DNA
                          organism = synthetic construct
SEQUENCE: 282
tatagccgga aaacctaccg gattgatgtt tgagagtagt gaaaactacg             50

SEQ ID NO: 283            moltype = DNA  length = 41
FEATURE                   Location/Qualifiers
misc_feature              1..41
                          note = Description of Artificial Sequence: Synthetic primer
misc_feature              1..41
                          note = Category: primer
misc_feature              1..41
                          note = Description: Amplify ABE8.17m_sgRNA spacer 1
source                    1..41
                          mol_type = other DNA
                          organism = synthetic construct
SEQUENCE: 283
atccacatct gtgaaagaaa ctatagtgag tcgtattagg a                      41

SEQ ID NO: 284            moltype = DNA  length = 45
FEATURE                   Location/Qualifiers
misc_feature              1..45
                          note = Description of Artificial Sequence: Synthetic primer
misc_feature              1..45
                          note = Category: primer
misc_feature              1..45
                          note = Description: Amplify ABE8.17m_sgRNA spacer 1
source                    1..45
                          mol_type = other DNA
                          organism = synthetic construct
SEQUENCE: 284
tttctttcac agatgtggat gttttagagc tagaaatagc aagtt                  45

SEQ ID NO: 285            moltype = DNA  length = 41
FEATURE                   Location/Qualifiers
misc_feature              1..41
                          note = Description of Artificial Sequence: Synthetic primer
misc_feature              1..41
                          note = Category: primer
misc_feature              1..41
                          note = Description: Amplify ABE8.17m_sgRNA spacer 2
source                    1..41
                          mol_type = other DNA
                          organism = synthetic construct
SEQUENCE: 285
ctcatccgcc acatatcctg ctatagtgag tcgtattagg a                      41

SEQ ID NO: 286            moltype = DNA  length = 45
FEATURE                   Location/Qualifiers
misc_feature              1..45
                          note = Description of Artificial Sequence: Synthetic primer
misc_feature              1..45
                          note = Category: primer
misc_feature              1..45
                          note = Description: Amplify ABE8.17m_sgRNA spacer 2
source                    1..45
                          mol_type = other DNA
                          organism = synthetic construct
SEQUENCE: 286
caggatatgt ggcggatgag gttttagagc tagaaatagc aagtt                  45
```

```
SEQ ID NO: 287         moltype = DNA  length = 41
FEATURE                Location/Qualifiers
misc_feature           1..41
                       note = Description of Artificial Sequence: Synthetic primer
misc_feature           1..41
                       note = Category: primer
misc_feature           1..41
                       note = Description: Amplify ABE8.17m_sgRNA spacer 3
source                 1..41
                       mol_type = other DNA
                       organism = synthetic construct
SEQUENCE: 287
atcgcgtggg cgtattcgca ctatagtgag tcgtattagg a                      41

SEQ ID NO: 288         moltype = DNA  length = 45
FEATURE                Location/Qualifiers
misc_feature           1..45
                       note = Description of Artificial Sequence: Synthetic primer
misc_feature           1..45
                       note = Category: primer
misc_feature           1..45
                       note = Description: Amplify ABE8.17m_sgRNA spacer 3
source                 1..45
                       mol_type = other DNA
                       organism = synthetic construct
SEQUENCE: 288
tgcgaatacg cccacgcgat gttttagagc tagaaatagc aagtt                  45

SEQ ID NO: 289         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC1-4_spacer 1
source                 1..50
                       mol_type = other DNA
                       organism = synthetic construct
SEQUENCE: 289
caaaacttgc accacagatg aaacgccgct atagtgagtc gtattaaggt             50

SEQ ID NO: 290         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC1-4_spacer 1
source                 1..50
                       mol_type = other DNA
                       organism = synthetic construct
SEQUENCE: 290
tatagcggcg tttcatctgt ggtgcaagtt ttgatttact cgaaagagtc             50

SEQ ID NO: 291         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC1-4_spacer 2
source                 1..50
                       mol_type = other DNA
                       organism = synthetic construct
SEQUENCE: 291
caaaacgacg gcaaacgact gtcctggcct atagtgagtc gtattaaggt             50

SEQ ID NO: 292         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC1-4_spacer 2
source                 1..50
```

```
                         mol_type = other DNA
                         organism = synthetic construct
SEQUENCE: 292
tataggccag gacagtcgtt tgccgtcgtt ttgatttact cgaaagagtc             50

SEQ ID NO: 293           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC1-4_spacer 3
source                   1..50
                         mol_type = other DNA
                         organism = synthetic construct
SEQUENCE: 293
caaaacgcct ccagtacagc gcggctgact atagtgagtc gtattaaggt             50

SEQ ID NO: 294           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC1-4_spacer 3
source                   1..50
                         mol_type = other DNA
                         organism = synthetic construct
SEQUENCE: 294
tatagtcagc cgcgctgtac tggaggcgtt ttgatttact cgaaagagtc             50

SEQ ID NO: 295           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC1-6_spacer 1
source                   1..50
                         mol_type = other DNA
                         organism = synthetic construct
SEQUENCE: 295
caaaacgctg cgcaactgtt gggaagggct atagtgagtc gtattaaggt             50

SEQ ID NO: 296           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC1-6_spacer 1
source                   1..50
                         mol_type = other DNA
                         organism = synthetic construct
SEQUENCE: 296
tagcccttcc caacagttgc gcagcgtttt gacttgaaaa agtcttaact             50

SEQ ID NO: 297           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC1-6_spacer 2
source                   1..50
                         mol_type = other DNA
                         organism = synthetic construct
SEQUENCE: 297
caaaaccagt ttgaggggac gacgacagct atagtgagtc gtattaaggt             50

SEQ ID NO: 298           moltype = DNA  length = 50
FEATURE                  Location/Qualifiers
misc_feature             1..50
                         note = Description of Artificial Sequence: Synthetic primer
```

```
misc_feature            1..50
                        note = Category: primer
misc_feature            1..50
                        note = Description: Amplify MGC1-6_spacer 2
source                  1..50
                        mol_type = other DNA
                        organism = synthetic construct
SEQUENCE: 298
tagctgtcgt cgtcccctca aactggtttt gacttgaaaa agtcttaact             50

SEQ ID NO: 299          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC1-6_spacer 3
source                  1..50
                        mol_type = other DNA
                        organism = synthetic construct
SEQUENCE: 299
caaaacggtt ttcgacgttc agacgtagct atagtgagtc gtattaaggt             50

SEQ ID NO: 300          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC1-6_spacer 3
source                  1..50
                        mol_type = other DNA
                        organism = synthetic construct
SEQUENCE: 300
tagctacgtc tgaacgtcga aaaccgtttt gacttgaaaa agtcttaact             50

SEQ ID NO: 301          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 1
source                  1..50
                        mol_type = other DNA
                        organism = synthetic construct
SEQUENCE: 301
ctcaactctt ccagataact gccgtcacct atagtgagtc gtattaaggt             50

SEQ ID NO: 302          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 1
source                  1..50
                        mol_type = other DNA
                        organism = synthetic construct
SEQUENCE: 302
aggtgacggc agttatctgg aagagttgag aatcgaaaga ttcttaataa             50

SEQ ID NO: 303          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 2
source                  1..50
                        mol_type = other DNA
                        organism = synthetic construct
SEQUENCE: 303
tcaacagtac agcgcggctg aaatcatcta tagtgagtcg tattaaggtc             50
```

```
SEQ ID NO: 304          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 2
source                  1..50
                        mol_type = other DNA
                        organism = synthetic construct
SEQUENCE: 304
agatgatttc agccgcgctg tactgttgag aatcgaaaga ttcttaataa             50

SEQ ID NO: 305          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 3
source                  1..50
                        mol_type = other DNA
                        organism = synthetic construct
SEQUENCE: 305
ctcaaccggt caaaacaggc ggcagtaact atagtgagtc gtattaaggt             50

SEQ ID NO: 306          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-6_spacer 3
source                  1..50
                        mol_type = other DNA
                        organism = synthetic construct
SEQUENCE: 306
tagttactgc cgcctgtttt gaccggttga gaatcgaaag attcttaata             50

SEQ ID NO: 307          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-7_spacer 1
source                  1..50
                        mol_type = other DNA
                        organism = synthetic construct
SEQUENCE: 307
cccaacaaac caggcaaagc gccattcgct atagtgagtc gtattaaggt             50

SEQ ID NO: 308          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify MGC3-7_spacer 1
source                  1..49
                        mol_type = other DNA
                        organism = synthetic construct
SEQUENCE: 308
cactatagcg aatggcgctt tgcctggttt gttgggaacc gaaaggttc              49

SEQ ID NO: 309          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-7_spacer 2
```

```
source                  1..50
                        mol_type = other DNA
                        organism = synthetic construct
SEQUENCE: 309
cccaactgca tctgccagtt tgaggggact atagtgagtc gtattaaggt             50

SEQ ID NO: 310          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify MGC3-7_spacer 2
source                  1..49
                        mol_type = other DNA
                        organism = synthetic construct
SEQUENCE: 310
cactatagtc ccctcaaact ggcagatgca gttgggaacc gaaaggttc              49

SEQ ID NO: 311          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-7_spacer 3
source                  1..50
                        mol_type = other DNA
                        organism = synthetic construct
SEQUENCE: 311
cccaacgata ggtcacgttg gtgtagatct atagtgagtc gtattaaggt             50

SEQ ID NO: 312          moltype = DNA  length = 49
FEATURE                 Location/Qualifiers
misc_feature            1..49
                        note = Description of Artificial Sequence: Synthetic primer
misc_feature            1..49
                        note = Category: primer
misc_feature            1..49
                        note = Description: Amplify MGC3-7_spacer 3
source                  1..49
                        mol_type = other DNA
                        organism = synthetic construct
SEQUENCE: 312
cactatagat ctacaccaac gtgacctatc gttgggaacc gaaaggttc              49

SEQ ID NO: 313          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC4-5_spacer 1
source                  1..50
                        mol_type = other DNA
                        organism = synthetic construct
SEQUENCE: 313
cacagcgtaa ccgacccagc gcccgttgct atagtgagtc gtattaaggt             50

SEQ ID NO: 314          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify MGC4-5_spacer 1
source                  1..48
                        mol_type = other DNA
                        organism = synthetic construct
SEQUENCE: 314
cactatagca acgggcgctg ggtcggttac gctgtggctt gcggggga               48

SEQ ID NO: 315          moltype = DNA  length = 50
FEATURE                 Location/Qualifiers
misc_feature            1..50
```

```
                        note = Description of Artificial Sequence: Synthetic primer
misc_feature            1..50
                        note = Category: primer
misc_feature            1..50
                        note = Description: Amplify MGC4-5_spacer 2
source                  1..50
                        mol_type = other DNA
                        organism = synthetic construct
SEQUENCE: 315
cacagcacat ggaaatcgct gatttgtgct atagtgagtc gtattaaggt            50

SEQ ID NO: 316          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify MGC4-5_spacer 2
source                  1..48
                        mol_type = other DNA
                        organism = synthetic construct
SEQUENCE: 316
cactatagca caaatcagcg atttccatgt gctgtggctt gcggggga              48

SEQ ID NO: 317          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC4-5_spacer 3
source                  1..50
                        mol_type = other DNA
                        organism = synthetic construct
SEQUENCE: 317
cacagcgtgg tgtcggctcc gccgccttct atagtgagtc gtattaaggt            50

SEQ ID NO: 318          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify MGC4-5_spacer 3
source                  1..48
                        mol_type = other DNA
                        organism = synthetic construct
SEQUENCE: 318
cactatagaa ggcggcggag ccgacaccac gctgtggctt gcggggga              48

SEQ ID NO: 319          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC14-1_spacer 1
source                  1..50
                        mol_type = other DNA
                        organism = synthetic construct
SEQUENCE: 319
caagacggaa caaacggcgg attgaccgct atagtgagtc gtattaaggt            50

SEQ ID NO: 320          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Amplify MGC14-1_spacer 1
source                  1..48
                        mol_type = other DNA
                        organism = synthetic construct
SEQUENCE: 320
```

```
cactatagcg gtcaatccgc cgtttgttcc gtcttgagcg aaagctcc              48

SEQ ID NO: 321         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC14-1_spacer 2
source                 1..50
                       mol_type = other DNA
                       organism = synthetic construct
SEQUENCE: 321
caagacgcgt gggcgtattc gcaaaggact atagtgagtc gtattaaggt            50

SEQ ID NO: 322         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify MGC14-1_spacer 2
source                 1..48
                       mol_type = other DNA
                       organism = synthetic construct
SEQUENCE: 322
cactatagtc ctttgcgaat acgcccacgc gtcttgagcg aaagctcc              48

SEQ ID NO: 323         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC14-1_spacer 3
source                 1..50
                       mol_type = other DNA
                       organism = synthetic construct
SEQUENCE: 323
caagacaaat caccgccgta agccgaccct atagtgagtc gtattaaggt            50

SEQ ID NO: 324         moltype = DNA  length = 48
FEATURE                Location/Qualifiers
misc_feature           1..48
                       note = Description of Artificial Sequence: Synthetic primer
misc_feature           1..48
                       note = Category: primer
misc_feature           1..48
                       note = Description: Amplify MGC14-1_spacer 3
source                 1..48
                       mol_type = other DNA
                       organism = synthetic construct
SEQUENCE: 324
cactataggg tcggcttacg gcggtgattt gtcttgagcg aaagctcc              48

SEQ ID NO: 325         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGC15-1_spacer 1
source                 1..50
                       mol_type = other DNA
                       organism = synthetic construct
SEQUENCE: 325
tacaacgacg tagtgtgacg cgatcggcct atagtgagtc gtattaaggt            50

SEQ ID NO: 326         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
```

```
                         note = Description: Amplify MGC15-1_spacer 1
source                   1..50
                         mol_type = other DNA
                         organism = synthetic construct
SEQUENCE: 326
ataggccgat cgcgtcacac tacgtcgttg taattcccta gaaataggtt              50

SEQ ID NO: 327           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC15-1_spacer 2
source                   1..50
                         mol_type = other DNA
                         organism = synthetic construct
SEQUENCE: 327
tacaactcgc cggtagccag cgcggatcct atagtgagtc gtattaaggt              50

SEQ ID NO: 328           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC15-1_spacer 2
source                   1..50
                         mol_type = other DNA
                         organism = synthetic construct
SEQUENCE: 328
ataggatccg cgctggctac cggcgagttg taattcccta gaaataggtt              50

SEQ ID NO: 329           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC15-1_spacer 3
source                   1..50
                         mol_type = other DNA
                         organism = synthetic construct
SEQUENCE: 329
tacaaccata ctgcaccggg cgggaaggct atagtgagtc gtattaaggt              50

SEQ ID NO: 330           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC15-1_spacer 3
source                   1..50
                         mol_type = other DNA
                         organism = synthetic construct
SEQUENCE: 330
atagccttcc cgcccggtgc agtatggttg taattcccta gaaataggtt              50

SEQ ID NO: 331           moltype = DNA  length = 50
FEATURE                  Location/Qualifiers
misc_feature             1..50
                         note = Description of Artificial Sequence: Synthetic primer
misc_feature             1..50
                         note = Category: primer
misc_feature             1..50
                         note = Description: Amplify MGC18-1_spacer 1
source                   1..50
                         mol_type = other DNA
                         organism = synthetic construct
SEQUENCE: 331
tcaaacgcct ccagtacagc gcggctgact atagtgagtc gtattaaggt              50

SEQ ID NO: 332           moltype = DNA  length = 50
FEATURE                  Location/Qualifiers
```

```
misc_feature          1..50
                      note = Description of Artificial Sequence: Synthetic primer
misc_feature          1..50
                      note = Category: primer
misc_feature          1..50
                      note = Description: Amplify MGC18-1_spacer 1
source                1..50
                      mol_type = other DNA
                      organism = synthetic construct
SEQUENCE: 332
ctatagtcag ccgcgctgta ctggaggcgt ttgagagtag tgaaaactac             50

SEQ ID NO: 333        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGC18-1_spacer 2
source                1..50
                      mol_type = other DNA
                      organism = synthetic construct
SEQUENCE: 333
tcaaacgcac agccgggaag ggctggtcct atagtgagtc gtattaaggt             50

SEQ ID NO: 334        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGC18-1_spacer 2
source                1..50
                      mol_type = other DNA
                      organism = synthetic construct
SEQUENCE: 334
ctataggacc agcccttccc ggctgtgcgt ttgagagtag tgaaaactac             50

SEQ ID NO: 335        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGC18-1_spacer 3
source                1..50
                      mol_type = other DNA
                      organism = synthetic construct
SEQUENCE: 335
tcaaacatgg tttgcccgga taaacggact atagtgagtc gtattaaggt             50

SEQ ID NO: 336        moltype = DNA  length = 50
FEATURE               Location/Qualifiers
misc_feature          1..50
                      note = Description of Artificial Sequence: Synthetic primer
misc_feature          1..50
                      note = Category: primer
misc_feature          1..50
                      note = Description: Amplify MGC18-1_spacer 3
source                1..50
                      mol_type = other DNA
                      organism = synthetic construct
SEQUENCE: 336
ctatagtccg tttatccggg caaaccatgt ttgagagtag tgaaaactac             50

SEQ ID NO: 337        moltype = DNA  length = 41
FEATURE               Location/Qualifiers
misc_feature          1..41
                      note = Description of Artificial Sequence: Synthetic primer
misc_feature          1..41
                      note = Category: primer
misc_feature          1..41
                      note = Description: Amplify BE3_sgRNA spacer 1
source                1..41
                      mol_type = other DNA
                      organism = synthetic construct
```

```
SEQUENCE: 337
tgtggagcga catccagagg ctatagtgag tcgtattagg a                      41

SEQ ID NO: 338         moltype = DNA  length = 45
FEATURE                Location/Qualifiers
misc_feature           1..45
                       note = Description of Artificial Sequence: Synthetic primer
misc_feature           1..45
                       note = Category: primer
misc_feature           1..45
                       note = Description: Amplify BE3_sgRNA spacer 1
source                 1..45
                       mol_type = other DNA
                       organism = synthetic construct
SEQUENCE: 338
cctctggatg tcgctccaca gttttagagc tagaaatagc aagtt                  45

SEQ ID NO: 339         moltype = DNA  length = 41
FEATURE                Location/Qualifiers
misc_feature           1..41
                       note = Description of Artificial Sequence: Synthetic primer
misc_feature           1..41
                       note = Category: primer
misc_feature           1..41
                       note = Description: Amplify BE3_sgRNA spacer 2
source                 1..41
                       mol_type = other DNA
                       organism = synthetic construct
SEQUENCE: 339
taattcaatt cgcgcgtccc ctatagtgag tcgtattagg a                      41

SEQ ID NO: 340         moltype = DNA  length = 45
FEATURE                Location/Qualifiers
misc_feature           1..45
                       note = Description of Artificial Sequence: Synthetic primer
misc_feature           1..45
                       note = Category: primer
misc_feature           1..45
                       note = Description: Amplify BE3_sgRNA spacer 2
source                 1..45
                       mol_type = other DNA
                       organism = synthetic construct
SEQUENCE: 340
gggacgcgcg aattgaatta gttttagagc tagaaatagc aagtt                  45

SEQ ID NO: 341         moltype = DNA  length = 41
FEATURE                Location/Qualifiers
misc_feature           1..41
                       note = Description of Artificial Sequence: Synthetic primer
misc_feature           1..41
                       note = Category: primer
misc_feature           1..41
                       note = Description: Amplify BE3_sgRNA spacer 3
source                 1..41
                       mol_type = other DNA
                       organism = synthetic construct
SEQUENCE: 341
agtcacgacg ttgtaaaacg ctatagtgag tcgtattagg a                      41

SEQ ID NO: 342         moltype = DNA  length = 45
FEATURE                Location/Qualifiers
misc_feature           1..45
                       note = Description of Artificial Sequence: Synthetic primer
misc_feature           1..45
                       note = Category: primer
misc_feature           1..45
                       note = Description: Amplify BE3_sgRNA spacer 3
source                 1..45
                       mol_type = other DNA
                       organism = synthetic construct
SEQUENCE: 342
cgttttacaa cgtcgtgact gttttagagc tagaaatagc aagtt                  45

SEQ ID NO: 343         moltype = DNA  length = 25
FEATURE                Location/Qualifiers
misc_feature           1..25
                       note = Description of Artificial Sequence: Synthetic primer
misc_feature           1..25
                       note = Category: primer
```

```
misc_feature           1..25
                       note = Description: For lacZ sequencing
source                 1..25
                       mol_type = other DNA
                       organism = synthetic construct
SEQUENCE: 343
cgaacatcca aaagtttgtg ttttt                                       25

SEQ ID NO: 344         moltype = DNA  length = 19
FEATURE                Location/Qualifiers
misc_feature           1..19
                       note = Description of Artificial Sequence: Synthetic primer
misc_feature           1..19
                       note = Category: primer
misc_feature           1..19
                       note = Description: For lacZ sequencing
source                 1..19
                       mol_type = other DNA
                       organism = synthetic construct
SEQUENCE: 344
tgagcgcatt tttacgcgc                                              19

SEQ ID NO: 345         moltype = DNA  length = 18
FEATURE                Location/Qualifiers
misc_feature           1..18
                       note = Description of Artificial Sequence: Synthetic primer
misc_feature           1..18
                       note = Category: primer
misc_feature           1..18
                       note = Description: For lacZ sequencing
source                 1..18
                       mol_type = other DNA
                       organism = synthetic construct
SEQUENCE: 345
gaaaacggca acccgtgg                                               18

SEQ ID NO: 346         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify sgRNA expression cassette
source                 1..50
                       mol_type = other DNA
                       organism = synthetic construct
SEQUENCE: 346
ccgccgccgc aaggaatggt ttaattaatt acggccagtc atgcataatc            50

SEQ ID NO: 347         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify sgRNA expression cassette
source                 1..50
                       mol_type = other DNA
                       organism = synthetic construct
SEQUENCE: 347
gactgttggg cgccatctcc ttgcatgctc actgagcctc cacctagcct            50

SEQ ID NO: 348         moltype = DNA  length = 50
FEATURE                Location/Qualifiers
misc_feature           1..50
                       note = Description of Artificial Sequence: Synthetic primer
misc_feature           1..50
                       note = Category: primer
misc_feature           1..50
                       note = Description: Amplify MGA3-8_sgRNA spacer 1
source                 1..50
                       mol_type = other DNA
                       organism = synthetic construct
SEQUENCE: 348
ctcaaccgcc cgttgcacca cagatgaact atagtgagtc gtattaaggt            50

SEQ ID NO: 349         moltype = DNA  length = 50
```

```
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-8_sgRNA spacer 1
source                  1..50
                        mol_type = other DNA
                        organism = synthetic construct
SEQUENCE: 349
tatagttcat ctgtggtgca acgggcggtt gagaatcttt cgaaagaaag            50

SEQ ID NO: 350          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-8_sgRNA spacer 2
source                  1..50
                        mol_type = other DNA
                        organism = synthetic construct
SEQUENCE: 350
ctcaacccat gcagaggatg atgctcgtct atagtgagtc gtattaaggt            50

SEQ ID NO: 351          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-8_sgRNA spacer 2
source                  1..50
                        mol_type = other DNA
                        organism = synthetic construct
SEQUENCE: 351
atagacgagc atcatcctct gcatgggttg agaatctttc gaaagaaaga            50

SEQ ID NO: 352          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-8_sgRNA spacer 3
source                  1..50
                        mol_type = other DNA
                        organism = synthetic construct
SEQUENCE: 352
ctcaacgcgt tagggtcaat gcgggtcgct atagtgagtc gtattaaggt            50

SEQ ID NO: 353          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGA3-8_sgRNA spacer 3
source                  1..50
                        mol_type = other DNA
                        organism = synthetic construct
SEQUENCE: 353
tatagcgacc cgcattgacc ctaacgcgtt gagaatcttt cgaaagaaag            50

SEQ ID NO: 354          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 1
source                  1..50
                        mol_type = other DNA
```

```
                        organism = synthetic construct
SEQUENCE: 354
ctcaaccgcc cgttgcacca cagatgaact atagtgagtc gtattaaggt             50

SEQ ID NO: 355          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 1
source                  1..50
                        mol_type = other DNA
                        organism = synthetic construct
SEQUENCE: 355
tatagttcat ctgtggtgca acgggcggtt gagaatcttt cgaaagaaag             50

SEQ ID NO: 356          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 2
source                  1..50
                        mol_type = other DNA
                        organism = synthetic construct
SEQUENCE: 356
ctcaacccat gcagaggatg atgctcgtct atagtgagtc gtattaaggt             50

SEQ ID NO: 357          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 2
source                  1..50
                        mol_type = other DNA
                        organism = synthetic construct
SEQUENCE: 357
atagacgagc atcatcctct gcatgggttg agaatctttc gaaagaaaga             50

SEQ ID NO: 358          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 3
source                  1..50
                        mol_type = other DNA
                        organism = synthetic construct
SEQUENCE: 358
ctcaacgcgt tagggtcaat gcgggtcgct atagtgagtc gtattaaggt             50

SEQ ID NO: 359          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Amplify MGC3-8_sgRNA spacer 3
source                  1..50
                        mol_type = other DNA
                        organism = synthetic construct
SEQUENCE: 359
tatagcgacc cgcattgacc ctaacgcgtt gagaatcttt cgaaagaaag             50

SEQ ID NO: 360          moltype =   length =
SEQUENCE: 360
000

SEQ ID NO: 361          moltype =   length =
```

```
SEQUENCE: 361
000

SEQ ID NO: 362          moltype =   length =
SEQUENCE: 362
000

SEQ ID NO: 363          moltype =   length =
SEQUENCE: 363
000

SEQ ID NO: 364          moltype =   length =
SEQUENCE: 364
000

SEQ ID NO: 365          moltype =   length =
SEQUENCE: 365
000

SEQ ID NO: 366          moltype =   length =
SEQUENCE: 366
000

SEQ ID NO: 367          moltype =   length =
SEQUENCE: 367
000

SEQ ID NO: 368          moltype =   length =
SEQUENCE: 368
000

SEQ ID NO: 369          moltype = AA  length = 7
FEATURE                 Location/Qualifiers
REGION                  1..7
                        note = Description of Artificial Sequence: Synthetic peptide
REGION                  1..7
                        note = Category: NLS
REGION                  1..7
                        note = Description: SV40
source                  1..7
                        mol_type = protein
                        organism = synthetic construct
SEQUENCE: 369
PKKKRKV                                                                   7

SEQ ID NO: 370          moltype = AA  length = 16
FEATURE                 Location/Qualifiers
REGION                  1..16
                        note = Description of Unknown: nucleoplasmin bipartite NLS
                         sequence
REGION                  1..16
                        note = Category: NLS
REGION                  1..16
                        note = Description: nucleoplasmin bipartite NLS
source                  1..16
                        mol_type = protein
                        organism = unidentified
SEQUENCE: 370
KRPAATKKAG QAKKKK                                                         16

SEQ ID NO: 371          moltype = AA  length = 9
FEATURE                 Location/Qualifiers
REGION                  1..9
                        note = Description of Unknown: c-myc NLS sequence
REGION                  1..9
                        note = Category: NLS
REGION                  1..9
                        note = Description: c-myc NLS
source                  1..9
                        mol_type = protein
                        organism = unidentified
SEQUENCE: 371
PAAKRVKLD                                                                 9

SEQ ID NO: 372          moltype = AA  length = 11
FEATURE                 Location/Qualifiers
REGION                  1..11
                        note = Description of Unknown: c-myc NLS sequence
REGION                  1..11
```

```
                        note = Category: NLS
REGION                  1..11
                        note = Description: c-myc NLS
source                  1..11
                        mol_type = protein
                        organism = unidentified
SEQUENCE: 372
RQRRNELKRS P                                                              11

SEQ ID NO: 373          moltype = AA  length = 38
FEATURE                 Location/Qualifiers
REGION                  1..38
                        note = Category: NLS
REGION                  1..38
                        note = Description: hRNPA1 M9 NLS
source                  1..38
                        mol_type = protein
                        organism = Homo sapiens
SEQUENCE: 373
NQSSNFGPMK GGNFGGRSSG PYGGGGQYFA KPRNQGGY                                 38

SEQ ID NO: 374          moltype = AA  length = 42
FEATURE                 Location/Qualifiers
REGION                  1..42
                        note = Description of Unknown: Importin-alpha IBB domain
                         sequence
REGION                  1..42
                        note = Category: NLS
REGION                  1..42
                        note = Description: Importin-alpha IBB domain
source                  1..42
                        mol_type = protein
                        organism = unidentified
SEQUENCE: 374
RMRIZFKNKG KDTAELRRRR VEVSVELRKA KKDEQILKRR NV                            42

SEQ ID NO: 375          moltype = AA  length = 8
FEATURE                 Location/Qualifiers
REGION                  1..8
                        note = Description of Unknown: Myoma T protein sequence
REGION                  1..8
                        note = Category: NLS
REGION                  1..8
                        note = Description: Myoma T protein
source                  1..8
                        mol_type = protein
                        organism = unidentified
SEQUENCE: 375
VSRKRPRP                                                                  8

SEQ ID NO: 376          moltype = AA  length = 8
FEATURE                 Location/Qualifiers
REGION                  1..8
                        note = Description of Unknown: Myoma T protein sequence
REGION                  1..8
                        note = Category: NLS
REGION                  1..8
                        note = Description: Myoma T protein
source                  1..8
                        mol_type = protein
                        organism = unidentified
SEQUENCE: 376
PPKKARED                                                                  8

SEQ ID NO: 377          moltype = AA  length = 8
FEATURE                 Location/Qualifiers
REGION                  1..8
                        note = Description of Unknown: p53 sequence
REGION                  1..8
                        note = Category: NLS
REGION                  1..8
                        note = Description: p53
source                  1..8
                        mol_type = protein
                        organism = unidentified
SEQUENCE: 377
PQPKKKPL                                                                  8

SEQ ID NO: 378          moltype = AA  length = 12
```

```
FEATURE                Location/Qualifiers
REGION                 1..12
                       note = Category: NLS
REGION                 1..12
                       note = Description: mouse c-abl IV
source                 1..12
                       mol_type = protein
                       organism = Mus sp.
SEQUENCE: 378
SALIKKKKKM AP                                                        12

SEQ ID NO: 379         moltype = AA  length = 5
FEATURE                Location/Qualifiers
REGION                 1..5
                       note = Category: NLS
REGION                 1..5
                       note = Description: influenza virus NS1
source                 1..5
                       mol_type = protein
                       organism = Influenza virus
SEQUENCE: 379
DRLRR                                                                5

SEQ ID NO: 380         moltype = AA  length = 7
FEATURE                Location/Qualifiers
REGION                 1..7
                       note = Category: NLS
REGION                 1..7
                       note = Description: influenza virus NS1
source                 1..7
                       mol_type = protein
                       organism = Influenza virus
SEQUENCE: 380
PKQKKRK                                                              7

SEQ ID NO: 381         moltype = AA  length = 10
FEATURE                Location/Qualifiers
REGION                 1..10
                       note = Category: NLS
REGION                 1..10
                       note = Description: Hepatitis virus delta antigen
source                 1..10
                       mol_type = protein
                       organism = Hepatitis delta virus
SEQUENCE: 381
RKLKKKIKKL                                                           10

SEQ ID NO: 382         moltype = AA  length = 10
FEATURE                Location/Qualifiers
REGION                 1..10
                       note = Category: NLS
REGION                 1..10
                       note = Description: mouse Mx1 protein
source                 1..10
                       mol_type = protein
                       organism = Mus sp.
SEQUENCE: 382
REKKKFLKRR                                                           10

SEQ ID NO: 383         moltype = AA  length = 20
FEATURE                Location/Qualifiers
REGION                 1..20
                       note = Category: NLS
REGION                 1..20
                       note = Description: human poly(ADP-ribose) polymerase
source                 1..20
                       mol_type = protein
                       organism = Homo sapiens
SEQUENCE: 383
KRKGDEVDGV DEVAKKKSKK                                                20

SEQ ID NO: 384         moltype = AA  length = 17
FEATURE                Location/Qualifiers
REGION                 1..17
                       note = Category: NLS
REGION                 1..17
                       note = Description: steroid hormone receptor (human)
                        glucocorticoid
source                 1..17
```

```
                         mol_type = protein
                         organism = Homo sapiens
SEQUENCE: 384
RKCLQAGMNL EARKTKK                                                  17

SEQ ID NO: 385           moltype = AA  length = 170
FEATURE                  Location/Qualifiers
REGION                   1..170
                         note = Description of Unknown: uncultivated organism
REGION                   1..170
                         note = Category: MG68 putative adenosine deaminase
                          (TadA-like)
REGION                   1..170
                         note = Description: MG68-3 deaminase
source                   1..170
                         mol_type = protein
                         organism = unidentified
SEQUENCE: 385
MNEQTSTDEQ FMQQALALAD EAERQGEVPV GALLVHQGTV IGRGFNQVIT QLDPSAHAEM  60
LAIRDAARYL QNYRILDTTL YVTLEPCPMC AGALVHARVK RLVYGASDPR TGACGSVFNV  120
VADTRLNHQL EVVAGVLGSQ CGERLSAFFR QRRAAQKALK KAAQNFQSPS            170

SEQ ID NO: 386           moltype = AA  length = 167
FEATURE                  Location/Qualifiers
REGION                   1..167
                         note = Description of Unknown: uncultivated organism
REGION                   1..167
                         note = Category: MG68 putative adenosine deaminase
                          (TadA-like)
REGION                   1..167
                         note = Description: MG68-4 deaminase
source                   1..167
                         mol_type = protein
                         organism = unidentified
SEQUENCE: 386
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAEDP KTGACGSVMD  120
IARHPALNHQ LQVDGGVMAA PCARLLSDFF RWRRAQKKAA RDNSSGN               167

SEQ ID NO: 387           moltype = AA  length = 173
FEATURE                  Location/Qualifiers
REGION                   1..173
                         note = Description of Unknown: uncultivated organism
REGION                   1..173
                         note = Category: MG68 putative adenosine deaminase
                          (TadA-like)
REGION                   1..173
                         note = Description: MG68-5 deaminase
source                   1..173
                         mol_type = protein
                         organism = unidentified
SEQUENCE: 387
MSTDFTSAAQ QELDIAYMRK AIALAAQAEA DGEVPVGAVL VHNNEIIGVG RNRVIGGCDP  60
SLHAEFEAIR QGAQEIGNYR LLETTLYVTL EPCPMCAGLL VHSRIGRLVY GTPDLKTGAA  120
GSLMNLLQHP ELNHQIAITS GVLQADCAAQ LSGFFSAQRE RKKALKKRLK PNL         173

SEQ ID NO: 388           moltype = AA  length = 182
FEATURE                  Location/Qualifiers
REGION                   1..182
                         note = Description of Unknown: uncultivated organism
REGION                   1..182
                         note = Category: MG68 putative adenosine deaminase
                          (TadA-like)
REGION                   1..182
                         note = Description: MG68-6 deaminase
source                   1..182
                         mol_type = protein
                         organism = unidentified
SEQUENCE: 388
MSEIPQVVTE QQTDERWMHY ALALADKAEQ AGEIPVGAVL VKDNQVIGEG WNMSICRHDP  60
SAHAEMLAIR EAAVRVQNYR LLDDTTLYVTL EPCAMCAGLL VHSRVKRLVF GAFDAKTGAA  120
GSVTDLVRHP VLNHQLEVTS GVLAEQCADK LSSFFRRRRQ EHKAAKALRQ AQDPENQGNS  180
ES                                                                  182

SEQ ID NO: 389           moltype = AA  length = 151
FEATURE                  Location/Qualifiers
REGION                   1..151
                         note = Description of Unknown: uncultivated organism
REGION                   1..151
```

```
                        note = Category: MG68 putative adenosine deaminase
                         (TadA-like)
REGION                  1..151
                        note = Description: MG68-7 deaminase
source                  1..151
                        mol_type = protein
                        organism = unidentified
SEQUENCE: 389
MSDEIWIKHA LTLADKAYQQ GEVPVGAVLV KNNQIIAEGW NQPIAHHDPS AHAEIMALRL  60
AGQAEQNYRL PETTLYVTLE PCVMCAGAMI HARIGRLVFG AYDPKTGAAG SVFDIFSDAR  120
HNHQIEVVSG VLSELCGDKL RAFFRERRKK R                                151

SEQ ID NO: 390          moltype = AA  length = 166
FEATURE                 Location/Qualifiers
REGION                  1..166
                        note = Description of Unknown: uncultivated organism
REGION                  1..166
                        note = Category: MG68 putative adenosine deaminase
                         (TadA-like)
REGION                  1..166
                        note = Description: MG68-8 deaminase
source                  1..166
                        mol_type = protein
                        organism = unidentified
SEQUENCE: 390
MPQSEQDIYW IRYAMQLAER AEQAGEVPVG AVLVLDNQAL GEGWNLSISR HDPCAHAEIM  60
AIRQAGERIG NYRLLGATLY VTLEPCVMCA GAMVHSRIAR VVYGASDLKT GAAGSVFDVL  120
SDPRHNHVVE ITGGVESEAC SQQLSDFFRR RRAEQKAEKQ RLKDNQ                166

SEQ ID NO: 391          moltype = AA  length = 168
FEATURE                 Location/Qualifiers
REGION                  1..168
                        note = Description of Unknown: uncultivated organism
REGION                  1..168
                        note = Category: MG68 putative adenosine deaminase
                         (TadA-like)
REGION                  1..168
                        note = Description: MG68-9 deaminase
source                  1..168
                        mol_type = protein
                        organism = unidentified
SEQUENCE: 391
MNVAADEQWM KEALRQAERA LLAGEVPVGA VVVSQNNIVG QGFNRNLLDR DPTAHAEIIA  60
LREAAANIGN HRLLDCELYA TIEPCAMCAG AITHARVRRL VYGAEDLKAG AVHSVMQVVN  120
HPALNHRVEV KGGVLAERCG ELLQQFFWAR RAEQSGISGA NEDQLRRG              168

SEQ ID NO: 392          moltype = AA  length = 143
FEATURE                 Location/Qualifiers
REGION                  1..143
                        note = Description of Unknown: uncultivated organism
REGION                  1..143
                        note = Category: MG68 putative adenosine deaminase
                         (TadA-like)
REGION                  1..143
                        note = Description: MG68-10 deaminase
source                  1..143
                        mol_type = protein
                        organism = unidentified
SEQUENCE: 392
MLLAMEQARA AEEAGEVPVG AVILSPEGEV VARGENRVLR DSDPTAHAEM VALRAAGRVL  60
GNYRLPGCTL YSTLEPCSMC SGAILHARVA RLVFAASDPK AGACGSVLEV MNHPRLNHQV  120
ELVGGVLALE CGQMLTEFFR ARR                                         143

SEQ ID NO: 393          moltype = AA  length = 210
FEATURE                 Location/Qualifiers
REGION                  1..210
                        note = Description of Unknown: uncultivated organism
REGION                  1..210
                        note = Category: MG68 putative adenosine deaminase
                         (TadA-like)
REGION                  1..210
                        note = Description: MG68-11 deaminase
source                  1..210
                        mol_type = protein
                        organism = unidentified
SEQUENCE: 393
MSAEIDLTDK AFMRQALDQA QNAWLLGEVP VGAVIVREGR VIATGYNRPI GDNDPTAHAE  60
IVALRQAASL LGNYRLPGCT LYVTLEPCAM CAMALMHARL DRVVFGAPDP KTGAAGSVIN  120
LFDEPRLNHH CALRGGVEAQ DCARLLQDFF RERRRQIQAL QQKPAIPADR ADPDEQHASL  180
```

```
HAEGPAPLAG IDVRHLDEPD AAATSNPESP                                210

SEQ ID NO: 394         moltype = AA  length = 159
FEATURE                Location/Qualifiers
REGION                 1..159
                       note = Description of Unknown: uncultivated organism
REGION                 1..159
                       note = Category: MG68 putative adenosine deaminase
                        (TadA-like)
REGION                 1..159
                       note = Description: MG68-12 deaminase
source                 1..159
                       mol_type = protein
                       organism = unidentified
SEQUENCE: 394
MEIKARMRDI MTDDERWMAK ALRLAKEGAQ AGEVPVGAIL VFSGEQLAAA YNSPIRLRDA  60
TAHAEILALR LGGERLQNYR LTGCTLYVTL EPCAMCAGAL VQARIARLVF GARDSRVGAA  120
GSALDLAREP RFNHQVTVVG GVLASECEQV LREFFRARR                      159

SEQ ID NO: 395         moltype = AA  length = 205
FEATURE                Location/Qualifiers
REGION                 1..205
                       note = Description of Unknown: uncultivated organism
REGION                 1..205
                       note = Category: MG68 putative adenosine deaminase
                        (TadA-like)
REGION                 1..205
                       note = Description: MG68-13 deaminase
source                 1..205
                       mol_type = protein
                       organism = unidentified
SEQUENCE: 395
MPEPFQGGDP ADPARAAAEA QDLADRAFMR LALDQAHNAW LLGEVPVGAV IVHEGRVLAT  60
GYNRPIGDSD PTAHAEIVAL RQAASLLGNY RLPGCTLYVT LEPCAMCAMA LLHARIERVV  120
FGASDPKTGA AGSVLDLFAQ PLLNHHASLR AGVEAQACGA LLQEFFRERR ARARAQQQLP  180
AHGGGIDVRH LDAPEPGDES DPFDE                                     205

SEQ ID NO: 396         moltype = AA  length = 159
FEATURE                Location/Qualifiers
REGION                 1..159
                       note = Description of Unknown: uncultivated organism
REGION                 1..159
                       note = Category: MG68 putative adenosine deaminase
                        (TadA-like)
REGION                 1..159
                       note = Description: MG68-14 deaminase
source                 1..159
                       mol_type = protein
                       organism = unidentified
SEQUENCE: 396
MGSDQDFMRL ALLEAEKAGA IGEVPVGAVI VKDGKVVARG HNQPVSGHDP TAHAEIMALR  60
EAGQVLGNYR LPACDLYVTL EPCAMCIGAM IHARIRRVIF GAHDPKTGAA GSVINLFEEK  120
TLNHHATVTG GILASDCAQL LKAFFAMRRK EAKTPSLSG                      159

SEQ ID NO: 397         moltype = AA  length = 168
FEATURE                Location/Qualifiers
REGION                 1..168
                       note = Description of Unknown: uncultivated organism
REGION                 1..168
                       note = Category: MG68 putative adenosine deaminase
                        (TadA-like)
REGION                 1..168
                       note = Description: MG68-15 deaminase
source                 1..168
                       mol_type = protein
                       organism = unidentified
SEQUENCE: 397
MEPMEEHRHF MGLAIEEAAR AYELNEVPVG AVLVGSAGEI LSRASNAPIR SADPSAHAEM  60
IALRQAARAS GNYRLPGSVL YVTLEPCVMC VGAMLHARIA TLVFGARDPR TGAAGSVVDL  120
TSVPAFNHYV RVIAGVRAEE CSELLRRFFR ERRREGKSGY GGEVPKRP             168

SEQ ID NO: 398         moltype = AA  length = 153
FEATURE                Location/Qualifiers
REGION                 1..153
                       note = Description of Unknown: uncultivated organism
REGION                 1..153
                       note = Category: MG68 putative adenosine deaminase
                        (TadA-like)
REGION                 1..153
```

```
                        note = Description: MG68-16 deaminase
source                  1..153
                        mol_type = protein
                        organism = unidentified
SEQUENCE: 398
MADEDIKFMR LALELAKKAE FIDEVPVGAL IIKDGEIIGT GMNSCISDHD PTSHAEIKAI  60
RDAANTIKNY RLNGCSIYVT LEPCAMCVGA IQHARIEKII YGANDPKTGA CGSVIDLMSI  120
KEINHHTEAI GGVLQKECGQ ILKDFFLSKR KKP                               153

SEQ ID NO: 399          moltype = AA  length = 148
FEATURE                 Location/Qualifiers
REGION                  1..148
                        note = Description of Unknown: uncultivated organism
REGION                  1..148
                        note = Category: MG68 putative adenosine deaminase
                         (TadA-like)
REGION                  1..148
                        note = Description: MG68-17 deaminase
source                  1..148
                        mol_type = protein
                        organism = unidentified
SEQUENCE: 399
MQRALGRAGD ARAQGEVPVG AVVVCAGEVV GEGCNRNISL DDPSAHAEIL ALRAAGQRLG  60
NYRLPGCTLY VTLEPCAMCV GAAIHSRLDG VVFGATDPKT GALGGAFDLP ASHAHNHVLS  120
VRGGLLADEC GALLKAFFRD RRKAPRAP                                     148

SEQ ID NO: 400          moltype = AA  length = 191
FEATURE                 Location/Qualifiers
REGION                  1..191
                        note = Description of Unknown: uncultivated organism
REGION                  1..191
                        note = Category: MG68 putative adenosine deaminase
                         (TadA-like)
REGION                  1..191
                        note = Description: MG68-18 deaminase
source                  1..191
                        mol_type = protein
                        organism = unidentified
SEQUENCE: 400
MQKKVDDFLK IVEPPDAERR TKGKLLQQRA VDEQWMGLAL QRGEEAGRQG EVPVGAVVVG  60
KDGFLTAAGN SPIGLADPSA HAEMLAIRAA AKLLGNYRLP EATLYVTLEP CIMCMGALIQ  120
ARISRLVFGA ADPKTGAAIS VYAIGTDQRL NHTVAVTGGI LAEACAQLLK NFFKKRRGHS  180
PVINSPFLKT P                                                       191

SEQ ID NO: 401          moltype = AA  length = 144
FEATURE                 Location/Qualifiers
REGION                  1..144
                        note = Description of Unknown: uncultivated organism
REGION                  1..144
                        note = Category: MG68 putative adenosine deaminase
                         (TadA-like)
REGION                  1..144
                        note = Description: MG68-19 deaminase
source                  1..144
                        mol_type = protein
                        organism = unidentified
SEQUENCE: 401
MREAYALALI AYEQGEVPVG AVLVGEDDEI LGRGWNQVIQ RHDPMAHAEC VAIQEAAAQL  60
RNYRLNGSTL YVTLEPCCMC AGAMVHARIA RLVFGARDVR SGAAGSAYNL LAGDLLNHRV  120
KIDEGILQQE CSHLLRNFFK QRRD                                         144

SEQ ID NO: 402          moltype = AA  length = 195
FEATURE                 Location/Qualifiers
REGION                  1..195
                        note = Description of Unknown: uncultivated organism
REGION                  1..195
                        note = Category: MG68 putative adenosine deaminase
                         (TadA-like)
REGION                  1..195
                        note = Description: MG68-20 deaminase
source                  1..195
                        mol_type = protein
                        organism = unidentified
SEQUENCE: 402
MTSQVSRQQP LSGNNLVHND LIASVCPPGL VPAQQDEFWM QQALVLARQA EMMGEVPVGA  60
VVVKNQQLIG YGYNQSITLN DPSAHAEVLA LRMAGQTLTN YRLPDTTLYV TLEPCAMCAT  120
TMVHARVARL VYGAADLKTG AAGSVLNLTN YTAFNHQLSC VSGVLQRDCS YLLSNFFKLR  180
RTQHKAKKVS GTFIR                                                   195
```

```
SEQ ID NO: 403          moltype = AA  length = 162
FEATURE                 Location/Qualifiers
REGION                  1..162
                        note = Description of Unknown: uncultivated organism
REGION                  1..162
                        note = Category: MG68 putative adenosine deaminase
                         (TadA-like)
REGION                  1..162
                        note = Description: MG68-21 deaminase
source                  1..162
                        mol_type = protein
                        organism = unidentified
SEQUENCE: 403
MDHERYMRRA IELAQQAESL GEVPVGAVIV HDHQIIGEGF NEVIRRNDPS AHAEAQAIRA  60
AGQHLANYRL VNTTLYVSLE PCAMCAGLIV HARVKTVVFA TPDPRTGATG TAIQVLNHPS  120
MNHHVEVVSG VLQEQSATIL QNFFRKKREL AKMKKFHEKR VN                     162

SEQ ID NO: 404          moltype = AA  length = 166
FEATURE                 Location/Qualifiers
REGION                  1..166
                        note = Description of Unknown: uncultivated organism
REGION                  1..166
                        note = Category: MG68 putative adenosine deaminase
                         (TadA-like)
REGION                  1..166
                        note = Description: MG68-22 deaminase
source                  1..166
                        mol_type = protein
                        organism = unidentified
SEQUENCE: 404
MSDEHFMRLA LAQAALAEAE GEIPVGAVVV LNGEVVGSGY NSPIGRHDPT AHAEIRALRA  60
AAATLGNYRL VGCELFVTLE PCLMCAGAIQ HARIARLVYG AADYKTGVCG STLDVFGELP  120
GSPVPRLNHH TQVTGGVLGD ECSRQLSAFF ARRRAEKNAA KNHVFQ                 166

SEQ ID NO: 405          moltype = AA  length = 161
FEATURE                 Location/Qualifiers
REGION                  1..161
                        note = Description of Unknown: uncultivated organism
REGION                  1..161
                        note = Category: MG68 putative adenosine deaminase
                         (TadA-like)
REGION                  1..161
                        note = Description: MG68-23 deaminase
source                  1..161
                        mol_type = protein
                        organism = unidentified
SEQUENCE: 405
MDSLVERHEH YMMLALRLAE KGADRGEVPV GAVVVSPKGQ ILSLAHNEPI DLHDPTGHAE  60
IIAIRKAAQR IGNYRLVGCS LYVTLEPCVM CYGAIIHARI KRLFFGAYDP KAGAGTVFGL  120
FSSPFFNHQP EVRGGILAEL CEKVLKEFFE KLRSSKCCSS G                      161

SEQ ID NO: 406          moltype = AA  length = 152
FEATURE                 Location/Qualifiers
REGION                  1..152
                        note = Description of Unknown: uncultivated organism
REGION                  1..152
                        note = Category: MG68 putative adenosine deaminase
                         (TadA-like)
REGION                  1..152
                        note = Description: MG68-24 deaminase
source                  1..152
                        mol_type = protein
                        organism = unidentified
SEQUENCE: 406
MTEDERWMEE ALALAREASN DGEAPVGAVV VHAGEIIGRG RNRIEGLADP TAHAELLALR  60
QASMNLGRWR LTGCALFVTL EPCAMCLGAC YAARVDRLVY GATSPKFGAA GSSVTLAGVE  120
RLNHRLEVVS GVLEKECARL LAKFFRGLRG KG                                152

SEQ ID NO: 407          moltype = AA  length = 168
FEATURE                 Location/Qualifiers
REGION                  1..168
                        note = Description of Unknown: uncultivated organism
REGION                  1..168
                        note = Category: MG68 putative adenosine deaminase
                         (TadA-like)
REGION                  1..168
                        note = Description: MG68-25 deaminase
source                  1..168
                        mol_type = protein
```

```
                         organism = unidentified
SEQUENCE: 407
MDDQHWMGRA LALAERAAEQ GEVPGGAVLV IENEIVGEGW SRPIATQDPS AHAEILALRD  60
AGLRRGNYRL SGSVLYVTLE PCVMCAGAIV HARVDTLVFG AADPKAGACG SVFDLLPSDG  120
RFNHHTQCRG PILADACGTI LRAFFANKRA SPRARANASA AHERPEND                168

SEQ ID NO: 408          moltype = AA  length = 173
FEATURE                 Location/Qualifiers
REGION                  1..173
                        note = Description of Unknown: uncultivated organism
REGION                  1..173
                        note = Category: MG68 putative adenosine deaminase
                         (TadA-like)
REGION                  1..173
                        note = Description: MG68-26 deaminase
source                  1..173
                        mol_type = protein
                        organism = unidentified
SEQUENCE: 408
MSESQFDETQ YRWMDRALEL AGQAANLGEV PVGAVIVSAE GELLGEGFNQ PIKVQDPTAH  60
AEIMAIRQAC RKTGNYRLPG AVLYVTLEPC AMCAGAIVHA RLARVVFATC EPKAGAVEST  120
LRFFDLPQLN HRVEYTGGLR RSEASSLLSH FFQSRREEKA LLKKNSRQQQ SDC          173

SEQ ID NO: 409          moltype = AA  length = 164
FEATURE                 Location/Qualifiers
REGION                  1..164
                        note = Description of Unknown: uncultivated organism
REGION                  1..164
                        note = Category: MG68 putative adenosine deaminase
                         (TadA-like)
REGION                  1..164
                        note = Description: MG68-27 deaminase
source                  1..164
                        mol_type = protein
                        organism = unidentified
SEQUENCE: 409
MREEKDLIFM KKALHLAEEA WRQGEVPVGA VVVDGEGQII GQGYNQSIAL LDPTAHAEIV  60
ALRQAAKKKK NYRLSGSTLY VTLEPCPMCL GAMVQARIDR LVFGAYDPKN GAVSSIMNFP  120
LDKMNHRFEI EGGLLSQECA TILKEFFQSR RGETNNKKET AKEE                    164

SEQ ID NO: 410          moltype = AA  length = 153
FEATURE                 Location/Qualifiers
REGION                  1..153
                        note = Description of Unknown: uncultivated organism
REGION                  1..153
                        note = Category: MG68 putative adenosine deaminase
                         (TadA-like)
REGION                  1..153
                        note = Description: MG68-28 deaminase
source                  1..153
                        mol_type = protein
                        organism = unidentified
SEQUENCE: 410
MDTDEQFMQH AIQLAHKAQS QGEVPVGAIL VKDNKIIGKG WNQPITRHDP SAHAEIMAIR  60
HAGQALKNYR LPDTTLYVTL EPCNMCAGMI IHARIKRLVF AAYDPKTGAA GSVFDTLTDP  120
RNNHTVEIEG GVLEEPCAEM LRHFFRQRRK KTP                                153

SEQ ID NO: 411          moltype = AA  length = 158
FEATURE                 Location/Qualifiers
REGION                  1..158
                        note = Description of Unknown: uncultivated organism
REGION                  1..158
                        note = Category: MG68 putative adenosine deaminase
                         (TadA-like)
REGION                  1..158
                        note = Description: MG68-29 deaminase
source                  1..158
                        mol_type = protein
                        organism = unidentified
SEQUENCE: 411
MSELENNNPQ HIKWMREAIK LAQKAQECGE VPVGALITKN DTLISSAYNQ PITKHDPTAH  60
AEIQALQQAG KILQNYRLND TVLYITLEPC AMCAGAIVHA RIGTVVFGAY DHKTGVAGSA  120
GNIFTAEFSN HKPKIIGGTL EKECSLIIRN FFQARRQK                          158

SEQ ID NO: 412          moltype = AA  length = 182
FEATURE                 Location/Qualifiers
REGION                  1..182
                        note = Description of Unknown: uncultivated organism
REGION                  1..182
```

```
                      note = Category: MG68 putative adenosine deaminase
                       (TadA-like)
REGION                1..182
                      note = Description: MG68-30 deaminase
source                1..182
                      mol_type = protein
                      organism = unidentified
SEQUENCE: 412
MPNFLKQLQQ IIAFETSCAA DWSEQQKHVF WMQQALKVAA YGEQLGEVPV GAVAVVENQL  60
IAVGWNASIS KHDPTAHAEV MALRAAGTVL KNYRQLQLTL YVTLEPCAMC AGAMVHARIA  120
QLVYGASDPK TGAVDSVFNL LRHPNLNHQA PVLGGVLATE CRTQLQDFFR RRRQEKKQAQ  180
QK                                                                182

SEQ ID NO: 413        moltype = AA  length = 167
FEATURE               Location/Qualifiers
REGION                1..167
                      note = Description of Unknown: uncultivated organism
REGION                1..167
                      note = Category: MG68 putative adenosine deaminase
                       (TadA-like)
REGION                1..167
                      note = Description: MG68-31 deaminase
source                1..167
                      mol_type = protein
                      organism = unidentified
SEQUENCE: 413
MESVDEQWMR YAIRLAQRAE EQGEVPVGAV LVKGDRCLAE GWNVPVQRHD PTAHAEMVAI  60
RDAGIALENY RLIDSTLYVT LEPCVMCMGA IAHARIKRLV FGAFDPKRGA VCNALSLTDA  120
SFLNHKVVWD GGVFEQECSE LLIDFFKARR KVTKPEVVVT NPQRHGM                167

SEQ ID NO: 414        moltype = AA  length = 160
FEATURE               Location/Qualifiers
REGION                1..160
                      note = Description of Unknown: uncultivated organism
REGION                1..160
                      note = Category: MG68 putative adenosine deaminase
                       (TadA-like)
REGION                1..160
                      note = Description: MG68-32 deaminase
source                1..160
                      mol_type = protein
                      organism = unidentified
SEQUENCE: 414
MYNQQAIDKH FMNCALELAT FAADSGEVPV GAVIVRKNTI VAKGSNSPIA DHDPTAHAEI  60
IAIRKATAQC ANYRTPDTTL YVTLEPCIMC MGAIIQARIG RLVFGAYDAK TGAAGSCYSI  120
GQDNLLNHSL EIAGGINEQQ CAILLKKFFK IRRKKGSKNN                        160

SEQ ID NO: 415        moltype = AA  length = 150
FEATURE               Location/Qualifiers
REGION                1..150
                      note = Description of Unknown: uncultivated organism
REGION                1..150
                      note = Category: MG68 putative adenosine deaminase
                       (TadA-like)
REGION                1..150
                      note = Description: MG68-33 deaminase
source                1..150
                      mol_type = protein
                      organism = unidentified
SEQUENCE: 415
MSDLEWMRRA ITLAQKAEQQ GEVPVGALLV REGVCVGEGW NQPILRHDPS AHAEINALRD  60
AGQATENYRL IDTVLYVTLE PCVMCMGAIA NARVRRLVFG ASDPARGAAG SILSLSNASF  120
LNHHIETEGG LLAEECSELL RSFFARRRRK                                   150

SEQ ID NO: 416        moltype = AA  length = 155
FEATURE               Location/Qualifiers
REGION                1..155
                      note = Description of Unknown: uncultivated organism
REGION                1..155
                      note = Category: MG68 putative adenosine deaminase
                       (TadA-like)
REGION                1..155
                      note = Description: MG68-34 deaminase
source                1..155
                      mol_type = protein
                      organism = unidentified
SEQUENCE: 416
MSPVVAESDR AWMRHALELA NRAGEEGEVP VGAVMVKDGQ LVGEGWNRVI GLNDPSAHAE  60
ILALREAGQR LGNYRLPGCS LYVTLEPCAM CAGAMLHARL ERVYFGTGDP KTGALGGTFD  120
```

```
LFADYPHNHR IETQGGLLEI ECSSLLKEFF RARRL                          155

SEQ ID NO: 417          moltype = AA  length = 194
FEATURE                 Location/Qualifiers
REGION                  1..194
                        note = Description of Unknown: uncultivated organism
REGION                  1..194
                        note = Category: MG68 putative adenosine deaminase
                         (TadA-like)
REGION                  1..194
                        note = Description: MG68-35 deaminase
source                  1..194
                        mol_type = protein
                        organism = unidentified
SEQUENCE: 417
MGLNGLTHHS PFIPISENID TSDKLALQIM SLKLSNPDEK WMRHAQSLAE HAAAQGEIPV  60
GAVIVQAGEC IAEGWNQPIA NNDPTAHAEI IALRKAAQYL NNYRLVNTLL YVTLEPCVMC  120
AGAIIQARVK RVIFGAYDPK AGAAGSRFDI LRDTRHNYQV ECISGVLAKE CSDYLSRFFK  180
NRRTRAKPSR FPKP                                                 194

SEQ ID NO: 418          moltype = AA  length = 174
FEATURE                 Location/Qualifiers
REGION                  1..174
                        note = Description of Unknown: uncultivated organism
REGION                  1..174
                        note = Category: MG68 putative adenosine deaminase
                         (TadA-like)
REGION                  1..174
                        note = Description: MG68-36 deaminase
source                  1..174
                        mol_type = protein
                        organism = unidentified
SEQUENCE: 418
MQDDTVPEEI DHERWMRQAL NEAMDAAEEG EVPVGAVVVY ENRIIGRGHN RTVATHDPSA  60
HAEILALGAA GAAVGDWRLT GVDIYVSLEP CAMCAGAIQL GRLRRAVFGP RDPKFGGCGS  120
VLDVLREPRL NHQVEVIEGV MAAESQHLLK EFFRRLRAKD RVPATPDPFP NAGE        174

SEQ ID NO: 419          moltype = AA  length = 149
FEATURE                 Location/Qualifiers
REGION                  1..149
                        note = Description of Unknown: uncultivated organism
REGION                  1..149
                        note = Category: MG68 putative adenosine deaminase
                         (TadA-like)
REGION                  1..149
                        note = Description: MG68-37 deaminase
source                  1..149
                        mol_type = protein
                        organism = unidentified
SEQUENCE: 419
MEEEYFMREA LKEAEKAAQE GEVPIGAVVV GPSREIIGRG YNRPIGLCDP TAHAEIMALR  60
EAAKRLGNYR LLDCEIYVTL EPCPMCAGAL VYARLKRLVF GAHDPKAGAC GSVYNIVQDK  120
RLNHQLEVAG GLLAEECRAL LQAFFKSRR                                 149

SEQ ID NO: 420          moltype = AA  length = 160
FEATURE                 Location/Qualifiers
REGION                  1..160
                        note = Description of Unknown: uncultivated organism
REGION                  1..160
                        note = Category: MG68 putative adenosine deaminase
                         (TadA-like)
REGION                  1..160
                        note = Description: MG68-38 deaminase
source                  1..160
                        mol_type = protein
                        organism = unidentified
SEQUENCE: 420
MFEFSDNKAE FFMKQAILQA IRAWKKGEVP VGAVVVSGAG QILASAHNCP ISLDDPTAHA  60
EILALRLAAG KVGNYRLTDS WLISTLEPCV MCAGAMVWAR VKGVVFGARD PVSGAFGSVM  120
DINEVPGLNH RIEVTEGVLA AECSQLLKDF FKRRRQSSAG                     160

SEQ ID NO: 421          moltype = AA  length = 148
FEATURE                 Location/Qualifiers
REGION                  1..148
                        note = Description of Unknown: uncultivated organism
REGION                  1..148
                        note = Category: MG68 putative adenosine deaminase
                         (TadA-like)
REGION                  1..148
```

```
                          note = Description: MG68-39 deaminase
source                    1..148
                          mol_type = protein
                          organism = unidentified
SEQUENCE: 421
MTDENWMQRA LQLAAQAEAV GEVPVGAVIV KNDTLVAEGF NQPIGAHDAT AHAEIVALRR  60
AGEALGNYRL VDTTLYVTLE PCSMCVGAMI HARVAKVVFG ASDPRTGALG GAFDLQQAGR  120
HNHRFDVVSG VMADSSRQLL QNFFRVRR                                     148

SEQ ID NO: 422            moltype = AA  length = 149
FEATURE                   Location/Qualifiers
REGION                    1..149
                          note = Description of Unknown: uncultivated organism
REGION                    1..149
                          note = Category: MG68 putative adenosine deaminase
                           (TadA-like)
REGION                    1..149
                          note = Description: MG68-40 deaminase
source                    1..149
                          mol_type = protein
                          organism = unidentified
SEQUENCE: 422
MTEDEKWMNL AIEQAIKAQD EDEVPVGAVL VKNGLLLSQA HNQPISTNDA TAHAEIQALR  60
KAGIKLQNYR LTDSTLYVTL EPCAMCLGAM MHARIARIVY GANDLKTGAC GSSENLLNAN  120
CFNHKIHLIS GVLENECKQL LKKFFNSRR                                    149

SEQ ID NO: 423            moltype = AA  length = 185
FEATURE                   Location/Qualifiers
REGION                    1..185
                          note = Description of Unknown: uncultivated organism
REGION                    1..185
                          note = Category: MG68 putative adenosine deaminase
                           (TadA-like)
REGION                    1..185
                          note = Description: MG68-41 deaminase
source                    1..185
                          mol_type = protein
                          organism = unidentified
SEQUENCE: 423
MNQVNCGRIG SRLIRTGGVN ISRAPIEEDP VNDLQYAQDT KWMRCALDCA RRAYSTEEVP  60
IGAVLVRNEQ IIGEGFNQTI RNLDPTSHAE IMAIRSAAEN IGNYRLSDTT LYVTIEPCMM  120
CLGAIIHARV ERLVFGAQEP KAGVLKSHPV FDGDFLNHQV KWSSGILESE CSRLMRDFFI  180
HKRTL                                                              185

SEQ ID NO: 424            moltype = AA  length = 203
FEATURE                   Location/Qualifiers
REGION                    1..203
                          note = Description of Unknown: uncultivated organism
REGION                    1..203
                          note = Category: MG68 putative adenosine deaminase
                           (TadA-like)
REGION                    1..203
                          note = Description: MG68-42 deaminase
source                    1..203
                          mol_type = protein
                          organism = unidentified
SEQUENCE: 424
MAPVPLKQPL AGESFDAHDH AMMRLAIDQA LNAQLHGEVP VGAVLVKGGQ VIATGYNHPI  60
GSHDPTAHAE IRTLRMAAEQ LGNYRLGEST LYVTLEPCMM CLGAMLHARI TRVVFGASDP  120
KTGVCGGVLD LPAEGRLNHQ TTVQGGLLAE ECGELLQRFF AERRAQRRAD REALRAQQDE  180
LLRWAATLPA EEEVGTLRLD EET                                          203

SEQ ID NO: 425            moltype = AA  length = 150
FEATURE                   Location/Qualifiers
REGION                    1..150
                          note = Description of Unknown: uncultivated organism
REGION                    1..150
                          note = Category: MG68 putative adenosine deaminase
                           (TadA-like)
REGION                    1..150
                          note = Description: MG68-43 deaminase
source                    1..150
                          mol_type = protein
                          organism = unidentified
SEQUENCE: 425
MAMALAEAEK AMQIGEVPIG AVVVGPDQQL LGTGYNQSIC LNDPSAHAEM LAIRAAAAQL  60
GNYRLRDCTL YVTLEPCAMC MGAILHSRIQ RVVFAAADPK TGACGSVLSL QSEPRLNHHC  120
SVTQGVLAER AASLIKGFFK ARRQVKKCRC                                   150
```

```
SEQ ID NO: 426          moltype = AA  length = 164
FEATURE                 Location/Qualifiers
REGION                  1..164
                        note = Description of Unknown: uncultivated organism
REGION                  1..164
                        note = Category: MG68 putative adenosine deaminase
                         (TadA-like)
REGION                  1..164
                        note = Description: MG68-44 deaminase
source                  1..164
                        mol_type = protein
                        organism = unidentified
SEQUENCE: 426
MLHMVYYEIN ETNSQDVFFM RRALTLAQKA ASADEVPVGA VAIANNEIIG EGFNCPIGTH  60
DPTAHAEIMA LRQAAQKSNN YRLPEVTLYV TLEPCVMCVG AMLHARIKRL VFGAIDQKTG  120
AVVSVFKILD EKNLNHRIQY QSGVLAVPCG KILSDFFKDR RGVI                   164

SEQ ID NO: 427          moltype = AA  length = 180
FEATURE                 Location/Qualifiers
REGION                  1..180
                        note = Description of Unknown: uncultivated organism
REGION                  1..180
                        note = Category: MG68 putative adenosine deaminase
                         (TadA-like)
REGION                  1..180
                        note = Description: MG68-45 deaminase
source                  1..180
                        mol_type = protein
                        organism = unidentified
SEQUENCE: 427
MTALITTSNI HDKMMSLALK EAFKAYKLGE IPVGCVITDE NNELVATGFN RTIIDNDPSA  60
HAEIVALRKA GEKLQNYRLV NLNLYVTLEP CTMCSGAIIH ARIKRVFFGA YDLKTGACGS  120
VFNVLNDDRH NHKVEIYGGI LKEECSSMLS DFFKARRKMQ KEGRDWIVES GKDRTWLNKD  180

SEQ ID NO: 428          moltype = AA  length = 153
FEATURE                 Location/Qualifiers
REGION                  1..153
                        note = Description of Unknown: uncultivated organism
REGION                  1..153
                        note = Category: MG68 putative adenosine deaminase
                         (TadA-like)
REGION                  1..153
                        note = Description: MG68-46 deaminase
source                  1..153
                        mol_type = protein
                        organism = unidentified
SEQUENCE: 428
MISDTEFMGA ALELALAASK LGEVPVGAVV VKGGRIIGTG SNAPISRHDP TAHAEILALR  60
AAASALENYR LTECTLYVTL EPCAMCAGAI QHARIARLVF GASDSKTGAC GSVVNLFGEP  120
MLNHHTQVQG GMLARDCGEL LSDFFRQRRA AVQ                               153

SEQ ID NO: 429          moltype = AA  length = 160
FEATURE                 Location/Qualifiers
REGION                  1..160
                        note = Description of Unknown: uncultivated organism
REGION                  1..160
                        note = Category: MG68 putative adenosine deaminase
                         (TadA-like)
REGION                  1..160
                        note = Description: MG68-47 deaminase
source                  1..160
                        mol_type = protein
                        organism = unidentified
SEQUENCE: 429
MSGSDAAASR ACMEQALACA RDAEAAGEVP VGAVIVDAAG AVVARAANAP IARNDPTAHA  60
ELLVLRAAGR VLGNYRLPGC VLYVTLEPCA MCVGALVHAR IARIVYGAPD PKTGACGSVF  120
DLAANSKMNH RIEVAGGVLA EECGALLKQF FAARRGRDAP                        160

SEQ ID NO: 430          moltype = AA  length = 151
FEATURE                 Location/Qualifiers
REGION                  1..151
                        note = Description of Unknown: uncultivated organism
REGION                  1..151
                        note = Category: MG68 putative adenosine deaminase
                         (TadA-like)
REGION                  1..151
                        note = Description: MG68-48 deaminase
source                  1..151
                        mol_type = protein
```

```
                         organism = unidentified
SEQUENCE: 430
MFSRADQVFM RQALELAKQA KGEGEVPVGA VLTLNDLPIA TAYNQSITHQ DPTAHAEIIV  60
LREAAKILKN YRLVNTVLYV TLEPCAMCAG ALIHARVKRL IYATADPRTG ACGSIFNLIN  120
HQALNHQIQY ESGLLAEESK LLLQQFFQKR R                                 151

SEQ ID NO: 431           moltype = AA  length = 148
FEATURE                  Location/Qualifiers
REGION                   1..148
                         note = Description of Unknown: uncultivated organism
REGION                   1..148
                         note = Category: MG68 putative adenosine deaminase
                          (TadA-like)
REGION                   1..148
                         note = Description: MG68-49 deaminase
source                   1..148
                         mol_type = protein
                         organism = unidentified
SEQUENCE: 431
MNDEHYIQYA LNLAQKAESE NEVPVGALIV CNNQIIAEGW NQPIQLHDSS AHAEMLALRK  60
ASHHIENYRL KNTTLYVTLE PCAMCVGAMI HARIQKLVFG AWDQKAGAVH SVFQLIDDTR  120
HNHAIEWRGG VMADACSRVL KNFFKQRR                                    148

SEQ ID NO: 432           moltype = AA  length = 153
FEATURE                  Location/Qualifiers
REGION                   1..153
                         note = Description of Unknown: uncultivated organism
REGION                   1..153
                         note = Category: MG68 putative adenosine deaminase
                          (TadA-like)
REGION                   1..153
                         note = Description: MG68-50 deaminase
source                   1..153
                         mol_type = protein
                         organism = unidentified
SEQUENCE: 432
MTSHDDTYWI IHALTLAKKA EQQGEVPVGA VIVHDHQIVG EGWNQPIGAG DPTAHAEIIA  60
MRNAAQHLKN YRLINCTLYV TLEPCAMCVG AMVHARISRL VFGAFDPKAG AVTSVMQLLD  120
APHFNHIVTH QGGICAEKCS EILKSFFAMK RKT                               153

SEQ ID NO: 433           moltype = AA  length = 155
FEATURE                  Location/Qualifiers
REGION                   1..155
                         note = Description of Unknown: uncultivated organism
REGION                   1..155
                         note = Category: MG68 putative adenosine deaminase
                          (TadA-like)
REGION                   1..155
                         note = Description: MG68-51 deaminase
source                   1..155
                         mol_type = protein
                         organism = unidentified
SEQUENCE: 433
MTDDRDLYWM QQALLLAVDA GRRGEVPVGA LLVLDEVSIG VGYNRPIGDR DPTAHAEIIA  60
LRDAAKKINN YRLLDTTLYV TLEPCMMCAA AMVHARIKRL VYGAPDPKAG AIVSQAQILD  120
APFFNHRVAY YGNLLAMPCG ELLRTFFKAK RLSST                             155

SEQ ID NO: 434           moltype = AA  length = 153
FEATURE                  Location/Qualifiers
REGION                   1..153
                         note = Description of Unknown: uncultivated organism
REGION                   1..153
                         note = Category: MG68 putative adenosine deaminase
                          (TadA-like)
REGION                   1..153
                         note = Description: MG68-52 deaminase
source                   1..153
                         mol_type = protein
                         organism = unidentified
SEQUENCE: 434
MRLAMDMAKE AYSIGEVPVG CVIADADGNV ISTGYNRSIT DNDPSAHAEM VAIRNAGSLL  60
KNYRMPGLSL YVTLEPCCMC SGAIIHARIA RVYYGASDLK TGACGSVFNV MSDPRHNHSV  120
ECIGGILADE CSKMLSDFFK ERRQQKKAEA TKL                               153

SEQ ID NO: 435           moltype = AA  length = 174
FEATURE                  Location/Qualifiers
REGION                   1..174
                         note = Description of Unknown: uncultivated organism
REGION                   1..174
```

```
                        note = Category: MG68 putative adenosine deaminase
                         (TadA-like)
REGION                  1..174
                        note = Description: MG68-53 deaminase
source                  1..174
                        mol_type = protein
                        organism = unidentified
SEQUENCE: 435
MTVNHEYFMR LAIEQALLAY QAGEIPVGAV IVDTDGNVIG RGFNRTILDN DPSAHAEIVA  60
LRDAGERVKN YRLINLDMYV TLEPCTMCSG ALIHSRLNNL YFGAYDLKTG ACGSRFNILG  120
SSEYNHIVNV TGGILKEECQ NIISDFFKAR RKMQKDGRDW IVESGKVRSW QKNV        174

SEQ ID NO: 436          moltype = AA  length = 172
FEATURE                 Location/Qualifiers
REGION                  1..172
                        note = Description of Unknown: uncultivated organism
REGION                  1..172
                        note = Category: MG68 putative adenosine deaminase
                         (TadA-like)
REGION                  1..172
                        note = Description: MG68-54 deaminase
source                  1..172
                        mol_type = protein
                        organism = unidentified
SEQUENCE: 436
MTSPTAGLGE TDEYWMNRAL ALAAEAGESG EVPVGAVVVL DGREVGAGYN GPIGSCDPTA  60
HAEIRALRDA GARAGNYRLP GATLYVTLEP CTMCVGAIVH ARINRLVYGT TEPKAGAVES  120
IRQTLRDDHF NWQVEATGGV LASQCREIIQ RFFAGRREYH RLRKQTLSVK EQ          172

SEQ ID NO: 437          moltype = AA  length = 158
FEATURE                 Location/Qualifiers
REGION                  1..158
                        note = Description of Unknown: uncultivated organism
REGION                  1..158
                        note = Category: MG68 putative adenosine deaminase
                         (TadA-like)
REGION                  1..158
                        note = Description: MG68-55 deaminase
source                  1..158
                        mol_type = protein
                        organism = unidentified
SEQUENCE: 437
MPDLDDGYWM QQALKLAAQA KDQGEVPVGA LVVGEQKLLG QGYNQVISLQ DPSAHAEVMA  60
LRGAGITQQN YRLVNTTLYV TLEPCMMCAG VLVHARIKRL VFGAYDPKAG AISSCAQLLT  120
LPHLNHQILV QGGILAKECG QQLTDFFKAK RQAKHDKG                          158

SEQ ID NO: 438          moltype = AA  length = 157
FEATURE                 Location/Qualifiers
REGION                  1..157
                        note = Description of Unknown: uncultivated organism
REGION                  1..157
                        note = Category: MG68 putative adenosine deaminase
                         (TadA-like)
REGION                  1..157
                        note = Description: MG68-56 deaminase
source                  1..157
                        mol_type = protein
                        organism = unidentified
SEQUENCE: 438
MTAAAEFDEH DLRWMRQALE LARRAERDHA EVPVGAVLVI DNEVIGSGMN RNIIDHDASA  60
HAEIVCLRDA GQRVANHRFP GSTLYVTLEP CVMCAGAIVH ARVGRVVYAA SDPKTGAAGS  120
VFDILTSERH NHRVAVRGGL LAEESARLLQ LFFRSRR                           157

SEQ ID NO: 439          moltype = AA  length = 176
FEATURE                 Location/Qualifiers
REGION                  1..176
                        note = Description of Unknown: uncultivated organism
REGION                  1..176
                        note = Category: MG68 putative adenosine deaminase
                         (TadA-like)
REGION                  1..176
                        note = Description: MG68-57 deaminase
source                  1..176
                        mol_type = protein
                        organism = unidentified
SEQUENCE: 439
MSESSAVYSD EYWLRYALQL AERAYQQGEV PVGAVLVRDN QILGEGWNQS ISQHDATAHA  60
EIMALRAAGL VAGNYRLPNT SLYVTLEPCV MCAGALLHAR VERVVFGAYD PKTGAVGSMF  120
DVLLDARHNH QVQLTGGVLQ ADCVAQLQAF FKERRLAQKL AKFNSVTISS PTSTEN      176
```

```
SEQ ID NO: 440          moltype = AA  length = 158
FEATURE                 Location/Qualifiers
REGION                  1..158
                        note = Description of Unknown: uncultivated organism
REGION                  1..158
                        note = Category: MG68 putative adenosine deaminase
                         (TadA-like)
REGION                  1..158
                        note = Description: MG68-58 deaminase
source                  1..158
                        mol_type = protein
                        organism = unidentified
SEQUENCE: 440
MSLADRHEMF MQMALQQAQL AYDCAEVPVG AVVVNSAGEV IGKGYNRTII DSDPTAHAEI  60
VALRQAAAHE QNYRLPDLTV YVTLEPCVMC IGALTHARIA HVVYGASDPK TGACGSVLCI  120
QANKKINHHT RITSGVLEQA CAEKLRHFFR ERRKGSKL                         158

SEQ ID NO: 441          moltype = AA  length = 154
FEATURE                 Location/Qualifiers
REGION                  1..154
                        note = Description of Unknown: uncultivated organism
REGION                  1..154
                        note = Category: MG68 putative adenosine deaminase
                         (TadA-like)
REGION                  1..154
                        note = Description: MG68-59 deaminase
source                  1..154
                        mol_type = protein
                        organism = unidentified
SEQUENCE: 441
MADDDFMALA IEQALLAQAQ GEVPVGAVLV DGSGHVIGRG ANAVIGLSDP TAHAEIVALR  60
SAAKLLGNYR LPQTTLFVTL EPCAMCLGAL FHARVSRIVF GAPDPKTGAC GSRLDLTAPD  120
LINFHASVRG GVMQEACGHL LTDFFKRKRS EKLS                             154

SEQ ID NO: 442          moltype = AA  length = 204
FEATURE                 Location/Qualifiers
REGION                  1..204
                        note = Description of Unknown: uncultivated organism
REGION                  1..204
                        note = Category: MG68 putative adenosine deaminase
                         (TadA-like)
REGION                  1..204
                        note = Description: MG68-60 deaminase
source                  1..204
                        mol_type = protein
                        organism = unidentified
SEQUENCE: 442
MRVALGAARE AQAAGEVPVG AVIVRDGVLI ATGRNAPRQQ HDPTAHAEIA ALRAAARRLG  60
NYRLDGCTLY VTLEPCLMCV GAMLHARLER VVFGAPDPKT GAAGSVFNAL AEPKLNHQTT  120
VEGGVLATEC AALLQVFFGQ RRLLQRISAQ PLRDDALRTS EARMAAFASP LSRWVCDLPA  180
LQGLRLHYLD MGPSTEGRAW LLLH                                        204

SEQ ID NO: 443          moltype = AA  length = 168
FEATURE                 Location/Qualifiers
REGION                  1..168
                        note = Description of Unknown: uncultivated organism
REGION                  1..168
                        note = Category: MG68 putative adenosine deaminase
                         (TadA-like)
REGION                  1..168
                        note = Description: MG68-61 deaminase
source                  1..168
                        mol_type = protein
                        organism = unidentified
SEQUENCE: 443
MNTEQSKPLL GDAHFMQQAL QLADAAFALQ EVPVGAVVVQ DGIIIGRGFN APITQHDPCA  60
HAEILALRDA AKNIGNYRLV GCELFVTLEP CVMCAGAMMH ARIARVVYGA YDLKTGACGS  120
VQNVFNEPRW NHHTICTGGV LAEQCGTKLS QFFALRRAQK KSLTATWT              168

SEQ ID NO: 444          moltype = AA  length = 283
FEATURE                 Location/Qualifiers
REGION                  1..283
                        note = Description of Unknown: uncultivated organism
REGION                  1..283
                        note = Category: MG121 deaminase
REGION                  1..283
                        note = Description: MG121-1 deaminase
source                  1..283
```

```
                         mol_type = protein
                         organism = unidentified
SEQUENCE: 444
MKVTLGGQTI DVEEVLKRIS STTVAAALIK DGEVVAVEET GGEHAEKKLV RKHDVEGAVI  60
FVTARPCRYC AEAMAEAGVA GVVYLGKGRG YGPYLLERLG VPCVEVHPSE PPAWRPVPRL  120
DVLITFGGNP YLTEEDVAAR TYALLTGIGV EAEVVPAPNN MAGRVEVMVK RGDPDRAHGR  180
LKETFGPVFK VRRFQLSGDY EDRESLAEDV LEVVEPLIED PFAVRANVAS PGPTFSGSKE  240
AEVFIGDVLT SAGHEVDLED PRTLVHVDVL GRRVSVGVER RDG                   283

SEQ ID NO: 445           moltype = AA  length = 279
FEATURE                  Location/Qualifiers
REGION                   1..279
                         note = Description of Unknown: uncultivated organism
REGION                   1..279
                         note = Category: MG121 deaminase
REGION                   1..279
                         note = Description: MG121-2 deaminase
source                   1..279
                         mol_type = protein
                         organism = unidentified
SEQUENCE: 445
VKITLAGETI DVEKVLREIP TRTVTAALIK DGEVKAYEEA DGEHAEKKLI RNHDVSDGVV  60
FVTIRPCLYC ARELAKAGVA GVVYIGRGRG LGPYYLARKG IEVVEVNPSR PLHYDPVERL  120
DVLVTFGGNP YLTEEDVAAR VYCLLTGKGI KAEIAPAPEN LAGRVEVMIT DGDSERAARV  180
IERELPTFNV RHFLLSDRFD DREELSKRVL EEIEPRVEDP FAVRARIARA GLFSSSRDAE  240
VFLGDVLTSA GHEVDLDEPR TVVHVDVLGD RVSVGVEKR                        279

SEQ ID NO: 446           moltype = AA  length = 283
FEATURE                  Location/Qualifiers
REGION                   1..283
                         note = Description of Unknown: uncultivated organism
REGION                   1..283
                         note = Category: MG121 deaminase
REGION                   1..283
                         note = Description: MG121-3 deaminase
source                   1..283
                         mol_type = protein
                         organism = unidentified
SEQUENCE: 446
MKVTLGGQTI DVEEVLKRIS STTVAAALIK DGEVVAVEET GGEHAEKKLV RKHDVEGAVI  60
FVTARPCRYC AEAMAEAGVA GVVYLGKGRG YGPYLLERLG VPCVEVHPSE PPAWRPVPRL  120
DVLITFGGNP YLTEEDVAAR TYALLTGIGI EAEVVPAPNN MAGRVEVMVK RGDPDRAHGR  180
LKETFGSVFK VRRFQLSGDY EDRESLAEDV LEVVEPLIED PFAVRANVAS PGPTFSGSKE  240
AEVFIGDVLT SAGHEVDLED PRTLVHVDVL GRRVSVGVER RDG                   283

SEQ ID NO: 447           moltype = AA  length = 280
FEATURE                  Location/Qualifiers
REGION                   1..280
                         note = Description of Unknown: uncultivated organism
REGION                   1..280
                         note = Category: MG121 deaminase
REGION                   1..280
                         note = Description: MG121-4 deaminase
source                   1..280
                         mol_type = protein
                         organism = unidentified
SEQUENCE: 447
MRSAEYLAYL RRRYGLRPNR RLGQHFMVDD RLLRFMVEAA GVGPEDTVLE IGPGPGLLTR  60
YLIERAGRVV AVELDERLVE VLERELGDAE NLEIVHADFL EYGVPEEVNK VVSNLPYQIS  120
SEATFEILRS DVERAVLTYQ REFAERMTAE PGTRGYGRLT VMVNLLARVE VLRAVPRRAF  180
VPPPRVSSAI VRLEPRPESE LPDVDPETLE AVCRGLFQHR RKTVRNALRL SAHEWGGDEE  240
VVEEVLRRLP EELLDKRPLH LTPEEVVRVA RCVERARGSS                       280

SEQ ID NO: 448           moltype = AA  length = 167
FEATURE                  Location/Qualifiers
REGION                   1..167
                         note = Description of Artificial Sequence: Synthetic
                          polypeptide
REGION                   1..167
                         note = Category: MG68 putative adenosine deaminase
                          (TadA-like)
REGION                   1..167
                         note = Description: MG68-4_V1
source                   1..167
                         mol_type = protein
                         organism = synthetic construct
SEQUENCE: 448
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
```

```
IARHPALNHQ LQVDGGVMAA PCARLLSDFF RWRRAQKKAA RDNSSGN              167

SEQ ID NO: 449         moltype = AA  length = 167
FEATURE                Location/Qualifiers
REGION                 1..167
                       note = Description of Artificial Sequence: Synthetic
                        polypeptide
REGION                 1..167
                       note = Category: MG68 putative adenosine deaminase
                        (TadA-like)
REGION                 1..167
                       note = Description: MG68-4_V2
source                 1..167
                       mol_type = protein
                       organism = synthetic construct
SEQUENCE: 449
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGVENP KTGACGSVMD  120
IARHPALNHQ LQVDGGVMAA PCARLLSDFF RWRRAQKKAA RDNSSGN              167

SEQ ID NO: 450         moltype = AA  length = 167
FEATURE                Location/Qualifiers
REGION                 1..167
                       note = Description of Artificial Sequence: Synthetic
                        polypeptide
REGION                 1..167
                       note = Category: MG68 putative adenosine deaminase
                        (TadA-like)
REGION                 1..167
                       note = Description: MG68-4_V3
source                 1..167
                       mol_type = protein
                       organism = synthetic construct
SEQUENCE: 450
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSYFF RWRRAQKKAA RDNSSGN              167

SEQ ID NO: 451         moltype = AA  length = 167
FEATURE                Location/Qualifiers
REGION                 1..167
                       note = Description of Artificial Sequence: Synthetic
                        polypeptide
REGION                 1..167
                       note = Category: MG68 putative adenosine deaminase
                        (TadA-like)
REGION                 1..167
                       note = Description: MG68-4_V4
source                 1..167
                       mol_type = protein
                       organism = synthetic construct
SEQUENCE: 451
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGAENP KTGACGSVMD  120
IARHPALNHQ LQVDGGVMAA PCARLLSDFF RWRRAQKKAA RDNSSGN              167

SEQ ID NO: 452         moltype = AA  length = 167
FEATURE                Location/Qualifiers
REGION                 1..167
                       note = Description of Artificial Sequence: Synthetic
                        polypeptide
REGION                 1..167
                       note = Category: MG68 putative adenosine deaminase
                        (TadA-like)
REGION                 1..167
                       note = Description: MG68-4_V5
source                 1..167
                       mol_type = protein
                       organism = synthetic construct
SEQUENCE: 452
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARYPALNHQ LQVDGGVMAA PCARLLSDFF RWRRAQKKAA RDNSSGN              167

SEQ ID NO: 453         moltype = AA  length = 167
FEATURE                Location/Qualifiers
REGION                 1..167
                       note = Description of Artificial Sequence: Synthetic
                        polypeptide
```

```
REGION                  1..167
                        note = Category: MG68 putative adenosine deaminase
                         (TadA-like)
REGION                  1..167
                        note = Description: MG68-4_V6
source                  1..167
                        mol_type = protein
                        organism = synthetic construct
SEQUENCE: 453
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCNRLLSDFF RWRRAQKKAA RDNSSGN                167

SEQ ID NO: 454          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V7
source                  1..167
                        mol_type = protein
                        organism = synthetic construct
SEQUENCE: 454
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLCDFF RWRRAQKKAA RDNSSGN                167

SEQ ID NO: 455          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V8
source                  1..167
                        mol_type = protein
                        organism = synthetic construct
SEQUENCE: 455
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSDFF RWRRAQKNAA RDNSSGN                167

SEQ ID NO: 456          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V9
source                  1..167
                        mol_type = protein
                        organism = synthetic construct
SEQUENCE: 456
MTDSQNDTDE YWMGEALKLA QKARDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSDFF RWRRAQKKAA RDNSSGN                167

SEQ ID NO: 457          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V10
source                  1..167
                        mol_type = protein
```

```
                         organism = synthetic construct
SEQUENCE: 457
MTDSQNDTDE YWMGEALKLA QKAWDEGEVP VGAILVRKGE VIGHGWNRSI GSHDPSAHAE  60
IMAIREAGVR IGNYRMLDTV LYSTLEPCAM CAGALVHGRI SRLVFGAENP KTGACGSVMD  120
IARHPALNHQ LQVDGGVMAA PCARLLSDFF RWRRAQKKAA RDNSSGN                167

SEQ ID NO: 458           moltype = AA  length = 167
FEATURE                  Location/Qualifiers
REGION                   1..167
                         note = Description of Artificial Sequence: Synthetic
                          polypeptide
REGION                   1..167
                         note = Category: MG68 putative adenosine deaminase
                          (TadA-like)
REGION                   1..167
                         note = Description: MG68-4_V11
source                   1..167
                         mol_type = protein
                         organism = synthetic construct
SEQUENCE: 458
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KRGACGSVMD  120
IARHPALNHQ LQVDGGVMAA PCARLLSDFF RWRRAQKKAA RDNSSGN                167

SEQ ID NO: 459           moltype = AA  length = 167
FEATURE                  Location/Qualifiers
REGION                   1..167
                         note = Description of Artificial Sequence: Synthetic
                          polypeptide
REGION                   1..167
                         note = Category: MG68 putative adenosine deaminase
                          (TadA-like)
REGION                   1..167
                         note = Description: MG68-4_V12
source                   1..167
                         mol_type = protein
                         organism = synthetic construct
SEQUENCE: 459
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSRFF RWRRAQKKAA RDNSSGN                167

SEQ ID NO: 460           moltype = AA  length = 167
FEATURE                  Location/Qualifiers
REGION                   1..167
                         note = Description of Artificial Sequence: Synthetic
                          polypeptide
REGION                   1..167
                         note = Category: MG68 putative adenosine deaminase
                          (TadA-like)
REGION                   1..167
                         note = Description: MG68-4_V13
source                   1..167
                         mol_type = protein
                         organism = synthetic construct
SEQUENCE: 460
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSDFF RWRPAQKKAA RDNSSGN                167

SEQ ID NO: 461           moltype = AA  length = 167
FEATURE                  Location/Qualifiers
REGION                   1..167
                         note = Description of Artificial Sequence: Synthetic
                          polypeptide
REGION                   1..167
                         note = Category: MG68 putative adenosine deaminase
                          (TadA-like)
REGION                   1..167
                         note = Description: MG68-4_V14
source                   1..167
                         mol_type = protein
                         organism = synthetic construct
SEQUENCE: 461
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGVENP KTGACGSVMD  120
IARHPALNHQ LQVDGGVMAA PCARLLSYFF RWRRAQKKAA RDNSSGN                167

SEQ ID NO: 462           moltype = AA  length = 167
```

```
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V15
source                  1..167
                        mol_type = protein
                        organism = synthetic construct
SEQUENCE: 462
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARHPALNHQ LQVDGGVMAA PCARLLSYFF RWRRAQKKAA RDNSSGN                167

SEQ ID NO: 463          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V16
source                  1..167
                        mol_type = protein
                        organism = synthetic construct
SEQUENCE: 463
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCARLLSDFF RWRRAQKKAA RDNSSGN                167

SEQ ID NO: 464          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V17
source                  1..167
                        mol_type = protein
                        organism = synthetic construct
SEQUENCE: 464
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCNRLLSYFF RWRRAQKKAA RDNSSGN                167

SEQ ID NO: 465          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V18
source                  1..167
                        mol_type = protein
                        organism = synthetic construct
SEQUENCE: 465
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCARLLCYFF RWRRAQKKAA RDNSSGN                167

SEQ ID NO: 466          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
```

```
REGION                  1..167
                        note = Description: MG68-4_V19
source                  1..167
                        mol_type = protein
                        organism = synthetic construct
SEQUENCE: 466
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCARLLSYFF RWRRAQKNAA RDNSSGN                167

SEQ ID NO: 467          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V20
source                  1..167
                        mol_type = protein
                        organism = synthetic construct
SEQUENCE: 467
MTDSQNDTDE YWMGEALKLA QKAWDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCARLLCYFF RWRRAQKNAA RDNSSGN                167

SEQ ID NO: 468          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V21
source                  1..167
                        mol_type = protein
                        organism = synthetic construct
SEQUENCE: 468
MTDSQNDTDE YWMGEALKLA QKARDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCARLLCYFF RWRRAQKNAA RDNSSGN                167

SEQ ID NO: 469          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V22
source                  1..167
                        mol_type = protein
                        organism = synthetic construct
SEQUENCE: 469
MTDSQNDTDE YWMGEALKLA QKARDEGEVP VGAILVRKGE VIGHGWNRSI GSHDPSAHAE  60
IMAIREAGVR IGNYRMLDTV LYVTFEPCAM CAGALVHGRI SRLVFGVENP KTGACGSVMD  120
IARYPALNHQ LQVDGGVMAA PCNRLLCYFF RWRRAQKNAA RDNSSGN                167

SEQ ID NO: 470          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V23
source                  1..167
                        mol_type = protein
                        organism = synthetic construct
SEQUENCE: 470
MTDSQNDTDE YWMGEALKLA QKARDEGEVP VGAILVRKGE VIGHGWNRSI GSHDPSAHAE  60
```

-continued

```
IMAIREAGVR IGNYRMLDTV LYVTFEPCAM CAGALVHGRI SRLVFGVENP KTGACGSVMD  120
IARYPALNHQ LQVDGGVMAA PCNRLLCYFF RWRPAQKNAA RDNSSGN                167

SEQ ID NO: 471          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V24
source                  1..167
                        mol_type = protein
                        organism = synthetic construct
SEQUENCE: 471
MTDSQNDTDE YWMGEALKLA QKARDEGEVP VGAILVRKGE VIGHGWNRSI GSHDPSAHAE  60
IMAIREAGVR IGNYRMLDTV LYSTFEPCAM CAGALVHGRI SRLVFGVENP KTGACGSVMD  120
IARYPALNHQ LQVDGGVMAA PCNRLLCYFF RWRPAQKNAA RDNSSGN                167

SEQ ID NO: 472          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V25
source                  1..167
                        mol_type = protein
                        organism = synthetic construct
SEQUENCE: 472
MTDSQNDTDE YWMGEALKLA QKARDEGEVP VGAILVRKGE VIGHGWNRSI GSHDPSAHAE  60
IMAIREAGVR IGNYRMLDTV LYSTFEPCAM CAGALVHGRI SRLVFGVENP KTGACGSVMD  120
IARHPALNHQ LQVDGGVMAA PCNRLLCYFF RWRPAQKNAA RDNSSGN                167

SEQ ID NO: 473          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V26
source                  1..167
                        mol_type = protein
                        organism = synthetic construct
SEQUENCE: 473
MTDSQNDTDE YWMGEALKLA QKARDEGEVP VGAILVRKGE VIGHGWNRSI GSHDPSAHAE  60
IMAIREAGVR IGNYRMLDTV LYSTFEPCAM CAGALVHGRI SRLVFGVENP KTGACGSVMD  120
IARHPALNHQ LQVDGGVMAA PCNRLLCRFF RWRPAQKNAA RDNSSGN                167

SEQ ID NO: 474          moltype = AA  length = 167
FEATURE                 Location/Qualifiers
REGION                  1..167
                        note = Description of Artificial Sequence: Synthetic
                         polypeptide
REGION                  1..167
                        note = Category: MG68 putative adenosine deaminase
                         (TadA-like)
REGION                  1..167
                        note = Description: MG68-4_V27
source                  1..167
                        mol_type = protein
                        organism = synthetic construct
SEQUENCE: 474
MTDSQNDTDE YWMGEALKLA QKARDEGEVP VGAILVRKGE VIGHGWNRSI GSHDPSAHAE  60
IMAIREAGVR IGNYRMLDTV LYSTFEPCAM CAGALVHGRI SRLVFGVENP KRGACGSVMD  120
IARHPALNHQ LQVDGGVMAA PCNRLLCRFF RWRPAQKNAA RDNSSGN                167

SEQ ID NO: 475          moltype = AA  length = 167
FEATURE                 Location/Qualifiers
REGION                  1..167
                        note = Description of Artificial Sequence: Synthetic
```

```
                         polypeptide
REGION                  1..167
                        note = Category: MG68 putative adenosine deaminase
                         (TadA-like)
REGION                  1..167
                        note = Description: MG68-4_V28
source                  1..167
                        mol_type = protein
                        organism = synthetic construct
SEQUENCE: 475
MTDSQNDTDE YWMGEALKLA QKARDEGEVP VGAILVRKGE VIGHGWNRSI GSHDPSAHAE  60
IMAIREAGVR IGNYRMLDTV LYSTFEPCAM CAGALVHGRI SRLVFGVENP KRGACGSVMD  120
IARHPALNHQ LQVDGGVMAA PCNRLLCDFF RWRPAQKNAA RDNSSGN               167

SEQ ID NO: 476          moltype = AA  length = 962
FEATURE                 Location/Qualifiers
REGION                  1..962
                        note = Description of Artificial Sequence: Synthetic
                         polypeptide
REGION                  1..962
                        note = Category: adenine base editor
REGION                  1..962
                        note = Description: MG68-4_V1-nMG34-1 (D10A)
source                  1..962
                        mol_type = protein
                        organism = synthetic construct
SEQUENCE: 476
MTDSQNDTDE YWMGEALKLA QKAWDEGEVP VGAILVRKGE VIGHGWNRSI GSHDPSAHAE  60
IMAIREAGVR IGNYRMLDTV LYVTLEPCAM CAGALVHGRI SRLVFGAENP KTGACGSVMD  120
IARHPALNHQ LQVDGGVMAA PCARLLSDFF RWRRAQKKAA RDNSSGNGTS GGSSGGSSGS  180
ETPGTSESAT PESSGGSSGG SMERELVLGI AYGGKYTGLA VVDRRHNQVL YANRLKMRDD  240
VAGILKDRRK QRGIRRTAQT KKKRLRELKN YLKSIGYNES TATFETVYSL AHKRGYDYAD  300
MPEEKTSEEI EAMDVEERKQ WEKEKQEWEE TKRNSRHRKE VVKDVHKAMI EGRATEEQIK  360
RVERIFNKQY RPKRFNNRIL TKCKVEDCGV NTPLRKNVRD LLIENIVRFF PIEQSEKDNL  420
KDAVLDKNRR EEVKSFFRKH KTDEHIRKQV YDIADNKLSG RTVFCKEHIL EHTEHSKEER  480
KVFRLAPSLK TKIENVLAVI KDEILPKFTV NKVVMESNNF DIAAKTQGKK RLAKEEYGKG  540
PREGKETRKE ALLRETDGRC IYCGKSIDIS NAHDDHIFPR KAGGLNIFAN LVACCAVCNE  600
NKKGRTPLES GISPKPEIIA FMKNDLKKKI LEDARNINTV DFNKYMSHAS IGWRYMRDRL  660
RESAGNKKLP IERQSGIYTA YFRRWWGFKK ERGNTLHHAL DAVILASRKG YSDDGLVDMT  720
LKPKYNKGGE FDPEKHLPEP IEFKMDKGSR GSALHDRNPL SYKKGIITRR FMVTEIECGK  780
EDDVISETYR EKLKEAFKRF DTKKGKCLTD KEAKEAGFCI KKNELVMSLK CSIKGTGPGQ  840
MIRINNNVFK TNVHNVGVDV YLDEKGKKKA YERKNPRLSK HFIEPPPQPN GRVSFTLKRR  900
DMVTVEGEDA IYRIKKLGTS PTIEAVVGSD GKTRTVSATK LTKANSAELE GSGGSPKKKR  960
KV                                                                962

SEQ ID NO: 477          moltype = AA  length = 1589
FEATURE                 Location/Qualifiers
REGION                  1..1589
                        note = Description of Artificial Sequence: Synthetic
                         polypeptide
REGION                  1..1589
                        note = Category: adenine base editor
REGION                  1..1589
                        note = Description: MG68-4_V1-nSpCas9 (D10A)
source                  1..1589
                        mol_type = protein
                        organism = synthetic construct
SEQUENCE: 477
MGSSHHHHHH MTDSQNDTDE YWMGEALKLA QKAWDEGEVP VGAILVRKGE VIGHGWNRSI  60
GSHDPSAHAE IMAIREAGVR IGNYRMLDTV LYVTLEPCAM CAGALVHGRI SRLVFGAENP  120
KTGACGSVMD IARHPALNHQ LQVDGGVMAA PCARLLSDFF RWRRAQKKAA RDNSSGNSGG  180
SSGGSSGSET PGTSESATPE SSGGSSGGSM DKKYSIGLAI GTNSVGWAVI TDEYKVPSKK  240
FKVLGNTDRH SIKKNLIGAL LFDSGETAEA TRLKRTARRR YTRRKNRICY LQEIFSNEMA  300
KVDDSFFHRL EESFLVEEDK KHERHPIFGN IVDEVAYHEK YPTIYHLRKK LVDSTDKADL  360
RLIYLALAHM IKFRGHFLIE GDLNPDNSDV DKLFIQLVQT YNQLFEENPI NASGVDAKAI  420
LSARLSKSRR LENLIAQLPG EKKNGLFGNL IALSLGLTPN FKSNFDLAED AKLQLSKDTY  480
DDDLDNLLAQ IGDQYADLFL AAKNLSDAIL LSDILRVNTE ITKAPLSASM IKRYDEHHQD  540
LTLLKALVRQ QLPEKYKEIF FDQSKNGYAG YIDGGASQEE FYKFIKPILE KMDGTEELLV  600
KLNREDLLRK QRTFDNGSIP HQIHLGELHA ILRRQEDFYP FLKDNREKIE KILTFRIPYY  660
VGPLARGNSR FAWMTRKSEE TITPWNFEEV VDKGASAQSF IERMTNFDKN LPNEKVLPKH  720
SLLYEYFTVY NELTKVKYVT EGMRKPAFLS GEQKKAIVDL LFKTNRKVTV KQLKEDYFKK  780
IECFDSVEIS GVEDRFNASL GTYHDLLKII KDKDFLDNEE NEDILEDIVL TLTLFEDREM  840
IEERLKTYAH LFDDKVMKQL KRRRYTGWGR LSRKLINGIR DKQSGKTILD FLKSDGFANR  900
NFMQLIHDDS LTFKEDIQKA QVSGQGDSLH EHIANLAGSP AIKKGILQTV KVVDELVKVM  960
GRHKPENIVI EMARENQTTQ KGQKNSRERM KRIEEGIKEL GSQILKEHPV ENTQLQNEKL  1020
YLYYLQNGRD MYVDQELDIN RLSDYDVDHI VPQSFLKDDS IDNKVLTRSD KNRGKSDNVP  1080
SEEVVKKMKN YWRQLLNAKL ITQRKFDNLT KAERGGLSEL DKAGFIKRQL VETRQITKHV  1140
AQILDSRMNT KYDENDKLIR EVKVITLKSK LVSDFRKDFQ FYKVREINNY HHAHDAYLNA  1200
VVGTALIKKY PKLESEFVYG DYKVYDVRKM IAKSEQEIGK ATAKYFFYSN IMNFFKTEIT  1260
```

```
LANGEIRKRP LIETNGETGE IVWDKGRDFA TVRKVLSMPQ VNIVKKTEVQ TGGFSKESIL  1320
PKRNSDKLIA RKKDWDPKKY GGFDSPTVAY SVLVVAKVEK GKSKKLKSVK ELLGITIMER  1380
SSFEKNPIDF LEAKGYKEVK KDLIIKLPKY SLFELENGRK RMLASAGELQ KGNELALPSK  1440
YVNFLYLASH YEKLKGSPED NEQKQLFVEQ HKHYLDEIIE QISEFSKRVI LADANLDKVL  1500
SAYNKHRDKP IREQAENIIH LFTLTNLGAP AAFKYFDTTI DRKRYTSTKE VLDATLIHQS  1560
ITGLYETRID LSQLGGDGSG GSPKKKRKV                                    1589

SEQ ID NO: 478          moltype = AA  length = 1361
FEATURE                 Location/Qualifiers
REGION                  1..1361
                        note = Description of Artificial Sequence: Synthetic
                         polypeptide
REGION                  1..1361
                        note = Category: cytosine base editor
REGION                  1..1361
                        note = Description: rAPOBEC1-nMG15-1 (D8A)
source                  1..1361
                        mol_type = protein
                        organism = synthetic construct
SEQUENCE: 478
MGSSHHHHHH GMSSETGPVA VDPTLRRRIE PHEFEVFFDP RELRKETCLL YEINWGGRHS  60
IWRHTSQNTN KHVEVNFIEK FTTERYFCPN TRCSITWFLS WSPCGECSRA ITEFLSRYPH  120
VTLFIYIARL YHHADPRNRQ GLRDLISSGV TIQIMTEQES GYCWRNFVNY SPSNEAHWPR  180
YPHLWVRLYV LELYCIILGL PPCLNILRRK QPQLTFFTIA LQSCHYQRLP PHILWATGLK  240
SGSETPGTSE SATPESGMNY VLGLAVGIAS VGWAVLELNE EDNPIRIEGL GARIFDKAEV  300
PKTGASLAAP RRMSRGIRRV IRRRRFRLQR VRSYLKKHNI LPAEKVDHLY DVPSAIDIYE  360
LRKRALTEKV TAEEWARLLI FFAKHRGFKS NRKKASGDAD EGEMLKAIAA NAEILKNYRT  420
VGEMLCDNEK FRKRKRNRDG AYNFTVSRAM LMEEIHTLFE IQRNLGQKFA DEKLEEEYVI  480
LFAAQRKFDE GPGENSPYAG NQIEKMIGSC TLEGKKEKRA PKASYAFMAF NLWQKINHLK  540
VNRRGSERFL TEEERRRIAD LAWKKEKLTY GSLRKVLSLD PEDRFVGLRY DLKKGKAENL  600
EEPVSEAEKR SFSWVKDYHS IRKALDKVEK NRILKLSHEQ LDTIATAFSV YKNEETIEKY  660
LEEGGIGKAD GEALLERLSG FSKFGHLSLK ACYKLLPFLE KGEVYSRACE LAGYDFSKSS  720
LENIDDIPNP VVKRSISQTL KVINAIILRY GNPVEVHIEL ARELARSFRD RKKMEKGMQE  780
NQAKNEKIRQ RLISEFGVLR PKGMDIVKFK LCEEQNGECA YSQKHFDMEK LLKDPSYAEV  840
DHIIPYSRSF DDSYNNKVLV LTKENREKRN RIPMEYLADA PERKNRFIHW VKSTIRNSRK  900
RENLLRTDYT ATTENEWKRR NLQDTQYISK YLYNYLRHHL VLAKGYTERK RRIIPVNGAV  960
TAYFRKRLGI NKIRENGDLH HAVDAVIIAC ATQGIVNKVS RYSKSRELWD YEVDMETGEV  1020
LQKKNKNTKD VFPEPWLNFR YELEQKVRVR PLDIPETADI TEMEEPFVSH MPNRKIHGPA  1080
HKETIRSGRL KEEGYTISKT ALIDLKLTED KEEIKGYYNK ESDRLLYEAL KKQLQRYGGK  1140
AKEAFKEPFH KPKADGTPGP IVNKVKIMEK STMLIPVNGG KGLASNGNMV RIDVFRAEEK  1200
GKKKYYFIPV YVADTVKEEL PNRAVLAHKP YEAWKIMKEE NFIFSLYPND LIFVDAGKEI  1260
PFKAALKGST LDPEKKASRF LMYYKGADIA TGSISGVNHD ETYKARGVGI QSLREIKKCC  1320
IDVLGNISFA SKEKRQTFRS GGSSSGGGAS SGGSPKKKRK V                      1361

SEQ ID NO: 479          moltype = AA  length = 1441
FEATURE                 Location/Qualifiers
REGION                  1..1441
                        note = Description of Artificial Sequence: Synthetic
                         polypeptide
REGION                  1..1441
                        note = Category: cytosine base editor
REGION                  1..1441
                        note = Description: rAPOBEC1-nMG15-1 (D8A)-UGI (PBS1)
source                  1..1441
                        mol_type = protein
                        organism = synthetic construct
SEQUENCE: 479
MGSSHHHHHH GMSSETGPVA VDPTLRRRIE PHEFEVFFDP RELRKETCLL YEINWGGRHS  60
IWRHTSQNTN KHVEVNFIEK FTTERYFCPN TRCSITWFLS WSPCGECSRA ITEFLSRYPH  120
VTLFIYIARL YHHADPRNRQ GLRDLISSGV TIQIMTEQES GYCWRNFVNY SPSNEAHWPR  180
YPHLWVRLYV LELYCIILGL PPCLNILRRK QPQLTFFTIA LQSCHYQRLP PHILWATGLK  240
SGSETPGTSE SATPESGMNY VLGLAVGIAS VGWAVLELNE EDNPIRIEGL GARIFDKAEV  300
PKTGASLAAP RRMSRGIRRV IRRRRFRLQR VRSYLKKHNI LPAEKVDHLY DVPSAIDIYE  360
LRKRALTEKV TAEEWARLLI FFAKHRGFKS NRKKASGDAD EGEMLKAIAA NAEILKNYRT  420
VGEMLCDNEK FRKRKRNRDG AYNFTVSRAM LMEEIHTLFE IQRNLGQKFA DEKLEEEYVI  480
LFAAQRKFDE GPGENSPYAG NQIEKMIGSC TLEGKKEKRA PKASYAFMAF NLWQKINHLK  540
VNRRGSERFL TEEERRRIAD LAWKKEKLTY GSLRKVLSLD PEDRFVGLRY DLKKGKAENL  600
EEPVSEAEKR SFSWVKDYHS IRKALDKVEK NRILKLSHEQ LDTIATAFSV YKNEETIEKY  660
LEEGGIGKAD GEALLERLSG FSKFGHLSLK ACYKLLPFLE KGEVYSRACE LAGYDFSKSS  720
LENIDDIPNP VVKRSISQTL KVINAIILRY GNPVEVHIEL ARELARSFRD RKKMEKGMQE  780
NQAKNEKIRQ RLISEFGVLR PKGMDIVKFK LCEEQNGECA YSQKHFDMEK LLKDPSYAEV  840
DHIIPYSRSF DDSYNNKVLV LTKENREKRN RIPMEYLADA PERKNRFIHW VKSTIRNSRK  900
RENLLRTDYT ATTENEWKRR NLQDTQYISK YLYNYLRHHL VLAKGYTERK RRIIPVNGAV  960
TAYFRKRLGI NKIRENGDLH HAVDAVIIAC ATQGIVNKVS RYSKSRELWD YEVDMETGEV  1020
LQKKNKNTKD VFPEPWLNFR YELEQKVRVR PLDIPETADI TEMEEPFVSH MPNRKIHGPA  1080
HKETIRSGRL KEEGYTISKT ALIDLKLTED KEEIKGYYNK ESDRLLYEAL KKQLQRYGGK  1140
AKEAFKEPFH KPKADGTPGP IVNKVKIMEK STMLIPVNGG KGLASNGNMV RIDVFRAEEK  1200
GKKKYYFIPV YVADTVKEEL PNRAVLAHKP YEAWKIMKEE NFIFSLYPND LIFVDAGKEI  1260
PFKAALKGST LDPEKKASRF LMYYKGADIA TGSISGVNHD ETYKARGVGI QSLREIKKCC  1320
```

```
IDVLGNISFA SKEKRQTFRS GGSSRTNLSD IIEKETGKQL VIQESILMLP EEVEEVIGNK  1380
PESDILVHTA YDESTDENVM LLTSDAPEYK PWALVIQDSN GENKIKMLAS SGGSPKKKRK  1440
V                                                                 1441

SEQ ID NO: 480         moltype = AA  length = 1442
FEATURE                Location/Qualifiers
REGION                 1..1442
                       note = Description of Artificial Sequence: Synthetic
                        polypeptide
REGION                 1..1442
                       note = Category: cytosine base editor
REGION                 1..1442
                       note = Description: rAPOBEC1-nMG15-1 (D8A)-MG69-1
source                 1..1442
                       mol_type = protein
                       organism = synthetic construct
SEQUENCE: 480
MGSSHHHHHH GMSSETGPVA VDPTLRRRIE PHEFEVFFDP RELRKETCLL YEINWGGRHS  60
IWRHTSQNTN KHVEVNFIEK FTTERYFCPN TRCSITWFLS WSPCGECSRA ITEFLSRYPH  120
VTLFIYIARL YHHADPRNRQ GLRDLISSGV TIQIMTEQES GYCWRNFVNY SPSNEAHWPR  180
YPHLWVRLYV LELYCIILGL PPCLNILRRK QPQLTFFTIA LQSCHYQRLP PHILWATGLK  240
SGSETPGTSE SATPESGMNY VLGLAVGIAS VGWAVLELNE EDNPIRIEGL GARIFDKAEV  300
PKTGASLAAP RRMSRGIRRV IRRRRFRLQR VRSYLKKHNI LPAEKVDHLY DVPSAIDIYE  360
LRKRALTEKV TAEEWARLLI FFAKHRGFKS NRKKASGDAD EGEMLKAIAA NAEILKNYRT  420
VGEMLCDNEK FRKRKRNRDG AYNFTVSRAM LMEEIHTLFE IQRNLGQKFA DEKLEEEYVI  480
LFAAQRKFDE GPGENSPYAG NQIEKMIGSC TLEGKKEKRA PKASYAFMAF NLWQKINHLK  540
VNRRGSERFL TEEERRRIAD LAWKKEKLTY GSLRKVLSLD PEDRFVGLRY DLKKGKAENL  600
EEPVSEAEKR SFSWVKDYHS IRKALDKVEK NRILKLSHEQ LDTIATAFSV YKNEETIEKY  660
LEEGGIGKAD GEALLERLSG FSKFGHLSLK ACYKLLPFLE KGEVYSRACE LAGYDFSKSS  720
LENIDDIPNP VVKRSISQTL KVINAIILRY GNPVEVHIEL ARELARSFRD RKKMEKGMQE  780
NQAKNEKIRQ RLISEFGVLR PKGMDIVKFK LCEEQNGECA YSQKHFDMEK LLKDPSYAEV  840
DHIIPYSRSF DDSYNNKVLV LTKENREKRN RIPMEYLADA PERKNRFIHW VKSTIRNSRK  900
RENLLRTDYT ATTENEWKRR NLQDTQYISK YLYNYLRHHL VLAKGYTERK RRIIPVNGAV  960
TAYFRKRLGI NKIRENGDLH HAVDAVIIAC ATQGIVNKVS RYSKSRELWD YEVDMETGEV  1020
LQKKNKNTKD VFPEPWLNFR YELEQKVRVR PLDIPETADI TEMEEPFVSH MPNRKIHGPA  1080
HKETIRSGRL KEEGYTISKT ALIDLKLTED KEEIKGYYNK ESDRLLYEAL KKQLQRYGGK  1140
AKEAFKEPFH KPKADGTPGP IVNKVKIMEK STMLIPVNGG KGLASNGNMV RIDVFRAEEK  1200
GKKKYYFIPV YVADTVKEEL PNRAVLAHKP YEAWKIMKEE NFIFSLYPND LIFVDAGKEI  1260
PFKAALKGST LDPEKKASRF LMYYKGADIA TGSISGVNHD ETYKARGVGI QSLREIKKCC  1320
IDVLGNISFA SKEKRQTFRS GGSSSKTIKD LEEFAAEKLG YDIVFQESIS MEPQEVEHLI  1380
TTDEKSVLVN STYDDNKEIT ISMISTPHPE YRPIALIIQD MEGEVQRKEL GSGGSPKKKR  1440
KV                                                                1442

SEQ ID NO: 481         moltype = AA  length = 1443
FEATURE                Location/Qualifiers
REGION                 1..1443
                       note = Description of Artificial Sequence: Synthetic
                        polypeptide
REGION                 1..1443
                       note = Category: cytosine base editor
REGION                 1..1443
                       note = Description: rAPOBEC1-nMG15-1 (D8A)-MG69-2
source                 1..1443
                       mol_type = protein
                       organism = synthetic construct
SEQUENCE: 481
MGSSHHHHHH GMSSETGPVA VDPTLRRRIE PHEFEVFFDP RELRKETCLL YEINWGGRHS  60
IWRHTSQNTN KHVEVNFIEK FTTERYFCPN TRCSITWFLS WSPCGECSRA ITEFLSRYPH  120
VTLFIYIARL YHHADPRNRQ GLRDLISSGV TIQIMTEQES GYCWRNFVNY SPSNEAHWPR  180
YPHLWVRLYV LELYCIILGL PPCLNILRRK QPQLTFFTIA LQSCHYQRLP PHILWATGLK  240
SGSETPGTSE SATPESGMNY VLGLAVGIAS VGWAVLELNE EDNPIRIEGL GARIFDKAEV  300
PKTGASLAAP RRMSRGIRRV IRRRRFRLQR VRSYLKKHNI LPAEKVDHLY DVPSAIDIYE  360
LRKRALTEKV TAEEWARLLI FFAKHRGFKS NRKKASGDAD EGEMLKAIAA NAEILKNYRT  420
VGEMLCDNEK FRKRKRNRDG AYNFTVSRAM LMEEIHTLFE IQRNLGQKFA DEKLEEEYVI  480
LFAAQRKFDE GPGENSPYAG NQIEKMIGSC TLEGKKEKRA PKASYAFMAF NLWQKINHLK  540
VNRRGSERFL TEEERRRIAD LAWKKEKLTY GSLRKVLSLD PEDRFVGLRY DLKKGKAENL  600
EEPVSEAEKR SFSWVKDYHS IRKALDKVEK NRILKLSHEQ LDTIATAFSV YKNEETIEKY  660
LEEGGIGKAD GEALLERLSG FSKFGHLSLK ACYKLLPFLE KGEVYSRACE LAGYDFSKSS  720
LENIDDIPNP VVKRSISQTL KVINAIILRY GNPVEVHIEL ARELARSFRD RKKMEKGMQE  780
NQAKNEKIRQ RLISEFGVLR PKGMDIVKFK LCEEQNGECA YSQKHFDMEK LLKDPSYAEV  840
DHIIPYSRSF DDSYNNKVLV LTKENREKRN RIPMEYLADA PERKNRFIHW VKSTIRNSRK  900
RENLLRTDYT ATTENEWKRR NLQDTQYISK YLYNYLRHHL VLAKGYTERK RRIIPVNGAV  960
TAYFRKRLGI NKIRENGDLH HAVDAVIIAC ATQGIVNKVS RYSKSRELWD YEVDMETGEV  1020
LQKKNKNTKD VFPEPWLNFR YELEQKVRVR PLDIPETADI TEMEEPFVSH MPNRKIHGPA  1080
HKETIRSGRL KEEGYTISKT ALIDLKLTED KEEIKGYYNK ESDRLLYEAL KKQLQRYGGK  1140
AKEAFKEPFH KPKADGTPGP IVNKVKIMEK STMLIPVNGG KGLASNGNMV RIDVFRAEEK  1200
GKKKYYFIPV YVADTVKEEL PNRAVLAHKP YEAWKIMKEE NFIFSLYPND LIFVDAGKEI  1260
PFKAALKGST LDPEKKASRF LMYYKGADIA TGSISGVNHD ETYKARGVGI QSLREIKKCC  1320
IDVLGNISFA SKEKRQTFRS GGSSSKTIKD LEEFAAEKLG YDIVFQESIS MEPQEVEHLI  1380
```

```
TTDEKSVLVN STYDDDKEIT ISVISTPHPE YRPIALVIQD MEGEVQRKEL YGSGGSPKKK  1440
RKV                                                               1443

SEQ ID NO: 482          moltype = AA  length = 1422
FEATURE                 Location/Qualifiers
REGION                  1..1422
                        note = Description of Artificial Sequence: Synthetic
                         polypeptide
REGION                  1..1422
                        note = Category: cytosine base editor
REGION                  1..1422
                        note = Description: rAPOBEC1-nMG15-1 (D8A)-MG69-
source                  1..1422
                        mol_type = protein
                        organism = synthetic construct
SEQUENCE: 482
MGSSHHHHHH GMSSETGPVA VDPTLRRRIE PHEFEVFFDP RELRKETCLL YEINWGGRHS  60
IWRHTSQNTN KHVEVNFIEK FTTERYFCPN TRCSITWFLS WSPCGECSRA ITEFLSRYPH  120
VTLFIYIARL YHHADPRNRQ GLRDLISSGV TIQIMTEQES GYCWRNFVNY SPSNEAHWPR  180
YPHLWVRLYV LELYCIILGL PPCLNILRRK QPQLTFFTIA LQSCHYQRLP PHILWATGLK  240
SGSETPGTSE SATPESGMNY VLGLAVGIAS VGWAVLELNE EDNPIRIEGL GARIFDKAEV  300
PKTGASLAAP RRMSRGIRRV IRRRRFRLQR VRSYLKKHNI LPAEKVDHLY DVPSAIDIYE  360
LRKRALTEKV TAEEWARLLI FFAKHRGFKS NRKKASGDAD EGEMLKAIAA NAEILKNYRT  420
VGEMLCDNEK FRKRKRNRDG AYNFTVSRAM LMEEIHTLFE IQRNLGQKFA DEKLEEEYVI  480
LFAAQRKFDE GPGENSPYAG NQIEKMIGSC TLEGKKEKRA PKASYAFMAF NLWQKINHLK  540
VNRRGSERFL TEEERRRIAD LAWKKEKLTY GSLRKVLSLD PEDRFVGLRY DLKKGKAENL  600
EEPVSEAEKR SFSWVKDYHS IRKALDKVEK NRILKLSHEQ LDTIATAFSV YKNEETIEKY  660
LEEGGIGKAD GEALLERLSG FSKFGHLSLK ACYKLLPFLE KGEVYSRACE LAGYDFSKSS  720
LENIDDIPNP VVKRSISQTL KVINAIILRY GNPVEVHIEL ARELARSFRD RKKMEKGMQE  780
NQAKNEKIRQ RLISEFGVLR PKGMDIVKFK LCEEQNGECA YSQKHFDMEK LLKDPSYAEV  840
DHIIPYSRSF DDSYNNKVLV LTKENREKRN RIPMEYLADA PERKNRFIHW VKSTIRNSRK  900
RENLLRTDYT ATTENEWKRR NLQDTQYISK YLYNYLRHHL VLAKGYTERK RRIIPVNGAV  960
TAYFRKRLGI NKIRENGDLH HAVDAVIIAC ATQGIVNKVS RYSKSRELWD YEVDMETGEV  1020
LQKKNKNTKD VFPEPWLNFR YELEQKVRVR PLDIPETADI TEMEEPFVSH MPNRKIHGPA  1080
HKETIRSGRL KEEGYTISKT ALIDLKLTED KEEIKGYYNK ESDRLLYEAL KKQLQRYGGK  1140
AKEAFKEPFH KPKADGTPGP IVNKVKIMEK STMLIPVNGG KGLASNGNMV RIDVFRAEEK  1200
GKKKYYFIPV YVADTVKEEL PNRAVLAHKP YEAWKIMKEE NFIFSLYPND LIFVDAGKEI  1260
PFKAALKGST LDPEKKASRF LMYYKGADIA TGSISGVNHD ETYKARGVGI QSLREIKKCC  1320
IDVLGNISFA SKEKRQTFRS GGSSIVRVTY NVEQEVEISN KFNKDVDIMK PEEYDDYIDD  1380
LMFALNEKLP EYAEISCVIN DNTGEVLFEG GSGGSPKKKR KV                    1422

SEQ ID NO: 483          moltype = DNA  length = 10943
FEATURE                 Location/Qualifiers
misc_feature            1..10943
                        note = Description of Artificial Sequence: Synthetic
                         polynucleotide
misc_feature            1..10943
                        note = Category: Plasmid
misc_feature            1..10943
                        note = Description: pET21-CAT (H193Y)-sgRNA-TadA-nSpCas9
                         (D10A)
source                  1..10943
                        mol_type = other DNA
                        organism = synthetic construct
SEQUENCE: 483
gaaataattt tgtttaactt taagaaggag atataccatg ggcagcagtc atcatcatca  60
ccatcacatg tctgaagtcg aatttagcca cgaatactgg atgcgtcacg cgctgacgct  120
ggcgaaacgt gcctgggatg agcgggaagt gccggtcggc gcggtattag tgcataacaa  180
tcgggtaatc ggcgaaggct ggaaccgccc gattggtcgc catgatccca ccgcacatgc  240
agaaatcatg gccctgcggc agggtggtct ggtgatgcaa aattatcgtc tgatcgacgc  300
cacgttgtat gtcacgcttg aaccatgtgt aatgtgtgcc ggagcgatga tccacagtcg  360
cattggtcgc gtggtctttg gtgcgcgtga cgcgaaaact ggcgctgcgg gatctttaat  420
ggatgtgctg catcatccgg gtatgaatca ccgagtggaa attacggaag gaatactggc  480
ggatgagtgc gcggcgttgc tcagtgactt ctttcgcatg cgccgccagg aaattaaagc  540
gcagaaaaaa gcgcaatcct cgacggattc aggcgggtcg tcgggaggaa gcagtggcag  600
cgagactccc ggaacttcgg agagcgctac accagaaagt agtggaggca gctctggtgg  660
gtccatggat aagaaatact caataggact ggcgattggc acaaatagcg tcggatgggc  720
tgtgatcact gatgaatata aggttccttc taaaaagttc aaggttctgg gaaatacaga  780
ccgccacagt atcaaaaaaa atcttatagg ggctcttctg tttgacagtg gagagacagc  840
cgaagctact agactcaaac ggacagctag gagaaggtat acaagacgga agaataggat  900
ttgttatctc caggagattt tttcaaatga gatggccaaa gtggatgata gtttctttca  960
tagacttgaa gagtcttttt tggtggaaga agacaagaag catgaaagac atcctatttt  1020
tggaaatata gtggatgaag ttgcttatca cgagaaatat ccaactatct atcatctgag  1080
aaaaaaattg gtggattcta ctgataaagc cgatttgcgc ctgatctatt tggccctggc  1140
ccacatgatt aagtttagag gtcatttttt gattgagggc gatctgaatc ctgataatag  1200
tgatgtggac aaactgttta tccagttggt gcaaacctac aatcaactgt ttgaagaaaa  1260
ccctattaac gcaagtggag tggatgctaa agccattctt tctgcaagat tgagtaaatc  1320
aagaagactg gaaaatctca ttgctcagct ccccggtgag aagaaaaatg gcctgtttgg  1380
gaatctcatt gctttgtcat tgggtttgac ccctaatttt aaatcaaatt ttgatttggc  1440
```

```
agaagatgct aaactccagc tttcaaaaga tacttacgat gatgatctgg ataatctgtt  1500
ggctcaaatt ggagatcaat atgctgattt gtttttggca gctaagaatc tgtcagatgc  1560
tattctgctt tcagacatcc tgagagtgaa tactgaaata actaaggctc ccctgtcagc  1620
ttcaatgatt aaacgctacg atgaacatca tcaagacttg actcttctga aagccctggt  1680
tagacaacaa cttccagaaa agtataaaga aatctttttt gatcaatcaa aaaacggata  1740
tgcaggttat attgatggcg gcgcaagcca agaagaattt tataaattta tcaaaccaat  1800
tctggaaaaa atggatggta ctgaggaact gttggtgaaa ctgaatagag aagatttgct  1860
gcgcaagcaa cggacctttg acaacggctc tattccccat caaattcact tgggtgagct  1920
gcatgctatt ttgagaagac aagaagactt ttatccattt ctgaaagaca atagagagaa  1980
gattgaaaaa atcttgactt ttaggattcc ttattatgtt ggtccattgg ccagaggcaa  2040
tagtaggttt gcatggatga ctcggaagtc tgaagaaaca attacccccat ggaattttga  2100
agaagttgtc gataaaggtg cttcagctca atcatttatt gaacgcatga caaactttga  2160
taaaaatctt ccaaatgaaa aagtgctgcc aaaacatagt ttgctttatg agtattttac  2220
cgtttataac gaattgacaa aggtcaaata tgttactgaa ggaatgagaa aaccagcatt  2280
tctttcaggt gaacagaaga aagccattgt tgatctgctc ttcaaaacaa ataggaaagt  2340
gaccgttaag caactgaaag aagattattt caaaaaaata gaatgttttg atagtgttga  2400
aatttcagga gttgaagata gatttaatgc ttcactgggt acataccatg atttgctgaa  2460
aattattaaa gataaagatt ttttggataa tgaagaaaat gaagacatcc tggaggatat  2520
tgttctgaca ttgaccctgt ttgaagatag ggagatgatt gaggaaagac ttaaaacata  2580
cgctcacctc tttgatgata aggtgatgaa acagcttaaa agacgcagat atactggttg  2640
gggaaggttg tccagaaaat tgattaatgg tattagggat aagcaatctg gcaaaacaat  2700
actggatttt ttgaaatcag atggttttgc caatcgcaat tttatgcagc tcatccatga  2760
tgatagtttg acatttaaag aagacatcca aaaagcacaa gtgtctggac aaggcgatag  2820
tctgcatgaa catattgcaa atctggctgg tagccctgct attaaaaaag gtattctcca  2880
gactgtgaaa gttgttgatg aattggtcaa agtgatgggg cggcataagc cagaaaatat  2940
cgttattgaa atggcaagag aaaatcagac aactcaaaag ggccagaaaa attccagaga  3000
gaggatgaaa agaatcgaag aaggtatcaa agaactggga agtcagattc ttaaagagca  3060
tcctgttgaa aatactcaat tgcaaaatga aaagctctat ctctattatc tccaaaatgg  3120
aagagatatg tatgtggacc aagaactgga tattaatagg ctgagtgatt atgatgtcga  3180
tcacattgtt ccacaaagtt tccttaaaga cgattcaata gacaataagg tcctgaccag  3240
gtctgataaa aatagaggta aatccgataa cgttccaagt gaagaagtgg tcaaaaagat  3300
gaaaaactat tggagacaac ttctgaacgc caagctgatc actcaaagga agtttgataa  3360
tctgaccaaa gctgaaagag gaggtttgag tgaacttgat aaagctggtt ttatcaaacg  3420
ccaattggtt gaaactcgcc aaatcactaa gcatgtggca caaattttgg atagtcgcat  3480
gaatactaaa tacgatgaaa atgataaact tattagagag gttaaagtga ttaccctgaa  3540
atctaaactg gtttctgact tcagaaaaga tttccaattc tataaagtga gagagattaa  3600
caattaccat catgcccatg atgcctatct gaatgccgtc gttggaactg ctttgattaa  3660
gaaatatcca aaacttgaaa gcgagtttgt ctatggtgat tataaagttt atgatgttag  3720
gaaaatgatt gctaagtctg agcaagaaat aggcaaagca accgcaaagt atttctttta  3780
ctctaatatc atgaacttct tcaaaacaga aattacactt gcaaatggag agattcgcaa  3840
acgccctctg atcgaaacta atggggaaac tggagaaatt gtctgggata aagggagaga  3900
ttttgccaca gtgcgcaaag tgttgtccat gccccaagtc aatatcgtca agaaaacaga  3960
agtgcagaca ggcggattct ctaaggagtc aattctgcca aaaagaaatt ccgacaagct  4020
gattgctagg aaaaaagact gggacccaaa aaaatatggt ggttttgata gtccaaccgt  4080
ggcttattca gtcctggtgg ttgctaaggt ggaaaaaggg aaatccaaga agctgaaatc  4140
cgttaaagag ctgctgggga tcacaattat ggaaagaagt tcctttgaaa aaaatcccat  4200
tgactttctg gaagctaaag gatataagga agttaaaaaa gacctgatca ttaaactgcc  4260
taaatatagt ctttttgagc tggaaaacgg taggaaacgg atgctggcta gtgccggaga  4320
actgcaaaaa ggaaatgagc tggctctgcc aagcaaatat gtgaattttc tgtatctggc  4380
tagtcattat gaaaagttga agggtagtcc agaagataac gaacaaaaac aattgtttgt  4440
ggagcagcat aagcattatc tggatgagat tattgagcaa atcagtgaat tttctaagag  4500
agttattctg gcagatgcca atctggataa agttcttagt gcatataaca aacatagaga  4560
caaaccaata agagaacaag cagaaaatat cattcatctg tttaccttga ccaatcttgg  4620
agcacccgct gcttttaaat actttgatac aacaattgat aggaaaagat atacctctac  4680
aaaagaagtt ctggatgcca ctcttatcca tcaatccatc actggtcttt atgaaacacg  4740
cattgatttg agtcagctgg gaggtgacgg ctctggcggg tctcccaaga agaagaggaa  4800
agtctaagat ccggctgcta acaaagcccg aaaggaagct gagttggctg ctgccaccgc  4860
tgagcaataa ctagcataac cccttggggc ctctaaacgg gtcttgaggg gttttttgct  4920
gaaaggagga actatatccg gattggcgaa tgggacgcgc cctgtagcgg cgcattaagc  4980
gcggcgggtg tggtggttac gcgcagcgtg accgctacac ttgccagcgc cctagcgccc  5040
gctcctttcg ctttcttccc ttcctttctc gccacgttcg ccggctttcc ccgtcaagct  5100
ctaaatcggg ggctcccttt agggttccga tttagtgctt tacggcacct cgaccccaaa  5160
aaacttgatt agggtgatgg ttcacgtagt gggccatcgc cctgatagac ggtttttcgc  5220
cctttgacgt tggagtccac gttctttaat agtggactct tgttccaaac tggaacaaca  5280
ctcaacccta tctcggtcta ttcttttgat ttataaggga ttttgccgat ttcggcctat  5340
tggttaaaaa atgagctgat ttaacaaaaa tttaacgcga attttaacaa aatattaacg  5400
cttacaattt aggtggcact tttcggggaa atgtgcgcgg aacccctatt tgtttatttt  5460
tctaaataca ttcaaatatg tatccgctca tgagacaata accctgataa atgcttcaat  5520
aatattgaaa aaggaagagt atgagtattc aacatttccg tgtcgccctt attccctttt  5580
ttgcggcatt ttgccttcct gtttttgctc acccagaaac gctggtgaaa gtaaaagatg  5640
ctgaagatca gttgggtgca cgagtgggtt acatcgaact ggatctcaac agcggtaaga  5700
tccttgagag ttttcgcccc gaagaacgtt ttccaatgat gagcactttt aaagttctgc  5760
tatgtggcgc ggtattatcc cgtattgacg ccgggcaaga gcaactcggt cgccgcatac  5820
actattctca gaatgacttg gttgagtact caccagtcac agaaaagcat cttacggatg  5880
gcatgacagt aagagaatta tgcagtgctg ccataaccat gagtgataac actgcggcca  5940
acttacttct gacaacgatc ggaggaccga aggagctaac cgcttttttg cacaacatgg  6000
gggatcatgt aactcgcctt gatcgttggg aaccggagct gaatgaagcc ataccaaacg  6060
acgagcgtga caccacgatg cctgcagcaa tggcaacaac gttgcgcaaa ctattaactg  6120
gcgaactact tactctagct tcccggcaac aattaataga ctggatggag gcggataaag  6180
```

```
ttgcaggacc acttctgcgc tcggcccttc cggctggctg gtttattgct gataaatctg  6240
gagccggtga gcgtgggtct cgcggtatca ttgcagcact ggggccagat ggtaagccct  6300
cccgtatcgt agttatctac acgacgggga gtcaggcaac tatggatgaa cgaaatagac  6360
agatcgctga gataggtgcc tcactgatta agcattggta actgtcagac caagtttact  6420
catatatact ttagattgat ttaaaacttc atttttaatt taaaaggatc taggtgaaga  6480
tcctttttga taatctcatg accaaaatcc cttaacgtga gttttcgttc cactgagcgt  6540
cagaccccgt agaaaagatc aaaggatctt cttgagatcc tttttttctg cgcgtaatct  6600
gctgcttgca aacaaaaaaa ccaccgctac cagcggtggt ttgtttgccg gatcaagagc  6660
taccaactct ttttccgaag gtaactggct tcagcagagc gcagatacca aatactgtcc  6720
ttctagtgta gccgtagtta ggccaccact tcaagaactc tgtagcaccg cctacatacc  6780
tcgctctgct aatcctgtta ccagtggctg ctgccagtgg cgataagtcg tgtcttaccg  6840
ggttggactc aagacgatag ttaccggata aggcgcagcg gtcgggctga acggggggtt  6900
cgtgcacaca gcccagcttg gagcgaacga cctacaccga actgagatac ctacagcgtg  6960
agctatgaga aagcgccacg cttcccgaag ggagaaaggc ggacaggtat ccggtaagcg  7020
gcagggtcgg aacaggagag cgcacgaggg agcttccagg gggaaacgcc tggtatcttt  7080
atagtcctgt cgggtttcgc cacctctgac ttgagcgtcg atttttgtga tgctcgtcag  7140
gggggcggag cctatggaaa aacgccagca acgcggcctt tttacggttc ctggcctttt  7200
gctggccttt tgctcacatg ttctttcctg cgttatcccc tgattctgtg gataaccgta  7260
ttaccgcctt tgagtgagct gataccgctc gccgcagccg aacgaccgag cgcagcgagt  7320
cagtgagcga ggaagcggaa gagcgcctga tgcggtattt tctccttacg catctgtgcg  7380
gtatttcaca ccgcaatggt gcactctcag tacaatctgc tctgatgccg catagttaag  7440
ccagtataca ctccgctatc gctacgtgac tgggtcatgg ctgcgccccg acacccgcca  7500
acacccgctg acgcgccctg acgggcttgt ctgctcccgg catccgctta cagacaagct  7560
gtgaccgtct ccgggagctg catgtgtcag aggttttcac cgtcatcacc gaaacgcgcg  7620
aggcagctgc ggtaaagctc atcagcgtgg tcgtgaagcg attcacagat gtctgcctgt  7680
tcatccgcgt ccagctcgtt gagtttctcc agaagcgtta atgtctggct tctgataaag  7740
cgggccatgt taagggcggt tttttcctgt ttggtcactg atgcctccgt gtaaggggga  7800
tttctgttca tgggggtaat gataccgatg aaacgagaga ggatgctcac gatacgggtt  7860
actgatgatg aacatgcccg gttactggaa cgttgtgagg gtaaacaact ggcggtatgg  7920
atgcggcggg accagagaaa aatcactcag ggtcaatgcc agcgcttcgt taatacagat  7980
gtaggtgttc cacagggtag ccagcagcat cctgcgatgc agatccggaa cataatggtg  8040
cagggcgctg acttccgcgt ttccagactt tacgaaacac ggaaaccgaa gaccattcat  8100
gttgttgctc aggtcgcaga cgttttgcag cagcagtcgc ttcacgttcg ctcgcgtatc  8160
ggtgattcat tctgctaacc agtaaggcaa ccccgccagc ctagccgggt cctcaacgac  8220
aggagcacga tcatgcgcac ccgtggggcc gccatgccgg cgataatggc ctgcttctcg  8280
ccgaaacgtt tggtggcggg accagtgacg aaggcttgag cgagggcgtg caagattccg  8340
aataccgcaa gcgacaggcc gatcatcgtc gcgctccagc gaaagcggtc ctcgccgaaa  8400
atgacccaga gcgctgccgg cacctgtcct acgagttgca tgataaagaa gacagtcata  8460
agtgcggcga cgatagtcat gccccgcgcc caccggaagg agctgactgg gttgaaggct  8520
ctcaagggca tcggtcgaga tcccggtgcc taatgagtga gctaacttac attaattgcg  8580
ttgcgctcac tgcccgcttt ccagtcggga aacctgtcgt gccagctgca ttaatgaatc  8640
ggccaacgcg cggggagagg cggtttgcgt attgggcgcc agggtggttt ttcttttcac  8700
cagtgagacg ggcaacagct gattgccctt caccgcctgg ccctgagaga gttgcagcaa  8760
gcggtccacg ctggtttgcc ccagcaggcg aaaatcctgt ttgatggtgg ttaacggcgg  8820
gatataacat gagctgtctt cggtatcgtc gtatcccact accgagatat ccgcaccaac  8880
gcgcagcccg gactcggtaa tggcgcgcat tgcgcccagc gccatctgat cgttggcaac  8940
cagcatcgca gtgggaacga tgccctcatt cagcatttgc atggtttgtt gaaaaccgga  9000
catggcactc cagtcgcctt cccgttccgc tatcggctga atttgattgc gagtgagata  9060
tttatgccag ccagccagac gcagacgcgc cgagacagaa cttaatgggc ccgctaacag  9120
cgcgatttgc tggtgaccca atgcgaccag atgctccacg cccagtcgcg taccgtcttc  9180
atgggagaaa ataatactgt tgatgggtgt ctggtcagag acatcaagaa ataacgccgg  9240
aacattagtg caggcagctt ccacagcaat ggcatcctgg tcatccagcg gatagttaat  9300
gatcagccca ctgacgcgtt gcgcgagaag attgtgcacc gccgctttac aggcttcgac  9360
gccgcttcgt tctaccatcg acaccaccac gctggcaccc agttgatcgg cgcgagattt  9420
aatcgccgcg acaatttgcg acggcgcgtg cagggccaga ctggaggtgg caacgccaat  9480
cagcaacgac tgtttgcccg ccagttgttg tgccacgcgg ttgggaatgt aattcagctc  9540
cgccatcgcc gcttccactt tttcccgcgt tttcgcagaa acgtggctgg cctggttcac  9600
cacgcgggaa acggtctgat aagagacacc ggcatactct gcgacatcgt ataacgttac  9660
tggtttcaca ttcaccaccc tgaattgact ctcttccggg cgctatcatg ccataccgcg  9720
aaaggttttg cgccattcga tggtgtccgg gatctcgacg ctctccctta tgcgactcct  9780
gcattaggaa gcagcccagt agtaggttga ggccgttgag caccgccgcc gcaaggaatg  9840
gtttaattaa tttgatcggc acgtaagagg ttccaacttt caccataatg aaataagatc  9900
actaccgggc gtattttttg agttatcgag attttcagga gctaaggaag ctaaaatgga  9960
gaaaaaaatc actggatata ccaccgttga tatatcccaa tggcatcgta aagaacattt  10020
tgaggcattt cagtcagttg ctcaatgtac ctataaccag accgttcagc tggatattac  10080
ggccttttta aagaccgtaa agaaaaataa gcacaagttt tatccggcct ttattcacat  10140
tcttgcccgc ctgatgaatg ctcatccgga attccgtatg gcaatgaaag acggtgagct  10200
ggtgatatgg gatagtgttc acccttgtta caccgttttc catgagcaaa ctgaaacgtt  10260
ttcatcgctc tggagtgaat accacgacga tttccggcag tttctacaca tatattcgca  10320
agatgtggcg tgttacggtg aaaacctggc ctatttccct aaagggttta ttgagaatat  10380
gtttttcgtc tcagccaatc cctgggtgag tttcaccagt tttgatttaa acgtggccaa  10440
tatggacaac ttcttcgccc ccgttttcac catgggcaaa tattatacgc aaggcgacaa  10500
ggtgctgatg ccgctggcga ttcaggttca ttatgccgtc tgtgatggct tccatgtcgg  10560
cagaatgctt aatgaattac aacagtactg cgatgagtgg cagggcgggg cgtaattttt  10620
ttaaggcagt tattggtgcc cttaaacgcc tggtgctacg cctgaataag tgaagcatgc  10680
aaggagatgg cgcccaacag tcccccggcc acggggcctg ccaccatacc cacgccgaaa  10740
caagcgctca tgagcccgaa gtggcgagcc cgatcttccc catcggtgat gtcggcgata  10800
taggcgccag caaccgcacc tgtggcgccg gtgatgccgg ccacgatgcg tccggcgtag  10860
aggatcgaga tctcgatccc gcgaaattaa tacgactcac tataggggaa ttgtgagcgg  10920
```

```
ataacaattc ccctctagga tcc                                          10943

SEQ ID NO: 484          moltype = DNA  length = 8520
FEATURE                 Location/Qualifiers
misc_feature            1..8520
                        note = Description of Artificial Sequence: Synthetic
                         polynucleotide
misc_feature            1..8520
                        note = Category: Plasmid
misc_feature            1..8520
                        note = Description: pET21-sgRNA-TadA (ABE8.17m)-nMG34-1
                         (D10A)
source                  1..8520
                        mol_type = other DNA
                        organism = synthetic construct
SEQUENCE: 484
gaaataattt tgtttaactt taagaaggag atataccatg ggcagcagtc atcatcatca  60
ccatcactcc gaggttgaat ttagtcatga atattggatg cgccacgcgc tgacgttagc  120
caaacgtgct cgtgatgagc gcgaagttcc agtcggggcc gtcttggtcc ttaacaatcg  180
tgtcattggc gaggggtgga accgcgctat tgggctgcac gatccaacag cgcatgctga  240
gattatggcc ttgcgtcaag gagggttagt aatgcaaaac taccgtctta ttgatgctac  300
gttatactct acattcgaac cctgtgtaat gtgtgcagga gcgatgatcc acagtcgtat  360
tggccgcgta gtatttggtg tacgcaatgc taaaactgga gccgccggat cgttgatgga  420
tgtcttgcat taccctggaa tgaaccatcg tgtagagatc actgaaggca tccttgccga  480
tgagtgtgcg gctttgcttt gctatttctt ccgtatgcca cgtcgtgttt ttaacgccca  540
aaaaaaggct caatccagta ccgattcagg cgggtcgtcg ggaggaagca gtggcagcga  600
gactcccgga acttcggaga gcgctacacc agaaagtagt ggaggcagct ctggtgggtc  660
catggagcgc gagctggtgc tggggatcgc gtatggtggt aagtacacgg gcttggcggt  720
ggtggatcgc cgccacaacc aagtgctgta cgcgaatcgt cttaaaatgc gtgatgacgt  780
ggcaggcatc ttgaaggacc gtcgcaaaca gcgcgggatt cgtcgcacgg cccagacgaa  840
gaagaaacgc cttcgcgagc tgaagaatta cctgaagagc atcgggtaca atgagtcgac  900
ggccaccttc gagaccgtgt attcactggc gcacaagcgt ggttacgact acgcagacat  960
gccagaggag aaaaccagtg aggagattga agcgatggac gttgaggaac gtaagcaatg  1020
ggagaaggaa aagcaagagt gggaagaaac taagcgcaac tctcgccatc gcaaagaggt  1080
agttaaggac gtacacaagg cgatgatcga gggccgtgcc acggaagaac aaattaagcg  1140
tgtggagcgc atcttcaaca agcaatatcg cccgaagcgt tttaacaacc gcatcttgac  1200
caagtgcaaa gtggaagact gtggtgtgaa cactcctttg cgtaagaacg tacgcgacct  1260
gctgattgag aacattgttc gtttctttcc gattgagcag agcgagaaag acaacctgaa  1320
ggacgccgta ttagacaaga atcgtcgcga agaggtgaag tccttctttc gcaagcacaa  1380
aaccgacgag cacatccgta aacaagtgta cgacattgcc gacaataaac tgagcgggcg  1440
tactgtattc tgcaaggagc acattctgga gcacacggaa cactccaagg aagagcgtaa  1500
agtctttcgc ctggcaccga gtctgaagac gaagattgaa aacgtgctgg cagtaatcaa  1560
ggatgaaatt ctccctaagt tcacggtgaa caaagtagtg atggaatcaa ataacttcga  1620
catcgccgcg aagacccaag gtaagaagcg tctcgccaag gaagagtacg gcaagggccc  1680
gcgtgagggt aaggaaacgc gcaaagaggc gctgctgcgc gagaccgacg ggcgctgcat  1740
ttattgcggc aagagcatcg atatttcgaa cgcacacgac gatcacatct tccctcgtaa  1800
agcgggcgga ttgaacattt tcgcgaacct cgtggcctgc tgtgcggtgt gcaacgaaaa  1860
caagaagggc cgcacgcctc tggagtcggg catttcacca aagccagaga ttattgcatt  1920
tatgaagaac gacctgaaga agaaaatctt ggaagatgct cgcaacatta acaccgtcga  1980
cttcaacaag tatatgagcc acgcttcgat tgggtggcgt tacatgcgcg atcgccttcg  2040
cgaatcggca ggtaacaaga aactgccgat cgaacgccaa agtggtattt atacggccta  2100
ctttcgtcgc tggtggggtt tcaagaaaga gcgcggtaat actttgcacc acgctctgga  2160
cgcggtgatt ttggcctcgc gtaagggcta ctcagacgac ggcttagtag acatgacttt  2220
aaaacccaag tacaataagg gcggcgaatt cgatccggag aagcacttac cggagcctat  2280
cgagttcaag atggacaagg ggtcacgcgg tagcgccctg cacgaccgta atccgttgag  2340
ttacaagaag ggtatcatca ctcgtcgctt catggtcact gaaatcgaat gtggcaagga  2400
agatgacgtg atctctgaaa cctaccgcga gaagttgaag gaagcgttca agcgcttcga  2460
caccaagaag ggcaagtgcc tgaccgataa agaagccaaa gaggcggggt tctgtatcaa  2520
gaagaacgag ctggtgatgt cgctgaagtg ttcaatcaag gggactggcc cgggccaaat  2580
gattcgcatt aacaacaacg tgttcaaaac caacgtacac aacgtaggag ttgacgtcta  2640
cctggacgag aagggcaaga agaaggcgta cgaacgcaag aacccacgct tatcgaagca  2700
ttttattgag ccgccgccac aaccgaacgg ccgcgtctct ttcacactga agcgtcgcga  2760
catggtgact gtagagggag aggatgccat ttaccgcatt aagaagttgg gtacttcccc  2820
gaccatcgag gcggtggtgg ggagcgacgg taagacgcgc acagtatcgg caacgaaatt  2880
gaccaaggcc aatagcgccg agctcgaggg ctctggcggg tctcccaaga agaagaggaa  2940
agtctaagat ccggctgcta acaaagcccg aaaggaagct gagttggctg ctgccaccgc  3000
tgagcaataa ctagcataac cccttggggc ctctaaacgg gtcttgaggg gttttttgct  3060
gaaaggagga actatatccg gattggcgaa tgggacgcgc cctgtagcgg cgcattaagc  3120
gcggcgggtg tggtggttac gcgcagcgtg accgctacac ttgccagcgc cctagcgccc  3180
gctcctttcg ctttcttccc ttcctttctc gccacgttcg ccggctttcc ccgtcaagct  3240
ctaaatcggg ggctcccttt agggttccga tttagtgctt tacggcacct cgaccccaaa  3300
aaacttgatt agggtgatgg ttcacgtagt gggccatcgc cctgatagac ggtttttcgc  3360
cctttgacgt tggagtccac gttctttaat agtggactct tgttccaaac tggaacaaca  3420
ctcaacccta tctcggtcta ttcttttgat ttataaggga ttttgccgat ttcggcctat  3480
tggttaaaaa atgagctgat ttaacaaaaa tttaacgcga attttaacaa aatattaacg  3540
cttacaattt aggtggcact tttcggggaa atgtgcgcgg aacccctatt tgtttatttt  3600
tctaaataca ttcaaatatg tatccgctca tgagacaata accctgataa atgcttcaat  3660
aatattgaaa aaggaagagt atgagtattc aacatttccg tgtcgccctt attccctttt  3720
ttgcggcatt ttgccttcct gtttttgctc acccagaaac gctggtgaaa gtaaaagatg  3780
```

```
ctgaagatca gttgggtgca cgagtgggtt acatcgaact ggatctcaac agcggtaaga  3840
tccttgagag ttttcgcccc gaagaacgtt ttccaatgat gagcactttt aaagttctgc  3900
tatgtggcgc ggtattatcc cgtattgacg ccgggcaaga gcaactcggt cgccgcatac  3960
actattctca gaatgacttg gttgagtact caccagtcac agaaaagcat cttacggatg  4020
gcatgacagt aagagaatta tgcagtgctg ccataaccat gagtgataac actgcggcca  4080
acttacttct gacaacgatc ggaggaccga aggagctaac cgcttttttg cacaacatgg  4140
gggatcatgt aactcgcctt gatcgttggg aaccggagct gaatgaagcc ataccaaacg  4200
acgagcgtga caccacgatg cctgcagcaa tggcaacaac gttgcgcaaa ctattaactg  4260
gcgaactact tactctagct tcccggcaac aattaataga ctggatggag gcggataaag  4320
ttgcaggacc acttctgcgc tcggcccttc cggctggctg gtttattgct gataaatctg  4380
gagccggtga gcgtgggtct cgcggtatca ttgcagcact ggggccagat ggtaagccct  4440
cccgtatcgt agttatctac acgacgggga gtcaggcaac tatggatgaa cgaaatagac  4500
agatcgctga gataggtgcc tcactgatta agcattggta actgtcagac caagtttact  4560
catatatact ttagattgat ttaaaacttc atttttaatt taaaaggatc taggtgaaga  4620
tcctttttga taatctcatg accaaaatcc cttaacgtga gttttcgttc cactgagcgt  4680
cagaccccgt agaaaagatc aaaggatctt cttgagatcc tttttttctg cgcgtaatct  4740
gctgcttgca aacaaaaaaa ccaccgctac cagcggtggt ttgtttgccg gatcaagagc  4800
taccaactct ttttccgaag gtaactggct tcagcagagc gcagatacca aatactgtcc  4860
ttctagtgta gccgtagtta ggccaccact tcaagaactc tgtagcaccg cctacatacc  4920
tcgctctgct aatcctgtta ccagtggctg ctgccagtgg cgataagtcg tgtcttaccg  4980
ggttggactc aagacgatag ttaccggata aggcgcagcg gtcgggctga acggggggtt  5040
cgtgcacaca gcccagcttg gagcgaacga cctacaccga actgagatac ctacagcgtg  5100
agctatgaga aagcgccacg cttcccgaag ggagaaaggc ggacaggtat ccggtaagcg  5160
gcagggtcgg aacaggagag cgcacgaggg agcttccagg gggaaacgcc tggtatcttt  5220
atagtcctgt cgggtttcgc cacctctgac ttgagcgtcg atttttgtga tgctcgtcag  5280
gggggcggag cctatggaaa aacgccagca acgcggcctt tttacggttc ctggcctttt  5340
gctggccttt tgctcacatg ttctttcctg cgttatcccc tgattctgtg gataaccgta  5400
ttaccgcctt tgagtgagct gataccgctc gccgcagccg aacgaccgag cgcagcgagt  5460
cagtgagcga ggaagcggaa gagcgcctga tgcggtattt tctccttacg catctgtgcg  5520
gtatttcaca ccgcaatggt gcactctcag tacaatctgc tctgatgccg catagttaag  5580
ccagtataca ctccgctatc gctacgtgac tgggtcatgg ctgcgccccg acacccgcca  5640
acacccgctg acgcgccctg acgggcttgt ctgctcccgg catccgctta cagacaagct  5700
gtgaccgtct ccgggagctg catgtgtcag aggttttcac cgtcatcacc gaaacgcgcg  5760
aggcagctgc ggtaaagctc atcagcgtgg tcgtgaagcg attcacagat gtctgcctgt  5820
tcatccgcgt ccagctcgtt gagtttctcc agaagcgtta atgtctggct tctgataaag  5880
cgggccatgt taagggcggt tttttcctgt ttggtcactg atgcctccgt gtaaggggga  5940
tttctgttca tgggggtaat gataccgatg aaacgagaga ggatgctcac gatacgggtt  6000
actgatgatg aacatgcccg gttactggaa cgttgtgagg gtaaacaact ggcggtatgg  6060
atgcggcggg accagagaaa aatcactcag ggtcaatgcc agcgcttcgt taatacagat  6120
gtaggtgttc cacagggtag ccagcagcat cctgcgatgc agatccggaa cataatggtg  6180
cagggcgctg acttccgcgt ttccagactt tacgaaacac ggaaaccgaa gaccattcat  6240
gttgttgctc aggtcgcaga cgttttgcag cagcagtcgc ttcacgttcg ctcgcgtatc  6300
ggtgattcat tctgctaacc agtaaggcaa ccccgccagc ctagccgggt cctcaacgac  6360
aggagcacga tcatgcgcac ccgtggggcc gccatgccgg cgataatggc ctgcttctcg  6420
ccgaaacgtt tggtggcggg accagtgacg aaggcttgag cgagggcgtg caagattccg  6480
aataccgcaa gcgacaggcc gatcatcgtc gcgctccagc gaaagcggtc ctcgccgaaa  6540
atgacccaga gcgctgccgg cacctgtcct acgagttgca tgataaagaa gacagtcata  6600
agtgcggcga cgatagtcat gccccgcgcc caccggaagg agctgactgg gttgaaggct  6660
ctcaagggca tcggtcgaga tcccggtgcc taatgagtga gctaacttac attaattgcg  6720
ttgcgctcac tgcccgcttt ccagtcggga aacctgtcgt gccagctgca ttaatgaatc  6780
ggccaacgcg cggggagagg cggtttgcgt attgggcgcc agggtggttt ttcttttcac  6840
cagtgagacg ggcaacagct gattgccctt caccgcctgg ccctgagaga gttgcagcaa  6900
gcggtccacg ctggtttgcc ccagcaggcg aaaatcctgt ttgatggtgg ttaacggcgg  6960
gatataacat gagctgtctt cggtatcgtc gtatcccact accgagatat ccgcaccaac  7020
gcgcagcccg gactcggtaa tggcgcgcat tgcgcccagc gccatctgat cgttggcaac  7080
cagcatcgca gtgggaacga tgccctcatt cagcatttgc atggtttgtt gaaaaccgga  7140
catggcactc cagtcgcctt cccgttccgc tatcggctga atttgattgc gagtgagata  7200
tttatgccag ccagccagac gcagacgcgc cgagacagaa cttaatgggc ccgctaacag  7260
cgcgatttgc tggtgaccca atgcgaccag atgctccacg cccagtcgcg taccgtcttc  7320
atgggagaaa ataatactgt tgatgggtgt ctggtcagag acatcaagaa ataacgccgg  7380
aacattagtg caggcagctt ccacagcaat ggcatcctgg tcatccagcg gatagttaat  7440
gatcagccca ctgacgcgtt gcgcgagaag attgtgcacc gccgctttac aggcttcgac  7500
gccgcttcgt tctaccatcg acaccaccac gctggcaccc agttgatcgg cgcgagattt  7560
aatcgccgcg acaatttgcg acggcgcgtg cagggccaga ctggaggtgg caacgccaat  7620
cagcaacgac tgtttgcccg ccagttgttg tgccacgcgg ttgggaatgt aattcagctc  7680
cgccatcgcc gcttccactt tttcccgcgt tttcgcagaa acgtggctgg cctggttcac  7740
cacgcgggaa acggtctgat aagagacacc ggcatactct gcgacatcgt ataacgttac  7800
tggtttcaca ttcaccaccc tgaattgact ctcttccggg cgctatcatg ccataccgcg  7860
aaaggttttg cgccattcga tggtgtccgg gatctcgacg ctctccctta tgcgactcct  7920
gcattaggaa gcagcccagt agtaggttga ggccgttgag caccgccgcc gcaaggaatg  7980
gtttaattaa ttacggccag tcatgcataa tccgcacgca tctggaataa ggaagtgcca  8040
ttccgcctga ccttaatacg actcactata gtctttatgg cagggtgaaa cgcgttacag  8100
ttaagaaatt aattgtaaaa cgcctataca gtgaagggat atacgcttgg gtttgtccag  8160
cctgagcctc tatgccagaa atggcgcctt catcgtgggt taggacattt aattttaaaa  8220
aaaaaccccg cttcggcggg gtttttttt agcatgcaag gagatggcgc ccaacagtcc  8280
cccggccacg gggcctgcca ccatacccac gccgaaacaa gcgctcatga gcccgaagtg  8340
gcgagcccga tcttccccat cggtgatgtc ggcgatatag gcgccagcaa ccgcacctgt  8400
ggcgccggtg atgccggcca cgatgcgtcc ggcgtagagg atcgagatct cgatcccgcg  8460
aaattaatac gactcactat aggggaattg tgagcggata acaattcccc tctaggatcc  8520
```

```
SEQ ID NO: 485         moltype = DNA  length = 8925
FEATURE                Location/Qualifiers
misc_feature           1..8925
                       note = Description of Artificial Sequence: Synthetic
                        polynucleotide
misc_feature           1..8925
                       note = Category: Plasmid
misc_feature           1..8925
                       note = Description: pET21-sgRNA-rAPOBEC1-nMG34-1 (D10A)-UGI
                        (PBS1)
source                 1..8925
                       mol_type = other DNA
                       organism = synthetic construct
SEQUENCE: 485
atgggcagca gtcatcatca tcaccatcac atgtcgtctg agaccgggcc tgttgccgtg  60
gaccctaccc ttcgccgccg tatcgaacca cacgagtttg aagtgttttt tgacccacgc  120
gaactgcgca aagagacttg tttgctttac gagattaact ggggaggccg tcactccatc  180
tggcgtcaca cttcacaaaa tactaataag cacgttgagg ttaatttcat tgagaaattt  240
actacagagc gctacttctg tccgaataca cgttgcagca tcacctggtt tctttcctgg  300
tccccgtgcg gtgaatgttc acgtgccatc accgaattct tatcgcgcta ccctcacgta  360
actttgttta tctatattgc ccgtttatat caccatgcag accctcgcaa tcgtcagggc  420
ctgcgcgacc ttatctcgag tggagtcacc atccaaatta tgactgaaca ggaatcgggg  480
tattgttggc gcaactttgt caattattct ccgagcaacg aggcacattg gccgcgttac  540
ccacacttat gggtgcgcct ttacgtgctg gaattgtatt gcatcattct tggtcttccc  600
ccatgtttga atatccttcg ccgcaaacag cctcagttga cgttttttac gattgctctt  660
cagtcctgtc actaccaacg tcttcccccg cacatcctgt gggcgaccgg tttgaaatcg  720
gggagtgaaa cacccggcac atccgaaagt gcgacacctg aatctgccat ggagcgcgag  780
ctggtgctgg ggatcgcgta tggtggtaag tacacgggct tggcggtggt ggatcgccgc  840
cacaaccaag tgctgtacgc gaatcgtctt aaaatgcgtg atgacgtggc aggcatcttg  900
aaggaccgtc gcaaacagcg cgggattcgt cgcacggccc agacgaagaa gaaacgcctt  960
cgcgagctga agaattacct gaagagcatc gggtacaatg agtcgacggc caccttcgag  1020
accgtgtatt cactggcgca caagcgtggt tacgactacg cagacatgcc agaggagaaa  1080
accagtgagg agattgaagc gatggacgtt gaggaacgta agcaatggga gaaggaaaag  1140
caagagtggg aagaaactaa gcgcaactct cgccatcgca aagaggtagt taaggacgta  1200
cacaaggcga tgatcgaggg ccgtgccacg gaagaacaaa ttaagcgtgt ggagcgcatc  1260
ttcaacaagc aatatcgccc gaagcgtttt aacaaccgca tcttgaccaa gtgcaaagtg  1320
gaagactgtg gtgtgaacac tcctttgcgt aagaacgtac gcgacctgct gattgagaac  1380
attgttcgtt tctttccgat tgagcagagc gagaaagaca acctgaagga cgccgtatta  1440
gacaagaatc gtcgcgaaga ggtgaagtcc ttctttcgca agcacaaaac cgacgagcac  1500
atccgtaaac aagtgtacga cattgccgac aataaactga gcgggcgtac tgtattctgc  1560
aaggagcaca ttctggagca cacggaacac tccaaggaag agcgtaaagt ctttcgcctg  1620
gcaccgagtc tgaagacgaa gattgaaaac gtgctggcag taatcaagga tgaaattctc  1680
cctaagttca cggtgaacaa agtagtgatg gaatcaaata acttcgacat cgccgcgaag  1740
acccaaggta agaagcgtct cgccaaggaa gagtacggca agggcccgcg tgagggtaag  1800
gaaacgcgca aagaggcgct gctgcgcgag accgacgggc gctgcattta ttgcggcaag  1860
agcatcgata tttcgaacgc acacgacgat cacatcttcc ctcgtaaagc gggcggattg  1920
aacattttcg cgaacctcgt ggcctgctgt gcggtgtgca acgaaaacaa gaagggccgc  1980
acgcctctgg agtcgggcat ttcaccaaag ccagagatta ttgcatttat gaagaacgac  2040
ctgaagaaga aaatcttgga agatgctcgc aacattaaca ccgtcgactt caacaagtat  2100
atgagccacg cttcgattgg gtggcgttac atgcgcgatc gccttcgcga atcggcaggt  2160
aacaagaaac tgccgatcga acgccaaagt ggtatttata cggcctactt tcgtcgctgg  2220
tggggtttca agaaagagcg cggtaatact ttgcaccacg ctctggacgc ggtgattttg  2280
gcctcgcgta agggctactc agacgacggc ttagtagaca tgactttaaa acccaagtac  2340
aataagggcg gcgaattcga tccggagaag cacttaccgg agcctatcga gttcaagatg  2400
gacaaggggt cacgcggtag cgccctgcac gaccgtaatc cgttgagtta caagaagggt  2460
atcatcactc gtcgcttcat ggtcactgaa atcgaatgtg gcaaggaaga tgacgtgatc  2520
tctgaaacct accgcgagaa gttgaaggaa gcgttcaagc gcttcgacac caagaagggc  2580
aagtgcctga ccgataaaga agccaaagag gcggggttct gtatcaagaa gaacgagctg  2640
gtgatgtcgc tgaagtgttc aatcaagggg actggcccgg gccaaatgat tcgcattaac  2700
aacaacgtgt tcaaaaccaa cgtacacaac gtaggagttg acgtctacct ggacgagaag  2760
ggcaagaaga aggcgtacga acgcaagaac ccacgcttat cgaagcattt tattgagccg  2820
ccgccacaac cgaacggccg cgtctctttc acactgaagc gtcgcgacat ggtgactgta  2880
gagggagagg atgccattta ccgcattaag aagttgggta cttccccgac catcgaggcg  2940
gtggtgggga gcgacggtaa gacgcgcaca gtatcggcaa cgaaattgac caaggccaat  3000
agcgccgagc tcgaggggtc tggtggttct accaatcttt cagatattat tgaaaaagag  3060
acaggaaagc agttggtcat tcaagagagt atcctgatgt taccggagga agttgaggag  3120
gtaatcggaa ataaacccga gagcgacatt ttagtccaca ctgcttatga cgagagtacg  3180
gatgagaatg tgatgctgct tacgtcagat gcgcccgagt ataagccgtg ggccctggtc  3240
attcaggaca gtaacggcga aaacaagatc aaaatgcttt ctggtggttc tcccaagaag  3300
aagaggaaag tctaagatcc ggctgctaac aaagcccgaa aggaagctga gttggctgct  3360
gccaccgctg agcaataact agcataaccc cttggggcct ctaaacgggt cttgaggggt  3420
tttttgctga aaggaggaac tatatccgga ttggcgaatg ggacgcgccc tgtagcggcg  3480
cattaagcgc ggcgggtgtg gtggttacgc gcagcgtgac cgctacactt gccagcgccc  3540
tagcgcccgc tcctttcgct ttcttccctt cctttctcgc cacgttcgcc ggctttcccc  3600
gtcaagctct aaatcggggg ctccctttag ggttccgatt tagtgcttta cggcacctcg  3660
accccaaaaa acttgattag ggtgatggtt cacgtagtgg gccatcgccc tgatagacgg  3720
tttttcgccc tttgacgttg gagtccacgt tctttaatag tggactcttg ttccaaactg  3780
gaacaacact caaccctatc tcggtctatt cttttgattt ataagggatt ttgccgattt  3840
```

```
cggcctattg gttaaaaaat gagctgattt aacaaaaatt taacgcgaat tttaacaaaa  3900
tattaacgct tacaatttag gtggcacttt tcggggaaat gtgcgcggaa cccctatttg  3960
tttatttttc taaatacatt caaatatgta tccgctcatg agacaataac cctgataaat  4020
gcttcaataa tattgaaaaa ggaagagtat gagtattcaa catttccgtg tcgcccttat  4080
tccctttttt gcggcatttt gccttcctgt ttttgctcac ccagaaacgc tggtgaaagt  4140
aaaagatgct gaagatcagt tgggtgcacg agtgggttac atcgaactgg atctcaacag  4200
cggtaagatc cttgagagtt ttcgccccga agaacgtttt ccaatgatga gcacttttaa  4260
agttctgcta tgtggcgcgg tattatcccg tattgacgcc gggcaagagc aactcggtcg  4320
ccgcatacac tattctcaga atgacttggt tgagtactca ccagtcacag aaaagcatct  4380
tacggatggc atgacagtaa gagaattatg cagtgctgcc ataaccatga gtgataacac  4440
tgcggccaac ttacttctga caacgatcgg aggaccgaag gagctaaccg cttttttgca  4500
caacatgggg gatcatgtaa ctcgccttga tcgttgggaa ccggagctga atgaagccat  4560
accaaacgac gagcgtgaca ccacgatgcc tgcagcaatg gcaacaacgt tgcgcaaact  4620
attaactggc gaactactta ctctagcttc ccggcaacaa ttaatagact ggatggaggc  4680
ggataaagtt gcaggaccac ttctgcgctc ggcccttccg gctggctggt ttattgctga  4740
taaatctgga gccggtgagc gtgggtctcg cggtatcatt gcagcactgg ggccagatgg  4800
taagccctcc cgtatcgtag ttatctacac gacggggagt caggcaacta tggatgaacg  4860
aaatagacag atcgctgaga taggtgcctc actgattaag cattggtaac tgtcagacca  4920
agtttactca tatatacttt agattgattt aaaacttcat ttttaattta aaaggatcta  4980
ggtgaagatc ctttttgata atctcatgac caaaatccct taacgtgagt tttcgttcca  5040
ctgagcgtca gaccccgtag aaaagatcaa aggatcttct tgagatcctt tttttctgcg  5100
cgtaatctgc tgcttgcaaa caaaaaaacc accgctacca gcggtggttt gtttgccgga  5160
tcaagagcta ccaactcttt ttccgaaggt aactggcttc agcagagcgc agataccaaa  5220
tactgtcctt ctagtgtagc cgtagttagg ccaccacttc aagaactctg tagcaccgcc  5280
tacatacctc gctctgctaa tcctgttacc agtggctgct gccagtggcg ataagtcgtg  5340
tcttaccggg ttggactcaa gacgatagtt accggataag gcgcagcggt cgggctgaac  5400
ggggggttcg tgcacacagc ccagcttgga gcgaacgacc tacaccgaac tgagatacct  5460
acagcgtgag ctatgagaaa gcgccacgct tcccgaaggg agaaaggcgg acaggtatcc  5520
ggtaagcggc agggtcggaa caggagagcg cacgagggag cttccagggg gaaacgcctg  5580
gtatctttat agtcctgtcg ggtttcgcca cctctgactt gagcgtcgat ttttgtgatg  5640
ctcgtcaggg gggcggagcc tatggaaaaa cgccagcaac gcggcctttt tacggttcct  5700
ggccttttgc tggccttttg ctcacatgtt ctttcctgcg ttatcccctg attctgtgga  5760
taaccgtatt accgcctttg agtgagctga taccgctcgc cgcagccgaa cgaccgagcg  5820
cagcgagtca gtgagcgagg aagcggaaga gcgcctgatg cggtattttc tccttacgca  5880
tctgtgcggt atttcacacc gcaatggtgc actctcagta caatctgctc tgatgccgca  5940
tagttaagcc agtatacact ccgctatcgc tacgtgactg ggtcatggct gcgccccgac  6000
acccgccaac acccgctgac gcgccctgac gggcttgtct gctcccggca tccgcttaca  6060
gacaagctgt gaccgtctcc gggagctgca tgtgtcagag gttttcaccg tcatcaccga  6120
aacgcgcgag gcagctgcgg taaagctcat cagcgtggtc gtgaagcgat tcacagatgt  6180
ctgcctgttc atccgcgtcc agctcgttga gtttctccag aagcgttaat gtctggcttc  6240
tgataaagcg ggccatgtta agggcggttt tttcctgttt ggtcactgat gcctccgtgt  6300
aagggggatt tctgttcatg gggtaatga taccgatgaa acgagagagg atgctcacga  6360
tacgggttac tgatgatgaa catgcccggt tactggaacg ttgtgagggt aaacaactgg  6420
cggtatggat gcggcgggac cagagaaaaa tcactcaggg tcaatgccag cgcttcgtta  6480
atacagatgt aggtgttcca cagggtagcc agcagcatcc tgcgatgcag atccggaaca  6540
taatggtgca gggcgctgac ttccgcgttt ccagacttta cgaaacacgg aaaccgaaga  6600
ccattcatgt tgttgctcag gtcgcagacg ttttgcagca gcagtcgctt cacgttcgct  6660
cgcgtatcgg tgattcattc tgctaaccag taaggcaacc ccgccagcct agccgggtcc  6720
tcaacgacag gagcacgatc atgcgcaccc gtggggccgc catgccggcg ataatggcct  6780
gcttctcgcc gaaacgtttg gtggcgggac cagtgacgaa ggcttgagcg agggcgtgca  6840
agattccgaa taccgcaagc gacaggccga tcatcgtcgc gctccagcga aagcggtcct  6900
cgccgaaaat gacccagagc gctgccggca cctgtcctac gagttgcatg ataaagaaga  6960
cagtcataag tgcggcgacg atagtcatgc cccgcgccca ccggaaggag ctgactgggt  7020
tgaaggctct caagggcatc ggtcgagatc ccggtgccta atgagtgagc taacttacat  7080
taattgcgtt gcgctcactg cccgctttcc agtcgggaaa cctgtcgtgc cagctgcatt  7140
aatgaatcgg ccaacgcgcg gggagaggcg gtttgcgtat tgggcgccag ggtggttttt  7200
cttttcacca gtgagacggg caacagctga ttgcccttca ccgcctggcc ctgagagagt  7260
tgcagcaagc ggtccacgct ggtttgcccc agcaggcgaa aatcctgttt gatggtggtt  7320
aacggcggga tataacatga gctgtcttcg gtatcgtcgt atcccactac cgagatatcc  7380
gcaccaacgc gcagcccgga ctcggtaatg gcgcgcattg cgcccagcgc catctgatcg  7440
ttggcaacca gcatcgcagt gggaacgatg ccctcattca gcatttgcat ggtttgttga  7500
aaaccggaca tggcactcca gtcgccttcc cgttccgcta tcggctgaat ttgattgcga  7560
gtgagatatt tatgccagcc agccagacgc agacgcgccg agacagaact taatgggccc  7620
gctaacagcg cgatttgctg gtgacccaat gcgaccagat gctccacgcc cagtcgcgta  7680
ccgtcttcat gggagaaaat aatactgttg atgggtgtct ggtcagagac atcaagaaat  7740
aacgccggaa cattagtgca ggcagcttcc acagcaatgg catcctggtc atccagcgga  7800
tagttaatga tcagcccact gacgcgttgc gcgagaagat tgtgcaccgc cgctttacag  7860
gcttcgacgc cgcttcgttc taccatcgac accaccacgc tggcacccag ttgatcggcg  7920
cgagatttaa tcgccgcgac aatttgcgac ggcgcgtgca gggccagact ggaggtggca  7980
acgccaatca gcaacgactg tttgcccgcc agttgttgtg ccacgcggtt gggaatgtaa  8040
ttcagctccg ccatcgccgc ttccactttt tcccgcgttt tcgcagaaac gtggctggcc  8100
tggttcacca cgcgggaaac ggtctgataa gagacaccgg catactctgc gacatcgtat  8160
aacgttactg gtttcacatt caccaccctg aattgactct cttccgggcg ctatcatgcc  8220
ataccgcgaa aggttttgcg ccattcgatg gtgtccggga tctcgacgct ctcccttatg  8280
cgactcctgc attaggaagc agcccagtag taggttgagg ccgttgagca ccgccgccgc  8340
aaggaatggt ttaattaatt acggccagtc atgcataatc cgcacgcatc tggaataagg  8400
aagtgccatt ccgcctgacc ttaatacgac tcactatagc gcgccggaga aaaccgcctc  8460
ggttacagtt aagaaattaa ttgtaaaacg cctatacagt gaagggatat acgcttgggt  8520
ttgtccagcc tgagcctcta tgccagaaat ggcgccttca tcgtgggtta ggacatttaa  8580
```

```
ttttaaaaaa aaaccccgct tcggcggggt tttttttttag catgcaagga gatggcgccc  8640
aacagtcccc cggccacggg gcctgccacc atacccacgc cgaaacaagc gctcatgagc  8700
ccgaagtggc gagcccgatc ttccccatcg gtgatgtcgg cgatataggc gccagcaacc  8760
gcacctgtgg cgccggtgat gccggccacg atgcgtccgg cgtagaggat cgagatctcg  8820
atcccgcgaa attaatacga ctcactatag ggaattgtg agcggataac aattcccctc  8880
taggatccga aataattttg tttaacttta agaaggagat atacc               8925

SEQ ID NO: 486          moltype = DNA  length = 9519
FEATURE                 Location/Qualifiers
misc_feature            1..9519
                        note = Description of Artificial Sequence: Synthetic
                         polynucleotide
misc_feature            1..9519
                        note = Category: Plasmid
misc_feature            1..9519
                        note = Description: pET21-CAT (H193Y)-sgRNA-MG68-4
                         (D109N)-nMG34-1 (D10A)
source                  1..9519
                        mol_type = other DNA
                        organism = synthetic construct
SEQUENCE: 486
ttaattaatt tgatcggcac gtaagaggtt ccaactttca ccataatgaa ataagatcac  60
taccgggcgt atttttttgag ttatcgagat tttcaggagc taaggaagct aaaatggaga  120
aaaaaatcac tggatatacc accgttgata tatcccaatg gcatcgtaaa gaacattttg  180
aggcatttca gtcagttgct caatgtacct ataaccagac cgttcagctg gatattacgg  240
cctttttaaa gaccgtaaag aaaaataagc acaagtttta tccggccttt attcacattc  300
ttgcccgcct gatgaatgct catccggaat tccgtatggc aatgaaagac ggtgagctgg  360
tgatatggga tagtgttcac ccttgttaca ccgttttcca tgagcaaact gaaacgtttt  420
catcgctctg gagtgaatac cacgacgatt tccggcagtt tctacacata tattcgcaag  480
atgtggcgtg ttacggtgaa aacctggcct atttccctaa agggtttatt gagaatatgt  540
tttttgtctc agccaatccc tgggtgagtt tcaccagttt tgatttaaac gtggccaata  600
tggacaactt cttcgccccc gttttcacca tgggcaaata ttatacgcaa ggcgacaagg  660
tgctgatgcc gctggcgatt caggttcatt atgccgtctg tgatggcttc catgtcggca  720
gaatgcttaa tgaattacaa cagtactgcg atgagtggca gggcggggcg taattttttt  780
aaggcagtta ttggtgccct taaacgcctg gtgctacgcc tgaataagtg aagcatgcaa  840
ggagatggcg cccaacagtc ccccggccac ggggcctgcc accataccca cgccgaaaca  900
agcgctcatg agcccgaagt ggcgagcccg atcttcccca tcggtgatgt cggcgatata  960
ggcgccagca accgcacctg tggcgccggt gatgccggcc acgatgcgtc cggcgtagag  1020
gatcgactcg agtgcggccg caagcttgtc gacggagctc gaattcggat cctaatacga  1080
ctcactatag taatgaacct gaatcgccag gttacagtta agaaattaat tgtaaaacgc  1140
ctatacagtg aagggatata cgcttgggtt tgtccagcct gagcctctat gccagaaatg  1200
gcgccttcat cgtgggttag gacatttaat tttaaaaaaa aaccccgctt cggcggggtt  1260
tttttttagc atgcaaggag atggcgccca acagtccccc ggccacgggg cctgccacca  1320
tacccacgcc gaaacaagcg ctcatgagcc cgaagtggcg agcccgatct tccccatcgg  1380
tgatgtcggc gatataggcg ccagcaaccg cacctgtggc gccggtgatg ccggccacga  1440
tgcgtccggc gtagaggatc gagatctcga tcccgcgaaa ttaatacgac tcactatagg  1500
ggaattgtga gcggataaca attcccctct aggatccgaa ataattttgt ttaactttaa  1560
gaaggagata taccccgcgg atgactgatt ctcaaaatga tacagatgaa tactggatgg  1620
gagaggccct gaagttggca caaaaggcat gggacgaagg agaggtgccc gtaggagcca  1680
tcttggttcg taagggcgaa gttatcggtc atggctggaa ccgtagcatc gggtcccatg  1740
acccctcggc gcatgctgaa attatggcta ttcgtgaagc cggggtgcgt atcggtaatt  1800
atcgcatgtt ggataccgta ttatacgtta cgctggagcc gtgtgcaatg tgcgcagggg  1860
cacttgttca cgggcgtatt tcacgcttgg tctttggtgc cgaaaacccc aagacagggg  1920
cgtgcgggtc agtcatggac attgctcgcc accctgcttt gaaccaccaa ttacaagttg  1980
atggtggggt aatggcggct ccttgtgcgc gtcttttatc tgacttcttt cgctggcgtc  2040
gcgctcagaa aaaggcggcc cgtgataata gttcggggaa cggtacctca ggcgggtcgt  2100
cgggaggaag cagtggcagc gagactcccg gaacttcgga gagcgctaca ccagaaagta  2160
gtggaggcag ctctggtggg tccatggagc gcgagctggt gctggggatc gcgtatggtg  2220
gtaagtacac gggcttggcg gtggtggatc gccgccacaa ccaagtgctg tacgcgaatc  2280
gtcttaaaat gcgtgatgac gtggcaggca tcttgaagga ccgtcgcaaa cagcgcggga  2340
ttcgtcgcac ggcccagacg aagaagaaac gccttcgcga gctgaagaat tacctgaaga  2400
gcatcgggta caatgagtcg acggccacct tcgagaccgt gtattcactg gcgcacaagc  2460
gtggttacga ctacgcagac atgccagagg agaaaaccag tgaggagatt gaagcgatgg  2520
acgttgagga acgtaagcaa tgggagaagg aaaagcaaga gtgggaagaa actaagcgca  2580
actctcgcca tcgcaaagag gtagttaagg acgtacacaa ggcgatgatc gagggccgtg  2640
ccacggaaga acaaattaag cgtgtggagc gcatcttcaa caagcaatat cgcccgaagc  2700
gttttaacaa ccgcatcttg accaagtgca aagtggaaga ctgtggtgtg aacactcctt  2760
tgcgtaagaa cgtacgcgac ctgctgattg agaacattgt tcgtttcttt ccgattgagc  2820
agagcgagaa agacaacctg aaggacgccg tattagacaa gaatcgtcgc gaagaggtga  2880
agtccttctt tcgcaagcac aaaaccgacg agcacatccg taaacaagtg tacgacattg  2940
ccgacaataa actgagcggg cgtactgtat tctgcaagga gcacattctg gagcacacgg  3000
aacactccaa ggaagagcgt aaagtctttc gcctggcacc gagtctgaag acgaagattg  3060
aaaacgtgct ggcagtaatc aaggatgaaa ttctccctaa gttcacggtg aacaaagtag  3120
tgatggaatc aaataacttc gacatcgccg cgaagaccca aggtaagaag cgtctcgcca  3180
aggaagagta cggcaagggc ccgcgtgagg gtaaggaaac gcgcaaagag gcgctgctgc  3240
gcgagaccga cgggcgctgc atttattgcg gcaagagcat cgatatttcg aacgcacacg  3300
acgatcacat cttccctcgt aaagcgggcg gattgaacat tttcgcgaac ctcgtggcct  3360
gctgtgcggt gtgcaacgaa aacaagaagg gccgcacgcc tctggagtcg ggcatttcac  3420
caaagccaga gattattgca tttatgaaga acgacctgaa gaagaaaatc ttggaagatg  3480
```

```
ctcgcaacat taacaccgtc gacttcaaca agtatatgag ccacgcttcg attgggtggc  3540
gttacatgcg cgatcgcctt cgcgaatcgg caggtaacaa gaaactgccg atcgaacgcc  3600
aaagtggtat ttatacggcc tactttcgtc gctggtgggg tttcaagaaa gagcgcggta  3660
atactttgca ccacgctctg gacgcggtga ttttggcctc gcgtaagggc tactcagacg  3720
acggcttagt agacatgact ttaaaaccca agtacaataa gggcggcgaa ttcgatccgg  3780
agaagcactt accggagcct atcgagttca agatggacaa ggggtcacgc ggtagcgccc  3840
tgcacgaccg taatccgttg agttacaaga agggtatcat cactcgtcgc ttcatggtca  3900
ctgaaatcga atgtggcaag gaagatgacg tgatctctga aacctaccgc gagaagttga  3960
aggaagcgtt caagcgcttc gacaccaaga agggcaagtg cctgaccgat aaagaagcca  4020
aagaggcggg gttctgtatc aagaagaacg agctggtgat gtcgctgaag tgttcaatca  4080
aggggactgg cccgggccaa atgattcgca ttaacaacaa cgtgttcaaa accaacgtac  4140
acaacgtagg agttgacgtc tacctggacg agaagggcaa gaagaaggcg tacgaacgca  4200
agaacccacg cttatcgaag cattttattg agccgccgcc acaaccgaac ggccgcgtct  4260
ctttcacact gaagcgtcgc gacatggtga ctgtagaggg agaggatgcc atttaccgca  4320
ttaagaagtt gggtacttcc ccgaccatcg aggcggtggt ggggagcgac ggtaagacgc  4380
gcacagtatc ggcaacgaaa ttgaccaagg ccaatagcgc cgagctcgag ggctctggcg  4440
ggtctcccaa gaagaagagg aaagtctaag atccggctgc taacaaagcc cgaaaggaag  4500
ctgagttggc tgctgccacc gctgagcaat aactagcata accccttggg gcctctaaac  4560
gggtcttgag gggttttttg ctgaaaggag gaactatatc cggattggcg aatgggacgc  4620
gccctgtagc ggcgcattaa gcgcggcggg tgtggtggtt acgcgcagcg tgaccgctac  4680
acttgccagc gccctagcgc ccgctccttt cgctttcttc ccttcctttc tcgccacgtt  4740
cgccggcttt ccccgtcaag ctctaaatcg ggggctccct ttagggttcc gatttagtgc  4800
tttacggcac ctcgacccca aaaaacttga ttagggtgat ggttcacgta gtgggccatc  4860
gccctgatag acggtttttc gccctttgac gttggagtcc acgttcttta atagtggact  4920
cttgttccaa actggaacaa cactcaaccc tatctcggtc tattcttttg atttataagg  4980
gattttgccg atttcggcct attggttaaa aaatgagctg atttaacaaa aatttaacgc  5040
gaattttaac aaaatattaa cgcttacaat ttaggtggca cttttcgggg aaatgtgcgc  5100
ggaaccccta tttgtttatt tttctaaata cattcaaata tgtatccgct catgagacaa  5160
taaccctgat aaatgcttca ataatattga aaaaggaaga gtatgagtat tcaacatttc  5220
cgtgtcgccc ttattccctt ttttgcggca ttttgccttc ctgtttttgc tcacccagaa  5280
acgctggtga aagtaaaaga tgctgaagat cagttgggtg cacgagtggg ttacatcgaa  5340
ctggatctca acagcggtaa gatccttgag agttttcgcc ccgaagaacg ttttccaatg  5400
atgagcactt ttaaagttct gctatgtggc gcggtattat cccgtattga cgccgggcaa  5460
gagcaactcg gtcgccgcat acactattct cagaatgact tggttgagta ctcaccagtc  5520
acagaaaagc atcttacgga tggcatgaca gtaagagaat tatgcagtgc tgccataacc  5580
atgagtgata acactgcggc caacttactt ctgacaacga tcggaggacc gaaggagcta  5640
accgcttttt tgcacaacat gggggatcat gtaactcgcc ttgatcgttg ggaaccggag  5700
ctgaatgaag ccataccaaa cgacgagcgt gacaccacga tgcctgcagc aatggcaaca  5760
acgttgcgca aactattaac tggcgaacta cttactctag cttcccggca acaattaata  5820
gactggatgg aggcggataa agttgcagga ccacttctgc gctcggccct tccggctggc  5880
tggtttattg ctgataaatc tggagccggt gagcgtgggt ctcgcggtat cattgcagca  5940
ctggggccag atggtaagcc ctcccgtatc gtagttatct acacgacggg gagtcaggca  6000
actatggatg aacgaaatag acagatcgct gagataggtg cctcactgat taagcattgg  6060
taactgtcag accaagttta ctcatatata ctttagattg atttaaaact tcatttttaa  6120
tttaaaagga tctaggtgaa gatccttttt gataatctca tgaccaaaat cccttaacgt  6180
gagttttcgt tccactgagc gtcagacccc gtagaaaaga tcaaaggatc ttcttgagat  6240
cctttttttc tgcgcgtaat ctgctgcttg caaacaaaaa aaccaccgct accagcggtg  6300
gtttgtttgc cggatcaaga gctaccaact ctttttccga aggtaactgg cttcagcaga  6360
gcgcagatac caaatactgt ccttctagtg tagccgtagt taggccacca cttcaagaac  6420
tctgtagcac cgcctacata cctcgctctg ctaatcctgt taccagtggc tgctgccagt  6480
ggcgataagt cgtgtcttac cgggttggac tcaagacgat agttaccgga taaggcgcag  6540
cggtcgggct gaacgggggg ttcgtgcaca cagcccagct tggagcgaac gacctacacc  6600
gaactgagat acctacagcg tgagctatga gaaagcgcca cgcttcccga agggagaaag  6660
gcggacaggt atccggtaag cggcagggtc ggaacaggag agcgcacgag ggagcttcca  6720
gggggaaacg cctggtatct ttatagtcct gtcgggtttc gccacctctg acttgagcgt  6780
cgatttttgt gatgctcgtc aggggggcgg agcctatgga aaaacgccag caacgcggcc  6840
tttttacggt tcctggcctt ttgctggcct tttgctcaca tgttctttcc tgcgttatcc  6900
cctgattctg tggataaccg tattaccgcc tttgagtgag ctgataccgc tcgccgcagc  6960
cgaacgaccg agcgcagcga gtcagtgagc gaggaagcgg aagagcgcct gatgcggtat  7020
tttctcctta cgcatctgtg cggtatttca caccgcaatg gtgcactctc agtacaatct  7080
gctctgatgc cgcatagtta agccagtata cactccgcta tcgctacgtg actgggtcat  7140
ggctgcgccc cgacacccgc caacacccgc tgacgcgccc tgacgggctt gtctgctccc  7200
ggcatccgct tacagacaag ctgtgaccgt ctccgggagc tgcatgtgtc agaggttttc  7260
accgtcatca ccgaaacgcg cgaggcagct gcggtaaagc tcatcagcgt ggtcgtgaag  7320
cgattcacag atgtctgcct gttcatccgc gtccagctcg ttgagtttct ccagaagcgt  7380
taatgtctgg cttctgataa agcgggccat gttaagggcg gttttttcct gtttggtcac  7440
tgatgcctcc gtgtaagggg gatttctgtt catgggggta atgataccga tgaaacgaga  7500
gaggatgctc acgatacggg ttactgatga tgaacatgcc cggttactgg aacgttgtga  7560
gggtaaacaa ctggcggtat ggatgcggcg ggaccagaga aaaatcactc agggtcaatg  7620
ccagcgcttc gttaatacag atgtaggtgt tccacagggt agccagcagc atcctgcgat  7680
gcagatccgg aacataatgg tgcagggcgc tgacttccgc gtttccagac tttacgaaac  7740
acggaaaccg aagaccattc atgttgttgc tcaggtcgca gacgttttgc agcagcagtc  7800
gcttcacgtt cgctcgcgta tcggtgattc attctgctaa ccagtaaggc aaccccgcca  7860
gcctagccgg gtcctcaacg acaggagcac gatcatgcgc acccgtgggg ccgccatgcc  7920
ggcgataatg gcctgcttct cgccgaaacg tttggtggcg ggaccagtga cgaaggcttg  7980
agcgagggcg tgcaagattc cgaataccgc aagcgacagg ccgatcatcg tcgcgctcca  8040
gcgaaagcgg tcctcgccga aaatgaccca gagcgctgcc ggcacctgtc ctacgagttg  8100
catgataaag aagacagtca taagtgcggc gacgatagtc atgccccgcg cccaccggaa  8160
ggagctgact gggttgaagg ctctcaaggg catcggtcga gatcccggtg cctaatgagt  8220
```

```
gagctaactt acattaattg cgttgcgctc actgcccgct ttccagtcgg gaaacctgtc  8280
gtgccagctg cattaatgaa tcggccaacg cgcggggaga ggcggtttgc gtattgggcg  8340
ccagggtggt ttttcttttc accagtgaga cgggcaacag ctgattgccc ttcaccgcct  8400
ggccctgaga gagttgcagc aagcggtcca cgctggtttg ccccagcagg cgaaaatcct  8460
gtttgatggt ggttaacggc gggatataac atgagctgtc ttcggtatcg tcgtatccca  8520
ctaccgagat atccgcacca acgcgcagcc cggactcggt aatggcgcgc attgcgccca  8580
gcgccatctg atcgttggca accagcatcg cagtgggaac gatgccctca ttcagcattt  8640
gcatggtttg ttgaaaaccg gacatggcac tccagtcgcc ttcccgttcc gctatcggct  8700
gaatttgatt gcgagtgaga tatttatgcc agccagccag acgcagacgc gccgagacag  8760
aacttaatgg gcccgctaac agcgcgattt gctggtgacc caatgcgacc agatgctcca  8820
cgcccagtcg cgtaccgtct tcatgggaga aaataatact gttgatgggt gtctggtcag  8880
agacatcaag aaataacgcc ggaacattag tgcaggcagc ttccacagca atggcatcct  8940
ggtcatccag cggatagtta atgatcagcc cactgacgcg ttgcgcgaga agattgtgca  9000
ccgccgcttt acaggcttcg acgccgcttc gttctaccat cgacaccacc acgctggcac  9060
ccagttgatc ggcgcgagat ttaatcgccg cgacaatttg cgacggcgcg tgcagggcca  9120
gactggaggt ggcaacgcca atcagcaacg actgtttgcc cgccagttgt tgtgccacgc  9180
ggttgggaat gtaattcagc tccgccatcg ccgcttccac tttttcccgc gttttcgcag  9240
aaacgtggct ggcctggttc accacgcggg aaacggtctg ataagagaca ccggcatact  9300
ctgcgacatc gtataacgtt actggtttca cattcaccac cctgaattga ctctcttccg  9360
ggcgctatca tgccataccg cgaaaggttt tgcgccattc gatggtgtcc gggatctcga  9420
cgctctccct tatgcgactc ctgcattagg aagcagccca gtagtaggtt gaggccgttg  9480
agcaccgccg ccgcaaggaa tggtttaatt aattctaga                         9519

SEQ ID NO: 487          moltype = DNA  length = 11211
FEATURE                 Location/Qualifiers
misc_feature            1..11211
                        note = Description of Artificial Sequence: Synthetic
                         polynucleotide
misc_feature            1..11211
                        note = Category: Plasmid
misc_feature            1..11211
                        note = Description: pET21-CAT (H193Y)-sgRNA-MG68-4
                         (D109N)-nSpCas9 (D10A)
source                  1..11211
                        mol_type = other DNA
                        organism = synthetic construct
SEQUENCE: 487
gaaataattt tgtttaactt taagaaggag atataccatg ggcagcagtc atcatcatca  60
ccatcacatg actgattctc aaaatgatac agatgaatac tggatgggag aggccctgaa  120
gttggcacaa aaggcatggg acgaaggaga ggtgcccgta ggagccatct tggttcgtaa  180
gggcgaagtt atcggtcatg gctggaaccg tagcatcggg tcccatgacc cctcggcgca  240
tgctgaaatt atggctattc gtgaagccgg ggtgcgtatc ggtaattatc gcatgttgga  300
taccgtatta tacgttacgc tggagccgtg tgcaatgtgc gcaggggcac ttgttcacgg  360
gcgtatttca cgcttggtct ttggtgccga aaaccccaag acaggggcgt gcgggtcagt  420
catggacatt gctcgccacc ctgctttgaa ccaccaatta caagttgatg gtggggtaat  480
ggcggctcct tgtgcgcgtc ttttatctga cttctttcgc tggcgtcgcg ctcagaaaaa  540
ggcggcccgt gataatagtt cggggaactc aggcgggtcg tcgggaggaa gcagtggcag  600
cgagactccc ggaacttcgg agagcgctac accagaaagt agtggaggca gctctggtgg  660
gtccatggat aagaaatact caataggact ggcgattggc acaaatagcg tcggatgggc  720
tgtgatcact gatgaatata aggttccttc taaaaagttc aaggttctgg gaaatacaga  780
ccgccacagt atcaaaaaaa atcttatagg ggctcttctg tttgacagtg gagagacagc  840
cgaagctact agactcaaac ggacagctag gagaaggtat acaagacgga agaataggat  900
ttgttatctc caggagattt tttcaaatga gatggccaaa gtggatgata gtttctttca  960
tagacttgaa gagtcttttt tggtggaaga agacaagaag catgaaagac atcctatttt  1020
tggaaatata gtggatgaag ttgcttatca cgagaaatat ccaactatct atcatctgag  1080
aaaaaaattg gtggattcta ctgataaagc cgatttgcgc ctgatctatt tggccctggc  1140
ccacatgatt aagtttagag gtcatttttt gattgagggc gatctgaatc ctgataatag  1200
tgatgtggac aaactgttta tccagttggt gcaaacctac aatcaactgt ttgaagaaaa  1260
ccctattaac gcaagtggag tggatgctaa agccattctt tctgcaagat tgagtaaatc  1320
aagaagactg gaaaatctca ttgctcagct ccccggtgag aagaaaaatg gcctgtttgg  1380
gaatctcatt gctttgtcat tgggtttgac ccctaatttt aaatcaaatt ttgatttggc  1440
agaagatgct aaactccagc tttcaaaaga tacttacgat gatgatctgg ataatctgtt  1500
ggctcaaatt ggagatcaat atgctgattt gtttttggca gctaagaatc tgtcagatgc  1560
tattctgctt tcagacatcc tgagagtgaa tactgaaata actaaggctc ccctgtcagc  1620
ttcaatgatt aaacgctacg atgaacatca tcaagacttg actcttctga aagccctggt  1680
tagacaacaa cttccagaaa agtataaaga aatctttttt gatcaatcaa aaaacggata  1740
tgcaggttat attgatggcg gcgcaagcca agaagaattt tataaattta tcaaaccaat  1800
tctggaaaaa atggatggta ctgaggaact gttggtgaaa ctgaatagag aagatttgct  1860
gcgcaagcaa cggacctttg acaacggctc tattccccat caaattcact tgggtgagct  1920
gcatgctatt ttgagaagac aagaagactt ttatccattt ctgaaagaca atagagagaa  1980
gattgaaaaa atcttgactt ttaggattcc ttattatgtt ggtccattgg ccagaggcaa  2040
tagtaggttt gcatggatga ctcggaagtc tgaagaaaca attaccccat ggaattttga  2100
agaagttgtc gataaaggtg cttcagctca atcatttatt gaacgcatga caaactttga  2160
taaaaatctt ccaaatgaaa aagtgctgcc aaaacatagt ttgctttatg agtattttac  2220
cgtttataac gaattgacaa aggtcaaata tgttactgaa ggaatgagaa aaccagcatt  2280
tctttcaggt gaacagaaga aagccattgt tgatctgctc ttcaaaacaa ataggaaagt  2340
gaccgttaag caactgaaag aagattattt caaaaaaata gaatgttttg atagtgttga  2400
aatttcagga gttgaagata gatttaatgc ttcactgggt acataccatg atttgctgaa  2460
aattattaaa gataaagatt ttttggataa tgaagaaaat gaagacatcc tggaggatat  2520
```

```
tgttctgaca ttgaccctgt ttgaagatag ggagatgatt gaggaaagac ttaaaacata  2580
cgctcacctc tttgatgata aggtgatgaa acagcttaaa agacgcagat atactggttg  2640
gggaaggttg tccagaaaat tgattaatgg tattagggat aagcaatctg gcaaaacaat  2700
actggatttt ttgaaatcag atggttttgc caatcgcaat tttatgcagc tcatccatga  2760
tgatagtttg acatttaaag aagacatcca aaaagcacaa gtgtctggac aaggcgatag  2820
tctgcatgaa catattgcaa atctggctgg tagccctgct attaaaaaag gtattctcca  2880
gactgtgaaa gttgttgatg aattggtcaa agtgatgggg cggcataagc cagaaaatat  2940
cgttattgaa atggcaagag aaaatcagac aactcaaaag ggccagaaaa attccagaga  3000
gaggatgaaa agaatcgaag aaggtatcaa agaactggga agtcagattc ttaaagagca  3060
tcctgttgaa aatactcaat tgcaaaatga aaagctctat ctctattatc tccaaaatgg  3120
aagagatatg tatgtggacc aagaactgga tattaatagg ctgagtgatt atgatgtcga  3180
tcacattgtt ccacaaagtt tccttaaaga cgattcaata gacaataagg tcctgaccag  3240
gtctgataaa aatagaggta aatccgataa cgttccaagt gaagaagtgg tcaaaaagat  3300
gaaaaactat tggagacaac ttctgaacgc caagctgatc actcaaagga agtttgataa  3360
tctgaccaaa gctgaaagag gaggtttgag tgaacttgat aaagctggtt ttatcaaacg  3420
ccaattggtt gaaactcgcc aaatcactaa gcatgtggca caaattttgg atagtcgcat  3480
gaatactaaa tacgatgaaa atgataaact tattagagag gttaaagtga ttaccctgaa  3540
atctaaactg gtttctgact tcagaaaaga tttccaattc tataaagtga gagagattaa  3600
caattaccat catgcccatg atgcctatct gaatgccgtc gttggaactg ctttgattaa  3660
gaaatatcca aaacttgaaa gcgagtttgt ctatggtgat tataaagttt atgatgttag  3720
gaaaatgatt gctaagtctg agcaagaaat aggcaaagca accgcaaagt atttctttta  3780
ctctaatatc atgaacttct tcaaaacaga aattacactt gcaaatggag agattcgcaa  3840
acgccctctg atcgaaacta atggggaaac tggagaaatt gtctgggata aagggagaga  3900
ttttgccaca gtgcgcaaag tgttgtccat gccccaagtc aatatcgtca agaaaacaga  3960
agtgcagaca ggcggattct ctaaggagtc aattctgcca aaaagaaatt ccgacaagct  4020
gattgctagg aaaaaagact gggacccaaa aaaatatggt ggttttgata gtccaaccgt  4080
ggcttattca gtcctggtgg ttgctaaggt ggaaaaaggg aaatccaaga agctgaaatc  4140
cgttaaagag ctgctgggga tcacaattat ggaaagaagt tcctttgaaa aaaatcccat  4200
tgactttctg gaagctaaag gatataagga agttaaaaaa gacctgatca ttaaactgcc  4260
taaatatagt ctttttgagc tggaaaacgg taggaaacgg atgctggcta gtgccggaga  4320
actgcaaaaa ggaaatgagc tggctctgcc aagcaaatat gtgaattttc tgtatctggc  4380
tagtcattat gaaaagttga agggtagtcc agaagataac gaacaaaaac aattgtttgt  4440
ggagcagcat aagcattatc tggatgagat tattgagcaa atcagtgaat tttctaagag  4500
agttattctg gcagatgcca atctggataa agttcttagt gcatataaca aacatagaga  4560
caaaccaata agagaacaag cagaaaatat cattcatctg tttaccttga ccaatcttgg  4620
agcacccgct gcttttaaat actttgatac aacaattgat aggaaaagat atacctctac  4680
aaaagaagtt ctggatgcca ctcttatcca tcaatccatc actggtcttt atgaaacacg  4740
cattgatttg agtcagctgg gaggtgacgg ctctggcggg tctcccaaga agaagaggaa  4800
agtctaagat ccggctgcta acaaagcccg aaaggaagct gagttggctg ctgccaccgc  4860
tgagcaataa ctagcataac cccttggggc ctctaaacgg gtcttgaggg gttttttgct  4920
gaaaggagga actatatccg gattggcgaa tgggacgcgc cctgtagcgg cgcattaagc  4980
gcggcgggtg tggtggttac gcgcagcgtg accgctacac ttgccagcgc cctagcgccc  5040
gctcctttcg ctttcttccc ttcctttctc gccacgttcg ccggctttcc ccgtcaagct  5100
ctaaatcggg ggctcccttt agggttccga tttagtgctt tacggcacct cgaccccaaa  5160
aaacttgatt agggtgatgg ttcacgtagt gggccatcgc cctgatagac ggtttttcgc  5220
cctttgacgt tggagtccac gttctttaat agtggactct tgttccaaac tggaacaaca  5280
ctcaacccta tctcggtcta ttcttttgat ttataaggga ttttgccgat ttcggcctat  5340
tggttaaaaa atgagctgat ttaacaaaaa tttaacgcga attttaacaa aatattaacg  5400
cttacaattt aggtggcact tttcggggaa atgtgcgcgg aacccctatt tgtttatttt  5460
tctaaataca ttcaaatatg tatccgctca tgagacaata accctgataa atgcttcaat  5520
aatattgaaa aaggaagagt atgagtattc aacatttccg tgtcgccctt attccctttt  5580
ttgcggcatt ttgccttcct gtttttgctc acccagaaac gctggtgaaa gtaaaagatg  5640
ctgaagatca gttgggtgca cgagtgggtt acatcgaact ggatctcaac agcggtaaga  5700
tccttgagag ttttcgcccc gaagaacgtt ttccaatgat gagcactttt aaagttctgc  5760
tatgtggcgc ggtattatcc cgtattgacg ccgggcaaga gcaactcggt cgccgcatac  5820
actattctca gaatgacttg gttgagtact caccagtcac agaaaagcat cttacggatg  5880
gcatgacagt aagagaatta tgcagtgctg ccataaccat gagtgataac actgcggcca  5940
acttacttct gacaacgatc ggaggaccga aggagctaac cgcttttttg cacaacatgg  6000
gggatcatgt aactcgcctt gatcgttggg aaccggagct gaatgaagcc ataccaaacg  6060
acgagcgtga caccacgatg cctgcagcaa tggcaacaac gttgcgcaaa ctattaactg  6120
gcgaactact tactctagct tcccggcaac aattaataga ctggatggag gcggataaag  6180
ttgcaggacc acttctgcgc tcggcccttc cggctggctg gtttattgct gataaatctg  6240
gagccggtga gcgtgggtct cgcggtatca ttgcagcact ggggccagat ggtaagccct  6300
cccgtatcgt agttatctac acgacgggga gtcaggcaac tatggatgaa cgaaatagac  6360
agatcgctga gataggtgcc tcactgatta agcattggta actgtcagac caagtttact  6420
catatatact ttagattgat ttaaaacttc atttttaatt taaaaggatc taggtgaaga  6480
tcctttttga taatctcatg accaaaatcc cttaacgtga gttttcgttc cactgagcgt  6540
cagaccccgt agaaaagatc aaaggatctt cttgagatcc tttttttctg cgcgtaatct  6600
gctgcttgca aacaaaaaaa ccaccgctac cagcggtggt ttgtttgccg gatcaagagc  6660
taccaactct ttttccgaag gtaactggct tcagcagagc gcagatacca aatactgtcc  6720
ttctagtgta gccgtagtta ggccaccact tcaagaactc tgtagcaccg cctacatacc  6780
tcgctctgct aatcctgtta ccagtggctg ctgccagtgg cgataagtcg tgtcttaccg  6840
ggttggactc aagacgatag ttaccggata aggcgcagcg gtcgggctga acggggggtt  6900
cgtgcacaca gcccagcttg gagcgaacga cctacaccga actgagatac ctacagcgtg  6960
agctatgaga aagcgccacg cttcccgaag ggagaaaggc ggacaggtat ccggtaagcg  7020
gcagggtcgg aacaggagag cgcacgaggg agcttccagg gggaaacgcc tggtatcttt  7080
atagtcctgt cgggtttcgc cacctctgac ttgagcgtcg atttttgtga tgctcgtcag  7140
gggggcggag cctatggaaa aacgccagca acgcggcctt tttacggttc ctggcctttt  7200
gctggccttt tgctcacatg ttctttcctg cgttatcccc tgattctgtg gataaccgta  7260
```

```
ttaccgcctt tgagtgagct gataccgctc gccgcagccg aacgaccgag cgcagcgagt  7320
cagtgagcga ggaagcggaa gagcgcctga tgcggtattt tctccttacg catctgtgcg  7380
gtatttcaca ccgcaatggt gcactctcag tacaatctgc tctgatgccg catagttaag  7440
ccagtataca ctccgctatc gctacgtgac tgggtcatgg ctgcgccccg acacccgcca  7500
acacccgctg acgcgccctg acgggcttgt ctgctcccgg catccgctta cagacaagct  7560
gtgaccgtct ccgggagctg catgtgtcag aggttttcac cgtcatcacc gaaacgcgcg  7620
aggcagctgc ggtaaagctc atcagcgtgg tcgtgaagcg attcacagat gtctgcctgt  7680
tcatccgcgt ccagctcgtt gagtttctcc agaagcgtta atgtctggct tctgataaag  7740
cgggccatgt taagggcggt tttttcctgt ttggtcactg atgcctccgt gtaaggggga  7800
tttctgttca tgggggtaat gataccgatg aaacgagaga ggatgctcac gatacgggtt  7860
actgatgatg aacatgcccg gttactggaa cgttgtgagg gtaaacaact ggcggtatgg  7920
atgcggcggg accagagaaa aatcactcag ggtcaatgcc agcgcttcgt taatacagat  7980
gtaggtgttc cacagggtag ccagcagcat cctgcgatgc agatccggaa cataatggtg  8040
cagggcgctg acttccgcgt ttccagactt tacgaaacac ggaaaccgaa gaccattcat  8100
gttgttgctc aggtcgcaga cgttttgcag cagcagtcgc ttcacgttcg ctcgcgtatc  8160
ggtgattcat tctgctaacc agtaaggcaa ccccgccagc ctagccgggt cctcaacgac  8220
aggagcacga tcatgcgcac ccgtggggcc gccatgccgg cgataatggc ctgcttctcg  8280
ccgaaacgtt tggtggcggg accagtgacg aaggcttgag cgagggcgtg caagattccg  8340
aataccgcaa gcgacaggcc gatcatcgtc gcgctccagc gaaagcggtc ctcgccgaaa  8400
atgacccaga gcgctgccgg cacctgtcct acgagttgca tgataaagaa gacagtcata  8460
agtgcggcga cgatagtcat gccccgcgcc caccggaagg agctgactgg gttgaaggct  8520
ctcaagggca tcggtcgaga tcccggtgcc taatgagtga gctaacttac attaattgcg  8580
ttgcgctcac tgcccgcttt ccagtcggga aacctgtcgt gccagctgca ttaatgaatc  8640
ggccaacgcg cggggagagg cggtttgcgt attgggcgcc agggtggttt ttcttttcac  8700
cagtgagacg ggcaacagct gattgccctt caccgcctgg ccctgagaga gttgcagcaa  8760
gcggtccacg ctggtttgcc ccagcaggcg aaaatcctgt ttgatggtgg ttaacggcgg  8820
gatataacat gagctgtctt cggtatcgtc gtatcccact accgagatat ccgcaccaac  8880
gcgcagcccg gactcggtaa tggcgcgcat tgcgcccagc gccatctgat cgttggcaac  8940
cagcatcgca gtgggaacga tgccctcatt cagcatttgc atggtttgtt gaaaaccgga  9000
catggcactc cagtcgcctt cccgttccgc tatcggctga atttgattgc gagtgagata  9060
tttatgccag ccagccagac gcagacgcgc cgagacagaa cttaatgggc ccgctaacag  9120
cgcgatttgc tggtgaccca atgcgaccag atgctccacg cccagtcgcg taccgtcttc  9180
atgggagaaa ataatactgt tgatgggtgt ctggtcagag acatcaagaa ataacgccgg  9240
aacattagtg caggcagctt ccacagcaat ggcatcctgg tcatccagcg gatagttaat  9300
gatcagccca ctgacgcgtt gcgcgagaag attgtgcacc gccgctttac aggcttcgac  9360
gccgcttcgt tctaccatcg acaccaccac gctggcaccc agttgatcgg cgcgagattt  9420
aatcgccgcg acaatttgcg acggcgcgtg cagggccaga ctggaggtgg caacgccaat  9480
cagcaacgac tgtttgcccg ccagttgttg tgccacgcgg ttgggaatgt aattcagctc  9540
cgccatcgcc gcttccactt tttcccgcgt tttcgcagaa acgtggctgg cctggttcac  9600
cacgcgggaa acggtctgat aagagacacc ggcatactct gcgacatcgt ataacgttac  9660
tggtttcaca ttcaccaccc tgaattgact ctcttccggg cgctatcatg ccataccgcg  9720
aaaggttttg cgccattcga tggtgtccgg gatctcgacg ctctccctta tgcgactcct  9780
gcattaggaa gcagcccagt agtaggttga ggccgttgag caccgccgcc gcaaggaatg  9840
gtttaattaa tttgatcggc acgtaagagg ttccaacttt caccataatg aaataagatc  9900
actaccgggc gtattttttg agttatcgag attttcagga gctaaggaag ctaaaatgga  9960
gaaaaaaatc actggatata ccaccgttga tatatcccaa tggcatcgta aagaacattt  10020
tgaggcattt cagtcagttg ctcaatgtac ctataaccag accgttcagc tggatattac  10080
ggccttttta aagaccgtaa agaaaaataa gcacaagttt tatccggcct ttattcacat  10140
tcttgcccgc ctgatgaatg ctcatccgga attccgtatg gcaatgaaag acggtgagct  10200
ggtgatatgg gatagtgttc acccttgtta caccgttttc catgagcaaa ctgaaacgtt  10260
ttcatcgctc tggagtgaat accacgacga tttccggcag tttctacaca tatattcgca  10320
agatgtggcg tgttacggtg aaaacctggc ctatttccct aaagggttta ttgagaatat  10380
gtttttcgtc tcagccaatc cctgggtgag tttcaccagt tttgatttaa acgtggccaa  10440
tatggacaac ttcttcgccc ccgttttcac catgggcaaa tattatacgc aaggcgacaa  10500
ggtgctgatg ccgctggcga ttcaggttca ttatgccgtc tgtgatggct tccatgtcgg  10560
cagaatgctt aatgaattac aacagtactg cgatgagtgg cagggcgggg cgtaattttt  10620
ttaaggcagt tattggtgcc cttaaacgcc tggtgctacg cctgaataag tgaagcatgc  10680
aaggagatgg cgcccaacag tcccccggcc acggggcctg ccaccatacc cacgccgaaa  10740
caagcgctca tgagcccgaa gtggcgagcc cgatcttccc catcggtgat gtcggcgata  10800
taggcgccag caaccgcacc tgtggcgccg gtgatgccgg ccacgatgcg tccggcgtag  10860
aggatcgact cgagtgcggc cgcaagcttg tcgacggagc tcgaattcgg atcctaatac  10920
gactcactat agtaatgaac ctgaatcgcc aggttttaga gctagaaata gcaagttaaa  10980
ataaggctag tccgttatca acttgaaaaa gtggcaccga gtcggtgctt ttttgtgaac  11040
ctgcaggagg catcaaataa aacgaaaggc tcagtcgaaa gactgggcct ttcgttttat  11100
ctgttgtttg tcggtgaacg ctctcctgag taggacaaat tcgatcccgc gaaattaata  11160
cgactcacta taggggaatt gtgagcggat aacaattccc ctctaggatc c           11211
```

```
SEQ ID NO: 488          moltype = DNA  length = 96
FEATURE                 Location/Qualifiers
misc_feature            1..96
                        note = Description of Artificial Sequence: Synthetic
                         oligonucleotide
misc_feature            1..96
                        note = Category: sgRNA scaffold sequence
misc_feature            1..96
                        note = Description: MG15-1
source                  1..96
                        mol_type = other DNA
                        organism = synthetic construct
```

```
SEQUENCE: 488
gttgtaattc cctagaaata ggttattaca ataaggtcca acaggagtgt tggtaccgta  60
aagctctaac ggcacccacg ggtgccgtta tctttt                            96

SEQ ID NO: 489         moltype = DNA  length = 123
FEATURE                Location/Qualifiers
misc_feature           1..123
                       note = Description of Artificial Sequence: Synthetic
                        polynucleotide
misc_feature           1..123
                       note = Category: sgRNA scaffold sequence
misc_feature           1..123
                       note = Description: MG34-1
source                 1..123
                       mol_type = other DNA
                       organism = synthetic construct
SEQUENCE: 489
gttacagtta agaaattaat tgtaaaacgc ctatacagtg aagggatata cgcttgggtt  60
tgtccagcct gagcctctat gccagaaatg gcgccttcat cgtgggttag gacatttaat  120
ttt                                                                123

SEQ ID NO: 490         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: rAPOBEC1-nMG15-1 (D8A) in E. coli
source                 1..22
                       mol_type = other DNA
                       organism = synthetic construct
SEQUENCE: 490
gatccgcgct ggctaccggc ga                                           22

SEQ ID NO: 491         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: rAPOBEC1-nMG15-1 (D8A)-UGI (PBS1) in E.
                        coli
source                 1..22
                       mol_type = other DNA
                       organism = synthetic construct
SEQUENCE: 491
gatccgcgct ggctaccggc ga                                           22

SEQ ID NO: 492         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: rAPOBEC1-nMG15-1 (D8A)-MG69-1 in E. coli
source                 1..22
                       mol_type = other DNA
                       organism = synthetic construct
SEQUENCE: 492
gatccgcgct ggctaccggc ga                                           22

SEQ ID NO: 493         moltype = DNA  length = 22
FEATURE                Location/Qualifiers
misc_feature           1..22
                       note = Description of Artificial Sequence: Synthetic
                        oligonucleotide
misc_feature           1..22
                       note = Category: spacer
misc_feature           1..22
                       note = Description: rAPOBEC1-nMG15-1 (D8A)-MG69-2 in E. coli
source                 1..22
                       mol_type = other DNA
                       organism = synthetic construct
```

```
SEQUENCE: 493
gatccgcgct ggctaccggc ga                                          22

SEQ ID NO: 494          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: rAPOBEC1-nMG15-1 (D8A)-MG69-3 in E. coli
source                  1..22
                        mol_type = other DNA
                        organism = synthetic construct
SEQUENCE: 494
gatccgcgct ggctaccggc ga                                          22

SEQ ID NO: 495          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: rAPOBEC1-nSpCas9 (D10A)-UGI (PBS1) in
                         HEK293T
source                  1..20
                        mol_type = other DNA
                        organism = synthetic construct
SEQUENCE: 495
ggcccagact gagcacgtga                                             20

SEQ ID NO: 496          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: rAPOBEC1-nSpCas9 (D10A) in HEK293T
source                  1..20
                        mol_type = other DNA
                        organism = synthetic construct
SEQUENCE: 496
ggcccagact gagcacgtga                                             20

SEQ ID NO: 497          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: rAPOBEC1-nSpCas9 (D10A)-MG69-1 in
                         HEK293T
source                  1..20
                        mol_type = other DNA
                        organism = synthetic construct
SEQUENCE: 497
ggcccagact gagcacgtga                                             20

SEQ ID NO: 498          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: rAPOBEC1-nSpCas9 (D10A)-MG69-2 in
                         HEK293T
source                  1..20
                        mol_type = other DNA
                        organism = synthetic construct
SEQUENCE: 498
```

```
ggcccagact gagcacgtga                                                20

SEQ ID NO: 499          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG1-4 (D9A)-MG69-1_site 1
                         in HEK293T
source                  1..22
                        mol_type = other DNA
                        organism = synthetic construct
SEQUENCE: 499
gattcccacc tctcaatacg tt                                             22

SEQ ID NO: 500          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG1-4 (D9A)-MG69-1_site 2
                         in HEK293T
source                  1..22
                        mol_type = other DNA
                        organism = synthetic construct
SEQUENCE: 500
cccaggcagg caggctctcc ga                                             22

SEQ ID NO: 501          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG1-4 (D9A)-MG69-1_site 3
                         in HEK293T
source                  1..22
                        mol_type = other DNA
                        organism = synthetic construct
SEQUENCE: 501
cacccccctct ccctccatca gt                                            22

SEQ ID NO: 502          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG1-4 (D9A)-MG69-1_site 4
                         in HEK293T
source                  1..22
                        mol_type = other DNA
                        organism = synthetic construct
SEQUENCE: 502
tgtacacagt ttcccaagct ac                                             22

SEQ ID NO: 503          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 1
                         in HEK293T
source                  1..22
                        mol_type = other DNA
                        organism = synthetic construct
```

```
SEQUENCE: 503
ctggactctg gccactccct gg                                            22

SEQ ID NO: 504          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 2
                         in HEK293T
source                  1..22
                        mol_type = other DNA
                        organism = synthetic construct
SEQUENCE: 504
catccagctc cagccccaga gc                                            22

SEQ ID NO: 505          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 3
                         in HEK293T
source                  1..22
                        mol_type = other DNA
                        organism = synthetic construct
SEQUENCE: 505
gattccggct ctgagggcca gt                                            22

SEQ ID NO: 506          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 4
                         in HEK293T
source                  1..22
                        mol_type = other DNA
                        organism = synthetic construct
SEQUENCE: 506
gcccttctgt ttgtcccact tg                                            22

SEQ ID NO: 507          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 5
                         in HEK293T
source                  1..22
                        mol_type = other DNA
                        organism = synthetic construct
SEQUENCE: 507
ttggccaagc caggcctaga at                                            22

SEQ ID NO: 508          moltype = DNA  length = 22
FEATURE                 Location/Qualifiers
misc_feature            1..22
                        note = Description of Artificial Sequence: Synthetic
                         oligonucleotide
misc_feature            1..22
                        note = Category: spacer
misc_feature            1..22
                        note = Description: A0A2K5RDN7-nMG3-6 (D13A)-MG69-1_site 6
                         in HEK293T
source                  1..22
                        mol_type = other DNA
```

```
                      organism = synthetic construct
SEQUENCE: 508
ctcagctggt acacggcagg gt                                          22

SEQ ID NO: 509        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: A0A2K5RDN7-nMG3-6 (D13A)-MG69-1_site 7
                       in HEK293T
source                1..22
                      mol_type = other DNA
                      organism = synthetic construct
SEQUENCE: 509
tcgcctatgg gaactctgga gg                                          22

SEQ ID NO: 510        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: A0A2K5RDN7-nMG4-2 (D28A)-MG69-1_site 1
                       in HEK293T
source                1..22
                      mol_type = other DNA
                      organism = synthetic construct
SEQUENCE: 510
cctaacatgg ataagtccag at                                          22

SEQ ID NO: 511        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: A0A2K5RDN7-nMG4-2 (D28A)-MG69-1_site 2
                       in HEK293T
source                1..22
                      mol_type = other DNA
                      organism = synthetic construct
SEQUENCE: 511
ggccctcaga gccggaatct ac                                          22

SEQ ID NO: 512        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: A0A2K5RDN7-nMG4-2 (D28A)-MG69-1_site 3
                       in HEK293T
source                1..22
                      mol_type = other DNA
                      organism = synthetic construct
SEQUENCE: 512
tgtcctccct caagatacag ga                                          22

SEQ ID NO: 513        moltype = DNA  length = 22
FEATURE               Location/Qualifiers
misc_feature          1..22
                      note = Description of Artificial Sequence: Synthetic
                       oligonucleotide
misc_feature          1..22
                      note = Category: spacer
misc_feature          1..22
                      note = Description: A0A2K5RDN7-nMG4-2 (D28A)-MG69-1_site 4
                       in HEK293T
source                1..22
```

```
                         mol_type = other DNA
                         organism = synthetic construct
SEQUENCE: 513
tgtgttcacc tgcccttctg tt                                              22

SEQ ID NO: 514           moltype = DNA  length = 22
FEATURE                  Location/Qualifiers
misc_feature             1..22
                         note = Description of Artificial Sequence: Synthetic
                          oligonucleotide
misc_feature             1..22
                         note = Category: spacer
misc_feature             1..22
                         note = Description: A0A2K5RDN7-nMG18-1 (D12A)-MG69-1_site 1
                          in HEK293T
source                   1..22
                         mol_type = other DNA
                         organism = synthetic construct
SEQUENCE: 514
cagtgtcccc cttccctatg gg                                              22

SEQ ID NO: 515           moltype = DNA  length = 22
FEATURE                  Location/Qualifiers
misc_feature             1..22
                         note = Description of Artificial Sequence: Synthetic
                          oligonucleotide
misc_feature             1..22
                         note = Category: spacer
misc_feature             1..22
                         note = Description: A0A2K5RDN7-nMG18-1 (D12A)-MG69-1_site 2
                          in HEK293T
source                   1..22
                         mol_type = other DNA
                         organism = synthetic construct
SEQUENCE: 515
ccccettccc tatgggaata at                                              22

SEQ ID NO: 516           moltype = DNA  length = 22
FEATURE                  Location/Qualifiers
misc_feature             1..22
                         note = Description of Artificial Sequence: Synthetic
                          oligonucleotide
misc_feature             1..22
                         note = Category: spacer
misc_feature             1..22
                         note = Description: A0A2K5RDN7-nMG18-1 (D12A)-MG69-1_site 3
                          in HEK293T
source                   1..22
                         mol_type = other DNA
                         organism = synthetic construct
SEQUENCE: 516
cagctccagc cccagagcct gg                                              22

SEQ ID NO: 517           moltype = DNA  length = 22
FEATURE                  Location/Qualifiers
misc_feature             1..22
                         note = Description of Artificial Sequence: Synthetic
                          oligonucleotide
misc_feature             1..22
                         note = Category: spacer
misc_feature             1..22
                         note = Description: A0A2K5RDN7-nMG18-1 (D12A)-MG69-1_site 4
                          in HEK293T
source                   1..22
                         mol_type = other DNA
                         organism = synthetic construct
SEQUENCE: 517
gtgcctctcc ctgcagacgg ta                                              22

SEQ ID NO: 518           moltype = DNA  length = 20
FEATURE                  Location/Qualifiers
misc_feature             1..20
                         note = Description of Artificial Sequence: Synthetic
                          oligonucleotide
misc_feature             1..20
                         note = Category: spacer
misc_feature             1..20
                         note = Description: A0A2K5RDN7-nSpCas9 (D10A)-MG69-1_site 1
                          in HEK293T
```

```
source                  1..20
                        mol_type = other DNA
                        organism = synthetic construct
SEQUENCE: 518
ttgccacgaa gcaggccaat                                              20

SEQ ID NO: 519          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: A0A2K5RDN7-nSpCas9 (D10A)-MG69-1_site 2
                         in HEK293T
source                  1..20
                        mol_type = other DNA
                        organism = synthetic construct
SEQUENCE: 519
cccggggccg ccattgacag                                              20

SEQ ID NO: 520          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: A0A2K5RDN7-nSpCas9 (D10A)-MG69-1_site 3
                         in HEK293T
source                  1..20
                        mol_type = other DNA
                        organism = synthetic construct
SEQUENCE: 520
tccggctctg agggccagtg                                              20

SEQ ID NO: 521          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: A0A2K5RDN7-nSpCas9 (D10A)-MG69-1_site 4
                         in HEK293T
source                  1..20
                        mol_type = other DNA
                        organism = synthetic construct
SEQUENCE: 521
caaccagtcc ccagtgactc                                              20

SEQ ID NO: 522          moltype = DNA  length = 20
FEATURE                 Location/Qualifiers
misc_feature            1..20
                        note = Description of Artificial Sequence: Synthetic
                         oligonucleotide
misc_feature            1..20
                        note = Category: spacer
misc_feature            1..20
                        note = Description: A0A2K5RDN7-nSpCas9 (D10A)-MG69-1_site 5
                         in HEK293T
source                  1..20
                        mol_type = other DNA
                        organism = synthetic construct
SEQUENCE: 522
gagtccgagc agaagaagaa                                              20

SEQ ID NO: 523          moltype = DNA  length = 21
FEATURE                 Location/Qualifiers
misc_feature            1..21
                        note = Description of Artificial Sequence: Synthetic primer
misc_feature            1..21
                        note = Category: primer
misc_feature            1..21
                        note = Description: Forward primer used to amplify lacZ of
                         E. coli and Sanger sequencing
```

```
source                  1..21
                        mol_type = other DNA
                        organism = synthetic construct
SEQUENCE: 523
ccaggcttta cactttatgc t                                           21

SEQ ID NO: 524          moltype = DNA  length = 25
FEATURE                 Location/Qualifiers
misc_feature            1..25
                        note = Description of Artificial Sequence: Synthetic primer
misc_feature            1..25
                        note = Category: primer
misc_feature            1..25
                        note = Description: Reverse primer used to amplify lacZ of
                         E. coli and Sanger sequencing
source                  1..25
                        mol_type = other DNA
                        organism = synthetic construct
SEQUENCE: 524
cgaacatcca aaagtttgtg ttttt                                       25

SEQ ID NO: 525          moltype = DNA  length = 18
FEATURE                 Location/Qualifiers
misc_feature            1..18
                        note = Description of Artificial Sequence: Synthetic primer
misc_feature            1..18
                        note = Category: primer
misc_feature            1..18
                        note = Description: Sanger sequencing of base edit of lacZ
                         of E. coli
source                  1..18
                        mol_type = other DNA
                        organism = synthetic construct
SEQUENCE: 525
ccgaaaggcg cggtgccg                                               18

SEQ ID NO: 526          moltype = DNA  length = 19
FEATURE                 Location/Qualifiers
misc_feature            1..19
                        note = Description of Artificial Sequence: Synthetic primer
misc_feature            1..19
                        note = Category: primer
misc_feature            1..19
                        note = Description: Sanger sequencing of base edit of lacZ
                         of E. coli
source                  1..19
                        mol_type = other DNA
                        organism = synthetic construct
SEQUENCE: 526
gtatgtggtg gatgaagcc                                              19

SEQ ID NO: 527          moltype = DNA  length = 18
FEATURE                 Location/Qualifiers
misc_feature            1..18
                        note = Description of Artificial Sequence: Synthetic primer
misc_feature            1..18
                        note = Category: primer
misc_feature            1..18
                        note = Description: Sanger sequencing of base edit of lacZ
                         of E. coli
source                  1..18
                        mol_type = other DNA
                        organism = synthetic construct
SEQUENCE: 527
ttgtggagcg acatccag                                               18

SEQ ID NO: 528          moltype = DNA  length = 19
FEATURE                 Location/Qualifiers
misc_feature            1..19
                        note = Description of Artificial Sequence: Synthetic primer
misc_feature            1..19
                        note = Category: primer
misc_feature            1..19
                        note = Description: Sanger sequencing of base edit of lacZ
                         of E. coli
source                  1..19
                        mol_type = other DNA
                        organism = synthetic construct
SEQUENCE: 528
```

```
tgagcgcatt tttacgcgc                                              19

SEQ ID NO: 529          moltype = DNA  length = 18
FEATURE                 Location/Qualifiers
misc_feature            1..18
                        note = Description of Artificial Sequence: Synthetic primer
misc_feature            1..18
                        note = Category: primer
misc_feature            1..18
                        note = Description: Sanger sequencing of base edit of lacZ
                         of E. coli
source                  1..18
                        mol_type = other DNA
                        organism = synthetic construct
SEQUENCE: 529
gaaaacggca acccgtgg                                               18

SEQ ID NO: 530          moltype = DNA  length = 20
FEATURE                 Location/Qualifiers
misc_feature            1..20
                        note = Description of Artificial Sequence: Synthetic primer
misc_feature            1..20
                        note = Category: primer
misc_feature            1..20
                        note = Description: Sanger sequencing of base edit of lacZ
                         of E. coli
source                  1..20
                        mol_type = other DNA
                        organism = synthetic construct
SEQUENCE: 530
ggattgaaaa tggtctgctg                                             20

SEQ ID NO: 531          moltype = DNA  length = 18
FEATURE                 Location/Qualifiers
misc_feature            1..18
                        note = Description of Artificial Sequence: Synthetic primer
misc_feature            1..18
                        note = Category: primer
misc_feature            1..18
                        note = Description: Sanger sequencing of base edit of lacZ
                         of E. coli
source                  1..18
                        mol_type = other DNA
                        organism = synthetic construct
SEQUENCE: 531
actgctgacg ccgctgcg                                               18

SEQ ID NO: 532          moltype = DNA  length = 48
FEATURE                 Location/Qualifiers
misc_feature            1..48
                        note = Description of Artificial Sequence: Synthetic primer
misc_feature            1..48
                        note = Category: primer
misc_feature            1..48
                        note = Description: Forward primer used to amplify CAT
                         (H193Y) of CAT (H193Y)-sgRNA- MG68-4 variant-nSpCas9 (D10A)
source                  1..48
                        mol_type = other DNA
                        organism = synthetic construct
SEQUENCE: 532
ccgccgccgc aaggaatggt ttaattaatt tgatcggcac gtaagagg              48

SEQ ID NO: 533          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Reverse primer used to amplify CAT
                         (H193Y) of CAT (H193Y)-sgRNA-MG68-4 variant-nSpCas9
source                  1..50
                        mol_type = other DNA
                        organism = synthetic construct
SEQUENCE: 533
ggactgttgg gcgccatctc cttgcatgct tcacttattc aggcgtagca            50

SEQ ID NO: 534          moltype = DNA  length = 50
FEATURE                 Location/Qualifiers
```

```
misc_feature            1..50
                        note = Description of Artificial Sequence: Synthetic primer
misc_feature            1..50
                        note = Category: primer
misc_feature            1..50
                        note = Description: Forward primer used to amplify CAT
                         (H193Y) of CAT (H193Y)-sgRNA-MG68-4 variant-nMG34-1 (D10A)
source                  1..50
                        mol_type = other DNA
                        organism = synthetic construct
SEQUENCE: 534
aaggaatggt ttaattaatt ctagattaat taatttgatc ggcacgtaag             50

SEQ ID NO: 535          moltype = DNA  length = 50
FEATURE                 Location/Qualifiers
misc_feature            1..50
                        note = Description of Artificial Sequence: Synthetic primer
misc_feature            1..50
                        note = Category: primer
misc_feature            1..50
                        note = Description: Sanger sequencing primer of CAT (H193Y)
source                  1..50
                        mol_type = other DNA
                        organism = synthetic construct
SEQUENCE: 535
ggactgttgg gcgccatctc cttgcatgct tcacttattc aggcgtagca             50

SEQ ID NO: 536          moltype = DNA  length = 18
FEATURE                 Location/Qualifiers
misc_feature            1..18
                        note = Description of Artificial Sequence: Synthetic primer
misc_feature            1..18
                        note = Category: primer
misc_feature            1..18
                        note = Description: Forward primer used to amplify BE3
                         target site in HEK293T cells and Sanger sequencing
source                  1..18
                        mol_type = other DNA
                        organism = synthetic construct
SEQUENCE: 536
gaggctggag aggcccgt                                                18

SEQ ID NO: 537          moltype = DNA  length = 22
FEATURE                 Location/Qualifiers
misc_feature            1..22
                        note = Description of Artificial Sequence: Synthetic primer
misc_feature            1..22
                        note = Category: primer
misc_feature            1..22
                        note = Description: Reverse primer used to amplify BE3
                         target site in HEK293T cells for Sanger sequencing
source                  1..22
                        mol_type = other DNA
                        organism = synthetic construct
SEQUENCE: 537
gattttcatg caggtgctga aa                                           22

SEQ ID NO: 538          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nSpCas9 (D10A)-MG69-1_site 1 in HEK293T cells
misc_difference         14..18
                        note = any nucleotide
source                  1..36
                        mol_type = other DNA
                        organism = synthetic construct
SEQUENCE: 538
gctcttccga tctnnnnnag gaggaagggc ctgagt                            36

SEQ ID NO: 539          moltype = DNA  length = 36
FEATURE                 Location/Qualifiers
misc_feature            1..36
                        note = Description of Artificial Sequence: Synthetic primer
misc_feature            1..36
```

```
                        note = Category: primer
misc_feature            1..36
                        note = Description: Reverse primer used to amplify
                         A0A2K5RDN7-nSpCas9 (D10A)-MG69-1_site 1 in HEK293T cells
misc_difference         14..18
                        note = any nucleotide
source                  1..36
                        mol_type = other DNA
                        organism = synthetic construct
SEQUENCE: 539
gctcttccga tctnnnnntc tgccctcgtg ggtttg                            36

SEQ ID NO: 540          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nSpCas9 (D10A)-MG69-1_site 2 in HEK293T cells
misc_difference         14..18
                        note = any nucleotide
source                  1..36
                        mol_type = other DNA
                        organism = synthetic construct
SEQUENCE: 540
gctcttccga tctnnnnnct ctggccactc cctggc                            36

SEQ ID NO: 541          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nSpCas9 (D10A)-MG69-1_site 2 in HEK293T cells
misc_difference         14..18
                        note = any nucleotide
source                  1..36
                        mol_type = other DNA
                        organism = synthetic construct
SEQUENCE: 541
gctcttccga tctnnnnngg caggctctcc gaggag                            36

SEQ ID NO: 542          moltype = DNA  length = 44
FEATURE                 Location/Qualifiers
misc_feature            1..44
                        note = Description of Artificial Sequence: Synthetic primer
misc_feature            1..44
                        note = Category: primer
misc_feature            1..44
                        note = Description: Forward primer used to amplify
                         A0A2K5RDN7-nSpCas9 (D10A)-MG69-1_site 3 in HEK293T cells
misc_difference         14..18
                        note = any nucleotide
source                  1..44
                        mol_type = other DNA
                        organism = synthetic construct
SEQUENCE: 542
gctcttccga tctnnnnngg gaataataaa agtctctctc ttaa                   44

SEQ ID NO: 543          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nSpCas9 (D10A)-MG69-1_site 3 in HEK293T cells
misc_difference         14..18
                        note = any nucleotide
source                  1..36
                        mol_type = other DNA
                        organism = synthetic construct
SEQUENCE: 543
gctcttccga tctnnnnncc ccctccacca gtaccc                            36
```

```
SEQ ID NO: 544          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nSpCas9 (D10A)-MG69-1_site 4 in HEK293T cells
misc_difference         14..18
                        note = any nucleotide
source                  1..36
                        mol_type = other DNA
                        organism = synthetic construct
SEQUENCE: 544
gctcttccga tctnnnnncc tgtccttgga gaaccg                            36

SEQ ID NO: 545          moltype = DNA  length = 37
FEATURE                 Location/Qualifiers
misc_feature            1..37
                        note = Description of Artificial Sequence: Synthetic primer
misc_feature            1..37
                        note = Category: primer
misc_feature            1..37
                        note = Description: Reverse primer used to amplify
                         A0A2K5RDN7-nSpCas9 (D10A)-MG69-1_site 4 in HEK293T cells
misc_difference         14..18
                        note = any nucleotide
source                  1..37
                        mol_type = other DNA
                        organism = synthetic construct
SEQUENCE: 545
gctcttccga tctnnnnngc aggtgaacac aagagct                           37

SEQ ID NO: 546          moltype = DNA  length = 37
FEATURE                 Location/Qualifiers
misc_feature            1..37
                        note = Description of Artificial Sequence: Synthetic primer
misc_feature            1..37
                        note = Category: primer
misc_feature            1..37
                        note = Description: Forward primer used to amplify
                         A0A2K5RDN7-nSpCas9 (D10A)-MG69-1_site 5 in HEK293T cells
misc_difference         14..18
                        note = any nucleotide
source                  1..37
                        mol_type = other DNA
                        organism = synthetic construct
SEQUENCE: 546
gctcttccga tctnnnnnga aggtgtggtt ccagaac                           37

SEQ ID NO: 547          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nSpCas9 (D10A)-MG69-1_site 5 in HEK293T cells
misc_difference         14..18
                        note = any nucleotide
source                  1..36
                        mol_type = other DNA
                        organism = synthetic construct
SEQUENCE: 547
gctcttccga tctnnnnntc gatgtcctcc ccattg                            36

SEQ ID NO: 548          moltype = DNA  length = 38
FEATURE                 Location/Qualifiers
misc_feature            1..38
                        note = Description of Artificial Sequence: Synthetic primer
misc_feature            1..38
                        note = Category: primer
misc_feature            1..38
                        note = Description: Forward primer used to amplify
                         A0A2K5RDN7-nMG1-4 (D9A)-MG69-1_site 1 in HEK293T cells
misc_difference         14..18
```

```
                         note = any nucleotide
source                   1..38
                         mol_type = other DNA
                         organism = synthetic construct
SEQUENCE: 548
gctcttccga tctnnnnnaa acaggctaga cataggga                          38

SEQ ID NO: 549           moltype = DNA  length = 37
FEATURE                  Location/Qualifiers
misc_feature             1..37
                         note = Description of Artificial Sequence: Synthetic primer
misc_feature             1..37
                         note = Category: primer
misc_feature             1..37
                         note = Description: Reverse primer used to amplify
                          A0A2K5RDN7-nMG1-4 (D9A)-MG69-1_site 1 in HEK293T cells
misc_difference          14..18
                         note = any nucleotide
source                   1..37
                         mol_type = other DNA
                         organism = synthetic construct
SEQUENCE: 549
gctcttccga tctnnnnnga agccaccaga gtctcta                           37

SEQ ID NO: 550           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Forward primer used to amplify
                          A0A2K5RDN7-nMG1-4 (D9A)-MG69-1_site 2 in HEK293T cells
misc_difference          14..18
                         note = any nucleotide
source                   1..36
                         mol_type = other DNA
                         organism = synthetic construct
SEQUENCE: 550
gctcttccga tctnnnnngc cgccattgac agaggg                            36

SEQ ID NO: 551           moltype = DNA  length = 41
FEATURE                  Location/Qualifiers
misc_feature             1..41
                         note = Description of Artificial Sequence: Synthetic primer
misc_feature             1..41
                         note = Category: primer
misc_feature             1..41
                         note = Description: Reverse primer used to amplify
                          A0A2K5RDN7-nMG1-4 (D9A)-MG69-1_site 2 in HEK293T cells
misc_difference          14..18
                         note = any nucleotide
source                   1..41
                         mol_type = other DNA
                         organism = synthetic construct
SEQUENCE: 551
gctcttccga tctnnnnngc atcaaaacaa aagggagatt g                      41

SEQ ID NO: 552           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Forward primer used to amplify
                          A0A2K5RDN7-nMG1-4 (D9A)-MG69-1_site 3 in HEK293T cells
misc_difference          14..18
                         note = any nucleotide
source                   1..36
                         mol_type = other DNA
                         organism = synthetic construct
SEQUENCE: 552
gctcttccga tctnnnnncc tctgcccacc tcactt                            36

SEQ ID NO: 553           moltype = DNA  length = 37
FEATURE                  Location/Qualifiers
misc_feature             1..37
                         note = Description of Artificial Sequence: Synthetic primer
```

```
misc_feature            1..37
                        note = Category: primer
misc_feature            1..37
                        note = Description: Reverse primer used to amplify
                         A0A2K5RDN7-nMG1-4 (D9A)-MG69-1_site 3 in HEK293T cells
misc_difference         14..18
                        note = any nucleotide
source                  1..37
                        mol_type = other DNA
                        organism = synthetic construct
SEQUENCE: 553
gctcttccga tctnnnnngc catgtgggtt aatctgg                            37

SEQ ID NO: 554          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG1-4 (D9A)-MG69-1_site 4 in HEK293T cells
misc_difference         14..18
                        note = any nucleotide
source                  1..36
                        mol_type = other DNA
                        organism = synthetic construct
SEQUENCE: 554
gctcttccga tctnnnnncc ggacgcacct acccat                             36

SEQ ID NO: 555          moltype = DNA  length = 37
FEATURE                 Location/Qualifiers
misc_feature            1..37
                        note = Description of Artificial Sequence: Synthetic primer
misc_feature            1..37
                        note = Category: primer
misc_feature            1..37
                        note = Description: Reverse primer used to amplify
                         A0A2K5RDN7-nMG1-4 (D9A)-MG69-1_site 4 in HEK293T cells
misc_difference         14..18
                        note = any nucleotide
source                  1..37
                        mol_type = other DNA
                        organism = synthetic construct
SEQUENCE: 555
gctcttccga tctnnnnnct agatgggaat ggatggg                            37

SEQ ID NO: 556          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG3-6 (D13A)-MG69-1_site 1 in HEK293T cells
misc_difference         14..18
                        note = any nucleotide
source                  1..36
                        mol_type = other DNA
                        organism = synthetic construct
SEQUENCE: 556
gctcttccga tctnnnnnaa ccacaaaccc acgagg                             36

SEQ ID NO: 557          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG3-6 (D13A)-MG69-1_site 1 in HEK293T cells
misc_difference         14..18
                        note = any nucleotide
source                  1..36
                        mol_type = other DNA
                        organism = synthetic construct
SEQUENCE: 557
```

```
gctcttccga tctnnnnntc aatggcggcc ccgggc                            36

SEQ ID NO: 558          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG3-6 (D13A)-MG69-1_site 2 in HEK293T cells
misc_difference         14..18
                        note = any nucleotide
source                  1..36
                        mol_type = other DNA
                        organism = synthetic construct
SEQUENCE: 558
gctcttccga tctnnnnnag tgatccccag tgtccc                            36

SEQ ID NO: 559          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG3-6 (D13A)-MG69-1_site 2 in HEK293T cells
misc_difference         14..18
                        note = any nucleotide
source                  1..36
                        mol_type = other DNA
                        organism = synthetic construct
SEQUENCE: 559
gctcttccga tctnnnnngc cctgaacgcg tttgct                            36

SEQ ID NO: 560          moltype = DNA  length = 42
FEATURE                 Location/Qualifiers
misc_feature            1..42
                        note = Description of Artificial Sequence: Synthetic primer
misc_feature            1..42
                        note = Category: primer
misc_feature            1..42
                        note = Description: Forward primer used to amplify
                         A0A2K5RDN7-nMG3-6 (D13A)-MG69-1_site 3 in HEK293T cells
misc_difference         14..18
                        note = any nucleotide
source                  1..42
                        mol_type = other DNA
                        organism = synthetic construct
SEQUENCE: 560
gctcttccga tctnnnnntg ggaataataa aagtctctct ct                     42

SEQ ID NO: 561          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG3-6 (D13A)-MG69-1_site 3 in HEK293T cells
misc_difference         14..18
                        note = any nucleotide
source                  1..36
                        mol_type = other DNA
                        organism = synthetic construct
SEQUENCE: 561
gctcttccga tctnnnnncc cctccaccag tacccc                            36

SEQ ID NO: 562          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG3-6 (D13A)-MG69-1_site 4 in HEK293T cells
```

```
misc_difference        14..18
                       note = any nucleotide
source                 1..36
                       mol_type = other DNA
                       organism = synthetic construct
SEQUENCE: 562
gctcttccga tctnnnnnca gggcctcctc agccca                           36

SEQ ID NO: 563         moltype = DNA  length = 38
FEATURE                Location/Qualifiers
misc_feature           1..38
                       note = Description of Artificial Sequence: Synthetic primer
misc_feature           1..38
                       note = Category: primer
misc_feature           1..38
                       note = Description: Reverse primer used to amplify
                        A0A2K5RDN7-nMG3-6 (D13A)-MG69-1_site 4 in HEK293T cells
misc_difference        14..18
                       note = any nucleotide
source                 1..38
                       mol_type = other DNA
                       organism = synthetic construct
SEQUENCE: 563
gctcttccga tctnnnnngt ctggatgtcg taagggaa                         38

SEQ ID NO: 564         moltype = DNA  length = 40
FEATURE                Location/Qualifiers
misc_feature           1..40
                       note = Description of Artificial Sequence: Synthetic primer
misc_feature           1..40
                       note = Category: primer
misc_feature           1..40
                       note = Description: Forward primer used to amplify
                        A0A2K5RDN7-nMG3-6 (D13A)-MG69-1_site 5 in HEK293T cells
misc_difference        14..18
                       note = any nucleotide
source                 1..40
                       mol_type = other DNA
                       organism = synthetic construct
SEQUENCE: 564
gctcttccga tctnnnnngg ggtgtaactc agaatgtttt                       40

SEQ ID NO: 565         moltype = DNA  length = 36
FEATURE                Location/Qualifiers
misc_feature           1..36
                       note = Description of Artificial Sequence: Synthetic primer
misc_feature           1..36
                       note = Category: primer
misc_feature           1..36
                       note = Description: Reverse primer used to amplify
                        A0A2K5RDN7-nMG3-6 (D13A)-MG69-1_site 5 in HEK293T cells
misc_difference        14..18
                       note = any nucleotide
source                 1..36
                       mol_type = other DNA
                       organism = synthetic construct
SEQUENCE: 565
gctcttccga tctnnnnngg gagtgagact cagaga                           36

SEQ ID NO: 566         moltype = DNA  length = 39
FEATURE                Location/Qualifiers
misc_feature           1..39
                       note = Description of Artificial Sequence: Synthetic primer
misc_feature           1..39
                       note = Category: primer
misc_feature           1..39
                       note = Description: Forward primer used to amplify
                        A0A2K5RDN7-nMG3-6 (D13A)-MG69-1_site 6 in HEK293T cells
misc_difference        14..18
                       note = any nucleotide
source                 1..39
                       mol_type = other DNA
                       organism = synthetic construct
SEQUENCE: 566
gctcttccga tctnnnnngc aaagagggaa atgagatca                        39

SEQ ID NO: 567         moltype = DNA  length = 41
FEATURE                Location/Qualifiers
misc_feature           1..41
```

```
                         note = Description of Artificial Sequence: Synthetic primer
misc_feature             1..41
                         note = Category: primer
misc_feature             1..41
                         note = Description: Reverse primer used to amplify
                          A0A2K5RDN7-nMG3-6 (D13A)-MG69-1_site 6 in HEK293T cells
misc_difference          14..18
                         note = any nucleotide
source                   1..41
                         mol_type = other DNA
                         organism = synthetic construct
SEQUENCE: 567
gctcttccga tctnnnnngt gacacatttg tttgagaatc a                        41

SEQ ID NO: 568           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Forward primer used to amplify
                          A0A2K5RDN7-nMG3-6 (D13A)-MG69-1_site 7 in HEK293T cells
misc_difference          14..18
                         note = any nucleotide
source                   1..36
                         mol_type = other DNA
                         organism = synthetic construct
SEQUENCE: 568
gctcttccga tctnnnnnct ttatccccgc acagag                              36

SEQ ID NO: 569           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Reverse primer used to amplify
                          A0A2K5RDN7-nMG3-6 (D13A)-MG69-1_site 7 in HEK293T cells
misc_difference          14..18
                         note = any nucleotide
source                   1..36
                         mol_type = other DNA
                         organism = synthetic construct
SEQUENCE: 569
gctcttccga tctnnnnnct tggcccatgg gaaatc                              36

SEQ ID NO: 570           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Forward primer used to amplify
                          A0A2K5RDN7-nMG4-2 (D28A)-MG69-1_site 1 in HEK293T cells
misc_difference          14..18
                         note = any nucleotide
source                   1..36
                         mol_type = other DNA
                         organism = synthetic construct
SEQUENCE: 570
gctcttccga tctnnnnngt cccatcccaa cacccc                              36

SEQ ID NO: 571           moltype = DNA  length = 36
FEATURE                  Location/Qualifiers
misc_feature             1..36
                         note = Description of Artificial Sequence: Synthetic primer
misc_feature             1..36
                         note = Category: primer
misc_feature             1..36
                         note = Description: Reverse primer used to amplify
                          A0A2K5RDN7-nMG4-2 (D28A)-MG69-1_site 1 in HEK293T cells
misc_difference          14..18
                         note = any nucleotide
source                   1..36
                         mol_type = other DNA
                         organism = synthetic construct
```

```
SEQUENCE: 571
gctcttccga tctnnnnntg ggcatgtgtg ctccca                          36

SEQ ID NO: 572          moltype = DNA  length = 42
FEATURE                 Location/Qualifiers
misc_feature            1..42
                        note = Description of Artificial Sequence: Synthetic primer
misc_feature            1..42
                        note = Category: primer
misc_feature            1..42
                        note = Description: Forward primer used to amplify
                         A0A2K5RDN7-nMG4-2 (D28A)-MG69-1_site 2 in HEK293T cells
misc_difference         14..18
                        note = any nucleotide
source                  1..42
                        mol_type = other DNA
                        organism = synthetic construct
SEQUENCE: 572
gctcttccga tctnnnnnct atgggaataa taaaagtctc tc                   42

SEQ ID NO: 573          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG4-2 (D28A)-MG69-1_site 2 in HEK293T cells
misc_difference         14..18
                        note = any nucleotide
source                  1..36
                        mol_type = other DNA
                        organism = synthetic construct
SEQUENCE: 573
gctcttccga tctnnnnnct ccaccagtac cccacc                          36

SEQ ID NO: 574          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG4-2 (D28A)-MG69-1_site 3 in HEK293T cells
misc_difference         14..18
                        note = any nucleotide
source                  1..36
                        mol_type = other DNA
                        organism = synthetic construct
SEQUENCE: 574
gctcttccga tctnnnnngg accctggtct ctacct                          36

SEQ ID NO: 575          moltype = DNA  length = 37
FEATURE                 Location/Qualifiers
misc_feature            1..37
                        note = Description of Artificial Sequence: Synthetic primer
misc_feature            1..37
                        note = Category: primer
misc_feature            1..37
                        note = Description: Reverse primer used to amplify
                         A0A2K5RDN7-nMG4-2 (D28A)-MG69-1_site 3 in HEK293T cells
misc_difference         14..18
                        note = any nucleotide
source                  1..37
                        mol_type = other DNA
                        organism = synthetic construct
SEQUENCE: 575
gctcttccga tctnnnnncc tctcccattg aactacc                         37

SEQ ID NO: 576          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
```

```
                       A0A2K5RDN7-nMG4-2 (D28A)-MG69-1_site 4 in HEK293T cells
misc_difference        14..18
                       note = any nucleotide
source                 1..36
                       mol_type = other DNA
                       organism = synthetic construct
SEQUENCE: 576
gctcttccga tctnnnnncc ccagtgactc agggcc                            36

SEQ ID NO: 577         moltype = DNA  length = 40
FEATURE                Location/Qualifiers
misc_feature           1..40
                       note = Description of Artificial Sequence: Synthetic primer
misc_feature           1..40
                       note = Category: primer
misc_feature           1..40
                       note = Description: Reverse primer used to amplify
                        A0A2K5RDN7-nMG4-2 (D28A)-MG69-1_site 4 in HEK293T cells
misc_difference        14..18
                       note = any nucleotide
source                 1..40
                       mol_type = other DNA
                       organism = synthetic construct
SEQUENCE: 577
gctcttccga tctnnnnntc gtaagggaaa gacttaggaa                        40

SEQ ID NO: 578         moltype = DNA  length = 42
FEATURE                Location/Qualifiers
misc_feature           1..42
                       note = Description of Artificial Sequence: Synthetic primer
misc_feature           1..42
                       note = Category: primer
misc_feature           1..42
                       note = Description: Forward primer used to amplify
                        A0A2K5RDN7-nMG18-1 (D12A)-MG69-1_site 1 in HEK293T cells
misc_difference        14..18
                       note = any nucleotide
source                 1..42
                       mol_type = other DNA
                       organism = synthetic construct
SEQUENCE: 578
gctcttccga tctnnnnntc tcccttttgt tttgatgcat tt                     42

SEQ ID NO: 579         moltype = DNA  length = 36
FEATURE                Location/Qualifiers
misc_feature           1..36
                       note = Description of Artificial Sequence: Synthetic primer
misc_feature           1..36
                       note = Category: primer
misc_feature           1..36
                       note = Description: Reverse primer used to amplify
                        A0A2K5RDN7-nMG18-1 (D12A)-MG69-1_site 1 in HEK293T cells
misc_difference        14..18
                       note = any nucleotide
source                 1..36
                       mol_type = other DNA
                       organism = synthetic construct
SEQUENCE: 579
gctcttccga tctnnnnncc accccaggct ctgggg                            36

SEQ ID NO: 580         moltype = DNA  length = 44
FEATURE                Location/Qualifiers
misc_feature           1..44
                       note = Description of Artificial Sequence: Synthetic primer
misc_feature           1..44
                       note = Category: primer
misc_feature           1..44
                       note = Description: Forward primer used to amplify
                        A0A2K5RDN7-nMG18-1 (D12A)-MG69-1_site 2 in HEK293T cells
misc_difference        14..18
                       note = any nucleotide
source                 1..44
                       mol_type = other DNA
                       organism = synthetic construct
SEQUENCE: 580
gctcttccga tctnnnnncc ttttgttttg atgcatttct gttt                   44

SEQ ID NO: 581         moltype = DNA  length = 36
FEATURE                Location/Qualifiers
```

```
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG18-1 (D12A)-MG69-1_site 2 in HEK293T cells
misc_difference         14..18
                        note = any nucleotide
source                  1..36
                        mol_type = other DNA
                        organism = synthetic construct
SEQUENCE: 581
gctcttccga tctnnnnnaa tctaccaccc caggct                            36

SEQ ID NO: 582          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG18-1 (D12A)-MG69-1_site 3 in HEK293T cells
misc_difference         14..18
                        note = any nucleotide
source                  1..36
                        mol_type = other DNA
                        organism = synthetic construct
SEQUENCE: 582
gctcttccga tctnnnnnat ccccagtgtc cccctt                            36

SEQ ID NO: 583          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Reverse primer used to amplify
                         A0A2K5RDN7-nMG18-1 (D12A)-MG69-1_site 3 in HEK293T cells
misc_difference         14..18
                        note = any nucleotide
source                  1..36
                        mol_type = other DNA
                        organism = synthetic construct
SEQUENCE: 583
gctcttccga tctnnnnncc aggccctgaa cgcgtt                            36

SEQ ID NO: 584          moltype = DNA  length = 36
FEATURE                 Location/Qualifiers
misc_feature            1..36
                        note = Description of Artificial Sequence: Synthetic primer
misc_feature            1..36
                        note = Category: primer
misc_feature            1..36
                        note = Description: Forward primer used to amplify
                         A0A2K5RDN7-nMG18-1 (D12A)-MG69-1_site 4 in HEK293T cells
misc_difference         14..18
                        note = any nucleotide
source                  1..36
                        mol_type = other DNA
                        organism = synthetic construct
SEQUENCE: 584
gctcttccga tctnnnnnag gccaggcctg cggggg                            36

SEQ ID NO: 585          moltype = DNA  length = 41
FEATURE                 Location/Qualifiers
misc_feature            1..41
                        note = Description of Artificial Sequence: Synthetic primer
misc_feature            1..41
                        note = Category: primer
misc_feature            1..41
                        note = Description: Reverse primer used to amplify
                         A0A2K5RDN7-nMG18-1 (D12A)-MG69-1_site 4 in HEK293T cells
misc_difference         14..18
                        note = any nucleotide
source                  1..41
                        mol_type = other DNA
```

```
                         organism = synthetic construct
SEQUENCE: 585
gctcttccga tctnnnnncc aaaaactccc aaattagcaa a                         41

SEQ ID NO: 586           moltype = AA  length = 969
FEATURE                  Location/Qualifiers
REGION                   1..969
                         note = Description of Artificial Sequence: Synthetic
                          polypeptide
REGION                   1..969
                         note = Category: adenine base editor
REGION                   1..969
                         note = Description: TadA (ABE8.17m)-nMG34-1 (D10A)
source                   1..969
                         mol_type = protein
                         organism = synthetic construct
SEQUENCE: 586
MGSSHHHHHH SEVEFSHEYW MRHALTLAKR ARDEREVPVG AVLVLNNRVI GEGWNRAIGL  60
HDPTAHAEIM ALRQGGLVMQ NYRLIDATLY STFEPCVMCA GAMIHSRIGR VVFGVRNAKT  120
GAAGSLMDVL HYPGMNHRVE ITEGILADEC AALLCYFFRM PRRVFNAQKK AQSSTDSGGS  180
SGGSSGSETP GTSESATPES SGGSSGGSME RELVLGIAYG GKYTGLAVVD RRHNQVLYAN  240
RLKMRDDVAG ILKDRRKQRG IRRTAQTKKK RLRELKNYLK SIGYNESTAT FETVYSLAHK  300
RGYDYADMPE EKTSEEIEAM DVEERKQWEK EKQEWEETKR NSRHRKEVVK DVHKAMIEGR  360
ATEEQIKRVE RIFNKQYRPK RFNNRILTKC KVEDCGVNTP LRKNVRDLLI ENIVRFFPIE  420
QSEKDNLKDA VLDKNRREEV KSFFRKHKTD EHIRKQVYDI ADNKLSGRTV FCKEHILEHT  480
EHSKEERKVF RLAPSLKTKI ENVLAVIKDE ILPKFTVNKV VMESNNFDIA AKTQGKKRLA  540
KEEYGKGPRE GKETRKEALL RETDGRCIYC GKSIDISNAH DDHIFPRKAG GLNIFANLVA  600
CCAVCNENKK GRTPLESGIS PKPEIIAFMK NDLKKKILED ARNINTVDFN KYMSHASIGW  660
RYMRDRLRES AGNKKLPIER QSGIYTAYFR RWWGFKKERG NTLHHALDAV ILASRKGYSD  720
DGLVDMTLKP KYNKGGEFDP EKHLPEPIEF KMDKGSRGSA LHDRNPLSYK KGIITRRFMV  780
TEIECGKEDD VISETYREKL KEAFKRFDTK KGKCLTDKEA KEAGFCIKKN ELVMSLKCSI  840
KGTGPGQMIR INNNVFKTNV HNVGVDVYLD EKGKKKAYER KNPRLSKHFI EPPPQPNGRV  900
SFTLKRRDMV TVEGEDAIYR IKKLGTSPTI EAVVGSDGKT RTVSATKLTK ANSAELEGSG  960
GSPKKKRKV                                                            969

SEQ ID NO: 587           moltype = AA  length = 1104
FEATURE                  Location/Qualifiers
REGION                   1..1104
                         note = Description of Artificial Sequence: Synthetic
                          polypeptide
REGION                   1..1104
                         note = Category: cytosine base editor
REGION                   1..1104
                         note = Description: rAPOBEC1-nMG34-1 (D10A)-UGI (PBS1)
source                   1..1104
                         mol_type = protein
                         organism = synthetic construct
SEQUENCE: 587
MGSSHHHHHH MSSETGPVAV DPTLRRRIEP HEFEVFFDPR ELRKETCLLY EINWGGRHSI  60
WRHTSQNTNK HVEVNFIEKF TTERYFCPNT RCSITWFLSW SPCGECSRAI TEFLSRYPHV  120
TLFIYIARLY HHADPRNRQG LRDLISSGVT IQIMTEQESG YCWRNFVNYS PSNEAHWPRY  180
PHLWVRLYVL ELYCIILGLP PCLNILRRKQ PQLTFFTIAL QSCHYQRLPP HILWATGLKS  240
GSETPGTSES ATPESAMERE LVLGIAYGGK YTGLAVVDRR HNQVLYANRL KMRDDVAGIL  300
KDRRKQRGIR RTAQTKKKRL RELKNYLKSI GYNESTATFE TVYSLAHKRG YDYADMPEEK  360
TSEEIEAMDV EERKQWEKEK QEWEETKRNS RHRKEVVKDV HKAMIEGRAT EEQIKRVERI  420
FNKQYRPKRF NNRILTKCKV EDCGVNTPLR KNVRDLLIEN IVRFFPIEQS EKDNLKDAVL  480
DKNRREEVKS FFRKHKTDEH IRKQVYDIAD NKLSGRTVFC KEHILEHTEH SKEERKVFRL  540
APSLKTKIEN VLAVIKDEIL PKFTVNKVVM ESNNFDIAAK TQGKKRLAKE EYGKGPREGK  600
ETRKEALLRE TDGRCIYCGK SIDISNAHDD HIFPRKAGGL NIFANLVACC AVCNENKKGR  660
TPLESGISPK PEIIAFMKND LKKKILEDAR NINTVDFNKY MSHASIGWRY MRDRLRESAG  720
NKKLPIERQS GIYTAYFRRW WGFKKERGNT LHHALDAVIL ASRKGYSDDG LVDMTLKPKY  780
NKGGEFDPEK HLPEPIEFKM DKGSRGSALH DRNPLSYKKG IITRRFMVTE IECGKEDDVI  840
SETYREKLKE AFKRFDTKKG KCLTDKEAKE AGFCIKKNEL VMSLKCSIKG TGPGQMIRIN  900
NNVFKTNVHN VGVDVYLDEK GKKKAYERKN PRLSKHFIEP PPQPNGRVSF TLKRRDMVTV  960
EGEDAIYRIK KLGTSPTIEA VVGSDGKTRT VSATKLTKAN SAELEGSGGS TNLSDIIEKE  1020
TGKQLVIQES ILMLPEEVEE VIGNKPESDI LVHTAYDEST DENVMLLTSD APEYKPWALV  1080
IQDSNGENKI KMLSGGSPKK KRKV                                           1104

SEQ ID NO: 588           moltype = AA  length = 1592
FEATURE                  Location/Qualifiers
REGION                   1..1592
                         note = Description of Artificial Sequence: Synthetic
                          polypeptide
REGION                   1..1592
                         note = Category: adenine base editor
REGION                   1..1592
                         note = Description: MG68-3-nSpCas9 (D10A)
source                   1..1592
                         mol_type = protein
```

```
                        organism = synthetic construct
SEQUENCE: 588
MGSSHHHHHH MNEQTSTDEQ FMQQALALAD EAERQGEVPV GALLVHQGTV IGRGFNQVIT  60
QLDPSAHAEM LAIRDAARYL QNYRILDTTL YVTLEPCPMC AGALVHARVK RLVYGASDPR  120
TGACGSVFNV VADTRLNHQL EVVAGVLGSQ CGERLSAFFR QRRAAQKALK KAAQNFQSPS  180
SGGSSGGSSG SETPGTSESA TPESSGGSSG GSMDKKYSIG LAIGTNSVGW AVITDEYKVP  240
SKKFKVLGNT DRHSIKKNLI GALLFDSGET AEATRLKRTA RRRYTRRKNR ICYLQEIFSN  300
EMAKVDDSFF HRLEESFLVE EDKKHERHPI FGNIVDEVAY HEKYPTIYHL RKKLVDSTDK  360
ADLRLIYLAL AHMIKFRGHF LIEGDLNPDN SDVDKLFIQL VQTYNQLFEE NPINASGVDA  420
KAILSARLSK SRRLENLIAQ LPGEKKNGLF GNLIALSLGL TPNFKSNFDL AEDAKLQLSK  480
DTYDDDLDNL LAQIGDQYAD LFLAAKNLSD AILLSDILRV NTEITKAPLS ASMIKRYDEH  540
HQDLTLLKAL VRQQLPEKYK EIFFDQSKNG YAGYIDGGAS QEEFYKFIKP ILEKMDGTEE  600
LLVKLNREDL LRKQRTFDNG SIPHQIHLGE LHAILRRQED FYPFLKDNRE KIEKILTFRI  660
PYYVGPLARG NSRFAWMTRK SEETITPWNF EEVVDKGASA QSFIERMTNF DKNLPNEKVL  720
PKHSLLYEYF TVYNELTKVK YVTEGMRKPA FLSGEQKKAI VDLLFKTNRK VTVKQLKEDY  780
FKKIECFDSV EISGVEDRFN ASLGTYHDLL KIIKDKDFLD NEENEDILED IVLTLTLFED  840
REMIEERLKT YAHLFDDKVM KQLKRRRYTG WGRLSRKLIN GIRDKQSGKT ILDFLKSDGF  900
ANRNFMQLIH DDSLTFKEDI QKAQVSGQGD SLHEHIANLA GSPAIKKGIL QTVKVVDELV  960
KVMGRHKPEN IVIEMARENQ TTQKGQKNSR ERMKRIEEGI KELGSQILKE HPVENTQLQN  1020
EKLYLYYLQN GRDMYVDQEL DINRLSDYDV DHIVPQSFLK DDSIDNKVLT RSDKNRGKSD  1080
NVPSEEVVKK MKNYWRQLLN AKLITQRKFD NLTKAERGGL SELDKAGFIK RQLVETRQIT  1140
KHVAQILDSR MNTKYDENDK LIREVKVITL KSKLVSDFRK DFQFYKVREI NNYHHAHDAY  1200
LNAVVGTALI KKYPKLESEF VYGDYKVYDV RKMIAKSEQE IGKATAKYFF YSNIMNFFKT  1260
EITLANGEIR KRPLIETNGE TGEIVWDKGR DFATVRKVLS MPQVNIVKKT EVQTGGFSKE  1320
SILPKRNSDK LIARKKDWDP KKYGGFDSPT VAYSVLVVAK VEKGKSKKLK SVKELLGITI  1380
MERSSFEKNP IDFLEAKGYK EVKKDLIIKL PKYSLFELEN GRKRMLASAG ELQKGNELAL  1440
PSKYVNFLYL ASHYEKLKGS PEDNEQKQLF VEQHKHYLDE IIEQISEFSK RVILADANLD  1500
KVLSAYNKHR DKPIREQAEN IIHLFTLTNL GAPAAFKYFD TTIDRKRYTS TKEVLDATLI  1560
HQSITGLYET RIDLSQLGGD GSGGSPKKKR KV                                1592

SEQ ID NO: 589          moltype = AA  length = 1588
FEATURE                 Location/Qualifiers
REGION                  1..1588
                        note = Description of Artificial Sequence: Synthetic
                         polypeptide
REGION                  1..1588
                        note = Category: adenine base editor
REGION                  1..1588
                        note = Description: MG68-8-nSpCas9 (D10A)
source                  1..1588
                        mol_type = protein
                        organism = synthetic construct
SEQUENCE: 589
MGSSHHHHHH MPQSEQDIYW IRYAMQLAER AEQAGEVPVG AVLVLDNQAL GEGWNLSISR  60
HDPCAHAEIM AIRQAGERIG NYRLLGATLY VTLEPCVMCA GAMVHSRIAR VVYGASDLKT  120
GAAGSVFDVL SDPRHNHVVE ITGGVESEAC SQQLSDFFRR RRAEQKAEKQ RLKDNQSGGS  180
SGGSSGSETP GTSESATPES SGGSSGGSMD KKYSIGLAIG TNSVGWAVIT DEYKVPSKKF  240
KVLGNTDRHS IKKNLIGALL FDSGETAEAT RLKRTARRRY TRRKNRICYL QEIFSNEMAK  300
VDDSFFHRLE ESFLVEEDKK HERHPIFGNI VDEVAYHEKY PTIYHLRKKL VDSTDKADLR  360
LIYLALAHMI KFRGHFLIEG DLNPDNSDVD KLFIQLVQTY NQLFEENPIN ASGVDAKAIL  420
SARLSKSRRL ENLIAQLPGE KKNGLFGNLI ALSLGLTPNF KSNFDLAEDA KLQLSKDTYD  480
DDLDNLLAQI GDQYADLFLA AKNLSDAILL SDILRVNTEI TKAPLSASMI KRYDEHHQDL  540
TLLKALVRQQ LPEKYKEIFF DQSKNGYAGY IDGGASQEEF YKFIKPILEK MDGTEELLVK  600
LNREDLLRKQ RTFDNGSIPH QIHLGELHAI LRRQEDFYPF LKDNREKIEK ILTFRIPYYV  660
GPLARGNSRF AWMTRKSEET ITPWNFEEVV DKGASAQSFI ERMTNFDKNL PNEKVLPKHS  720
LLYEYFTVYN ELTKVKYVTE GMRKPAFLSG EQKKAIVDLL FKTNRKVTVK QLKEDYFKKI  780
ECFDSVEISG VEDRFNASLG TYHDLLKIIK DKDFLDNEEN EDILEDIVLT LTLFEDREMI  840
EERLKTYAHL FDDKVMKQLK RRRYTGWGRL SRKLINGIRD KQSGKTILDF LKSDGFANRN  900
FMQLIHDDSL TFKEDIQKAQ VSGQGDSLHE HIANLAGSPA IKKGILQTVK VVDELVKVMG  960
RHKPENIVIE MARENQTTQK GQKNSRERMK RIEEGIKELG SQILKEHPVE NTQLQNEKLY  1020
LYYLQNGRDM YVDQELDINR LSDYDVDHIV PQSFLKDDSI DNKVLTRSDK NRGKSDNVPS  1080
EEVVKKMKNY WRQLLNAKLI TQRKFDNLTK AERGGLSELD KAGFIKRQLV ETRQITKHVA  1140
QILDSRMNTK YDENDKLIRE VKVITLKSKL VSDFRKDFQF YKVREINNYH HAHDAYLNAV  1200
VGTALIKKYP KLESEFVYGD YKVYDVRKMI AKSEQEIGKA TAKYFFYSNI MNFFKTEITL  1260
ANGEIRKRPL IETNGETGEI VWDKGRDFAT VRKVLSMPQV NIVKKTEVQT GGFSKESILP  1320
KRNSDKLIAR KKDWDPKKYG GFDSPTVAYS VLVVAKVEKG KSKKLKSVKE LLGITIMERS  1380
SFEKNPIDFL EAKGYKEVKK DLIIKLPKYS LFELENGRKR MLASAGELQK GNELALPSKY  1440
VNFLYLASHY EKLKGSPEDN EQKQLFVEQH KHYLDEIIEQ ISEFSKRVIL ADANLDKVLS  1500
AYNKHRDKPI REQAENIIHL FTLTNLGAPA AFKYFDTTID RKRYTSTKEV LDATLIHQSI  1560
TGLYETRIDL SQLGGDGSGG SPKKKRKV                                     1588

SEQ ID NO: 590          moltype = AA  length = 16
FEATURE                 Location/Qualifiers
REGION                  1..16
                        note = Description of Artificial Sequence: Synthetic peptide
REGION                  1..16
                        note = Category: Linker
source                  1..16
                        mol_type = protein
```

```
                        organism = synthetic construct
SEQUENCE: 590
SGSETPGTSE SATPES                                                  16

SEQ ID NO: 591          moltype = AA  length = 17
FEATURE                 Location/Qualifiers
REGION                  1..17
                        note = Description of Artificial Sequence: Synthetic peptide
REGION                  1..17
                        note = Category: Linker
source                  1..17
                        mol_type = protein
                        organism = synthetic construct
SEQUENCE: 591
SGSETPGTSE SATPESA                                                 17

SEQ ID NO: 592          moltype = AA  length = 32
FEATURE                 Location/Qualifiers
REGION                  1..32
                        note = Description of Artificial Sequence: Synthetic peptide
REGION                  1..32
                        note = Category: Linker
source                  1..32
                        mol_type = protein
                        organism = synthetic construct
SEQUENCE: 592
SGGSSGGSSG SETPGTSESA TPESSGGSSG GS                                32

SEQ ID NO: 593          moltype = AA  length = 34
FEATURE                 Location/Qualifiers
REGION                  1..34
                        note = Description of Artificial Sequence: Synthetic peptide
REGION                  1..34
                        note = Category: Linker
source                  1..34
                        mol_type = protein
                        organism = synthetic construct
SEQUENCE: 593
GTSGGSSGGS SGSETPGTSE SATPESSGGS SGGS                              34

SEQ ID NO: 594          moltype = AA  length = 206
FEATURE                 Location/Qualifiers
REGION                  1..206
                        note = Description: CMP/dCMP-type deaminase
                         domain-containing protein (uniprot accession A0A2K5RDN7)
source                  1..206
                        mol_type = protein
                        organism = Cebus imitator
SEQUENCE: 594
MEASPASRPR PLMGPRTFTE NFTNNPEVFG RHQTYLCYEV KCQGPDGTRD LMTEQRDFLC  60
NQARNLLSGF DGRHAERCFL DRVPSWRLDP AQTYRVTCFI SWSPCFSCAR EVAEFLQENP  120
HVNLRIFAAR IYDCRPRYEE GLQMLQNAGA QVSIMTSEEF RHCWDTFVDH QGHPFQPWEG  180
LDEHSQALSR RLQAILQGNR WMILSL                                       206

SEQ ID NO: 595          moltype = AA  length = 167
FEATURE                 Location/Qualifiers
REGION                  1..167
                        note = Description of Unknown: Adenosine deaminase sequence
REGION                  1..167
                        note = Description: TadA* (ABE8.17m)
source                  1..167
                        mol_type = protein
                        organism = unidentified
SEQUENCE: 595
MSEVEFSHEY WMRHALTLAK RARDEREVPV GAVLVLNNRV IGEGWNRAIG LHDPTAHAEI  60
MALRQGGLVM QNYRLIDATL YSTFEPCVMC AGAMIHSRIG RVVFGVRNAK TGAAGSLMDV  120
LHYPGMNHRV EITEGILADE CAALLCYFFR MPRRVFNAQK KAQSSTD                167

SEQ ID NO: 596          moltype = AA  length = 747
FEATURE                 Location/Qualifiers
REGION                  1..747
                        note = Description of Unknown: uncultivated organism
                         sequence
REGION                  1..747
                        note = Description: MG34-1 effector
source                  1..747
                        mol_type = protein
                        organism = unidentified
SEQUENCE: 596
```

-continued

```
MERELVLGID YGGKYTGLAV VDRRHNQVLY ANRLKMRDDV AGILKDRRKQ RGIRRTAQTK  60
KKRLRELKNY LKSIGYNEST ATFETVYSLA HKRGYDYADM PEEKTSEEIE AMDVEERKQW  120
EKEKQEWEET KRNSRHRKEV VKDVHKAMIE GRATEEQIKR VERIFNKQYR PKRFNNRILT  180
KCKVEDCGVN TPLRKNVRDL LIENIVRFFP IEQSEKDNLK DAVLDKNRRE EVKSFFRKHK  240
TDEHIRKQVY DIADNKLSGR TVFCKEHILE HTEHSKEERK VFRLAPSLKT KIENVLAVIK  300
DEILPKFTVN KVVMESNNFD IAAKTQGKKR LAKEEYGKGP REGKETRKEA LLRETDGRCI  360
YCGKSIDISN AHDDHIFPRK AGGLNIFANL VACCAVCNEN KKGRTPLESG ISPKPEIIAF  420
MKNDLKKKIL EDARNINTVD FNKYMSHASI GWRYMRDRLR ESAGNKKLPI ERQSGIYTAY  480
FRRWWGFKKE RGNTLHHALD AVILASRKGY SDDGLVDMTL KPKYNKGGEF DPEKHLPEPI  540
EFKMDKGSRG SALHDRNPLS YKKGIITRRF MVTEIECGKE DDVISETYRE KLKEAFKRFD  600
TKKGKCLTDK EAKEAGFCIK KNELVMSLKC SIKGTGPGQM IRINNNVFKT NVHNVGVDVY  660
LDEKGKKKAY ERKNPRLSKH FIEPPPQPNG RVSFTLKRRD MVTVEGEDAI YRIKKLGTSP  720
TIEAVVGSDG KTRTVSATKL TKANSAE                                    747

SEQ ID NO: 597         moltype = AA  length = 747
FEATURE                Location/Qualifiers
REGION                 1..747
                       note = Description of Unknown: uncultivated organism
                        sequence
REGION                 1..747
                       note = Description: MG34-1 (D10A)
source                 1..747
                       mol_type = protein
                       organism = unidentified
SEQUENCE: 597
MERELVLGIA YGGKYTGLAV VDRRHNQVLY ANRLKMRDDV AGILKDRRKQ RGIRRTAQTK  60
KKRLRELKNY LKSIGYNEST ATFETVYSLA HKRGYDYADM PEEKTSEEIE AMDVEERKQW  120
EKEKQEWEET KRNSRHRKEV VKDVHKAMIE GRATEEQIKR VERIFNKQYR PKRFNNRILT  180
KCKVEDCGVN TPLRKNVRDL LIENIVRFFP IEQSEKDNLK DAVLDKNRRE EVKSFFRKHK  240
TDEHIRKQVY DIADNKLSGR TVFCKEHILE HTEHSKEERK VFRLAPSLKT KIENVLAVIK  300
DEILPKFTVN KVVMESNNFD IAAKTQGKKR LAKEEYGKGP REGKETRKEA LLRETDGRCI  360
YCGKSIDISN AHDDHIFPRK AGGLNIFANL VACCAVCNEN KKGRTPLESG ISPKPEIIAF  420
MKNDLKKKIL EDARNINTVD FNKYMSHASI GWRYMRDRLR ESAGNKKLPI ERQSGIYTAY  480
FRRWWGFKKE RGNTLHHALD AVILASRKGY SDDGLVDMTL KPKYNKGGEF DPEKHLPEPI  540
EFKMDKGSRG SALHDRNPLS YKKGIITRRF MVTEIECGKE DDVISETYRE KLKEAFKRFD  600
TKKGKCLTDK EAKEAGFCIK KNELVMSLKC SIKGTGPGQM IRINNNVFKT NVHNVGVDVY  660
LDEKGKKKAY ERKNPRLSKH FIEPPPQPNG RVSFTLKRRD MVTVEGEDAI YRIKKLGTSP  720
TIEAVVGSDG KTRTVSATKL TKANSAE                                    747

SEQ ID NO: 598         moltype =   length =
SEQUENCE: 598
000

SEQ ID NO: 599         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 599
SGSETPGTSE SATPES                                                16

SEQ ID NO: 600         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 600
SGGSS                                                            5

SEQ ID NO: 601         moltype = AA  length = 25
FEATURE                Location/Qualifiers
source                 1..25
                       mol_type = protein
                       organism = Staphylococcus aureus
SEQUENCE: 601
MKRNYILGLD IGITSVGYGI IDYET                                      25

SEQ ID NO: 602         moltype = AA  length = 24
FEATURE                Location/Qualifiers
REGION                 1..24
                       note = Description of Artificial Sequence: Synthetic peptide
source                 1..24
                       mol_type = protein
                       organism = synthetic construct
SEQUENCE: 602
```

```
MKKKVFAFDL GKASIGYCVR DGFN                                        24

SEQ ID NO: 603          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 603
MEKEKNNHVW GFDIGKGSLG EAVRVGGD                                    28

SEQ ID NO: 604          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 604
MSTDMKNYRI GVDVGDRSVG LAAIEFDD                                    28

SEQ ID NO: 605          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 605
MSEHTKYRIG IDVGDRSVGL AAIEFDD                                     27

SEQ ID NO: 606          moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 606
MSTDMKNYRI GVDVGDRSVG LAAIEFDD                                    28

SEQ ID NO: 607          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 607
MGDQQTLQAT SYCLGLDVGV QGVGWAVIDL DD                               32

SEQ ID NO: 608          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 608
MSNKTILGLD LGVSSIGWAI IERND                                       25

SEQ ID NO: 609          moltype = AA  length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 609
MEITINREIG KLGLPRHLVL GMDPGIASCG FALIDTAN                         38

SEQ ID NO: 610          moltype = AA  length = 23
FEATURE                 Location/Qualifiers
REGION                  1..23
                        note = Description of Artificial Sequence: Synthetic peptide
source                  1..23
```

```
                        mol_type = protein
                        organism = synthetic construct
SEQUENCE: 610
MNYVLGLDVG IASVGWAVLE LNE                                            23

SEQ ID NO: 611          moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 611
MIKNILGLDL GVGSIGWALI QTED                                           24

SEQ ID NO: 612          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 612
MDQSKEYYIG LDGGTDSVGW AVLNPDY                                        27

SEQ ID NO: 613          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 613
cgtttgccgt ctgaatttga cc                                             22

SEQ ID NO: 614          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 614
gaagatcagg atatgtggcg ga                                             22

SEQ ID NO: 615          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 615
acgggtaaca gtttctttat gg                                             22

SEQ ID NO: 616          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 616
cgttgctgca taaaccgact ac                                             22

SEQ ID NO: 617          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 617
aaaacccgaa actgtggagc gc                                             22
```

```
SEQ ID NO: 618         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 618
gattgaaaat ggtctgctgc tg                                           22

SEQ ID NO: 619         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 619
tacgggtaac agtttcttta tg                                           22

SEQ ID NO: 620         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 620
gcgttggcaa tttaaccgcc ag                                           22

SEQ ID NO: 621         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 621
ctgaatatcg acggtttcca ta                                           22

SEQ ID NO: 622         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 622
cacatttaat gttgatgaaa gc                                           22

SEQ ID NO: 623         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 623
acacaaatca gcgatttcca tg                                           22

SEQ ID NO: 624         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 624
atggatgagc agacgatggt gc                                           22

SEQ ID NO: 625         moltype = DNA  length = 22
```

```
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 625
ttcatctgtg gtgcaacggg cg                                           22

SEQ ID NO: 626          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 626
acgagcatca tcctctgcat gg                                           22

SEQ ID NO: 627          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 627
cgacccgcat tgaccctaac gc                                           22

SEQ ID NO: 628          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 628
cacaaatcag cgatttccat gt                                           22

SEQ ID NO: 629          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 629
tgatgaagca gaacaacttt aa                                           22

SEQ ID NO: 630          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 630
aatattgaaa cccacggcat gg                                           22

SEQ ID NO: 631          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 631
aacgtcgaaa acccgaaact gt                                           22

SEQ ID NO: 632          moltype = DNA  length = 22
FEATURE                 Location/Qualifiers
misc_feature            1..22
```

```
                        note = Description of Artificial Sequence: Synthetic
                         oligonucleotide
source                  1..22
                        mol_type = other DNA
                        organism = synthetic construct
SEQUENCE: 632
aaacccacgg catggtgcca at                                            22

SEQ ID NO: 633          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 633
tcaaaaaatg gctttcgcta cc                                            22

SEQ ID NO: 634          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 634
aagcagcgtt gttgcagtgc ac                                            22

SEQ ID NO: 635          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 635
tcagccggaa aacctaccgg at                                            22

SEQ ID NO: 636          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 636
gccagctggc gtaatagcga ag                                            22

SEQ ID NO: 637          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 637
agggtgaaac gcaggtcgcc ag                                            22

SEQ ID NO: 638          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 638
ctacgtctga acgtcgaaaa cc                                            22

SEQ ID NO: 639          moltype = DNA  length = 22
FEATURE                 Location/Qualifiers
misc_feature            1..22
                        note = Description of Artificial Sequence: Synthetic
                         oligonucleotide
```

```
source                  1..22
                        mol_type = other DNA
                        organism = synthetic construct
SEQUENCE: 639
ggcaactctg gctcacagta cg                                          22

SEQ ID NO: 640          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 640
ccggaaaacc taccggattg at                                          22

SEQ ID NO: 641          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 641
tttctttcac agatgtggat                                             20

SEQ ID NO: 642          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 642
caggatatgt ggcggatgag                                             20

SEQ ID NO: 643          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 643
tgcgaatacg cccacgcgat                                             20

SEQ ID NO: 644          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 644
cggcgtttca tctgtggtgc aa                                          22

SEQ ID NO: 645          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 645
gccaggacag tcgtttgccg tc                                          22

SEQ ID NO: 646          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
```

```
                         organism = synthetic construct
SEQUENCE: 646
tcagccgcgc tgtactggag gc                                              22

SEQ ID NO: 647           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 647
cccttcccaa cagttgcgca gc                                              22

SEQ ID NO: 648           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 648
ctgtcgtcgt cccctcaaac tg                                              22

SEQ ID NO: 649           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 649
gtgacggcag ttatctggaa ga                                              22

SEQ ID NO: 650           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 650
atgatttcag ccgcgctgta ct                                              22

SEQ ID NO: 651           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 651
ttactgccgc ctgttttgac cg                                              22

SEQ ID NO: 652           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 652
cgaatggcgc tttgcctggt tt                                              22

SEQ ID NO: 653           moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 653
```

```
tcccctcaaa ctggcagatg ca                                           22

SEQ ID NO: 654         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 654
atctacacca acgtgaccta tc                                           22

SEQ ID NO: 655         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 655
caacgggcgc tgggtcggtt ac                                           22

SEQ ID NO: 656         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 656
aaggcggcgg agccgacacc ac                                           22

SEQ ID NO: 657         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 657
gccgatcgcg tcacactacg tc                                           22

SEQ ID NO: 658         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 658
gatccgcgct ggctaccggc ga                                           22

SEQ ID NO: 659         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 659
ccttcccgcc cggtgcagta tg                                           22

SEQ ID NO: 660         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 660
cggtcaatcc gccgtttgtt cc                                           22
```

```
SEQ ID NO: 661         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 661
tcctttgcga atacgcccac gc                                           22

SEQ ID NO: 662         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 662
ggtcggctta cggcggtgat tt                                           22

SEQ ID NO: 663         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 663
acgtgaccta tcccattacg gt                                           22

SEQ ID NO: 664         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 664
atccgccgtt tgttcccacg ga                                           22

SEQ ID NO: 665         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 665
cgacggcacg ctgattgaag ca                                           22

SEQ ID NO: 666         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 666
gaccagccct tcccggctgt gc                                           22

SEQ ID NO: 667         moltype = DNA  length = 22
FEATURE                Location/Qualifiers
misc_feature           1..22
                       note = Description of Artificial Sequence: Synthetic
                        oligonucleotide
source                 1..22
                       mol_type = other DNA
                       organism = synthetic construct
SEQUENCE: 667
tccgtttatc cgggcaaacc at                                           22

SEQ ID NO: 668         moltype = DNA  length = 20
FEATURE                Location/Qualifiers
```

```
misc_feature          1..20
                      note = Description of Artificial Sequence: Synthetic
                       oligonucleotide
source                1..20
                      mol_type = other DNA
                      organism = synthetic construct
SEQUENCE: 668
cctctggatg tcgctccaca                                              20

SEQ ID NO: 669        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 669
gggacgcgcg aattgaatta                                              20

SEQ ID NO: 670        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 670
cgttttacaa cgtcgtgact                                              20

SEQ ID NO: 671        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 671
ggactctggc cactccctgg                                              20

SEQ ID NO: 672        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 672
cgtattgaga ggtgggaatc                                              20

SEQ ID NO: 673        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 673
gtgtcccccct tccctatggg                                              20

SEQ ID NO: 674        moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 674
tccagctcca gccccagagc                                              20

SEQ ID NO: 675        moltype = DNA  length = 20
FEATURE               Location/Qualifiers
misc_feature          1..20
                      note = Description of Artificial Sequence: Synthetic
```

```
                         oligonucleotide
source                  1..20
                        mol_type = other DNA
                        organism = synthetic construct
SEQUENCE: 675
ggagagcctg cctgcctggg                                          20

SEQ ID NO: 676          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 676
cccttcccta tgggaataat                                          20

SEQ ID NO: 677          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 677
ttccggctct gagggccagt                                          20

SEQ ID NO: 678          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 678
ccccctctcc ctccatcagt                                          20

SEQ ID NO: 679          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 679
gctccagccc cagagcctgg                                          20

SEQ ID NO: 680          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 680
ccttctgttt gtcccacttg                                          20

SEQ ID NO: 681          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 681
tacacagttt cccaagctac                                          20

SEQ ID NO: 682          moltype = DNA  length = 20
FEATURE                 Location/Qualifiers
misc_feature            1..20
                        note = Description of Artificial Sequence: Synthetic
                         oligonucleotide
source                  1..20
```

```
                        mol_type = other DNA
                        organism = synthetic construct
SEQUENCE: 682
gcctctccct gcagacggta                                                  20

SEQ ID NO: 683          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 683
tctaggcctg gcttggccaa                                                  20

SEQ ID NO: 684          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 684
cctgccgtgt accagctgag                                                  20

SEQ ID NO: 685          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 685
gcctatggga actctggagg                                                  20

SEQ ID NO: 686          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 686
ttgccacgaa gcaggccaat                                                  20

SEQ ID NO: 687          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 687
ggcccagact gagcacgtga                                                  20

SEQ ID NO: 688          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 688
cccggggccg ccattgacag                                                  20

SEQ ID NO: 689          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
```

```
SEQUENCE: 689
tccggctctg agggccagtg                                              20

SEQ ID NO: 690         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 690
caaccagtcc ccagtgactc                                              20

SEQ ID NO: 691         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 691
gagtccgagc agaagaagaa                                              20

SEQ ID NO: 692         moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 692
HHHHHH                                                             6

SEQ ID NO: 693         moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 693
ctggcgattc aggttcatta t                                            21

SEQ ID NO: 694         moltype = DNA  length = 21
FEATURE                Location/Qualifiers
source                 1..21
                       mol_type = other DNA
                       organism = Escherichia coli
SEQUENCE: 694
ctggcgattc aggttcatca t                                            21

SEQ ID NO: 695         moltype = DNA  length = 22
FEATURE                Location/Qualifiers
source                 1..22
                       mol_type = other DNA
                       organism = synthetic construct
SEQUENCE: 695
acgggtgaca gtttctttat gg                                           22

SEQ ID NO: 696         moltype = DNA  length = 22
FEATURE                Location/Qualifiers
source                 1..22
                       mol_type = other DNA
                       organism = synthetic construct
SEQUENCE: 696
gcgggtgaca gtttctttat gg                                           22

SEQ ID NO: 697         moltype = DNA  length = 22
FEATURE                Location/Qualifiers
source                 1..22
                       mol_type = other DNA
                       organism = synthetic construct
SEQUENCE: 697
cacatttgat gttgatgaaa gc                                           22

SEQ ID NO: 698         moltype = DNA  length = 22
```

```
FEATURE                Location/Qualifiers
source                 1..22
                       mol_type = other DNA
                       organism = synthetic construct
SEQUENCE: 698
cacatttagt gttgatgaaa gc                                          22

SEQ ID NO: 699         moltype = DNA  length = 22
FEATURE                Location/Qualifiers
source                 1..22
                       mol_type = other DNA
                       organism = synthetic construct
SEQUENCE: 699
acacgagtca gcgatttcca tg                                          22

SEQ ID NO: 700         moltype = DNA  length = 22
FEATURE                Location/Qualifiers
source                 1..22
                       mol_type = other DNA
                       organism = synthetic construct
SEQUENCE: 700
acacaagtca gcgatttcca tg                                          22

SEQ ID NO: 701         moltype = DNA  length = 22
FEATURE                Location/Qualifiers
source                 1..22
                       mol_type = other DNA
                       organism = synthetic construct
SEQUENCE: 701
atgggtgggc agacgatggt gc                                          22

SEQ ID NO: 702         moltype = DNA  length = 22
FEATURE                Location/Qualifiers
source                 1..22
                       mol_type = other DNA
                       organism = synthetic construct
SEQUENCE: 702
atggatgagc ggacgatggt gc                                          22

SEQ ID NO: 703         moltype = DNA  length = 22
FEATURE                Location/Qualifiers
source                 1..22
                       mol_type = other DNA
                       organism = synthetic construct
SEQUENCE: 703
aaaacccgag gctgtggagc gc                                          22

SEQ ID NO: 704         moltype = DNA  length = 22
FEATURE                Location/Qualifiers
source                 1..22
                       mol_type = other DNA
                       organism = synthetic construct
SEQUENCE: 704
ggcggctctg gctcacagta cg                                          22

SEQ ID NO: 705         moltype = DNA  length = 22
FEATURE                Location/Qualifiers
source                 1..22
                       mol_type = other DNA
                       organism = synthetic construct
SEQUENCE: 705
ctacgtttga acgttgaaaa cc                                          22

SEQ ID NO: 706         moltype = DNA  length = 22
FEATURE                Location/Qualifiers
source                 1..22
                       mol_type = other DNA
                       organism = synthetic construct
SEQUENCE: 706
cgaatggcgc tttgcttggt tt                                          22

SEQ ID NO: 707         moltype = DNA  length = 22
FEATURE                Location/Qualifiers
source                 1..22
                       mol_type = other DNA
                       organism = synthetic construct
SEQUENCE: 707
tttccttaaa ctggcagatg ca                                          22
```

```
SEQ ID NO: 708         moltype = DNA  length = 22
FEATURE                Location/Qualifiers
source                 1..22
                       mol_type = other DNA
                       organism = synthetic construct
SEQUENCE: 708
ttcccttaaa ctggcagatg ca                                            22

SEQ ID NO: 709         moltype = DNA  length = 22
FEATURE                Location/Qualifiers
source                 1..22
                       mol_type = other DNA
                       organism = synthetic construct
SEQUENCE: 709
cacaaattag cgatttccat gt                                            22

SEQ ID NO: 710         moltype = DNA  length = 22
FEATURE                Location/Qualifiers
source                 1..22
                       mol_type = other DNA
                       organism = synthetic construct
SEQUENCE: 710
cacaaattag cgattttcat gt                                            22

SEQ ID NO: 711         moltype = DNA  length = 22
FEATURE                Location/Qualifiers
source                 1..22
                       mol_type = other DNA
                       organism = synthetic construct
SEQUENCE: 711
cggttaatcc gccgtttgtt cc                                            22

SEQ ID NO: 712         moltype = DNA  length = 22
FEATURE                Location/Qualifiers
source                 1..22
                       mol_type = other DNA
                       organism = synthetic construct
SEQUENCE: 712
gatttgcgct ggctaccggc ga                                            22

SEQ ID NO: 713         moltype = DNA  length = 22
FEATURE                Location/Qualifiers
source                 1..22
                       mol_type = other DNA
                       organism = synthetic construct
SEQUENCE: 713
gattcgcgct ggctaccggc ga                                            22

SEQ ID NO: 714         moltype = DNA  length = 22
FEATURE                Location/Qualifiers
source                 1..22
                       mol_type = other DNA
                       organism = synthetic construct
SEQUENCE: 714
ttagccgcgc tgtactggag gc                                            22

SEQ ID NO: 715         moltype = DNA  length = 22
FEATURE                Location/Qualifiers
source                 1..22
                       mol_type = other DNA
                       organism = synthetic construct
SEQUENCE: 715
ttagctgcgc tgtactggag gc                                            22

SEQ ID NO: 716         moltype = DNA  length = 22
FEATURE                Location/Qualifiers
source                 1..22
                       mol_type = other DNA
                       organism = synthetic construct
SEQUENCE: 716
ttagccgtgc tgtactggag gc                                            22

SEQ ID NO: 717         moltype = DNA  length = 22
FEATURE                Location/Qualifiers
source                 1..22
                       mol_type = other DNA
                       organism = synthetic construct
SEQUENCE: 717
gaccagccct tttcggctgt gc                                            22
```

-continued

```
SEQ ID NO: 718          moltype = DNA  length = 22
FEATURE                 Location/Qualifiers
source                  1..22
                        mol_type = other DNA
                        organism = synthetic construct
SEQUENCE: 718
gaccagccct ttccggctgt gc                                         22

SEQ ID NO: 719          moltype = DNA  length = 22
FEATURE                 Location/Qualifiers
source                  1..22
                        mol_type = other DNA
                        organism = synthetic construct
SEQUENCE: 719
tttgtttatt tgggcaaacc at                                         22

SEQ ID NO: 720          moltype = DNA  length = 22
FEATURE                 Location/Qualifiers
source                  1..22
                        mol_type = other DNA
                        organism = synthetic construct
SEQUENCE: 720
tttgtttatt cgggcaaacc at                                         22
```